United States Patent
Egen et al.

(10) Patent No.: US 10,005,848 B2
(45) Date of Patent: Jun. 26, 2018

(54) METHOD OF REDUCING BLOOD GLUCOSE BY ADMINISTERING RON AGONISTS

(71) Applicant: Genentech, Inc., South San Francisco, CA (US)

(72) Inventors: Jackson G Egen, San Mateo, CA (US); Jo-Anne Hongo, Redwood City, CA (US); Steven Kauder, San Mateo, CA (US); Robert A Lazarus, Millbrae, CA (US); Lydia Santell, Foster City, CA (US); Yan Wu, Foster City, CA (US); Meredith Hazen, Belmont, CA (US); Wei-Ching Liang, Foster City, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days. days.

(21) Appl. No.: 14/725,412

(22) Filed: May 29, 2015

(65) Prior Publication Data
US 2016/0032013 A1 Feb. 4, 2016

Related U.S. Application Data

(63) Continuation of application No. PCT/US2013/072364, filed on Nov. 27, 2013.

(60) Provisional application No. 61/823,744, filed on May 15, 2013, provisional application No. 61/732,048, filed on Nov. 30, 2012.

(51) Int. Cl.
| | |
|---|---|
| *C07K 16/40* | (2006.01) |
| *C07K 14/705* | (2006.01) |
| *C07K 16/28* | (2006.01) |
| *C07K 14/52* | (2006.01) |
| *C12Q 1/68* | (2006.01) |
| *G01N 33/74* | (2006.01) |
| *C12Q 1/6883* | (2018.01) |
| *A61K 39/00* | (2006.01) |

(52) U.S. Cl.
CPC .............. *C07K 16/40* (2013.01); *C07K 14/52* (2013.01); *C07K 14/70596* (2013.01); *C07K 16/2863* (2013.01); *C12Q 1/6883* (2013.01); *G01N 33/74* (2013.01); *A61K 2039/505* (2013.01); *C07K 2317/55* (2013.01); *C07K 2317/74* (2013.01); *C07K 2317/75* (2013.01); *C07K 2317/76* (2013.01); *C07K 2317/92* (2013.01); *C07K 2319/30* (2013.01); *C12Q 2600/106* (2013.01); *C12Q 2600/156* (2013.01); *G01N 2333/71* (2013.01); *G01N 2333/912* (2013.01); *G01N 2800/065* (2013.01); *G01N 2800/20* (2013.01); *G01N 2800/52* (2013.01)

(58) Field of Classification Search
CPC .... C07K 16/40; C07K 14/52; C07K 16/2863; C07K 14/70596; C07K 2317/92; C07K 2317/74; C07K 2319/30; C12Q 1/6883; C12Q 2600/106; G01N 33/74; G01N 2333/912; G01N 2800/065; G01N 2333/71; G01N 2800/20; G01N 2800/52

See application file for complete search history.

(56) References Cited

U.S. PATENT DOCUMENTS

| 5,948,892 A | 9/1999 | Wahl | |
|---|---|---|---|
| 7,947,811 B2 * | 5/2011 | Pereira | ................ A61K 31/337 424/130.1 |
| 2004/0260064 A1 * | 12/2004 | Wahl | .................. C07K 14/4753 530/351 |

FOREIGN PATENT DOCUMENTS

| WO | WO 96/14082 | * | 5/1996 |

OTHER PUBLICATIONS

Hauser F, et al. Genes and Immunity. 13:321-327. 2012.*
Goyette P, et al. Mucosal Immunology. 1(2):131-138. Mar. 2008.*
Santoro MM, et al. Developmental Cell. 5(2):257-271. Aug. 2003.*
Anderson et al., "Investigation of Crohn's disease risk loci in ulcerative colitis further defines their molecular relationship" Gastrenterology 136(2)::532-9.e3 ( 2009).
Anderson et al., "Meta-analysis identifies 29 additional ulcerative colitis risk loci, increasing the number of confirmed association to 47" Nat Genet. 43(3):246-52 ( 2011).
Ashkenazi and Chamow, "Immunoadhesins as research tools and therapeutic agents" Curr Op Immunol 9:195-200 ( 1997).
Barrett et al., "Genome-wide association defines more than 30 distinct susceptibility loci for Crohn's disease" Nat Genet 40(8):955-962 (Aug. 2008).
Carafoli et al., "Crystal structure of the beta-chain of human hepatocyte growth factor-like/macrophage stimulating protein" FEBS J. 272(22):5799-807 ( 2005).
Chao et al., "Crystal structure of the Sema-PSI extracellular domain of human RON receptor tyrosine kinase" PLoS One 7(7):e41912 ( 2012).
Chaudhuri et al., "Distinct involvement of the Gab 1 and Grb2 adaptor proteins in signal transduction by the related receptor tyrosine kinases RON and MET" J Biol Chem. 286(37):32762-74 ( 2011).
Chen et al., "Activation of the RON receptor tyrosine kinase inhibits inducible nitric oxide synthase (iNOS) expression by murine peritoneal exudate macrophages: phosphatigylinositol-3 kinase is required for RON-mediated inhibition of iNOS expression" J Immunol. 161(9):4950-9 ( 1998).

(Continued)

*Primary Examiner* — Robert Landsman
(74) *Attorney, Agent, or Firm* — Y. Elaine Chang

(57) ABSTRACT

This invention relates to RON compositions, in particular RON composition comprising a RON agonist, and methods of using the compositions for the treatment of diseases. The invention also relates to diagnosis of RON-associated or MSP-associated diseases.

5 Claims, 30 Drawing Sheets

(56) References Cited

OTHER PUBLICATIONS

Danilkovitch et al. et al., "Interaction of Macrophage-stimulating Protein with Its Receptor" J Biol Chem 274:29937-29943 ( 1999).
Danilkovitch et al., "Macrophage stimulating protein-induced epithelial cell adhesion is mediated by a PI3-K-dependent, but FAK-independent mechanism" Exp Cell Res. 248(2):575-82 ( 1999).
Danilkovitch et al., "Two independent signaling pathways mediate the antiapoptotic action of macrophage-stimulating protein on epithelial cells" Mol Cell Biol. 20(6):2218-27 ( 2000).
Egen et al., "Macrophage and T cell dynamics during the development and disintegration of mycobacterial granulomas" Immunity 28(2):271-84 ( 2008).
Ganesan et al., "An allosteric anti-hepsin antibody derived from a constrained phage display library" Protein engineering, Design & Selection 25(3):127-133 ( 2012).
Gaudino et al. et al., "Ron is a Heterodimeric Tyrosine Kinase Receptor Activated by the HGF Homologue MSP" EMBO J 13(15):3524-3532 ( 1994).
Gaudino et al., "The proto-oncogene RON is involved in development of epithelial, bone and neuro-endocrine tissues" Oncogene 11(12):2627-37 ( 1995).
Gherardi et al., "Functional map and domain structure of MET, the product of the c-met protooncogene and receptor for hepatocyte growth factor/scatter factor" P Natl Acad Sci USA 100(21):12039-12044 (Oct. 14, 2003).
Gong et al., "Importance of cellular microenvironment and circulatory dynamics in B cell immunotherapy" J Immunol. 174:817-826 ( 2005).
Gorlatova et al., "Protein Characterization of a Candidate Mechanism SNP for Crohn's Disease: The Macrophage Stimulating Protein R689C Substitution" PLOS One 6(11):e27269 (Nov. 7, 2011).
Goyette et al., "Gene-centric association mapping of chromosome 3p implicates MST1 in IBD pathogenesis" Mucosal Immunol. 1(2)::131-8 ( 2008).
Häuser et al., "Macrophage-stimulating protein polymorphism rs3197999 is associated with a gain of function: implications for inflammatory bowel disease" Genes and Immunity 13(4):321-327 (Jun. 1, 2012).
Iwama et al., "Terminal differentiation of murine resident peritoneal macrophages is characterized by expression of the STK protein tyrosine kinase, a receptor for macrophage-stimulating protein" Blood 86(9):3394-403 ( 1995).
Khor et al., "Genetics and pathogenesis of inflammatory bowel disease" Nature 474(7351):307-17 ( 2011).
Lu et al., "Multiple variants of the RON receptor tyrosine kinase: biochemical properties, tumorigenic activities, and potential drug targets" Cancer Lett. 257(2):157-64 ( 2007).
Moran et al., "Pro-urokinase-type plasminogen activator is a substrate for hepsin" J Biol Chem. 281(41):30439-46 (Oct. 13, 2006).
Nanney et al., "Proteolytic cleavage and activation of pro-macrophage-stimulating protein and upregulation of its receptor in tissue injury" Journal of Investigative Dermatology 111(4):573-581 (Oct. 1, 1988).
Ronsin et al., "A Novel Putative Receptor Protein Tyrosine Kinase of the Met Family" Oncogene 8:1195-1202 ( 1993).

Santoro et al., "The MSP receptor regulates alpha6beta4 and alpha3beta 1 integrins via 14-3-3 proteins in keratinocyte migration" Dev Cell. 5(2):257-71 ( 2003).
Shields et al. et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Stamos et al., "Crystal structure of the HGF beta-chain in complex with the Sema domain of the Met receptor" EMBO J 23(12):2325-2335 (Jun. 16, 2004).
Wahl et al., "Mutation of Cys672 allows recombinant expression of activatible macrophage-stimulating protein"J Biol Chem. 272(24):15053-6 ( 1997).
Waltz et al., "Ron-mediated cytoplasmic signaling is dispensable for viability but is required to limit inflammatory responses" J Clin Invest. 108(4):567-76 ( 2001).
Wang et al. et al., "Identification of the ron Gene Product as the Receptor for the Human Macrophage Stimulating Protein" Science 266:117-119 (Oct. 7, 1994).
Wang et al. et al., "Macrophage Stimulating Protein (MSP) Binds to Its Receptor via the MSP β Chain" J Biol Chem 272(27):16999-17004 (Jul. 4, 1997).
Wang et al. et al., "Proteolytic Conversion of Single Chain Precursor Macrophage-stimulating Protein to a Biologically Active Heterodimer by Contact Enzymes of the Coagulation Cascade" J Biol Chem 269(5):3436-3440 (Feb. 4, 1994).
Wellcome Trust Case Control Consortium, "Genome-wide association study of 14,000 cases of seven common diseases and 3,000 shared control" Nature 447(7145):661-78 ( 2007).
Wilson et al., "The RON receptor tyrosine kinase regulates IFN-gamma production and responses in innate immunity" J Immunol. 181(4)::2303-10 ( 2008).
Yoshimura et al. et al., "Cloning, Sequencing, and Expression of Human Macrophage Stimulating Protein (MSP,MST1) Confirms MSP as a Member of the Family of Kringle Proteins and Locates the MSP Gene on Chromosome 3" J Biol Chem 268(21):15461-15468 (Jul. 25, 1993).
Camp et al., "RON, a Tyrosine Kinase Receptor Involved in Tumor Progression and Metastasis" Annals of Surgical Oncology 12(4):273-281 (Apr. 1, 2005).
ISR (Jan. 28, 2014).
Kauder et al., "Functional Consequences of the Macrophage Stimulating Protein 689C Inflammatory Bowel Disease Risk Allele" PLOS One 8(12):e83958 (Dec. 23, 2013).
Michieli et al., "An HGF-MSP chimera disassociates the trophic properties of scatter factors from their pro-invasive activity" Nature Biotechnology 20(5):488-495 (May 1, 2002).
Secco et al., "Characterization of a single-chain intrabody directed against the human receptor tyrosine kinase Ron" Journal of Immunological Methods 285(1):99-109 (Feb. 1, 2004)
Takahara et al., "Metron factor-1 prevents liver injury without promoting metastasis" Hepatology 47(6):2010-2025 (Jun. 1, 2008).
Xue et al., "Protective effects of HGF-MSP chimer (metron factor-1) on liver ischemia-reperfusion injury in rat model" Journal of Digestive Diseases 11(5):299-305 (Oct. 28, 2010).
Yao et al, "Agonistic monoclonal antibodies potentiate tumorigenic and invasive activities of splicing variant of the RON receptor tyrosine kinase" Cancer Biology & Therapy 5(9):1179-1186 (2006).

\* cited by examiner

C

SEQUENCE LISTING

```
<160> NUMBER OF SEQ ID NOS: 93

<210> SEQ ID NO 1
<211> LENGTH: 2160
<212> TYPE: DNA
<213> ORGANISM: Artificial Sequence
<220> FEATURE:
<223> OTHER INFORMATION: Synthetic human MSP polypeptide
<220> FEATURE:
<221> NAME/KEY: CDS
<222> LOCATION: (1)..(2160)

<400> SEQUENCE: 1 atg ggg tgg ctc cca ctc ctg ctt ctg act caa tgc tta ggg gtc         48
Met Gly Trp Leu Pro Leu Leu Leu Leu Thr Gln Cys Leu Gly Val
1               5                   10                  15 cct ggg cag cgc tcg cca ttg aat gac ttc caa gtg ctc cgg ggc aca     96
Pro Gly Gln Arg Ser Pro Leu Asn Asp Phe Gln Val Leu Arg Gly Thr
            20                  25                  30 gag cta cag cac ctg cta cat gcg gtg gtg ccc ggg cct tgg cag gag    144
Glu Leu Gln His Leu Leu His Ala Val Val Pro Gly Pro Trp Gln Glu
        35                  40                  45 gat gtg gca gat gct gaa gag tgt gct ggt cgc tgt ggg ccc tta atg    192
Asp Val Ala Asp Ala Glu Glu Cys Ala Gly Arg Cys Gly Pro Leu Met
    50                  55                  60 gac tgc cgg gcc ttc cac tac aac gtg agc agc cat ggt tgc caa ctg    240
Asp Cys Arg Ala Phe His Tyr Asn Val Ser Ser His Gly Cys Gln Leu
65                  70                  75                  80 ctg cca tgg act caa cac tcg ccc cac acg agg ctg cgg cgt tct ggg    288
Leu Pro Trp Thr Gln His Ser Pro His Thr Arg Leu Arg Arg Ser Gly
                85                  90                  95 cgc tgt gac ctc ttc cag aag aaa gac tac gta cgg acc tgc atc atg    336
Arg Cys Asp Leu Phe Gln Lys Lys Asp Tyr Val Arg Thr Cys Ile Met
            100                 105                 110 aac aat ggg gtt ggg tac cgg ggc acc atg gcc acg acc gtg ggt ggc    384
Asn Asn Gly Val Gly Tyr Arg Gly Thr Met Ala Thr Thr Val Gly Gly
        115                 120                 125 ctg ccc tgc cag gct tgg agc cac aag ttc ccg aat gat cac aag tac    432
Leu Pro Cys Gln Ala Trp Ser His Lys Phe Pro Asn Asp His Lys Tyr
    130                 135                 140 acg ccc act ctc cgg aat ggc ctg gaa gag aac ttc tgc cgt aac cct    480
Thr Pro Thr Leu Arg Asn Gly Leu Glu Glu Asn Phe Cys Arg Asn Pro
145                 150                 155                 160 gat ggc gac ccc gga ggt cct tgg tgc tac aca aca gac cct gct gtg    528
Asp Gly Asp Pro Gly Gly Pro Trp Cys Tyr Thr Thr Asp Pro Ala Val
                165                 170                 175 cgc ttc cag agc tgc ggc atc aaa tcc tgc cgg gag gcc gcg tgt gtc    576
Arg Phe Gln Ser Cys Gly Ile Lys Ser Cys Arg Glu Ala Ala Cys Val
            180                 185                 190 tgg tgc aat ggc gag gaa tac cgc ggc gcg gta gac cgc acg gag tca    624
Trp Cys Asn Gly Glu Glu Tyr Arg Gly Ala Val Asp Arg Thr Glu Ser
        195                 200                 205 ggg cgc gag tgc cag cgc tgg gat ctt cag cac ccg cac cag cac ccc    672
Gly Arg Glu Cys Gln Arg Trp Asp Leu Gln His Pro His Gln His Pro
    210                 215                 220
```

```
ttc gag ccg ggc aag ttc ctc gac caa ggt ctg gac gac aac tat tgc    720
Phe Glu Pro Gly Lys Phe Leu Asp Gln Gly Leu Asp Asp Asn Tyr Cys
225                 230                 235                 240 cgg aat cct gac ggc tcc gag cgg cca tgg tgc tac act acg gat ccg    768
Arg Asn Pro Asp Gly Ser Glu Arg Pro Trp Cys Tyr Thr Thr Asp Pro
                245                 250                 255 cag atc gag cga gag ttc tgt gac ctc ccc cgc tgc ggg tcc gag gca    816
Gln Ile Glu Arg Glu Phe Cys Asp Leu Pro Arg Cys Gly Ser Glu Ala
                260                 265                 270 cag ccc cgc caa gag gcc aca act gtc agc tgc ttc cgc ggg aag ggt    864
Gln Pro Arg Gln Glu Ala Thr Thr Val Ser Cys Phe Arg Gly Lys Gly
        275                 280                 285 gag ggc tac cgg ggc aca gcc aat acc acc act gcg ggc gta cct tgc    912
Glu Gly Tyr Arg Gly Thr Ala Asn Thr Thr Thr Ala Gly Val Pro Cys
        290                 295                 300 cag cgt tgg gac gcg caa atc cct cat cag cac cga ttt acg cca gaa    960
Gln Arg Trp Asp Ala Gln Ile Pro His Gln His Arg Phe Thr Pro Glu
305                 310                 315                 320 aaa tac gcg tgc aaa gac ctt cgg gag aac ttc tgc cgg aac ccc gac   1008
Lys Tyr Ala Cys Lys Asp Leu Arg Glu Asn Phe Cys Arg Asn Pro Asp
                325                 330                 335 ggc tca gag gcg ccc tgg tgc ttc aca ctg cgg ccc ggc atg cgc gcg   1056
Gly Ser Glu Ala Pro Trp Cys Phe Thr Leu Arg Pro Gly Met Arg Ala
                340                 345                 350 gcc ttt tgc tac cag atc cgg cgt tgt aca gac gac gtg cgg ccc cag   1104
Ala Phe Cys Tyr Gln Ile Arg Arg Cys Thr Asp Asp Val Arg Pro Gln
        355                 360                 365 gac tgc tac cac ggc gca ggg gag cag tac cgc ggc acg gtc agc aag   1152
Asp Cys Tyr His Gly Ala Gly Glu Gln Tyr Arg Gly Thr Val Ser Lys
        370                 375                 380 acc cgc aag ggt gtc cag tgc cag cgc tgg tcc gct gag acg ccg cac   1200
Thr Arg Lys Gly Val Gln Cys Gln Arg Trp Ser Ala Glu Thr Pro His
385                 390                 395                 400 aag ccg cag ttc acg ttt acc tcc gaa ccg cat gca caa ctg gag gag   1248
Lys Pro Gln Phe Thr Phe Thr Ser Glu Pro His Ala Gln Leu Glu Glu
                405                 410                 415 aac ttc tgc cgg aac cca gat ggg gat agc cat ggg ccc tgg tgc tac   1296
Asn Phe Cys Arg Asn Pro Asp Gly Asp Ser His Gly Pro Trp Cys Tyr
                420                 425                 430 acg atg gac cca agg acc cca ttc gac tac tgt gcc ctg cga cgc tgc   1344
Thr Met Asp Pro Arg Thr Pro Phe Asp Tyr Cys Ala Leu Arg Arg Cys
        435                 440                 445 gct gat gac cag ccg cca tca atc ctg gac ccc cca gac cag gtg cag   1392
Ala Asp Asp Gln Pro Pro Ser Ile Leu Asp Pro Pro Asp Gln Val Gln
        450                 455                 460 ttt gag aag tgt ggc aag agg gtg gat cgg ctg gat cag cgg cgt tcc   1440
Phe Glu Lys Cys Gly Lys Arg Val Asp Arg Leu Asp Gln Arg Arg Ser
465                 470                 475                 480 aag ctg cgc gtg gtt ggg ggc cat ccg ggc aac tca ccc tgg aca gtc   1488
Lys Leu Arg Val Val Gly Gly His Pro Gly Asn Ser Pro Trp Thr Val
                485                 490                 495 agc ttg cgg aat cgg cag ggc cag cat ttc tgc ggg ggg tct cta gtg   1536
Ser Leu Arg Asn Arg Gln Gly Gln His Phe Cys Gly Gly Ser Leu Val
                500                 505                 510 aag gag cag tgg ata ctg act gcc cgg cag tgc ttc tcc tcc tgc cat   1584
Lys Glu Gln Trp Ile Leu Thr Ala Arg Gln Cys Phe Ser Ser Cys His
        515                 520                 525 atg cct ctc acg ggc tat gag gta tgg ttg ggc acc ctg ttc cag aac   1632
Met Pro Leu Thr Gly Tyr Glu Val Trp Leu Gly Thr Leu Phe Gln Asn
        530                 535                 540
```

```
cca cag cat gga gag cca agc cta cag cgg gtc cca gta gcc aag atg    1680
Pro Gln His Gly Glu Pro Ser Leu Gln Arg Val Pro Val Ala Lys Met
545                 550                 555                 560 gtg tgt ggg ccc tca ggc tcc cag ctt gtc ctg ctc aag ctg gag aga    1728
Val Cys Gly Pro Ser Gly Ser Gln Leu Val Leu Leu Lys Leu Glu Arg
                565                 570                 575 tct gtg acc ctg aac cag cgt gtg gcc ctg atc tgc ctg ccc cct gaa    1776
Ser Val Thr Leu Asn Gln Arg Val Ala Leu Ile Cys Leu Pro Pro Glu
            580                 585                 590 tgg tat gtg gtg cct cca ggg acc aag tgt gag att gca ggc tgg ggt    1824
Trp Tyr Val Val Pro Pro Gly Thr Lys Cys Glu Ile Ala Gly Trp Gly
        595                 600                 605 gag acc aaa ggt acg ggt aat gac aca gtc cta aat gtg gcc ttg ctg    1872
Glu Thr Lys Gly Thr Gly Asn Asp Thr Val Leu Asn Val Ala Leu Leu
    610                 615                 620 aat gtc atc tcc aac cag gag tgt aac atc aag cac cga gga cgt gtg    1920
Asn Val Ile Ser Asn Gln Glu Cys Asn Ile Lys His Arg Gly Arg Val
625                 630                 635                 640 cgg gag agt gag atg tgc act gag gga ctg ttg gcc cct gtg ggg gcc    1968
Arg Glu Ser Glu Met Cys Thr Glu Gly Leu Leu Ala Pro Val Gly Ala
                645                 650                 655 tgt gag ggt gac tac ggg ggc cca ctt gcc tgc ttt acc cac aac gcc    2016
Cys Glu Gly Asp Tyr Gly Gly Pro Leu Ala Cys Phe Thr His Asn Ala
            660                 665                 670 tgg gtc ctg gaa gga att ata atc ccc aac cga gta tgc gca agg tcc    2064
Trp Val Leu Glu Gly Ile Ile Ile Pro Asn Arg Val Cys Ala Arg Ser
        675                 680                 685 cgc tgg cca gct gtc ttc acg cgt gtc tct gtg ttt gtg gac tgg att    2112
Arg Trp Pro Ala Val Phe Thr Arg Val Ser Val Phe Val Asp Trp Ile
    690                 695                 700 cac aag gtc atg aga ctg ggt cat cat cat cat cat cat cat tga        2160
His Lys Val Met Arg Leu Gly His His His His His His His
705                 710                 715

<210> SEQ ID NO 2
<211> LENGTH: 719
<212> TYPE: PRT
<213> ORGANISM: Artificial Sequence
<220> FEATURE:
<223> OTHER INFORMATION: Synthetic human MSP polypeptide

<400> SEQUENCE: 2

Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
            35                  40                  45

Asp Val Ala Asp Ala Glu Glu Cys Ala Gly Arg Cys Gly Pro Leu Met
        50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
                100                 105                 110

Asn Asn Gly Val Gly Tyr Arg Gly Thr Met Ala Thr Thr Val Gly Gly
            115                 120                 125
```

```
Leu Pro Cys Gln Ala Trp Ser His Lys Phe Pro Asn Asp His Lys Tyr
130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
                180                 185                 190

Trp Cys Asn Gly Glu Glu Tyr Arg Gly Ala Val Asp Arg Thr Glu Ser
            195                 200                 205

Gly Arg Glu Cys Gln Arg Trp Asp Leu Gln His Pro His Gln His Pro
210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
            275                 280                 285

Glu Gly Tyr Arg Gly Thr Ala Asn Thr Thr Ala Gly Val Pro Cys
290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350

Ala Phe Cys Tyr Gln Ile Arg Arg Cys Thr Asp Asp Val Arg Pro Gln
            355                 360                 365

Asp Cys Tyr His Gly Ala Gly Glu Gln Tyr Arg Gly Thr Val Ser Lys
    370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
            435                 440                 445

Ala Asp Asp Gln Pro Pro Ser Ile Leu Asp Pro Pro Asp Gln Val Gln
450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
            500                 505                 510

Lys Glu Gln Trp Ile Leu Thr Ala Arg Gln Cys Phe Ser Ser Cys His
            515                 520                 525

Met Pro Leu Thr Gly Tyr Glu Val Trp Leu Gly Thr Leu Phe Gln Asn
530                 535                 540

Pro Gln His Gly Glu Pro Ser Leu Gln Arg Val Pro Val Ala Lys Met
```

```
                545                 550                 555                 560
Val Cys Gly Pro Ser Gly Ser Gln Leu Val Leu Leu Lys Leu Glu Arg
                    565                 570                 575

Ser Val Thr Leu Asn Gln Arg Val Ala Leu Ile Cys Leu Pro Pro Glu
                580                 585                 590

Trp Tyr Val Pro Pro Gly Thr Lys Cys Glu Ile Ala Gly Trp Gly
            595                 600                 605

Glu Thr Lys Gly Thr Gly Asn Asp Thr Val Leu Asn Val Ala Leu Leu
        610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                    645                 650                 655

Cys Glu Gly Asp Tyr Gly Gly Pro Leu Ala Cys Phe Thr His Asn Ala
                660                 665                 670

Trp Val Leu Glu Gly Ile Ile Ile Pro Asn Arg Val Cys Ala Arg Ser
            675                 680                 685

Arg Trp Pro Ala Val Phe Thr Arg Val Ser Val Phe Val Asp Trp Ile
        690                 695                 700

His Lys Val Met Arg Leu Gly His His His His His His
705                 710                 715

<210> SEQ ID NO 3
<211> LENGTH: 2160
<212> TYPE: DNA
<213> ORGANISM: Artificial Sequence
<220> FEATURE:
<223> OTHER INFORMATION: Synthetic human MSP polypeptide
<220> FEATURE:
<221> NAME/KEY: CDS
<222> LOCATION: (1)..(2160)

<400> SEQUENCE: 3 atg ggg tgg ctc cca ctc ctg ctg ctt ctg act caa tgc tta ggg gtc      48
Met Gly Trp Leu Pro Leu Leu Leu Leu Thr Gln Cys Leu Gly Val
1               5                   10                  15 cct ggg cag cgc tcg cca ttg aat gac ttc caa gtg ctc cgg ggc aca      96
Pro Gly Gln Arg Ser Pro Leu Asn Asp Phe Gln Val Leu Arg Gly Thr
            20                  25                  30 gag cta cag cac ctg cta cat gcg gtg gtg ccc ggg cct tgg cag gag     144
Glu Leu Gln His Leu Leu His Ala Val Val Pro Gly Pro Trp Gln Glu
        35                  40                  45 gat gtg gca gat gct gaa gag tgt gct ggt cgc tgt ggg ccc tta atg     192
Asp Val Ala Asp Ala Glu Glu Cys Ala Gly Arg Cys Gly Pro Leu Met
    50                  55                  60 gac tgc cgg gcc ttc cac tac aac gtg agc agc cat ggt tgc caa ctg     240
Asp Cys Arg Ala Phe His Tyr Asn Val Ser Ser His Gly Cys Gln Leu
65                  70                  75                  80 ctg cca tgg act caa cac tcg ccc cac acg agg ctg cgg cgt tct ggg     288
Leu Pro Trp Thr Gln His Ser Pro His Thr Arg Leu Arg Arg Ser Gly
                85                  90                  95 cgc tgt gac ctc ttc cag aag aaa gac tac gta cgg acc tgc atc atg     336
Arg Cys Asp Leu Phe Gln Lys Lys Asp Tyr Val Arg Thr Cys Ile Met
            100                 105                 110 aac aat ggg gtt ggg tac cgg ggc acc atg gcc acg acc gtg ggt ggc     384
Asn Asn Gly Val Gly Tyr Arg Gly Thr Met Ala Thr Thr Val Gly Gly
        115                 120                 125 ctg ccc tgc cag gct tgg agc cac aag ttc ccg aat gat cac aag tac     432
Leu Pro Cys Gln Ala Trp Ser His Lys Phe Pro Asn Asp His Lys Tyr
```

-continued

```
            130                 135                 140
acg ccc act ctc cgg aat ggc ctg gaa gag aac ttc tgc cgt aac cct    480
Thr Pro Thr Leu Arg Asn Gly Leu Glu Glu Asn Phe Cys Arg Asn Pro
145                 150                 155                 160 gat ggc gac ccc gga ggt cct tgg tgc tac aca aca gac cct gct gtg    528
Asp Gly Asp Pro Gly Gly Pro Trp Cys Tyr Thr Thr Asp Pro Ala Val
                165                 170                 175 cgc ttc cag agc tgc ggc atc aaa tcc tgc cgg gag gcc gcg tgt gtc    576
Arg Phe Gln Ser Cys Gly Ile Lys Ser Cys Arg Glu Ala Ala Cys Val
            180                 185                 190 tgg tgc aat ggc gag gaa tac cgc ggc gcg gta gac cgc acg gag tca    624
Trp Cys Asn Gly Glu Glu Tyr Arg Gly Ala Val Asp Arg Thr Glu Ser
        195                 200                 205 ggg cgc gag tgc cag cgc tgg gat ctt cag cac ccg cac cag cac ccc    672
Gly Arg Glu Cys Gln Arg Trp Asp Leu Gln His Pro His Gln His Pro
    210                 215                 220 ttc gag ccg ggc aag ttc ctc gac caa ggt ctg gac gac aac tat tgc    720
Phe Glu Pro Gly Lys Phe Leu Asp Gln Gly Leu Asp Asp Asn Tyr Cys
225                 230                 235                 240 cgg aat cct gac ggc tcc gag cgg cca tgg tgc tac act acg gat ccg    768
Arg Asn Pro Asp Gly Ser Glu Arg Pro Trp Cys Tyr Thr Thr Asp Pro
                245                 250                 255 cag atc gag cga gag ttc tgt gac ctc ccc cgc tgc ggg tcc gag gca    816
Gln Ile Glu Arg Glu Phe Cys Asp Leu Pro Arg Cys Gly Ser Glu Ala
            260                 265                 270 cag ccc cgc caa gag gcc aca act gtc agc tgc ttc cgc ggg aag ggt    864
Gln Pro Arg Gln Glu Ala Thr Thr Val Ser Cys Phe Arg Gly Lys Gly
        275                 280                 285 gag ggc tac cgg ggc aca gcc aat acc acc act gcg ggc gta cct tgc    912
Glu Gly Tyr Arg Gly Thr Ala Asn Thr Thr Thr Ala Gly Val Pro Cys
    290                 295                 300 cag cgt tgg gac gcg caa atc cct cat cag cac cga ttt acg cca gaa    960
Gln Arg Trp Asp Ala Gln Ile Pro His Gln His Arg Phe Thr Pro Glu
305                 310                 315                 320 aaa tac gcg tgc aaa gac ctt cgg gag aac ttc tgc cgg aac ccc gac   1008
Lys Tyr Ala Cys Lys Asp Leu Arg Glu Asn Phe Cys Arg Asn Pro Asp
                325                 330                 335 ggc tca gag gcg ccc tgg tgc ttc aca ctg cgg ccc ggc atg cgc gcg   1056
Gly Ser Glu Ala Pro Trp Cys Phe Thr Leu Arg Pro Gly Met Arg Ala
            340                 345                 350 gcc ttt tgc tac cag atc cgg cgt tgt aca gac gac gtg cgg ccc cag   1104
Ala Phe Cys Tyr Gln Ile Arg Arg Cys Thr Asp Asp Val Arg Pro Gln
        355                 360                 365 gac tgc tac cac ggc gca ggg gag cag tac cgc ggc acg gtc agc aag   1152
Asp Cys Tyr His Gly Ala Gly Glu Gln Tyr Arg Gly Thr Val Ser Lys
    370                 375                 380 acc cgc aag ggt gtc cag tgc cag cgc tgg tcc gct gag acg ccg cac   1200
Thr Arg Lys Gly Val Gln Cys Gln Arg Trp Ser Ala Glu Thr Pro His
385                 390                 395                 400 aag ccg cag ttc acg ttt acc tcc gaa ccg cat gca caa ctg gag gag   1248
Lys Pro Gln Phe Thr Phe Thr Ser Glu Pro His Ala Gln Leu Glu Glu
                405                 410                 415 aac ttc tgc cgg aac cca gat ggg gat agc cat ggg ccc tgg tgc tac   1296
Asn Phe Cys Arg Asn Pro Asp Gly Asp Ser His Gly Pro Trp Cys Tyr
            420                 425                 430 acg atg gac cca agg acc cca ttc gac tac tgt gcc ctg cga cgc tgc   1344
Thr Met Asp Pro Arg Thr Pro Phe Asp Tyr Cys Ala Leu Arg Arg Cys
        435                 440                 445 gct gat gac cag ccg cca tca atc ctg gac ccc cca gac cag gtg cag   1392
```

| | | | | | | | | | | | | |
|---|---|---|---|---|---|---|---|---|---|---|---|---|
| Ala | Asp | Asp | Gln | Pro | Pro | Ser | Ile | Leu | Asp | Pro | Pro | Asp | Gln | Val | Gln |
| | 450 | | | | | 455 | | | | | 460 | | | | |

```
ttt gag aag tgt ggc aag agg gtg gat cgg ctg gat cag cgg cgt tcc         1440
Phe Glu Lys Cys Gly Lys Arg Val Asp Arg Leu Asp Gln Arg Arg Ser
465                 470                 475                 480 aag ctg cgc gtg gtt ggg ggc cat ccg ggc aac tca ccc tgg aca gtc         1488
Lys Leu Arg Val Val Gly Gly His Pro Gly Asn Ser Pro Trp Thr Val
            485                 490                 495 agc ttg cgg aat cgg cag ggc cag cat ttc tgc ggg ggg tct cta gtg         1536
Ser Leu Arg Asn Arg Gln Gly Gln His Phe Cys Gly Gly Ser Leu Val
        500                 505                 510 aag gag cag tgg ata ctg act gcc cgg cag tgc ttc tcc tcc tgc cat         1584
Lys Glu Gln Trp Ile Leu Thr Ala Arg Gln Cys Phe Ser Ser Cys His
    515                 520                 525 atg cct ctc acg ggc tat gag gta tgg ttg ggc acc ctg ttc cag aac         1632
Met Pro Leu Thr Gly Tyr Glu Val Trp Leu Gly Thr Leu Phe Gln Asn
530                 535                 540 cca cag cat gga gag cca agc cta cag cgg gtc cca gta gcc aag atg         1680
Pro Gln His Gly Glu Pro Ser Leu Gln Arg Val Pro Val Ala Lys Met
545                 550                 555                 560 gtg tgt ggg ccc tca ggc tcc cag ctt gtc ctg ctc aag ctg gag aga         1728
Val Cys Gly Pro Ser Gly Ser Gln Leu Val Leu Leu Lys Leu Glu Arg
            565                 570                 575 tct gtg acc ctg aac cag cgt gtg gcc ctg atc tgc ctg ccc cct gaa         1776
Ser Val Thr Leu Asn Gln Arg Val Ala Leu Ile Cys Leu Pro Pro Glu
        580                 585                 590 tgg tat gtg gtg cct cca ggg acc aag tgt gag att gca ggc tgg ggt         1824
Trp Tyr Val Val Pro Pro Gly Thr Lys Cys Glu Ile Ala Gly Trp Gly
    595                 600                 605 gag acc aaa ggt acg ggt aat gac aca gtc cta aat gtg gcc ttg ctg         1872
Glu Thr Lys Gly Thr Gly Asn Asp Thr Val Leu Asn Val Ala Leu Leu
610                 615                 620 aat gtc atc tcc aac cag gag tgt aac atc aag cac cga gga cgt gtg         1920
Asn Val Ile Ser Asn Gln Glu Cys Asn Ile Lys His Arg Gly Arg Val
625                 630                 635                 640 cgg gag agt gag atg tgc act gag gga ctg ttg gcc cct gtg ggg gcc         1968
Arg Glu Ser Glu Met Cys Thr Glu Gly Leu Leu Ala Pro Val Gly Ala
            645                 650                 655 tgt gag ggt gac tac ggg ggc cca ctt gcc tgc ttt acc cac aac gcc         2016
Cys Glu Gly Asp Tyr Gly Gly Pro Leu Ala Cys Phe Thr His Asn Ala
        660                 665                 670 tgg gtc ctg gaa gga att ata atc ccc aac cga gta tgc gca agg tcc         2064
Trp Val Leu Glu Gly Ile Ile Ile Pro Asn Arg Val Cys Ala Arg Ser
    675                 680                 685 tgc tgg cca gct gtc ttc acg cgt gtc tct gtg ttt gtg gac tgg att         2112
Cys Trp Pro Ala Val Phe Thr Arg Val Ser Val Phe Val Asp Trp Ile
690                 695                 700 cac aag gtc atg aga ctg ggt cat cat cat cat cat cat cat cat tga         2160
His Lys Val Met Arg Leu Gly His His His His His His His His
705                 710                 715
```

<210> SEQ ID NO 4
<211> LENGTH: 719
<212> TYPE: PRT
<213> ORGANISM: Artificial Sequence
<220> FEATURE:
<223> OTHER INFORMATION: Synthetic human MSP polypeptide

<400> SEQUENCE: 4

```
Met Gly Trp Leu Pro Leu Leu Leu Leu Leu Thr Gln Cys Leu Gly Val
1               5                   10                  15
```

```
Pro Gly Gln Arg Ser Pro Leu Asn Asp Phe Gln Val Leu Arg Gly Thr
            20                  25                  30

Glu Leu Gln His Leu Leu His Ala Val Val Pro Gly Pro Trp Gln Glu
        35                  40                  45

Asp Val Ala Asp Ala Glu Glu Cys Ala Gly Arg Cys Gly Pro Leu Met
50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
            85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
            115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
        195                 200                 205

Gly Arg Glu Cys Gln Arg Trp Asp Leu Gln His Pro His Gln His Pro
    210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
        275                 280                 285

Glu Gly Tyr Arg Gly Thr Ala Asn Thr Thr Thr Ala Gly Val Pro Cys
    290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350

Ala Phe Cys Tyr Gln Ile Arg Arg Cys Thr Asp Asp Val Arg Pro Gln
        355                 360                 365

Asp Cys Tyr His Gly Ala Gly Glu Gln Tyr Arg Gly Thr Val Ser Lys
    370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430
```

Thr Met Asp Pro Arg Thr Pro Phe Asp Tyr Cys Ala Leu Arg Arg Cys
              435                 440                 445

Ala Asp Asp Gln Pro Pro Ser Ile Leu Asp Pro Asp Gln Val Gln
    450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
                500                 505                 510

Lys Glu Gln Trp Ile Leu Thr Ala Arg Gln Cys Phe Ser Ser␣ Cys His
            515                 520                 525

Met Pro Leu Thr Gly Tyr Glu Val Trp Leu Gly Thr Leu Phe Gln Asn
            530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
                580                 585                 590

Trp Tyr Val Val Pro Pro Gly Thr Lys Cys Glu Ile Ala Gly Trp Gly
                595                 600                 605

Glu Thr Lys Gly Thr Gly Asn Asp Thr Val Leu Asn Val Ala Leu Leu
            610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                645                 650                 655

Cys Glu Gly Asp Tyr Gly Gly Pro Leu Ala Cys Phe Thr His Asn Ala
                660                 665                 670

Trp Val Leu Glu Gly Ile Ile Ile Pro Asn Arg Val Cys Ala Arg Ser
            675                 680                 685

Cys Trp Pro Ala Val Phe Thr Arg Val Ser Val Phe Val Asp Trp Ile
690                 695                 700

His Lys Val Met Arg Leu Gly His His His His His His
705                 710                 715

```
<210> SEQ ID NO 5
<211> LENGTH: 2154
<212> TYPE: DNA
<213> ORGANISM: Artificial Sequence
<220> FEATURE:
<223> OTHER INFORMATION: Synthetic human MSP polypeptide
<220> FEATURE:
<221> NAME/KEY: CDS
<222> LOCATION: (1)..(2154)

<400> SEQUENCE: 5 atg ggg tgg ctc cca ctc ctg ctg ctt ctg act caa tgc tta ggg gtc     48
Met Gly Trp Leu Pro Leu Leu Leu Leu Leu Thr Gln Cys Leu Gly Val
1               5                   10                  15 cct ggg cag cgc tcg cca ttg aat gac ttc caa gtg ctc cgg ggc aca     96
Pro Gly Gln Arg Ser Pro Leu Asn Asp Phe Gln Val Leu Arg Gly Thr
                20                  25                  30 gag cta cag cac ctg cta cat gcg gtg gtg ccc ggg cct tgg cag gag    144
Glu Leu Gln His Leu Leu His Ala Val Val Pro Gly Pro Trp Gln Glu
            35                  40                  45
```

-continued

| | |
|---|---|
| gat gtg gca gat gct gaa gag tgt gct ggt cgc tgt ggg ccc tta atg<br>Asp Val Ala Asp Ala Glu Glu Cys Ala Gly Arg Cys Gly Pro Leu Met<br>50                        55                       60 | 192 |
| gac tgc cgg gcc ttc cac tac aac gtg agc agc cat ggt tgc caa ctg<br>Asp Cys Arg Ala Phe His Tyr Asn Val Ser Ser His Gly Cys Gln Leu<br>65                        70                      75                   80 | 240 |
| ctg cca tgg act caa cac tcg ccc cac acg agg ctg cgg cgt tct ggg<br>Leu Pro Trp Thr Gln His Ser Pro His Thr Arg Leu Arg Arg Ser Gly<br>                     85                       90                      95 | 288 |
| cgc tgt gac ctc ttc cag aag aaa gac tac gta cgg acc tgc atc atg<br>Arg Cys Asp Leu Phe Gln Lys Lys Asp Tyr Val Arg Thr Cys Ile Met<br>                   100                 105                110 | 336 |
| aac aat ggg gtt ggg tac cgg ggc acc atg gcc acg acc gtg ggt ggc<br>Asn Asn Gly Val Gly Tyr Arg Gly Thr Met Ala Thr Thr Val Gly Gly<br>               115                 120                125 | 384 |
| ctg ccc tgc cag gct tgg agc cac aag ttc ccg aat gat cac aag tac<br>Leu Pro Cys Gln Ala Trp Ser His Lys Phe Pro Asn Asp His Lys Tyr<br>130                       135                 140 | 432 |
| acg ccc act ctc cgg aat ggc ctg gaa gag aac ttc tgc cgt aac cct<br>Thr Pro Thr Leu Arg Asn Gly Leu Glu Glu Asn Phe Cys Arg Asn Pro<br>145                       150                 155                160 | 480 |
| gat ggc gac ccc gga ggt cct tgg tgc tac aca aca gac cct gct gtg<br>Asp Gly Asp Pro Gly Gly Pro Trp Cys Tyr Thr Thr Asp Pro Ala Val<br>                   165                 170                175 | 528 |
| cgc ttc cag agc tgc ggc atc aaa tcc tgc cgg gag gcc gcg tgt gtc<br>Arg Phe Gln Ser Cys Gly Ile Lys Ser Cys Arg Glu Ala Ala Cys Val<br>                   180                 185                190 | 576 |
| tgg tgc aat ggc gag gaa tac cgc ggc gcg gta gac cgc acg gag tca<br>Trp Cys Asn Gly Glu Glu Tyr Arg Gly Ala Val Asp Arg Thr Glu Ser<br>                   195                 200                205 | 624 |
| ggg cgc gag tgc cag cgc tgg gat ctt cag cac ccg cac cag cac ccc<br>Gly Arg Glu Cys Gln Arg Trp Asp Leu Gln His Pro His Gln His Pro<br>210                       215                 220 | 672 |
| ttc gag ccg ggc aag ttc ctc gac caa ggt ctg gac gac aac tat tgc<br>Phe Glu Pro Gly Lys Phe Leu Asp Gln Gly Leu Asp Asp Asn Tyr Cys<br>225                       230                 235                240 | 720 |
| cgg aat cct gac ggc tcc gag cgg cca tgg tgc tac act acg gat ccg<br>Arg Asn Pro Asp Gly Ser Glu Arg Pro Trp Cys Tyr Thr Thr Asp Pro<br>                   245                 250                255 | 768 |
| cag atc gag cga gag ttc tgt gac ctc ccc cgc tgc ggg tcc gag gca<br>Gln Ile Glu Arg Glu Phe Cys Asp Leu Pro Arg Cys Gly Ser Glu Ala<br>                   260                 265                270 | 816 |
| cag ccc cgc caa gag gcc aca act gtc agc tgc ttc cgc ggg aag ggt<br>Gln Pro Arg Gln Glu Ala Thr Thr Val Ser Cys Phe Arg Gly Lys Gly<br>275                       280                 285 | 864 |
| gag ggc tac cgg ggc aca gcc aat acc acc act gcg ggc gta cct tgc<br>Glu Gly Tyr Arg Gly Thr Ala Asn Thr Thr Thr Ala Gly Val Pro Cys<br>290                       295                 300 | 912 |
| cag cgt tgg gac gcg caa atc cct cat cag cac cga ttt acg cca gaa<br>Gln Arg Trp Asp Ala Gln Ile Pro His Gln His Arg Phe Thr Pro Glu<br>305                       310                 315                320 | 960 |
| aaa tac gcg tgc aaa gac ctt cgg gag aac ttc tgc cgg aac ccc gac<br>Lys Tyr Ala Cys Lys Asp Leu Arg Glu Asn Phe Cys Arg Asn Pro Asp<br>                   325                 330                335 | 1008 |
| ggc tca gag gcg ccc tgg tgc ttc aca ctg cgg ccc ggc atg cgc gcg<br>Gly Ser Glu Ala Pro Trp Cys Phe Thr Leu Arg Pro Gly Met Arg Ala<br>                   340                 345                350 | 1056 |
| gcc ttt tgc tac cag atc cgg cgt tgt aca gac gac gtg cgg ccc cag<br>Ala Phe Cys Tyr Gln Ile Arg Arg Cys Thr Asp Asp Val Arg Pro Gln<br>                   355                 360                365 | 1104 |

```
gac tgc tac cac ggc gca ggg gag cag tac cgc ggc acg gtc agc aag      1152
Asp Cys Tyr His Gly Ala Gly Glu Gln Tyr Arg Gly Thr Val Ser Lys
370                 375                 380 acc cgc aag ggt gtc cag tgc cag cgc tgg tcc gct gag acg ccg cac      1200
Thr Arg Lys Gly Val Gln Cys Gln Arg Trp Ser Ala Glu Thr Pro His
385                 390                 395                 400 aag ccg cag ttc acg ttt acc tcc gaa ccg cat gca caa ctg gag gag      1248
Lys Pro Gln Phe Thr Phe Thr Ser Glu Pro His Ala Gln Leu Glu Glu
                405                 410                 415 aac ttc tgc cgg aac cca gat ggg gat agc cat ggg ccc tgg tgc tac      1296
Asn Phe Cys Arg Asn Pro Asp Gly Asp Ser His Gly Pro Trp Cys Tyr
            420                 425                 430 acg atg gac cca agg acc cca ttc gac tac tgt gcc ctg cga cgc tgc      1344
Thr Met Asp Pro Arg Thr Pro Phe Asp Tyr Cys Ala Leu Arg Arg Cys
        435                 440                 445 gct gat gac cag ccg cca tca atc ctg gac ccc cca gac cag gtg cag      1392
Ala Asp Asp Gln Pro Pro Ser Ile Leu Asp Pro Pro Asp Gln Val Gln
450                 455                 460 ttt gag aag tgt ggc aag agg gtg gat cgg ctg gat cag cgg cgt tcc      1440
Phe Glu Lys Cys Gly Lys Arg Val Asp Arg Leu Asp Gln Arg Arg Ser
465                 470                 475                 480 aag ctg gaa gtg gtt ggg ggc cat ccg ggc aac tca ccc tgg aca gtc      1488
Lys Leu Glu Val Val Gly Gly His Pro Gly Asn Ser Pro Trp Thr Val
                485                 490                 495 agc ttg cgg aat cgg cag ggc cag cat ttc tgc ggg ggg tct cta gtg      1536
Ser Leu Arg Asn Arg Gln Gly Gln His Phe Cys Gly Gly Ser Leu Val
            500                 505                 510 aag gag cag tgg ata ctg act gcc cgg cag tgc ttc tcc tcc tgc cat      1584
Lys Glu Gln Trp Ile Leu Thr Ala Arg Gln Cys Phe Ser Ser Cys His
        515                 520                 525 atg cct ctc acg ggc tat gag gta tgg ttg ggc acc ctg ttc cag aac      1632
Met Pro Leu Thr Gly Tyr Glu Val Trp Leu Gly Thr Leu Phe Gln Asn
    530                 535                 540 cca cag cat gga gag cca agc cta cag cgg gtc cca gta gcc aag atg      1680
Pro Gln His Gly Glu Pro Ser Leu Gln Arg Val Pro Val Ala Lys Met
545                 550                 555                 560 gtg tgt ggg ccc tca ggc tcc cag ctt gtc ctg ctc aag ctg gag aga      1728
Val Cys Gly Pro Ser Gly Ser Gln Leu Val Leu Leu Lys Leu Glu Arg
                565                 570                 575 tct gtg acc ctg aac cag cgt gtg gcc ctg atc tgc ctg ccc cct gaa      1776
Ser Val Thr Leu Asn Gln Arg Val Ala Leu Ile Cys Leu Pro Pro Glu
            580                 585                 590 tgg tat gtg gtg cct cca ggg acc aag tgt gag att gca ggc tgg ggt      1824
Trp Tyr Val Val Pro Pro Gly Thr Lys Cys Glu Ile Ala Gly Trp Gly
        595                 600                 605 gag acc aaa ggt acg ggt aat gac aca gtc cta aat gtg gcc ttg ctg      1872
Glu Thr Lys Gly Thr Gly Asn Asp Thr Val Leu Asn Val Ala Leu Leu
    610                 615                 620 aat gtc atc tcc aac cag gag tgt aac atc aag cac cga gga cgt gtg      1920
Asn Val Ile Ser Asn Gln Glu Cys Asn Ile Lys His Arg Gly Arg Val
625                 630                 635                 640 cgg gag agt gag atg tgc act gag gga ctg ttg gcc cct gtg ggg gcc      1968
Arg Glu Ser Glu Met Cys Thr Glu Gly Leu Leu Ala Pro Val Gly Ala
                645                 650                 655 tgt gag ggt gac tac ggg ggc cca ctt gcc tgc ttt acc cac aac gcc      2016
Cys Glu Gly Asp Tyr Gly Gly Pro Leu Ala Cys Phe Thr His Asn Ala
            660                 665                 670 tgg gtc ctg gaa gga att ata atc ccc aac cga gta tgc gca agg tcc      2064
Trp Val Leu Glu Gly Ile Ile Ile Pro Asn Arg Val Cys Ala Arg Ser
```

```
                      675                 680                 685
cgc tgg cca gct gtc ttc acg cgt gtc tct gtg ttt gtg gac tgg att        2112
Arg Trp Pro Ala Val Phe Thr Arg Val Ser Val Phe Val Asp Trp Ile
690                 695                 700 cac aag gtc atg aga ctg ggt cat cat cat cat cat cat tag                2154
His Lys Val Met Arg Leu Gly His His His His His His
705                 710                 715

<210> SEQ ID NO 6
<211> LENGTH: 717
<212> TYPE: PRT
<213> ORGANISM: Artificial Sequence
<220> FEATURE:
<223> OTHER INFORMATION: Synthetic human MSP polypeptide

<400> SEQUENCE: 6

Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
            35                  40                  45

Asp Val Ala Asp Ala Glu Glu Cys Ala Gly Arg Cys Gly Pro Leu Met
    50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
        115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
        195                 200                 205

Gly Arg Glu Cys Gln Arg Trp Asp Leu Gln His Pro His Gln His Pro
    210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
        275                 280                 285

Glu Gly Tyr Arg Gly Thr Ala Asn Thr Thr Thr Ala Gly Val Pro Cys
    290                 295                 300

Gln Arg Trp Asp Ala Gln Ile Pro His Gln His Arg Phe Thr Pro Glu
305                 310                 315                 320
```

Lys Tyr Ala Cys Lys Asp Leu Arg Glu Asn Phe Cys Arg Asn Pro Asp
            325                 330                 335

Gly Ser Glu Ala Pro Trp Cys Phe Thr Leu Arg Pro Gly Met Arg Ala
        340                 345                 350

Ala Phe Cys Tyr Gln Ile Arg Arg Cys Thr Asp Asp Val Arg Pro Gln
            355                 360                 365

Asp Cys Tyr His Gly Ala Gly Glu Gln Tyr Arg Gly Thr Val Ser Lys
        370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
            405                 410                 415

Asn Phe Cys Arg Asn Pro Asp Gly Asp Ser His Gly Pro Trp Cys Tyr
        420                 425                 430

Thr Met Asp Pro Arg Thr Pro Phe Asp Tyr Cys Ala Leu Arg Arg Cys
            435                 440                 445

Ala Asp Asp Gln Pro Pro Ser Ile Leu Asp Pro Pro Asp Gln Val Gln
        450                 455                 460

Phe Glu Lys Cys Gly Lys Arg Val Asp Arg Leu Asp Gln Arg Arg Ser
465                 470                 475                 480

Lys Leu Glu Val Val Gly Gly His Pro Gly Asn Ser Pro Trp Thr Val
            485                 490                 495

Ser Leu Arg Asn Arg Gln Gly Gln His Phe Cys Gly Gly Ser Leu Val
        500                 505                 510

Lys Glu Gln Trp Ile Leu Thr Ala Arg Gln Cys Phe Ser Ser Cys His
            515                 520                 525

Met Pro Leu Thr Gly Tyr Glu Val Trp Leu Gly Thr Leu Phe Gln Asn
        530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
            565                 570                 575

Ser Val Thr Leu Asn Gln Arg Val Ala Leu Ile Cys Leu Pro Pro Glu
        580                 585                 590

Trp Tyr Val Val Pro Pro Gly Thr Lys Cys Glu Ile Ala Gly Trp Gly
            595                 600                 605

Glu Thr Lys Gly Thr Gly Asn Asp Thr Val Leu Asn Val Ala Leu Leu
        610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
            645                 650                 655

Cys Glu Gly Asp Tyr Gly Gly Pro Leu Ala Cys Phe Thr His Asn Ala
        660                 665                 670

Trp Val Leu Glu Gly Ile Ile Ile Pro Asn Arg Val Cys Ala Arg Ser
            675                 680                 685

Arg Trp Pro Ala Val Phe Thr Arg Val Ser Val Phe Val Asp Trp Ile
        690                 695                 700

His Lys Val Met Arg Leu Gly His His His His His
705                 710                 715

<210> SEQ ID NO 7
<211> LENGTH: 804

<212> TYPE: DNA
<213> ORGANISM: Artificial Sequence
<220> FEATURE:
<223> OTHER INFORMATION: Synthetic human MSP polypeptide
<220> FEATURE:
<221> NAME/KEY: CDS
<222> LOCATION: (1)..(804)

<400> SEQUENCE: 7

```
atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg      96
Leu His Leu Leu Leu Leu Pro Ile Ala Ile Pro Tyr Ala Glu Gly Val
            20                  25                  30 gtt ggg ggc cat ccg ggc aac tca ccc tgg aca gtc agc ttg cgg aat     144
Val Gly Gly His Pro Gly Asn Ser Pro Trp Thr Val Ser Leu Arg Asn
        35                  40                  45 cgg cag ggc cag cat ttc tgc ggg ggg tct cta gtg aag gag cag tgg     192
Arg Gln Gly Gln His Phe Cys Gly Gly Ser Leu Val Lys Glu Gln Trp
    50                  55                  60 ata ctg act gcc cgg cag tgc ttc tcc tcc tgc cat atg cct ctc acg     240
Ile Leu Thr Ala Arg Gln Cys Phe Ser Ser Cys His Met Pro Leu Thr
65                  70                  75                  80 ggc tat gag gta tgg ttg ggc acc ctg ttc cag aac cca cag cat gga     288
Gly Tyr Glu Val Trp Leu Gly Thr Leu Phe Gln Asn Pro Gln His Gly
                85                  90                  95 gag cca agc cta cag cgg gtc cca gta gcc aag atg gtg tgt ggg ccc     336
Glu Pro Ser Leu Gln Arg Val Pro Val Ala Lys Met Val Cys Gly Pro
            100                 105                 110 tca ggc tcc cag ctt gtc ctg ctc aag ctg gag aga tct gtg acc ctg     384
Ser Gly Ser Gln Leu Val Leu Leu Lys Leu Glu Arg Ser Val Thr Leu
        115                 120                 125 aac cag cgt gtg gcc ctg atc tcc ctg ccc cct gaa tgg tat gtg gtg     432
Asn Gln Arg Val Ala Leu Ile Ser Leu Pro Pro Glu Trp Tyr Val Val
130                 135                 140 cct cca ggg acc aag tgt gag att gca ggc tgg ggt gag acc aaa ggt     480
Pro Pro Gly Thr Lys Cys Glu Ile Ala Gly Trp Gly Glu Thr Lys Gly
145                 150                 155                 160 acg ggt aat gac aca gtc cta aat gtg gcc ttg ctg aat gtc atc tcc     528
Thr Gly Asn Asp Thr Val Leu Asn Val Ala Leu Leu Asn Val Ile Ser
                165                 170                 175 aac cag gag tgt aac atc aag cac cga gga cgt gtg cgg gag agt gag     576
Asn Gln Glu Cys Asn Ile Lys His Arg Gly Arg Val Arg Glu Ser Glu
            180                 185                 190 atg tgc act gag gga ctg ttg gcc cct gtg ggg gcc tgt gag ggt gac     624
Met Cys Thr Glu Gly Leu Leu Ala Pro Val Gly Ala Cys Glu Gly Asp
        195                 200                 205 tac ggg ggc cca ctt gcc tgc ttt acc cac aac tgc tgg gtc ctg gaa     672
Tyr Gly Gly Pro Leu Ala Cys Phe Thr His Asn Cys Trp Val Leu Glu
    210                 215                 220 gga att ata atc ccc aac cga gta tgc gca agg tcc cgc tgg cca gct     720
Gly Ile Ile Ile Pro Asn Arg Val Cys Ala Arg Ser Arg Trp Pro Ala
225                 230                 235                 240 gtc ttc acg cgt gtc tct gtg ttt gtg gac tgg att cac aag gtc atg     768
Val Phe Thr Arg Val Ser Val Phe Val Asp Trp Ile His Lys Val Met
                245                 250                 255 aga ctg ggt cat cat cat cat cat cat cat tag                         804
Arg Leu Gly His His His His His His His
            260                 265
```

```
<210> SEQ ID NO 8
<211> LENGTH: 267
<212> TYPE: PRT
<213> ORGANISM: Artificial Sequence
<220> FEATURE:
<223> OTHER INFORMATION: Synthetic human MSP polypeptide

<400> SEQUENCE: 8

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
        50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
                85                  90                  95

Glu Pro Ser Leu Gln Arg Val Pro Val Ala Lys Met Val Cys Gly Pro
            100                 105                 110

Ser Gly Ser Gln Leu Val Leu Leu Lys Leu Glu Arg Ser Val Thr Leu
        115                 120                 125

Asn Gln Arg Val Ala Leu Ile Ser Leu Pro Pro Glu Trp Tyr Val Val
130                 135                 140

Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
                165                 170                 175

Asn Gln Glu Cys Asn Ile Lys His Arg Gly Arg Val Arg Glu Ser Glu
            180                 185                 190

Met Cys Thr Glu Gly Leu Leu Ala Pro Val Gly Ala Cys Glu Gly Asp
        195                 200                 205

Tyr Gly Gly Pro Leu Ala Cys Phe Thr His Asn Cys Trp Val Leu Glu
    210                 215                 220

Gly Ile Ile Ile Pro Asn Arg Val Cys Ala Arg Ser Arg Trp Pro Ala
225                 230                 235                 240

Val Phe Thr Arg Val Ser Val Phe Val Asp Trp Ile His Lys Val Met
                245                 250                 255

Arg Leu Gly His His His His His His
            260                 265

<210> SEQ ID NO 9
<211> LENGTH: 267
<212> TYPE: PRT
<213> ORGANISM: Artificial Sequence
<220> FEATURE:
<223> OTHER INFORMATION: Synthetic human MSP polypeptide

<400> SEQUENCE: 9

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
            35                  40                  45
```

Arg Gln Gly Gln His Phe Cys Gly Gly Ser Leu Val Lys Glu Gln Trp
    50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
                85                  90                  95

Glu Pro Ser Leu Gln Arg Val Pro Val Ala Lys Met Val Cys Gly Pro
            100                 105                 110

Ser Gly Ser Gln Leu Val Leu Leu Lys Leu Glu Arg Ser Val Thr Leu
        115                 120                 125

Asn Gln Arg Val Ala Leu Ile Ser Leu Pro Pro Glu Trp Tyr Val Val
    130                 135                 140

Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
                165                 170                 175

Asn Gln Glu Cys Asn Ile Lys His Arg Gly Arg Val Arg Glu Ser Glu
            180                 185                 190

Met Cys Thr Glu Gly Leu Leu Ala Pro Val Gly Ala Cys Glu Gly Asp
        195                 200                 205

Tyr Gly Gly Pro Leu Ala Cys Phe Thr His Asn Ala Trp Val Leu Glu
    210                 215                 220

Gly Ile Ile Ile Pro Asn Arg Val Cys Ala Arg Ser Arg Trp Pro Ala
225                 230                 235                 240

Val Phe Thr Arg Val Ser Val Phe Val Asp Trp Ile His Lys Val Met
                245                 250                 255

Arg Leu Gly His His His His His His His
            260                 265

<210> SEQ ID NO 10
<211> LENGTH: 267
<212> TYPE: PRT
<213> ORGANISM: Artificial Sequence
<220> FEATURE:
<223> OTHER INFORMATION: Synthetic human MSP polypeptide

<400> SEQUENCE: 10

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
        35                  40                  45

Arg Gln Gly Gln His Phe Cys Gly Gly Ser Leu Val Lys Glu Gln Trp
    50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
                85                  90                  95

Glu Pro Ser Leu Gln Arg Val Pro Val Ala Lys Met Val Cys Gly Pro
            100                 105                 110

Ser Gly Ser Gln Leu Val Leu Leu Lys Leu Glu Arg Ser Val Thr Leu
        115                 120                 125

Asn Gln Arg Val Ala Leu Ile Ser Leu Pro Pro Glu Trp Tyr Val Val
    130                 135                 140

```
Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
            165                 170                 175

Asn Gln Glu Cys Asn Ile Lys His Arg Gly Arg Val Arg Glu Ser Glu
            180                 185                 190

Met Cys Thr Glu Gly Leu Leu Ala Pro Val Gly Ala Cys Glu Gly Asp
            195                 200                 205

Tyr Gly Gly Pro Leu Ala Cys Phe Thr His Asn Cys Trp Val Leu Glu
            210                 215                 220

Gly Ile Ile Ile Pro Asn Arg Val Cys Ala Arg Ser Cys Trp Pro Ala
225                 230                 235                 240

Val Phe Thr Arg Val Ser Val Phe Val Asp Trp Ile His Lys Val Met
            245                 250                 255

Arg Leu Gly His His His His His His
            260                 265

<210> SEQ ID NO 11
<211> LENGTH: 267
<212> TYPE: PRT
<213> ORGANISM: Artificial Sequence
<220> FEATURE:
<223> OTHER INFORMATION: Synthetic human MSP polypeptide

<400> SEQUENCE: 11

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
            85                  90                  95

Glu Pro Ser Leu Gln Arg Val Pro Val Ala Lys Met Val Cys Gly Pro
            100                 105                 110

Ser Gly Ser Gln Leu Val Leu Leu Lys Leu Glu Arg Ser Val Thr Leu
            115                 120                 125

Asn Gln Arg Val Ala Leu Ile Ser Leu Pro Pro Glu Trp Tyr Val Val
130                 135                 140

Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
            165                 170                 175

Asn Gln Glu Cys Asn Ile Lys His Arg Gly Arg Val Arg Glu Ser Glu
            180                 185                 190

Met Cys Thr Glu Gly Leu Leu Ala Pro Val Gly Ala Cys Glu Gly Asp
            195                 200                 205

Tyr Gly Gly Pro Leu Ala Cys Phe Thr His Asn Ala Trp Val Leu Glu
            210                 215                 220

Gly Ile Ile Ile Pro Asn Arg Val Cys Ala Arg Ser Cys Trp Pro Ala
225                 230                 235                 240
```

```
Val Phe Thr Arg Val Ser Val Phe Val Asp Trp Ile His Lys Val Met
                245                 250                 255

Arg Leu Gly His His His His His His His
            260                 265

<210> SEQ ID NO 12
<211> LENGTH: 711
<212> TYPE: PRT
<213> ORGANISM: Homo sapiens

<400> SEQUENCE: 12

Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
            35                  40                  45

Asp Val Ala Asp Ala Glu Glu Cys Ala Gly Arg Cys Gly Pro Leu Met
50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
        115                 120                 125

Leu Pro Cys Gln Ala Trp Ser His Lys Phe Pro Asn Asp His Lys Tyr
130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
        195                 200                 205

Gly Arg Glu Cys Gln Arg Trp Asp Leu Gln His Pro His Gln His Pro
210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
        275                 280                 285

Glu Gly Tyr Arg Gly Thr Ala Asn Thr Thr Thr Ala Gly Val Pro Cys
290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350
```

Ala Phe Cys Tyr Gln Ile Arg Arg Cys Thr Asp Asp Val Arg Pro Gln
            355                 360                 365

Asp Cys Tyr His Gly Ala Gly Glu Gln Tyr Arg Gly Thr Val Ser Lys
        370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
        435                 440                 445

Ala Asp Asp Gln Pro Pro Ser Ile Leu Asp Pro Pro Asp Gln Val Gln
    450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
            500                 505                 510

Lys Glu Gln Trp Ile Leu Thr Ala Arg Gln Cys Phe Ser Ser Cys His
        515                 520                 525

Met Pro Leu Thr Gly Tyr Glu Val Trp Leu Gly Thr Leu Phe Gln Asn
    530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
            580                 585                 590

Trp Tyr Val Val Pro Pro Gly Thr Lys Cys Glu Ile Ala Gly Trp Gly
        595                 600                 605

Glu Thr Lys Gly Thr Gly Asn Asp Thr Val Leu Asn Val Ala Leu Leu
    610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                645                 650                 655

Cys Glu Gly Asp Tyr Gly Gly Pro Leu Ala Cys Phe Thr His Asn Cys
            660                 665                 670

Trp Val Leu Glu Gly Ile Ile Ile Pro Asn Arg Val Cys Ala Arg Ser
        675                 680                 685

Arg Trp Pro Ala Val Phe Thr Arg Val Ser Val Phe Val Asp Trp Ile
    690                 695                 700

His Lys Val Met Arg Leu Gly
705                 710

<210> SEQ ID NO 13
<211> LENGTH: 2151
<212> TYPE: DNA
<213> ORGANISM: Mus musculus
<220> FEATURE:
<221> NAME/KEY: CDS
<222> LOCATION: (1)..(2151)

<400> SEQUENCE: 13

```
atg ggg tgg ctc cca ctt ctg ctg ctt ctg gta cag tgt tca agg gct      48
Met Gly Trp Leu Pro Leu Leu Leu Leu Leu Val Gln Cys Ser Arg Ala
 1               5                  10                  15 ctt ggg cag cgc tca cca ctg aat gac ttc cag ctg ttc cgg ggc aca      96
Leu Gly Gln Arg Ser Pro Leu Asn Asp Phe Gln Leu Phe Arg Gly Thr
             20                  25                  30 gag tta agg aac ctg tta cac aca gcg gtg ccg ggg cca tgg cag gag     144
Glu Leu Arg Asn Leu Leu His Thr Ala Val Pro Gly Pro Trp Gln Glu
         35                  40                  45 gat gtg gca gat gct gag gag tgt gct agg cgc tgt ggg ccc ctt ctg     192
Asp Val Ala Asp Ala Glu Glu Cys Ala Arg Arg Cys Gly Pro Leu Leu
     50                  55                  60 gac tgt cgg gcc ttc cac tac aac atg agc agc cat ggt tgc cag ctg     240
Asp Cys Arg Ala Phe His Tyr Asn Met Ser Ser His Gly Cys Gln Leu
 65                  70                  75                  80 ctg ccg tgg acc cag cac tcg ctg cac aca cag cta tac cac tcg agt     288
Leu Pro Trp Thr Gln His Ser Leu His Thr Gln Leu Tyr His Ser Ser
                 85                  90                  95 ctg tgc cat ctc ttc cag aag aaa gat tat gtg cgg acc tgc att atg     336
Leu Cys His Leu Phe Gln Lys Lys Asp Tyr Val Arg Thr Cys Ile Met
            100                 105                 110 gac aat ggg gtc agc tac cgg ggc act gtg gcc agg aca gct ggt ggc     384
Asp Asn Gly Val Ser Tyr Arg Gly Thr Val Ala Arg Thr Ala Gly Gly
        115                 120                 125 ctg ccc tgc caa gcc tgg agt cgc agg ttc ccc aat gac cac aag tat     432
Leu Pro Cys Gln Ala Trp Ser Arg Arg Phe Pro Asn Asp His Lys Tyr
    130                 135                 140 acg ccc acg cca aag aat ggc ctg gaa gag aac ttc tgt agg aac cct     480
Thr Pro Thr Pro Lys Asn Gly Leu Glu Glu Asn Phe Cys Arg Asn Pro
145                 150                 155                 160 gat ggg gat ccc aga ggt ccc tgg tgc tac aca aca aac cgc agt gtg     528
Asp Gly Asp Pro Arg Gly Pro Trp Cys Tyr Thr Thr Asn Arg Ser Val
                165                 170                 175 cgt ttc cag agc tgt ggc atc aaa acc tgc agg gag gct gtt tgt gtt     576
Arg Phe Gln Ser Cys Gly Ile Lys Thr Cys Arg Glu Ala Val Cys Val
            180                 185                 190 ctg tgc aac ggt gag gat tac cgt ggc gag gta gac gtt aca gag tca     624
Leu Cys Asn Gly Glu Asp Tyr Arg Gly Glu Val Asp Val Thr Glu Ser
        195                 200                 205 ggg cgg gag tgt caa cgc tgg gac ctg cag cac ccc cac tcg cac cct     672
Gly Arg Glu Cys Gln Arg Trp Asp Leu Gln His Pro His Ser His Pro
    210                 215                 220 ttc cag cct gaa aag ttc cta gac aaa gat ctg aaa gac aac tat tgt     720
Phe Gln Pro Glu Lys Phe Leu Asp Lys Asp Leu Lys Asp Asn Tyr Cys
225                 230                 235                 240 cgt aat ccg gac gga tct gag cgg ccc tgg tgc tac acc aca gac ccg     768
Arg Asn Pro Asp Gly Ser Glu Arg Pro Trp Cys Tyr Thr Thr Asp Pro
                245                 250                 255 aat gtt gag cga gaa ttc tgc gac ctg ccc agt tgc ggg cct aac ctg     816
Asn Val Glu Arg Glu Phe Cys Asp Leu Pro Ser Cys Gly Pro Asn Leu
            260                 265                 270 cct ccg acc gtc aaa gga tcc aag tca cag cgg cgc aac aag ggc aag     864
Pro Pro Thr Val Lys Gly Ser Lys Ser Gln Arg Arg Asn Lys Gly Lys
        275                 280                 285 gct ctt aac tgc ttc cgc gga aaa ggt gaa gac tat cga ggc aca acc     912
Ala Leu Asn Cys Phe Arg Gly Lys Gly Glu Asp Tyr Arg Gly Thr Thr
    290                 295                 300 aat acc acc tct gcg ggc gtg ccc tgc cag cgg tgg gat gcg cag agt     960
```

```
Asn Thr Thr Ser Ala Gly Val Pro Cys Gln Arg Trp Asp Ala Gln Ser
305                 310                 315                 320 cca cac cag cac cgc ttt gtg cca gag aaa tat gct tgc aag gac ctt    1008
Pro His Gln His Arg Phe Val Pro Glu Lys Tyr Ala Cys Lys Asp Leu
                    325                 330                 335 cgt gag aat ttc tgc cgg aat cct gat ggc tcc gag gcg cct tgg tgc    1056
Arg Glu Asn Phe Cys Arg Asn Pro Asp Gly Ser Glu Ala Pro Trp Cys
                340                 345                 350 ttc aca tct cga cct ggt ttg cgc atg gcc ttc tgc cac cag atc cca    1104
Phe Thr Ser Arg Pro Gly Leu Arg Met Ala Phe Cys His Gln Ile Pro
            355                 360                 365 cgc tgc act gaa gaa ctg gtg cca gag gga tgc tac cac ggc tca ggt    1152
Arg Cys Thr Glu Glu Leu Val Pro Glu Gly Cys Tyr His Gly Ser Gly
        370                 375                 380 gaa cag tat cgt ggc tca gtc agc aag acg cgc aag ggc gtt cag tgc    1200
Glu Gln Tyr Arg Gly Ser Val Ser Lys Thr Arg Lys Gly Val Gln Cys
385                 390                 395                 400 cag cac tgg tcc tct gag aca ccg cac aag cca caa ttt aca ccc acc    1248
Gln His Trp Ser Ser Glu Thr Pro His Lys Pro Gln Phe Thr Pro Thr
                405                 410                 415 tcg gca ccg cag gcg gga ctg gag gcc aac ttc tgc agg aat cct gat    1296
Ser Ala Pro Gln Ala Gly Leu Glu Ala Asn Phe Cys Arg Asn Pro Asp
            420                 425                 430 ggg gat agc cat ggg ccc tgg tgc tat acc ttg gac ccg gat atc ctg    1344
Gly Asp Ser His Gly Pro Trp Cys Tyr Thr Leu Asp Pro Asp Ile Leu
        435                 440                 445 ttt gac tac tgt gcc cta cag cgc tgt gat gat gac cag cca cca tcc    1392
Phe Asp Tyr Cys Ala Leu Gln Arg Cys Asp Asp Asp Gln Pro Pro Ser
450                 455                 460 att ctg gac ccc cca gac cag gtg gtg ttt gaa aag tgt ggc aag aga    1440
Ile Leu Asp Pro Pro Asp Gln Val Val Phe Glu Lys Cys Gly Lys Arg
                465                 470                 475                 480 gtt gac aag agt aat aaa ctt cgt gtg gtg gga ggc cat cct ggg aac    1488
Val Asp Lys Ser Asn Lys Leu Arg Val Val Gly Gly His Pro Gly Asn
                485                 490                 495 tcc cca tgg acg gtc agc ttg cgg aat cga cag ggc cag cat ttc tgt    1536
Ser Pro Trp Thr Val Ser Leu Arg Asn Arg Gln Gly Gln His Phe Cys
            500                 505                 510 ggg ggc tcc cta gtg aag gag cag tgg gta ctg act gcc cgg caa tgc    1584
Gly Gly Ser Leu Val Lys Glu Gln Trp Val Leu Thr Ala Arg Gln Cys
        515                 520                 525 atc tgg tca tgc cac gaa cct ctc aca gga tac gag gta tgg ttg ggt    1632
Ile Trp Ser Cys His Glu Pro Leu Thr Gly Tyr Glu Val Trp Leu Gly
    530                 535                 540 aca att aac cag aac cca cag cct gga gag gca aac ctg cag agg gtc    1680
Thr Ile Asn Gln Asn Pro Gln Pro Gly Glu Ala Asn Leu Gln Arg Val
545                 550                 555                 560 cca gtg gcc aag gca gtg tgc ggc cct gca ggc tcc cag ctt gtt ctg    1728
Pro Val Ala Lys Ala Val Cys Gly Pro Ala Gly Ser Gln Leu Val Leu
                565                 570                 575 ctc aag ctg gag aga cct gtg atc ctg aac cat cac gtg gcc ctg att    1776
Leu Lys Leu Glu Arg Pro Val Ile Leu Asn His His Val Ala Leu Ile
            580                 585                 590 tgc ctg cct cct gaa cag tat gtg gta cct cca ggg acc aag tgt gag    1824
Cys Leu Pro Pro Glu Gln Tyr Val Val Pro Pro Gly Thr Lys Cys Glu
        595                 600                 605 atc gca ggc tgg ggt gaa tcc atc ggt aca agc aat aac aca gtc ctt    1872
Ile Ala Gly Trp Gly Glu Ser Ile Gly Thr Ser Asn Asn Thr Val Leu
    610                 615                 620
```

-continued

| | | | | | | | | | | | | | | | | |
|---|---|---|---|---|---|---|---|---|---|---|---|---|---|---|---|---|
| cat | gtg | gcc | tcg | atg | aat | gtc | atc | tcc | aac | cag | gaa | tgt | aac | acg | aag | 1920 |
| His | Val | Ala | Ser | Met | Asn | Val | Ile | Ser | Asn | Gln | Glu | Cys | Asn | Thr | Lys | |
| 625 | | | | 630 | | | | | 635 | | | | | 640 | | |

| | | | | | | | | | | | | | | | | |
|---|---|---|---|---|---|---|---|---|---|---|---|---|---|---|---|---|
| tac | cga | gga | cac | ata | caa | gag | agt | gag | ata | tgc | acc | cag | gga | ctg | gtg | 1968 |
| Tyr | Arg | Gly | His | Ile | Gln | Glu | Ser | Glu | Ile | Cys | Thr | Gln | Gly | Leu | Val | |
| | | | | 645 | | | | | 650 | | | | | 655 | | |

| | | | | | | | | | | | | | | | | |
|---|---|---|---|---|---|---|---|---|---|---|---|---|---|---|---|---|
| gtc | cct | gtg | ggg | gct | tgt | gag | ggt | gac | tac | ggg | ggc | cca | ctt | gcc | tgc | 2016 |
| Val | Pro | Val | Gly | Ala | Cys | Glu | Gly | Asp | Tyr | Gly | Gly | Pro | Leu | Ala | Cys | |
| | | | 660 | | | | | 665 | | | | | 670 | | | |

| | | | | | | | | | | | | | | | | |
|---|---|---|---|---|---|---|---|---|---|---|---|---|---|---|---|---|
| tat | acc | cat | gac | tgc | tgg | gtc | cta | cag | gga | ctt | atc | atc | ccg | aac | aga | 2064 |
| Tyr | Thr | His | Asp | Cys | Trp | Val | Leu | Gln | Gly | Leu | Ile | Ile | Pro | Asn | Arg | |
| | | 675 | | | | | 680 | | | | | 685 | | | | |

| | | | | | | | | | | | | | | | | |
|---|---|---|---|---|---|---|---|---|---|---|---|---|---|---|---|---|
| gtg | tgt | gca | cgg | ccc | cgc | tgg | cca | gct | atc | ttc | aca | cgg | gtg | tct | gtg | 2112 |
| Val | Cys | Ala | Arg | Pro | Arg | Trp | Pro | Ala | Ile | Phe | Thr | Arg | Val | Ser | Val | |
| | 690 | | | | 695 | | | | | 700 | | | | | | |

| | | | | | | | | | | | | |
|---|---|---|---|---|---|---|---|---|---|---|---|---|
| ttc | gtg | gac | tgg | att | aac | aag | gtc | atg | cag | ctg | gag | tag | 2151 |
| Phe | Val | Asp | Trp | Ile | Asn | Lys | Val | Met | Gln | Leu | Glu | | |
| 705 | | | | | 710 | | | | | 715 | | | |

<210> SEQ ID NO 14
<211> LENGTH: 716
<212> TYPE: PRT
<213> ORGANISM: Mus musculus

<400> SEQUENCE: 14

Met Gly Trp Leu Pro Leu Leu Leu Leu Val Gln Cys Ser Arg Ala
1               5                   10                  15

Leu Gly Gln Arg Ser Pro Leu Asn Asp Phe Gln Leu Phe Arg Gly Thr
        20                  25                  30

Glu Leu Arg Asn Leu Leu His Thr Ala Val Pro Gly Pro Trp Gln Glu
    35                  40                  45

Asp Val Ala Asp Ala Glu Glu Cys Ala Arg Arg Cys Gly Pro Leu Leu
50                  55                  60

Asp Cys Arg Ala Phe His Tyr Asn Met Ser Ser His Gly Cys Gln Leu
65                  70                  75                  80

Leu Pro Trp Thr Gln His Ser Leu His Thr Gln Leu Tyr His Ser Ser
                85                  90                  95

Leu Cys His Leu Phe Gln Lys Lys Asp Tyr Val Arg Thr Cys Ile Met
                100                 105                 110

Asp Asn Gly Val Ser Tyr Arg Gly Thr Val Ala Arg Thr Ala Gly Gly
            115                 120                 125

Leu Pro Cys Gln Ala Trp Ser Arg Arg Phe Pro Asn Asp His Lys Tyr
    130                 135                 140

Thr Pro Thr Pro Lys Asn Gly Leu Glu Glu Asn Phe Cys Arg Asn Pro
145                 150                 155                 160

Asp Gly Asp Pro Arg Gly Pro Trp Cys Tyr Thr Thr Asn Arg Ser Val
                165                 170                 175

Arg Phe Gln Ser Cys Gly Ile Lys Thr Cys Arg Glu Ala Val Cys Val
                180                 185                 190

Leu Cys Asn Gly Glu Asp Tyr Arg Gly Glu Val Asp Val Thr Glu Ser
            195                 200                 205

Gly Arg Glu Cys Gln Arg Trp Asp Leu Gln His Pro His Ser His Pro
    210                 215                 220

Phe Gln Pro Glu Lys Phe Leu Asp Lys Asp Leu Lys Asp Asn Tyr Cys
225                 230                 235                 240

Arg Asn Pro Asp Gly Ser Glu Arg Pro Trp Cys Tyr Thr Thr Asp Pro
                245                 250                 255

```
Asn Val Glu Arg Glu Phe Cys Asp Leu Pro Ser Cys Gly Pro Asn Leu
            260                 265                 270

Pro Pro Thr Val Lys Gly Ser Lys Ser Gln Arg Arg Asn Lys Gly Lys
            275                 280                 285

Ala Leu Asn Cys Phe Arg Gly Lys Gly Glu Asp Tyr Arg Gly Thr Thr
            290                 295                 300

Asn Thr Thr Ser Ala Gly Val Pro Cys Gln Arg Trp Asp Ala Gln Ser
305                 310                 315                 320

Pro His Gln His Arg Phe Val Pro Glu Lys Tyr Ala Cys Lys Asp Leu
                    325                 330                 335

Arg Glu Asn Phe Cys Arg Asn Pro Asp Gly Ser Glu Ala Pro Trp Cys
                340                 345                 350

Phe Thr Ser Arg Pro Gly Leu Arg Met Ala Phe Cys His Gln Ile Pro
            355                 360                 365

Arg Cys Thr Glu Glu Leu Val Pro Glu Gly Cys Tyr His Gly Ser Gly
            370                 375                 380

Glu Gln Tyr Arg Gly Ser Val Ser Lys Thr Arg Lys Gly Val Gln Cys
385                 390                 395                 400

Gln His Trp Ser Ser Glu Thr Pro His Lys Pro Gln Phe Thr Pro Thr
                    405                 410                 415

Ser Ala Pro Gln Ala Gly Leu Glu Ala Asn Phe Cys Arg Asn Pro Asp
                420                 425                 430

Gly Asp Ser His Gly Pro Trp Cys Tyr Thr Leu Asp Pro Asp Ile Leu
            435                 440                 445

Phe Asp Tyr Cys Ala Leu Gln Arg Cys Asp Asp Gln Pro Pro Ser
450                 455                 460

Ile Leu Asp Pro Pro Asp Gln Val Val Phe Glu Lys Cys Gly Lys Arg
465                 470                 475                 480

Val Asp Lys Ser Asn Lys Leu Arg Val Val Gly Gly His Pro Gly Asn
                485                 490                 495

Ser Pro Trp Thr Val Ser Leu Arg Asn Arg Gln Gly Gln His Phe Cys
                500                 505                 510

Gly Gly Ser Leu Val Lys Glu Gln Trp Val Leu Thr Ala Arg Gln Cys
            515                 520                 525

Ile Trp Ser Cys His Glu Pro Leu Thr Gly Tyr Glu Val Trp Leu Gly
            530                 535                 540

Thr Ile Asn Gln Asn Pro Gln Pro Gly Glu Ala Asn Leu Gln Arg Val
545                 550                 555                 560

Pro Val Ala Lys Ala Val Cys Gly Pro Ala Gly Ser Gln Leu Val Leu
                565                 570                 575

Leu Lys Leu Glu Arg Pro Val Ile Leu Asn His His Val Ala Leu Ile
                580                 585                 590

Cys Leu Pro Pro Glu Gln Tyr Val Val Pro Pro Gly Thr Lys Cys Glu
            595                 600                 605

Ile Ala Gly Trp Gly Glu Ser Ile Gly Thr Ser Asn Asn Thr Val Leu
            610                 615                 620

His Val Ala Ser Met Asn Val Ile Ser Asn Gln Glu Cys Asn Thr Lys
625                 630                 635                 640

Tyr Arg Gly His Ile Gln Glu Ser Glu Ile Cys Thr Gln Gly Leu Val
                645                 650                 655

Val Pro Val Gly Ala Cys Glu Gly Asp Tyr Gly Gly Pro Leu Ala Cys
                660                 665                 670
```

```
Tyr Thr His Asp Cys Trp Val Leu Gln Gly Leu Ile Ile Pro Asn Arg
        675                 680                 685

Val Cys Ala Arg Pro Arg Trp Pro Ala Ile Phe Thr Arg Val Ser Val
    690                 695                 700

Phe Val Asp Trp Ile Asn Lys Val Met Gln Leu Glu
705                 710                 715

<210> SEQ ID NO 15
<211> LENGTH: 801
<212> TYPE: DNA
<213> ORGANISM: Artificial Sequence
<220> FEATURE:
<223> OTHER INFORMATION: Synthetic mouse MSP polypeptide
<220> FEATURE:
<221> NAME/KEY: CDS
<222> LOCATION: (1)..(801)

<400> SEQUENCE: 15 atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg      96
Leu His Leu Leu Leu Leu Pro Ile Ala Ile Pro Tyr Ala Glu Gly Val
            20                  25                  30 gtg gga ggc cat cct ggg aac tcc cca tgg acg gtc agc ttg cgg aat     144
Val Gly Gly His Pro Gly Asn Ser Pro Trp Thr Val Ser Leu Arg Asn
        35                  40                  45 cga cag ggc cag cat ttc tgt ggg ggc tcc cta gtg aag gag cag tgg     192
Arg Gln Gly Gln His Phe Cys Gly Gly Ser Leu Val Lys Glu Gln Trp
    50                  55                  60 gta ctg act gcc cgg caa tgc atc tgg tca tgc cac gaa cct ctc aca     240
Val Leu Thr Ala Arg Gln Cys Ile Trp Ser Cys His Glu Pro Leu Thr
65                  70                  75                  80 gga tac gag gta tgg ttg ggt aca att aac cag aac cca cag cct gga     288
Gly Tyr Glu Val Trp Leu Gly Thr Ile Asn Gln Asn Pro Gln Pro Gly
                85                  90                  95 gag gca aac ctg cag agg gtc cca gtg gcc aag gca gtg tgc ggc cct     336
Glu Ala Asn Leu Gln Arg Val Pro Val Ala Lys Ala Val Cys Gly Pro
            100                 105                 110 gca ggc tcc cag ctt gtt ctc ctc aag ctg gag aga cct gtg atc ctg     384
Ala Gly Ser Gln Leu Val Leu Leu Lys Leu Glu Arg Pro Val Ile Leu
        115                 120                 125 aac cat cac gtg gcc ctg att gcc ctg cct cct gaa cag tat gtg gta     432
Asn His His Val Ala Leu Ile Ala Leu Pro Pro Glu Gln Tyr Val Val
    130                 135                 140 cct cca ggg acc aag tgt gag atc gca ggc tgg ggt gaa tcc atc ggt     480
Pro Pro Gly Thr Lys Cys Glu Ile Ala Gly Trp Gly Glu Ser Ile Gly
145                 150                 155                 160 aca agc aat aac aca gtc ctt cat gtg gcc tcg atg aat gtc atc tcc     528
Thr Ser Asn Asn Thr Val Leu His Val Ala Ser Met Asn Val Ile Ser
                165                 170                 175 aac cag gaa tgt aac acg aag tac cga gga cac ata caa gag agt gag     576
Asn Gln Glu Cys Asn Thr Lys Tyr Arg Gly His Ile Gln Glu Ser Glu
            180                 185                 190 ata tgc acc cag gga ctg gtg gtc cct gtg ggg gct tgt gag ggt gac     624
Ile Cys Thr Gln Gly Leu Val Val Pro Val Gly Ala Cys Glu Gly Asp
        195                 200                 205 tac ggg ggc cca ctt gcc tgc tat acc cat gac gca tgg gtc cta cag     672
Tyr Gly Gly Pro Leu Ala Cys Tyr Thr His Asp Ala Trp Val Leu Gln
    210                 215                 220 gga ctt atc atc ccg aac aga gtg tgt gca cgg ccc cgc tgg cca gct     720
```

```
Gly Leu Ile Ile Pro Asn Arg Val Cys Ala Arg Pro Arg Trp Pro Ala
225                 230                 235                 240 atc ttc aca cgg gtg tct gtg ttc gtg gac tgg att aac aag gtc atg      768
Ile Phe Thr Arg Val Ser Val Phe Val Asp Trp Ile Asn Lys Val Met
                    245                 250                 255 ctg gag cat cat cat cat cat cat cat tga                               801
Leu Glu His His His His His His His
            260                 265
```

<210> SEQ ID NO 16
<211> LENGTH: 266
<212> TYPE: PRT
<213> ORGANISM: Artificial Sequence
<220> FEATURE:
<223> OTHER INFORMATION: Synthetic mouse MSP polypeptide

<400> SEQUENCE: 16

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
        50                  55                  60

Val Leu Thr Ala Arg Gln Cys Ile Trp Ser Cys His Glu Pro Leu Thr
65                  70                  75                  80

Gly Tyr Glu Val Trp Leu Gly Thr Ile Asn Gln Asn Pro Gln Pro Gly
                85                  90                  95

Glu Ala Asn Leu Gln Arg Val Pro Val Ala Lys Ala Val Cys Gly Pro
            100                 105                 110

Ala Gly Ser Gln Leu Val Leu Leu Lys Leu Glu Arg Pro Val Ile Leu
        115                 120                 125

Asn His His Val Ala Leu Ile Ala Leu Pro Pro Glu Gln Tyr Val Val
    130                 135                 140

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Leu Glu His His His His His His His
            260                 265
```

<210> SEQ ID NO 17
<211> LENGTH: 266
<212> TYPE: PRT
<213> ORGANISM: Artificial Sequence
<220> FEATURE:
<223> OTHER INFORMATION: Synthetic mouse MSP polypeptide

<400> SEQUENCE: 17

| | | | | | | | | | | | | | | |
|---|---|---|---|---|---|---|---|---|---|---|---|---|---|---|
|Met|Trp|Val|Thr|Lys|Leu|Leu|Pro|Ala|Leu|Leu|Leu|Gln|His|Val|Leu
1| | | |5| | | | |10| | | | |15| |

Leu His Leu Leu Leu Pro Ile Ala Ile Pro Tyr Ala Glu Gly Val
         20                  25                30

Val Gly Gly His Pro Gly Asn Ser Pro Trp Thr Val Ser Leu Arg Asn
           35                 40                45

Arg Gln Gly Gln His Phe Cys Gly Gly Ser Leu Val Lys Glu Gln Trp
 50                     55                  60

Val Leu Thr Ala Arg Gln Cys Ile Trp Ser Cys His Glu Pro Leu Thr
65              70                75                80

Gly Tyr Glu Val Trp Leu Gly Thr Ile Asn Gln Asn Pro Gln Pro Gly
               85                90              95

Glu Ala Asn Leu Gln Arg Val Pro Val Ala Lys Ala Val Cys Gly Pro
          100              105             110

Ala Gly Ser Gln Leu Val Leu Leu Lys Leu Glu Arg Pro Val Ile Leu
         115              120             125

Asn His His Val Ala Leu Ile Ala Leu Pro Pro Glu Gln Tyr Val Val
    130              135             140

Pro Pro Gly Thr Lys Cys Glu Ile Ala Gly Trp Gly Glu Ser Ile Gly
145             150              155            160

Thr Ser Asn Asn Thr Val Leu His Val Ala Ser Met Asn Val Ile Ser
             165             170            175

Asn Gln Glu Cys Asn Thr Lys Tyr Arg Gly His Ile Gln Glu Ser Glu
       180            185             190

Ile Cys Thr Gln Gly Leu Val Val Pro Val Gly Ala Cys Glu Gly Asp
         195            200            205

Tyr Gly Gly Pro Leu Ala Cys Tyr Thr His Asp Cys Trp Val Leu Gln
210             215             220

Gly Leu Ile Ile Pro Asn Arg Val Cys Ala Arg Pro Arg Trp Pro Ala
225             230            235          240

Ile Phe Thr Arg Val Ser Val Phe Val Asp Trp Ile Asn Lys Val Met
           245            250             255

Leu Glu His His His His His His His
       260            265

<210> SEQ ID NO 18
<211> LENGTH: 716
<212> TYPE: PRT
<213> ORGANISM: Mus musculus

<400> SEQUENCE: 18

Met Gly Trp Leu Pro Leu Leu Leu Leu Val Gln Cys Ser Arg Ala
1         5              10             15

Leu Gly Gln Arg Ser Pro Leu Asn Asp Phe Gln Leu Phe Arg Gly Thr
         20                25             30

Glu Leu Arg Asn Leu Leu His Thr Ala Val Pro Gly Pro Trp Gln Glu
           35              40            45

Asp Val Ala Asp Ala Glu Glu Cys Ala Arg Arg Cys Gly Pro Leu Leu
 50                    55               60

Asp Cys Arg Ala Phe His Tyr Asn Met Ser Ser His Gly Cys Gln Leu
65             70              75             80

Leu Pro Trp Thr Gln His Ser Leu His Thr Gln Leu Tyr His Ser Ser
           85              90             95

```
Leu Cys His Leu Phe Gln Lys Lys Asp Tyr Val Arg Thr Cys Ile Met
            100                 105                 110

Asp Asn Gly Val Ser Tyr Arg Gly Thr Val Ala Arg Thr Ala Gly Gly
            115                 120                 125

Leu Pro Cys Gln Ala Trp Ser Arg Arg Phe Pro Asn Asp His Lys Tyr
            130                 135                 140

Thr Pro Thr Pro Lys Asn Gly Leu Glu Glu Asn Phe Cys Arg Asn Pro
145                 150                 155                 160

Asp Gly Asp Pro Arg Gly Pro Trp Cys Tyr Thr Thr Asn Arg Ser Val
                165                 170                 175

Arg Phe Gln Ser Cys Gly Ile Lys Thr Cys Arg Glu Ala Val Cys Val
            180                 185                 190

Leu Cys Asn Gly Glu Asp Tyr Arg Gly Glu Val Asp Val Thr Glu Ser
            195                 200                 205

Gly Arg Glu Cys Gln Arg Trp Asp Leu Gln His Pro His Ser His Pro
            210                 215                 220

Phe Gln Pro Glu Lys Phe Leu Asp Lys Asp Leu Lys Asp Asn Tyr Cys
225                 230                 235                 240

Arg Asn Pro Asp Gly Ser Glu Arg Pro Trp Cys Tyr Thr Thr Asp Pro
                245                 250                 255

Asn Val Glu Arg Glu Phe Cys Asp Leu Pro Ser Cys Gly Pro Asn Leu
            260                 265                 270

Pro Pro Thr Val Lys Gly Ser Lys Ser Gln Arg Arg Asn Lys Gly Lys
            275                 280                 285

Ala Leu Asn Cys Phe Arg Gly Lys Gly Asp Tyr Arg Gly Thr Thr
            290                 295                 300

Asn Thr Thr Ser Ala Gly Val Pro Cys Gln Arg Trp Asp Ala Gln Ser
305                 310                 315                 320

Pro His Gln His Arg Phe Val Pro Glu Lys Tyr Ala Cys Lys Asp Leu
            325                 330                 335

Arg Glu Asn Phe Cys Arg Asn Pro Asp Gly Ser Glu Ala Pro Trp Cys
            340                 345                 350

Phe Thr Ser Arg Pro Gly Leu Arg Met Ala Phe Cys His Gln Ile Pro
            355                 360                 365

Arg Cys Thr Glu Glu Leu Val Pro Glu Gly Cys Tyr His Gly Ser Gly
            370                 375                 380

Glu Gln Tyr Arg Gly Ser Val Ser Lys Thr Arg Lys Gly Val Gln Cys
385                 390                 395                 400

Gln His Trp Ser Ser Glu Thr Pro His Lys Pro Gln Phe Thr Pro Thr
            405                 410                 415

Ser Ala Pro Gln Ala Gly Leu Glu Ala Asn Phe Cys Arg Asn Pro Asp
            420                 425                 430

Gly Asp Ser His Gly Pro Trp Cys Tyr Thr Leu Asp Pro Asp Ile Leu
            435                 440                 445

Phe Asp Tyr Cys Ala Leu Gln Arg Cys Asp Asp Gln Pro Pro Ser
            450                 455                 460

Ile Leu Asp Pro Pro Asp Gln Val Val Phe Glu Lys Cys Gly Lys Arg
465                 470                 475                 480

Val Asp Lys Ser Asn Lys Leu Arg Val Gly Gly His Pro Gly Asn
                485                 490                 495

Ser Pro Trp Thr Val Ser Leu Arg Asn Arg Gln Gly Gln His Phe Cys
            500                 505                 510
```

-continued

```
Gly Gly Ser Leu Val Lys Glu Gln Trp Val Leu Thr Ala Arg Gln Cys
            515                 520                 525
Ile Trp Ser Cys His Glu Pro Leu Thr Gly Tyr Glu Val Trp Leu Gly
530                 535                 540
Thr Ile Asn Gln Asn Pro Gln Pro Gly Glu Ala Asn Leu Gln Arg Val
545                 550                 555                 560
Pro Val Ala Lys Ala Val Cys Gly Pro Ala Gly Ser Gln Leu Val Leu
                565                 570                 575
Leu Lys Leu Glu Arg Pro Val Ile Leu Asn His His Val Ala Leu Ile
            580                 585                 590
Cys Leu Pro Pro Glu Gln Tyr Val Val Pro Pro Gly Thr Lys Cys Glu
        595                 600                 605
Ile Ala Gly Trp Gly Glu Ser Ile Gly Thr Ser Asn Asn Thr Val Leu
    610                 615                 620
His Val Ala Ser Met Asn Val Ile Ser Asn Gln Glu Cys Asn Thr Lys
625                 630                 635                 640
Tyr Arg Gly His Ile Gln Glu Ser Glu Ile Cys Thr Gln Gly Leu Val
                645                 650                 655
Val Pro Val Gly Ala Cys Glu Gly Asp Tyr Gly Gly Pro Leu Ala Cys
            660                 665                 670
Tyr Thr His Asp Cys Trp Val Leu Gln Gly Leu Ile Ile Pro Asn Arg
        675                 680                 685
Val Cys Ala Arg Pro Arg Trp Pro Ala Ile Phe Thr Arg Val Ser Val
    690                 695                 700
Phe Val Asp Trp Ile Asn Lys Val Met Gln Leu Glu
705                 710                 715

<210> SEQ ID NO 19
<211> LENGTH: 1482
<212> TYPE: DNA
<213> ORGANISM: Artificial Sequence
<220> FEATURE:
<223> OTHER INFORMATION: Synthetic human MSP fusion protein
<220> FEATURE:
<221> NAME/KEY: CDS
<222> LOCATION: (1)..(1482)

<400> SEQUENCE: 19 atg tgg gtg acc aaa ctc ctg cca gcc ctg ctg ctg cag cat gtc ctc     48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg     96
Leu His Leu Leu Leu Leu Pro Ile Ala Ile Pro Tyr Ala Glu Gly Val
            20                  25                  30 gtt ggg ggc cat ccg ggc aac tca ccc tgg aca gtc agc ttg cgg aat    144
Val Gly Gly His Pro Gly Asn Ser Pro Trp Thr Val Ser Leu Arg Asn
        35                  40                  45 cgg cag ggc cag cat ttc tgc ggg ggg tct cta gtg aag gag cag tgg    192
Arg Gln Gly Gln His Phe Cys Gly Gly Ser Leu Val Lys Glu Gln Trp
    50                  55                  60 ata ctg act gcc cgg cag tgc ttc tcc tcc tgc cat atg cct ctc acg    240
Ile Leu Thr Ala Arg Gln Cys Phe Ser Ser Cys His Met Pro Leu Thr
65                  70                  75                  80 ggc tat gag gta tgg ttg ggc acc ctg ttc cag aac cca cag cat gga    288
Gly Tyr Glu Val Trp Leu Gly Thr Leu Phe Gln Asn Pro Gln His Gly
                85                  90                  95 gag cca agc cta cag cgg gtc cca gta gcc aag atg gtg tgt ggg ccc    336
Glu Pro Ser Leu Gln Arg Val Pro Val Ala Lys Met Val Cys Gly Pro
            100                 105                 110
```

-continued

```
tca ggc tcc cag ctt gtc ctg ctc aag ctg gag aga tct gtg acc ctg     384
Ser Gly Ser Gln Leu Val Leu Leu Lys Leu Glu Arg Ser Val Thr Leu
        115                 120                 125 aac cag cgt gtg gcc ctg atc tcc ctg ccc cct gaa tgg tat gtg gtg     432
Asn Gln Arg Val Ala Leu Ile Ser Leu Pro Pro Glu Trp Tyr Val Val
130                 135                 140 cct cca ggg acc aag tgt gag att gca ggc tgg ggt gag acc aaa ggt     480
Pro Pro Gly Thr Lys Cys Glu Ile Ala Gly Trp Gly Glu Thr Lys Gly
145                 150                 155                 160 acg ggt aat gac aca gtc cta aat gtg gcc ttg ctg aat gtc atc tcc     528
Thr Gly Asn Asp Thr Val Leu Asn Val Ala Leu Leu Asn Val Ile Ser
                165                 170                 175 aac cag gag tgt aac atc aag cac cga gga cgt gtg cgg gag agt gag     576
Asn Gln Glu Cys Asn Ile Lys His Arg Gly Arg Val Arg Glu Ser Glu
            180                 185                 190 atg tgc act gag gga ctg ttg gcc cct gtg ggg gcc tgt gag ggt gac     624
Met Cys Thr Glu Gly Leu Leu Ala Pro Val Gly Ala Cys Glu Gly Asp
        195                 200                 205 tac ggg ggc cca ctt gcc tgc ttt acc cac aac gcc tgg gtc ctg gaa     672
Tyr Gly Gly Pro Leu Ala Cys Phe Thr His Asn Ala Trp Val Leu Glu
    210                 215                 220 gga att ata atc ccc aac cga gta tgc gca agg tcc cgc tgg cca gct     720
Gly Ile Ile Ile Pro Asn Arg Val Cys Ala Arg Ser Arg Trp Pro Ala
225                 230                 235                 240 gtc ttc acg cgt gtc tct gtg ttt gtg gac tgg att cac aag gtc atg     768
Val Phe Thr Arg Val Ser Val Phe Val Asp Trp Ile His Lys Val Met
                245                 250                 255 aga ctg ggt tcc gga gga tcc cag gtc acc gac aaa act cac aca tgc     816
Arg Leu Gly Ser Gly Gly Ser Gln Val Thr Asp Lys Thr His Thr Cys
            260                 265                 270 cca ccg tgc cca gca cct gaa ctc ctg ggg gga ccg tca gtc ttc ctc     864
Pro Pro Cys Pro Ala Pro Glu Leu Leu Gly Gly Pro Ser Val Phe Leu
        275                 280                 285 ttc ccc cca aaa ccc aag gac acc ctc atg atc tcc cgg acc cct gag     912
Phe Pro Pro Lys Pro Lys Asp Thr Leu Met Ile Ser Arg Thr Pro Glu
    290                 295                 300 gtc aca tgc gtg gtg gtg gac gtg agc cac gaa gac cct gag gtc aag     960
Val Thr Cys Val Val Val Asp Val Ser His Glu Asp Pro Glu Val Lys
305                 310                 315                 320 ttc aac tgg tac gtg gac ggc gtg gag gtg cat aat gcc aag aca aag    1008
Phe Asn Trp Tyr Val Asp Gly Val Glu Val His Asn Ala Lys Thr Lys
                325                 330                 335 ccg cgg gag gag cag tac aac agc acg tac cgt gtg gtc agc gtc ctc    1056
Pro Arg Glu Glu Gln Tyr Asn Ser Thr Tyr Arg Val Val Ser Val Leu
            340                 345                 350 acc gtc ctg cac cag gac tgg ctg aat ggc aag gag tac aag tgc aag    1104
Thr Val Leu His Gln Asp Trp Leu Asn Gly Lys Glu Tyr Lys Cys Lys
        355                 360                 365 gtc tcc aac aaa gcc ctc cca gcc ccc atc gag aaa acc atc tcc aaa    1152
Val Ser Asn Lys Ala Leu Pro Ala Pro Ile Glu Lys Thr Ile Ser Lys
    370                 375                 380 gcc aaa ggg cag ccc cga gaa cca cag gtg tac acc ctg ccc cca tcc    1200
Ala Lys Gly Gln Pro Arg Glu Pro Gln Val Tyr Thr Leu Pro Pro Ser
385                 390                 395                 400 cgg gaa gag atg acc aag aac cag gtc agc ctg acc tgc ctg gtc aaa    1248
Arg Glu Glu Met Thr Lys Asn Gln Val Ser Leu Thr Cys Leu Val Lys
                405                 410                 415 ggc ttc tat ccc agc gac atc gcc gtg gag tgg gag agc aat ggg cag    1296
Gly Phe Tyr Pro Ser Asp Ile Ala Val Glu Trp Glu Ser Asn Gly Gln
```

```
                      420               425                430
ccg gag aac aac tac aag acc acg cct ccc gtg ctg gac tcc gac ggc    1344
Pro Glu Asn Asn Tyr Lys Thr Thr Pro Pro Val Leu Asp Ser Asp Gly
        435                 440                 445 tcc ttc ttc ctc tac agc aag ctc acc gtg gac aag agc agg tgg cag    1392
Ser Phe Phe Leu Tyr Ser Lys Leu Thr Val Asp Lys Ser Arg Trp Gln
450                 455                 460 cag ggg aac gtc ttc tca tgc tcc gtg atg cat gag gct ctg cac aac    1440
Gln Gly Asn Val Phe Ser Cys Ser Val Met His Glu Ala Leu His Asn
465                 470                 475                 480 cac tac acg cag aag agc ctc tcc ctg tct ccg ggt aaa tga            1482
His Tyr Thr Gln Lys Ser Leu Ser Leu Ser Pro Gly Lys
                485                 490

<210> SEQ ID NO 20
<211> LENGTH: 493
<212> TYPE: PRT
<213> ORGANISM: Artificial Sequence
<220> FEATURE:
<223> OTHER INFORMATION: Synthetic human MSP fusion protein

<400> SEQUENCE: 20

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
    50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
                85                  90                  95

Glu Pro Ser Leu Gln Arg Val Pro Val Ala Lys Met Val Cys Gly Pro
                100                 105                 110

Ser Gly Ser Gln Leu Val Leu Leu Lys Leu Glu Arg Ser Val Thr Leu
            115                 120                 125

Asn Gln Arg Val Ala Leu Ile Ser Leu Pro Pro Glu Trp Tyr Val Val
    130                 135                 140

Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
                165                 170                 175

Asn Gln Glu Cys Asn Ile Lys His Arg Gly Arg Val Arg Glu Ser Glu
                180                 185                 190

Met Cys Thr Glu Gly Leu Leu Ala Pro Val Gly Ala Cys Glu Gly Asp
            195                 200                 205

Tyr Gly Gly Pro Leu Ala Cys Phe Thr His Asn Ala Trp Val Leu Glu
    210                 215                 220

Gly Ile Ile Ile Pro Asn Arg Val Cys Ala Arg Ser Arg Trp Pro Ala
225                 230                 235                 240

Val Phe Thr Arg Val Ser Val Phe Val Asp Trp Ile His Lys Val Met
                245                 250                 255

Arg Leu Gly Ser Gly Gly Ser Gln Val Thr Asp Lys Thr His Thr Cys
                260                 265                 270
```

```
Pro Pro Cys Pro Ala Pro Glu Leu Leu Gly Gly Pro Ser Val Phe Leu
            275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430

Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 21
<211> LENGTH: 1500
<212> TYPE: DNA
<213> ORGANISM: Artificial Sequence
<220> FEATURE:
<223> OTHER INFORMATION: Synthetic human MSP fusion protein
<220> FEATURE:
<221> NAME/KEY: CDS
<222> LOCATION: (1)..(1500)

<400> SEQUENCE: 21 atg tgg gtg acc aaa ctc ctg cca gcc ctg ctg ctg cag cat gtc ctc    48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg    96
Leu His Leu Leu Leu Leu Pro Ile Ala Ile Pro Tyr Ala Glu Gly Val
                20                  25                  30 gtt ggg ggc cat ccg ggc aac tca ccc tgg aca gtc agc ttg cgg aat   144
Val Gly Gly His Pro Gly Asn Ser Pro Trp Thr Val Ser Leu Arg Asn
            35                  40                  45 cgg cag ggc cag cat ttc tgc ggg ggg tct cta gtg aag gag cag tgg   192
Arg Gln Gly Gln His Phe Cys Gly Gly Ser Leu Val Lys Glu Gln Trp
50                  55                  60 ata ctg act gcc cgg cag tgc ttc tcc tcc tgc cat atg cct ctc acg   240
Ile Leu Thr Ala Arg Gln Cys Phe Ser Ser Cys His Met Pro Leu Thr
65                  70                  75                  80 ggc tat gag gta tgg ttg ggc acc ctg ttc cag aac cca cag cat gga   288
Gly Tyr Glu Val Trp Leu Gly Thr Leu Phe Gln Asn Pro Gln His Gly
                85                  90                  95
```

-continued

| | | |
|---|---|---|
| gag cca agc cta cag cgg gtc cca gta gcc aag atg gtg tgt ggg ccc<br>Glu Pro Ser Leu Gln Arg Val Pro Val Ala Lys Met Val Cys Gly Pro<br>100 105 110 | 336 | |
| tca ggc tcc cag ctt gtc ctg ctc aag ctg gag aga tct gtg acc ctg<br>Ser Gly Ser Gln Leu Val Leu Leu Lys Leu Glu Arg Ser Val Thr Leu<br>115 120 125 | 384 | |
| aac cag cgt gtg gcc ctg atc tcc ctg ccc cct gaa tgg tat gtg gtg<br>Asn Gln Arg Val Ala Leu Ile Ser Leu Pro Pro Glu Trp Tyr Val Val<br>130 135 140 | 432 | |
| cct cca ggg acc aag tgt gag att gca ggc tgg ggt gag acc aaa ggt<br>Pro Pro Gly Thr Lys Cys Glu Ile Ala Gly Trp Gly Glu Thr Lys Gly<br>145 150 155 160 | 480 | |
| acg ggt aat gac aca gtc cta aat gtg gcc ttg ctg aat gtc atc tcc<br>Thr Gly Asn Asp Thr Val Leu Asn Val Ala Leu Leu Asn Val Ile Ser<br>165 170 175 | 528 | |
| aac cag gag tgt aac atc aag cac cga gga cgt gtg cgg gag agt gag<br>Asn Gln Glu Cys Asn Ile Lys His Arg Gly Arg Val Arg Glu Ser Glu<br>180 185 190 | 576 | |
| atg tgc act gag gga ctg ttg gcc cct gtg ggg gcc tgt gag ggt gac<br>Met Cys Thr Glu Gly Leu Leu Ala Pro Val Gly Ala Cys Glu Gly Asp<br>195 200 205 | 624 | |
| tac ggg ggc cca ctt gcc tgc ttt acc cac aac gcc tgg gtc ctg gaa<br>Tyr Gly Gly Pro Leu Ala Cys Phe Thr His Asn Ala Trp Val Leu Glu<br>210 215 220 | 672 | |
| gga att ata atc ccc aac cga gta tgc gca agg tcc cgc tgg cca gct<br>Gly Ile Ile Ile Pro Asn Arg Val Cys Ala Arg Ser Arg Trp Pro Ala<br>225 230 235 240 | 720 | |
| gtc ttc acg cgt gtc tct gtg ttt gtg gac tgg att cac aag gtc atg<br>Val Phe Thr Arg Val Ser Val Phe Val Asp Trp Ile His Lys Val Met<br>245 250 255 | 768 | |
| aga ctg ggt cag gtc acc gac aag aaa att gag ccc aga ggg ccc aca<br>Arg Leu Gly Gln Val Thr Asp Lys Lys Ile Glu Pro Arg Gly Pro Thr<br>260 265 270 | 816 | |
| atc aag ccc tgt cct cca tgc aaa tgc cca gca cct aac ctc ttg ggt<br>Ile Lys Pro Cys Pro Pro Cys Lys Cys Pro Ala Pro Asn Leu Leu Gly<br>275 280 285 | 864 | |
| gga cca tcc gtc ttc atc ttc cct cca aag atc aag gat gta ctc atg<br>Gly Pro Ser Val Phe Ile Phe Pro Pro Lys Ile Lys Asp Val Leu Met<br>290 295 300 | 912 | |
| atc tcc ctg agc ccc ata gtc aca tgt gtg gtg gtg gat gtg agc gag<br>Ile Ser Leu Ser Pro Ile Val Thr Cys Val Val Val Asp Val Ser Glu<br>305 310 315 320 | 960 | |
| gat gac cca gat gtc cag atc agc tgg ttt gtg aac aac gtg gaa gta<br>Asp Asp Pro Asp Val Gln Ile Ser Trp Phe Val Asn Asn Val Glu Val<br>325 330 335 | 1008 | |
| cac aca gct cag aca caa acc cat aga gag gat tac aac agt act cta<br>His Thr Ala Gln Thr Gln Thr His Arg Glu Asp Tyr Asn Ser Thr Leu<br>340 345 350 | 1056 | |
| cgc gtg gtc agt gcc ctc ccc atc cag cac cag gac tgg atg agt ggc<br>Arg Val Val Ser Ala Leu Pro Ile Gln His Gln Asp Trp Met Ser Gly<br>355 360 365 | 1104 | |
| aag gag ttc aaa tgc aag gtc aac aac aaa gac ctc cca gcg ccc atc<br>Lys Glu Phe Lys Cys Lys Val Asn Asn Lys Asp Leu Pro Ala Pro Ile<br>370 375 380 | 1152 | |
| gag aga acc atc tca aaa ccc aaa ggg tca gta aga gct cca cag gta<br>Glu Arg Thr Ile Ser Lys Pro Lys Gly Ser Val Arg Ala Pro Gln Val<br>385 390 395 400 | 1200 | |
| tat gtc ttg cct cca cca gaa gaa gag atg act aag aaa cag gtc act<br>Tyr Val Leu Pro Pro Pro Glu Glu Glu Met Thr Lys Lys Gln Val Thr<br>405 410 415 | 1248 | |

-continued

```
ctg acc tgc atg gtc aca gac ttc atg cct gaa gac att tac gtg gag    1296
Leu Thr Cys Met Val Thr Asp Phe Met Pro Glu Asp Ile Tyr Val Glu
        420                 425                 430 tgg acc aac aac ggg aaa aca gag cta aac tac aag aac act gaa cca    1344
Trp Thr Asn Asn Gly Lys Thr Glu Leu Asn Tyr Lys Asn Thr Glu Pro
        435                 440                 445 gtc ctg gac tct gat ggt tct tac ttc atg tac agc aag ctg aga gtg    1392
Val Leu Asp Ser Asp Gly Ser Tyr Phe Met Tyr Ser Lys Leu Arg Val
    450                 455                 460 gaa aag aag aac tgg gtg gaa aga aat agc tac tcc tgt tca gtg gtc    1440
Glu Lys Lys Asn Trp Val Glu Arg Asn Ser Tyr Ser Cys Ser Val Val
465                 470                 475                 480 cac gag ggt ctg cac aat cac cac acg act aag agc ttc tcc cgg act    1488
His Glu Gly Leu His Asn His His Thr Thr Lys Ser Phe Ser Arg Thr
                485                 490                 495 ccg ggt aaa tga                                                    1500
Pro Gly Lys
```

<210> SEQ ID NO 22
<211> LENGTH: 499
<212> TYPE: PRT
<213> ORGANISM: Artificial Sequence
<220> FEATURE:
<223> OTHER INFORMATION: Synthetic human MSP fusion protein

<400> SEQUENCE: 22

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
        50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
                85                  90                  95

Glu Pro Ser Leu Gln Arg Val Pro Val Ala Lys Met Val Cys Gly Pro
            100                 105                 110

Ser Gly Ser Gln Leu Val Leu Leu Lys Leu Glu Arg Ser Val Thr Leu
        115                 120                 125

Asn Gln Arg Val Ala Leu Ile Ser Leu Pro Pro Glu Trp Tyr Val Val
        130                 135                 140

Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
                165                 170                 175

Asn Gln Glu Cys Asn Ile Lys His Arg Gly Arg Val Arg Glu Ser Glu
            180                 185                 190

Met Cys Thr Glu Gly Leu Leu Ala Pro Val Gly Ala Cys Glu Gly Asp
        195                 200                 205

Tyr Gly Gly Pro Leu Ala Cys Phe Thr His Asn Ala Trp Val Leu Glu
    210                 215                 220

Gly Ile Ile Ile Pro Asn Arg Val Cys Ala Arg Ser Arg Trp Pro Ala
225                 230                 235                 240
```

```
Val Phe Thr Arg Val Ser Val Phe Val Asp Trp Ile His Lys Val Met
            245                 250                 255

Arg Leu Gly Gln Val Thr Asp Lys Lys Ile Glu Pro Arg Gly Pro Thr
        260                 265                 270

Ile Lys Pro Cys Pro Pro Cys Lys Cys Pro Ala Pro Asn Leu Leu Gly
    275                 280                 285

Gly Pro Ser Val Phe Ile Phe Pro Pro Lys Ile Lys Asp Val Leu Met
    290                 295                 300

Ile Ser Leu Ser Pro Ile Val Thr Cys Val Val Asp Val Ser Glu
305                 310                 315                 320

Asp Asp Pro Asp Val Gln Ile Ser Trp Phe Val Asn Asn Val Glu Val
                325                 330                 335

His Thr Ala Gln Thr Gln Thr His Arg Glu Asp Tyr Asn Ser Thr Leu
            340                 345                 350

Arg Val Val Ser Ala Leu Pro Ile Gln His Gln Asp Trp Met Ser Gly
        355                 360                 365

Lys Glu Phe Lys Cys Lys Val Asn Asn Lys Asp Leu Pro Ala Pro Ile
    370                 375                 380

Glu Arg Thr Ile Ser Lys Pro Lys Gly Ser Val Arg Ala Pro Gln Val
385                 390                 395                 400

Tyr Val Leu Pro Pro Pro Glu Glu Met Thr Lys Lys Gln Val Thr
                405                 410                 415

Leu Thr Cys Met Val Thr Asp Phe Met Pro Glu Asp Ile Tyr Val Glu
            420                 425                 430

Trp Thr Asn Asn Gly Lys Thr Glu Leu Asn Tyr Lys Asn Thr Glu Pro
        435                 440                 445

Val Leu Asp Ser Asp Gly Ser Tyr Phe Met Tyr Ser Lys Leu Arg Val
    450                 455                 460

Glu Lys Lys Asn Trp Val Glu Arg Asn Ser Tyr Ser Cys Ser Val Val
465                 470                 475                 480

His Glu Gly Leu His Asn His His Thr Thr Lys Ser Phe Ser Arg Thr
                485                 490                 495

Pro Gly Lys

<210> SEQ ID NO 23
<211> LENGTH: 1500
<212> TYPE: DNA
<213> ORGANISM: Artificial Sequence
<220> FEATURE:
<223> OTHER INFORMATION: Synthetic human MSP fusion protein
<220> FEATURE:
<221> NAME/KEY: CDS
<222> LOCATION: (1)..(1500)

<400> SEQUENCE: 23 atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
1               5                   10                  15 ctg cat ctc ctg ctc ccc atc gcc atc ccc tat gca gag gga gtg          96
Leu His Leu Leu Leu Pro Ile Ala Ile Pro Tyr Ala Glu Gly Val
            20                  25                  30 gtt ggg ggc cat ccg ggc aac tca ccc tgg aca gtc agc ttg cgg aat     144
Val Gly Gly His Pro Gly Asn Ser Pro Trp Thr Val Ser Leu Arg Asn
        35                  40                  45 cgg cag ggc cag cat ttc tgc ggg ggg tct cta gtg aag gag cag tgg     192
Arg Gln Gly Gln His Phe Cys Gly Gly Ser Leu Val Lys Glu Gln Trp
    50                  55                  60
```

```
ata ctg act gcc cgg cag tgc ttc tcc tcc tgc cat atg cct ctc acg        240
Ile Leu Thr Ala Arg Gln Cys Phe Ser Ser Cys His Met Pro Leu Thr
 65                  70                  75                  80 ggc tat gag gta tgg ttg ggc acc ctg ttc cag aac cca cag cat gga        288
Gly Tyr Glu Val Trp Leu Gly Thr Leu Phe Gln Asn Pro Gln His Gly
                 85                  90                  95 gag cca agc cta cag cgg gtc cca gta gcc aag atg gtg tgt ggg ccc        336
Glu Pro Ser Leu Gln Arg Val Pro Val Ala Lys Met Val Cys Gly Pro
            100                 105                 110 tca ggc tcc cag ctt gtc ctg ctc aag ctg gag aga tct gtg acc ctg        384
Ser Gly Ser Gln Leu Val Leu Leu Lys Leu Glu Arg Ser Val Thr Leu
        115                 120                 125 aac cag cgt gtg gcc ctg atc tcc ctg ccc cct gaa tgg tat gtg gtg        432
Asn Gln Arg Val Ala Leu Ile Ser Leu Pro Pro Glu Trp Tyr Val Val
    130                 135                 140 cct cca ggg acc aag tgt gag att gca ggc tgg ggt gag acc aaa ggt        480
Pro Pro Gly Thr Lys Cys Glu Ile Ala Gly Trp Gly Glu Thr Lys Gly
145                 150                 155                 160 acg ggt aat gac aca gtc cta aat gtg gcc ttg ctg aat gtc atc tcc        528
Thr Gly Asn Asp Thr Val Leu Asn Val Ala Leu Leu Asn Val Ile Ser
                165                 170                 175 aac cag gag tgt aac atc aag cac cga gga cgt gtg cgg gag agt gag        576
Asn Gln Glu Cys Asn Ile Lys His Arg Gly Arg Val Arg Glu Ser Glu
            180                 185                 190 atg tgc act gag gga ctg ttg gcc cct gtg ggg gcc tgt gag ggt gac        624
Met Cys Thr Glu Gly Leu Leu Ala Pro Val Gly Ala Cys Glu Gly Asp
        195                 200                 205 tac ggg ggc cca ctt gcc tgc ttt acc cac aac tcc tgg gtc ctg gaa        672
Tyr Gly Gly Pro Leu Ala Cys Phe Thr His Asn Ser Trp Val Leu Glu
    210                 215                 220 gga att ata atc ccc aac cga gta tgc gca agg tcc cgc tgg cca gct        720
Gly Ile Ile Ile Pro Asn Arg Val Cys Ala Arg Ser Arg Trp Pro Ala
225                 230                 235                 240 gtc ttc acg cgt gtc tct gtg ttt gtg gac tgg att cac aag gtc atg        768
Val Phe Thr Arg Val Ser Val Phe Val Asp Trp Ile His Lys Val Met
                245                 250                 255 aga ctg ggt cag gtc acc gac aag aaa att gag ccc aga gga ccc aca        816
Arg Leu Gly Gln Val Thr Asp Lys Lys Ile Glu Pro Arg Gly Pro Thr
            260                 265                 270 atc aag ccc tgt cct cca tgc aaa tgc cca gca cct aac ctc ttg ggt        864
Ile Lys Pro Cys Pro Pro Cys Lys Cys Pro Ala Pro Asn Leu Leu Gly
        275                 280                 285 gga cca tcc gtc ttc atc ttc cct cca aag atc aag gat gta ctc atg        912
Gly Pro Ser Val Phe Ile Phe Pro Pro Lys Ile Lys Asp Val Leu Met
    290                 295                 300 atc tcc ctg agc ccc ata gtc aca tgt gtg gtg gtg gct gtg agc gag        960
Ile Ser Leu Ser Pro Ile Val Thr Cys Val Val Val Ala Val Ser Glu
305                 310                 315                 320 gat gac cca gat gtc cag atc agc tgg ttt gtg aac aac gtg gaa gta       1008
Asp Asp Pro Asp Val Gln Ile Ser Trp Phe Val Asn Asn Val Glu Val
                325                 330                 335 cac aca gct cag aca caa acc cat aga gag gat tac gcc agt act cta       1056
His Thr Ala Gln Thr Gln Thr His Arg Glu Asp Tyr Ala Ser Thr Leu
            340                 345                 350 cgc gtg gtc agt gcc ctc ccc atc cag cac cag gac tgg atg agt ggc       1104
Arg Val Val Ser Ala Leu Pro Ile Gln His Gln Asp Trp Met Ser Gly
        355                 360                 365 aag gag ttc aaa tgc aag gtc aac aac aaa gac ctc cca gcg ccc atc       1152
Lys Glu Phe Lys Cys Lys Val Asn Asn Lys Asp Leu Pro Ala Pro Ile
    370                 375                 380
```

```
gag aga acc atc tca aaa ccc aaa ggg tca gta aga gct cca cag gta      1200
Glu Arg Thr Ile Ser Lys Pro Lys Gly Ser Val Arg Ala Pro Gln Val
385                 390                 395                 400 tat gtc ttg cct cca cca gaa gaa gag atg act aag aaa cag gtc act      1248
Tyr Val Leu Pro Pro Pro Glu Glu Glu Met Thr Lys Lys Gln Val Thr
                405                 410                 415 ctg acc tgc atg gtc aca gac ttc atg cct gaa gac att tac gtg gag      1296
Leu Thr Cys Met Val Thr Asp Phe Met Pro Glu Asp Ile Tyr Val Glu
            420                 425                 430 tgg acc aac aac ggg aaa aca gag cta aac tac aag aac act gaa cca      1344
Trp Thr Asn Asn Gly Lys Thr Glu Leu Asn Tyr Lys Asn Thr Glu Pro
        435                 440                 445 gtc ctg gac tct gat ggt tct tac ttc atg tac agc aag ctg aga gtg      1392
Val Leu Asp Ser Asp Gly Ser Tyr Phe Met Tyr Ser Lys Leu Arg Val
    450                 455                 460 gaa aag aag aac tgg gtg gaa aga aat agc tac tcc tgt tca gtg gtc      1440
Glu Lys Lys Asn Trp Val Glu Arg Asn Ser Tyr Ser Cys Ser Val Val
465                 470                 475                 480 cac gag ggt ctg cac aat cac cac acg act aag agc ttc tcc cgg act      1488
His Glu Gly Leu His Asn His His Thr Thr Lys Ser Phe Ser Arg Thr
                485                 490                 495 ccg ggt aaa tga                                                      1500
Pro Gly Lys
```

<210> SEQ ID NO 24
<211> LENGTH: 499
<212> TYPE: PRT
<213> ORGANISM: Artificial Sequence
<220> FEATURE:
<223> OTHER INFORMATION: Synthetic human MSP fusion protein

<400> SEQUENCE: 24

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
        50                  55                  60

Ile Leu Thr Ala Arg Gln Cys Phe Ser Ser Cys His Met Pro Leu Thr
65                  70                  75                  80

Gly Tyr Glu Val Trp Leu Gly Thr Leu Phe Gln Asn Pro Gln His Gly
                85                  90                  95

Glu Pro Ser Leu Gln Arg Val Pro Val Ala Lys Met Val Cys Gly Pro
            100                 105                 110

Ser Gly Ser Gln Leu Val Leu Leu Lys Leu Glu Arg Ser Val Thr Leu
        115                 120                 125

Asn Gln Arg Val Ala Leu Ile Ser Leu Pro Pro Glu Trp Tyr Val Val
    130                 135                 140

Pro Pro Gly Thr Lys Cys Glu Ile Ala Gly Trp Gly Glu Thr Lys Gly
145                 150                 155                 160

Thr Gly Asn Asp Thr Val Leu Asn Val Ala Leu Leu Asn Val Ile Ser
                165                 170                 175

Asn Gln Glu Cys Asn Ile Lys His Arg Gly Arg Val Arg Glu Ser Glu
            180                 185                 190

Met Cys Thr Glu Gly Leu Leu Ala Pro Val Gly Ala Cys Glu Gly Asp
```

```
                    195                 200                 205
Tyr Gly Gly Pro Leu Ala Cys Phe Thr His Asn Ser Trp Val Leu Glu
    210                 215                 220

Gly Ile Ile Ile Pro Asn Arg Val Cys Ala Arg Ser Arg Trp Pro Ala
225                 230                 235                 240

Val Phe Thr Arg Val Ser Val Phe Val Asp Trp Ile His Lys Val Met
                245                 250                 255

Arg Leu Gly Gln Val Thr Asp Lys Lys Ile Glu Pro Arg Gly Pro Thr
            260                 265                 270

Ile Lys Pro Cys Pro Pro Cys Lys Cys Pro Ala Pro Asn Leu Leu Gly
        275                 280                 285

Gly Pro Ser Val Phe Ile Phe Pro Pro Lys Ile Lys Asp Val Leu Met
    290                 295                 300

Ile Ser Leu Ser Pro Ile Val Thr Cys Val Val Val Ala Val Ser Glu
305                 310                 315                 320

Asp Asp Pro Asp Val Gln Ile Ser Trp Phe Val Asn Asn Val Glu Val
                325                 330                 335

His Thr Ala Gln Thr Gln Thr His Arg Glu Asp Tyr Ala Ser Thr Leu
            340                 345                 350

Arg Val Val Ser Ala Leu Pro Ile Gln His Gln Asp Trp Met Ser Gly
        355                 360                 365

Lys Glu Phe Lys Cys Lys Val Asn Asn Lys Asp Leu Pro Ala Pro Ile
    370                 375                 380

Glu Arg Thr Ile Ser Lys Pro Lys Gly Ser Val Arg Ala Pro Gln Val
385                 390                 395                 400

Tyr Val Leu Pro Pro Pro Glu Glu Glu Met Thr Lys Lys Gln Val Thr
                405                 410                 415

Leu Thr Cys Met Val Thr Asp Phe Met Pro Glu Asp Ile Tyr Val Glu
            420                 425                 430

Trp Thr Asn Asn Gly Lys Thr Glu Leu Asn Tyr Lys Asn Thr Glu Pro
        435                 440                 445

Val Leu Asp Ser Asp Gly Ser Tyr Phe Met Tyr Ser Lys Leu Arg Val
    450                 455                 460

Glu Lys Lys Asn Trp Val Glu Arg Asn Ser Tyr Ser Cys Ser Val Val
465                 470                 475                 480

His Glu Gly Leu His Asn His Thr Thr Lys Ser Phe Ser Arg Thr
                485                 490                 495

Pro Gly Lys
```

<210> SEQ ID NO 25
<211> LENGTH: 1464
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1464)

<400> SEQUENCE: 25

```
atg tgg gtg acc aaa ctc ctg cca gcc ctg ctg ctg cag cat gtc ctc    48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg    96
Leu His Leu Leu Leu Leu Pro Ile Ala Ile Pro Tyr Ala Glu Gly Val
            20                  25                  30
```

| | | | | | | | | | | | | | | | | |
|---|---|---|---|---|---|---|---|---|---|---|---|---|---|---|---|---|
| gtg | gga | ggc | cat | cct | ggg | aac | tcc | cca | tgg | acg | gtc | agc | ttg | cgg | aat | 144 |
| Val | Gly | Gly | His | Pro | Gly | Asn | Ser | Pro | Trp | Thr | Val | Ser | Leu | Arg | Asn | |
| | | 35 | | | | 40 | | | | 45 | | | | | | |
| cga | cag | ggc | cag | cat | ttc | tgt | ggg | ggc | tcc | cta | gtg | aag | gag | cag | tgg | 192 |
| Arg | Gln | Gly | Gln | His | Phe | Cys | Gly | Gly | Ser | Leu | Val | Lys | Glu | Gln | Trp | |
| 50 | | | | | 55 | | | | | 60 | | | | | | |
| gta | ctg | act | gcc | cgg | caa | tgc | atc | tgg | tca | tgc | cac | gaa | cct | ctc | aca | 240 |
| Val | Leu | Thr | Ala | Arg | Gln | Cys | Ile | Trp | Ser | Cys | His | Glu | Pro | Leu | Thr | |
| 65 | | | | | 70 | | | | | 75 | | | | | 80 | |
| gga | tac | gag | gta | tgg | ttg | ggt | aca | att | aac | cag | aac | cca | cag | cct | gga | 288 |
| Gly | Tyr | Glu | Val | Trp | Leu | Gly | Thr | Ile | Asn | Gln | Asn | Pro | Gln | Pro | Gly | |
| | | | | 85 | | | | | 90 | | | | | 95 | | |
| gag | gca | aac | ctg | cag | agg | gtc | cca | gtg | gcc | aag | gca | gtg | tgc | ggc | cct | 336 |
| Glu | Ala | Asn | Leu | Gln | Arg | Val | Pro | Val | Ala | Lys | Ala | Val | Cys | Gly | Pro | |
| | | | 100 | | | | | 105 | | | | | 110 | | | |
| gca | ggc | tcc | cag | ctt | gtt | ctg | ctc | aag | ctg | gag | aga | cct | gtg | atc | ctg | 384 |
| Ala | Gly | Ser | Gln | Leu | Val | Leu | Leu | Lys | Leu | Glu | Arg | Pro | Val | Ile | Leu | |
| | | | 115 | | | | | 120 | | | | | 125 | | | |
| aac | cat | cac | gtg | gcc | ctg | att | gcc | ctg | cct | cct | gaa | cag | tat | gtg | gta | 432 |
| Asn | His | His | Val | Ala | Leu | Ile | Ala | Leu | Pro | Pro | Glu | Gln | Tyr | Val | Val | |
| | 130 | | | | | 135 | | | | | 140 | | | | | |
| cct | cca | ggg | acc | aag | tgt | gag | atc | gca | ggc | tgg | ggt | gaa | tcc | atc | ggt | 480 |
| Pro | Pro | Gly | Thr | Lys | Cys | Glu | Ile | Ala | Gly | Trp | Gly | Glu | Ser | Ile | Gly | |
| 145 | | | | | 150 | | | | | 155 | | | | | 160 | |
| aca | agc | aat | aac | aca | gtc | ctt | cat | gtg | gcc | tcg | atg | aat | gtc | atc | tcc | 528 |
| Thr | Ser | Asn | Asn | Thr | Val | Leu | His | Val | Ala | Ser | Met | Asn | Val | Ile | Ser | |
| | | | | 165 | | | | | 170 | | | | | 175 | | |
| aac | cag | gaa | tgt | aac | acg | aag | tac | cga | gga | cac | ata | caa | gag | agt | gag | 576 |
| Asn | Gln | Glu | Cys | Asn | Thr | Lys | Tyr | Arg | Gly | His | Ile | Gln | Glu | Ser | Glu | |
| | | | 180 | | | | | 185 | | | | | 190 | | | |
| ata | tgc | acc | cag | gga | ctg | gtg | gtc | cct | gtg | ggg | gct | tgt | gag | ggt | gac | 624 |
| Ile | Cys | Thr | Gln | Gly | Leu | Val | Val | Pro | Val | Gly | Ala | Cys | Glu | Gly | Asp | |
| | | | 195 | | | | | 200 | | | | | 205 | | | |
| tac | ggg | ggc | cca | ctt | gcc | tgc | tat | acc | cat | gac | gca | tgg | gtc | cta | cag | 672 |
| Tyr | Gly | Gly | Pro | Leu | Ala | Cys | Tyr | Thr | His | Asp | Ala | Trp | Val | Leu | Gln | |
| | 210 | | | | | 215 | | | | | 220 | | | | | |
| gga | ctt | atc | atc | ccg | aac | aga | gtg | tgt | gca | cgg | ccc | cgc | tgg | cca | gct | 720 |
| Gly | Leu | Ile | Ile | Pro | Asn | Arg | Val | Cys | Ala | Arg | Pro | Arg | Trp | Pro | Ala | |
| 225 | | | | | 230 | | | | | 235 | | | | | 240 | |
| atc | ttc | aca | cgg | gtg | tct | gtg | ttc | gtg | gac | tgg | att | aac | aag | gtc | atg | 768 |
| Ile | Phe | Thr | Arg | Val | Ser | Val | Phe | Val | Asp | Trp | Ile | Asn | Lys | Val | Met | |
| | | | | 245 | | | | | 250 | | | | | 255 | | |
| cag | ctg | gag | aca | atc | aag | ccc | tgt | cct | cca | tgc | aaa | tgc | cca | gca | cct | 816 |
| Gln | Leu | Glu | Thr | Ile | Lys | Pro | Cys | Pro | Pro | Cys | Lys | Cys | Pro | Ala | Pro | |
| | | | 260 | | | | | 265 | | | | | 270 | | | |
| aac | ctc | ttg | ggt | gga | cca | tcc | gtc | ttc | atc | ttc | cct | cca | aag | atc | aag | 864 |
| Asn | Leu | Leu | Gly | Gly | Pro | Ser | Val | Phe | Ile | Phe | Pro | Pro | Lys | Ile | Lys | |
| | | 275 | | | | | 280 | | | | | 285 | | | | |
| gat | gta | ctc | atg | atc | tcc | ctg | agc | ccc | ata | gtc | aca | tgt | gtg | gtg | gtg | 912 |
| Asp | Val | Leu | Met | Ile | Ser | Leu | Ser | Pro | Ile | Val | Thr | Cys | Val | Val | Val | |
| | 290 | | | | | 295 | | | | | 300 | | | | | |
| gat | gtg | agc | gag | gat | gac | cca | gat | gtc | cag | atc | agc | tgg | ttt | gtg | aac | 960 |
| Asp | Val | Ser | Glu | Asp | Asp | Pro | Asp | Val | Gln | Ile | Ser | Trp | Phe | Val | Asn | |
| 305 | | | | | 310 | | | | | 315 | | | | | 320 | |
| aac | gtg | gaa | gta | cac | aca | gct | cag | aca | caa | acc | cat | aga | gag | gat | tac | 1008 |
| Asn | Val | Glu | Val | His | Thr | Ala | Gln | Thr | Gln | Thr | His | Arg | Glu | Asp | Tyr | |
| | | | | 325 | | | | | 330 | | | | | 335 | | |
| aac | agt | act | cta | cgc | gtg | gtc | agt | gcc | ctc | ccc | atc | cag | cac | cag | gac | 1056 |
| Asn | Ser | Thr | Leu | Arg | Val | Val | Ser | Ala | Leu | Pro | Ile | Gln | His | Gln | Asp | |
| | | | 340 | | | | | 345 | | | | | 350 | | | |

```
tgg atg agt ggc aag gag ttc aaa tgc aag gtc aac aac aaa gac ctc    1104
Trp Met Ser Gly Lys Glu Phe Lys Cys Lys Val Asn Asn Lys Asp Leu
        355                 360                 365 cca gcg ccc atc gag aga acc atc tca aaa ccc aaa ggg tca gta aga    1152
Pro Ala Pro Ile Glu Arg Thr Ile Ser Lys Pro Lys Gly Ser Val Arg
370                 375                 380 gct cca cag gta tat gtc ttg cct cca cca gaa gaa gag atg act aag    1200
Ala Pro Gln Val Tyr Val Leu Pro Pro Pro Glu Glu Glu Met Thr Lys
385                 390                 395                 400 aaa cag gtc act ctg acc tgc atg gtc aca gac ttc atg cct gaa gac    1248
Lys Gln Val Thr Leu Thr Cys Met Val Thr Asp Phe Met Pro Glu Asp
                405                 410                 415 att tac gtg gag tgg acc aac aac ggg aaa aca gag cta aac tac aag    1296
Ile Tyr Val Glu Trp Thr Asn Asn Gly Lys Thr Glu Leu Asn Tyr Lys
                420                 425                 430 aac act gaa cca gtc ctg gac tct gat ggt tct tac ttc atg tac agc    1344
Asn Thr Glu Pro Val Leu Asp Ser Asp Gly Ser Tyr Phe Met Tyr Ser
                435                 440                 445 aag ctg aga gtg gaa aag aag aac tgg gtg gaa aga aat agc tac tcc    1392
Lys Leu Arg Val Glu Lys Lys Asn Trp Val Glu Arg Asn Ser Tyr Ser
450                 455                 460 tgt tca gtg gtc cac gag ggt ctg cac aat cac cac acg act aag agc    1440
Cys Ser Val Val His Glu Gly Leu His Asn His His Thr Thr Lys Ser
465                 470                 475                 480 ttc tcc cgg act ccg ggt aaa tga                                    1464
Phe Ser Arg Thr Pro Gly Lys
                485
```

<210> SEQ ID NO 26
<211> LENGTH: 487
<212> TYPE: PRT
<213> ORGANISM: Artificial Sequence
<220> FEATURE:
<223> OTHER INFORMATION: Synthetic mouse MSP fusion protein

<400> SEQUENCE: 26

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
        35                  40                  45

Arg Gln Gly Gln His Phe Cys Gly Gly Ser Leu Val Lys Glu Gln Trp
    50                  55                  60

Val Leu Thr Ala Arg Gln Cys Ile Trp Ser Cys His Glu Pro Leu Thr
65                  70                  75                  80

Gly Tyr Glu Val Trp Leu Gly Thr Ile Asn Gln Asn Pro Gln Pro Gly
                85                  90                  95

Glu Ala Asn Leu Gln Arg Val Pro Val Ala Lys Ala Val Cys Gly Pro
            100                 105                 110

Ala Gly Ser Gln Leu Val Leu Leu Lys Leu Glu Arg Pro Val Ile Leu
        115                 120                 125

Asn His His Val Ala Leu Ile Ala Leu Pro Pro Glu Gln Tyr Val Val
    130                 135                 140

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175
```

```
Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Thr Ile Lys Pro Cys Pro Pro Cys Lys Cys Pro Ala Pro
            260                 265                 270

Asn Leu Leu Gly Gly Pro Ser Val Phe Ile Phe Pro Pro Lys Ile Lys
        275                 280                 285

Asp Val Leu Met Ile Ser Leu Ser Pro Ile Val Thr Cys Val Val Val
    290                 295                 300

Asp Val Ser Glu Asp Asp Pro Asp Val Gln Ile Ser Trp Phe Val Asn
305                 310                 315                 320

Asn Val Glu Val His Thr Ala Gln Thr Gln Thr His Arg Glu Asp Tyr
                325                 330                 335

Asn Ser Thr Leu Arg Val Val Ser Ala Leu Pro Ile Gln His Gln Asp
            340                 345                 350

Trp Met Ser Gly Lys Glu Phe Lys Cys Lys Val Asn Asn Lys Asp Leu
        355                 360                 365

Pro Ala Pro Ile Glu Arg Thr Ile Ser Lys Pro Lys Gly Ser Val Arg
    370                 375                 380

Ala Pro Gln Val Tyr Val Leu Pro Pro Glu Glu Glu Met Thr Lys
385                 390                 395                 400

Lys Gln Val Thr Leu Thr Cys Met Val Thr Asp Phe Met Pro Glu Asp
                405                 410                 415

Ile Tyr Val Glu Trp Thr Asn Asn Gly Lys Thr Glu Leu Asn Tyr Lys
            420                 425                 430

Asn Thr Glu Pro Val Leu Asp Ser Asp Gly Ser Tyr Phe Met Tyr Ser
        435                 440                 445

Lys Leu Arg Val Glu Lys Lys Asn Trp Val Glu Arg Asn Ser Tyr Ser
    450                 455                 460

Cys Ser Val Val His Glu Gly Leu His Asn His His Thr Thr Lys Ser
465                 470                 475                 480

Phe Ser Arg Thr Pro Gly Lys
                485

<210> SEQ ID NO 27
<211> LENGTH: 1476
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1476)

<400> SEQUENCE: 27 atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg      96
```

```
                Leu His Leu Leu Leu Pro Ile Ala Ile Pro Tyr Ala Glu Gly Val
                         20                  25                  30 gtg gga ggc cat cct ggg aac tcc cca tgg acg gtc agc ttg cgg aat        144
Val Gly Gly His Pro Gly Asn Ser Pro Trp Thr Val Ser Leu Arg Asn
         35                  40                  45 cga cag ggc cag cat ttc tgt ggg ggc tcc cta gtg aag gag cag tgg        192
Arg Gln Gly Gln His Phe Cys Gly Gly Ser Leu Val Lys Glu Gln Trp
 50                  55                  60 gta ctg act gcc cgg caa tgc atc tgg tca tgc cac gaa cct ctc aca        240
Val Leu Thr Ala Arg Gln Cys Ile Trp Ser Cys His Glu Pro Leu Thr
 65                  70                  75                  80 gga tac gag gta tgg ttg ggt aca att aac cag aac cca cag cct gga        288
Gly Tyr Glu Val Trp Leu Gly Thr Ile Asn Gln Asn Pro Gln Pro Gly
                 85                  90                  95 gag gca aac ctg cag agg gtc cca gtg gcc aag gca gtg tgc ggc cct        336
Glu Ala Asn Leu Gln Arg Val Pro Val Ala Lys Ala Val Cys Gly Pro
            100                 105                 110 gca ggc tcc cag ctt gtt ctg ctc aag ctg gag aga cct gtg atc ctg        384
Ala Gly Ser Gln Leu Val Leu Leu Lys Leu Glu Arg Pro Val Ile Leu
        115                 120                 125 aac cat cac gtg gcc ctg att gcc ctg cct cct gaa cag tat gtg gta        432
Asn His His Val Ala Leu Ile Ala Leu Pro Pro Glu Gln Tyr Val Val
    130                 135                 140 cct cca ggg acc aag tgt gag atc gca ggc tgg ggt gaa tcc atc ggt        480
Pro Pro Gly Thr Lys Cys Glu Ile Ala Gly Trp Gly Glu Ser Ile Gly
145                 150                 155                 160 aca agc aat aac aca gtc ctt cat gtg gcc tcg atg aat gtc atc tcc        528
Thr Ser Asn Asn Thr Val Leu His Val Ala Ser Met Asn Val Ile Ser
                165                 170                 175 aac cag gaa tgt aac acg aag tac cga gga cac ata caa gag agt gag        576
Asn Gln Glu Cys Asn Thr Lys Tyr Arg Gly His Ile Gln Glu Ser Glu
            180                 185                 190 ata tgc acc cag gga ctg gtg gtc cct gtg ggg gct tgt gag ggt gac        624
Ile Cys Thr Gln Gly Leu Val Val Pro Val Gly Ala Cys Glu Gly Asp
        195                 200                 205 tac ggg ggc cca ctt gcc tgc tat acc cat gac gca tgg gtc cta cag        672
Tyr Gly Gly Pro Leu Ala Cys Tyr Thr His Asp Ala Trp Val Leu Gln
    210                 215                 220 gga ctt atc atc ccg aac aga gtg tgt gca cgg ccc cgc tgg cca gct        720
Gly Leu Ile Ile Pro Asn Arg Val Cys Ala Arg Pro Arg Trp Pro Ala
225                 230                 235                 240 atc ttc aca cgg gtg tct gtg ttc gtg gac tgg att aac aag gtc atg        768
Ile Phe Thr Arg Val Ser Val Phe Val Asp Trp Ile Asn Lys Val Met
                245                 250                 255 cag ctg gag ccc aga ggg ccc aca atc aag ccc tgt cct cca tgc aaa        816
Gln Leu Glu Pro Arg Gly Pro Thr Ile Lys Pro Cys Pro Pro Cys Lys
            260                 265                 270 tgc cca gca cct aac ctc ttg ggt gga cca tcc gtc ttc atc ttc cct        864
Cys Pro Ala Pro Asn Leu Leu Gly Gly Pro Ser Val Phe Ile Phe Pro
        275                 280                 285 cca aag atc aag gat gta ctc atg atc tcc ctg agc ccc ata gtc aca        912
Pro Lys Ile Lys Asp Val Leu Met Ile Ser Leu Ser Pro Ile Val Thr
    290                 295                 300 tgt gtg gtg gtg gat gtg agc gag gat gac cca gat gtc cag atc agc        960
Cys Val Val Val Asp Val Ser Glu Asp Asp Pro Asp Val Gln Ile Ser
305                 310                 315                 320 tgg ttt gtg aac aac gtg gaa gta cac aca gct cag aca caa acc cat       1008
Trp Phe Val Asn Asn Val Glu Val His Thr Ala Gln Thr Gln Thr His
                325                 330                 335
```

-continued

```
aga gag gat tac aac agt act cta cgc gtg gtc agt gcc ctc ccc atc      1056
Arg Glu Asp Tyr Asn Ser Thr Leu Arg Val Val Ser Ala Leu Pro Ile
            340                 345                 350 cag cac cag gac tgg atg agt ggc aag gag ttc aaa tgc aag gtc aac      1104
Gln His Gln Asp Trp Met Ser Gly Lys Glu Phe Lys Cys Lys Val Asn
        355                 360                 365 aac aaa gac ctc cca gcg ccc atc gag aga acc atc tca aaa ccc aaa      1152
Asn Lys Asp Leu Pro Ala Pro Ile Glu Arg Thr Ile Ser Lys Pro Lys
    370                 375                 380 ggg tca gta aga gct cca cag gta tat gtc ttg cct cca cca gaa gaa      1200
Gly Ser Val Arg Ala Pro Gln Val Tyr Val Leu Pro Pro Pro Glu Glu
385                 390                 395                 400 gag atg act aag aaa cag gtc act ctg acc tgc atg gtc aca gac ttc      1248
Glu Met Thr Lys Lys Gln Val Thr Leu Thr Cys Met Val Thr Asp Phe
                405                 410                 415 atg cct gaa gac att tac gtg gag tgg acc aac aac ggg aaa aca gag      1296
Met Pro Glu Asp Ile Tyr Val Glu Trp Thr Asn Asn Gly Lys Thr Glu
            420                 425                 430 cta aac tac aag aac act gaa cca gtc ctg gac tct gat ggt tct tac      1344
Leu Asn Tyr Lys Asn Thr Glu Pro Val Leu Asp Ser Asp Gly Ser Tyr
        435                 440                 445 ttc atg tac agc aag ctg aga gtg gaa aag aag aac tgg gtg gaa aga      1392
Phe Met Tyr Ser Lys Leu Arg Val Glu Lys Lys Asn Trp Val Glu Arg
    450                 455                 460 aat agc tac tcc tgt tca gtg gtc cac gag ggt ctg cac aat cac cac      1440
Asn Ser Tyr Ser Cys Ser Val Val His Glu Gly Leu His Asn His His
465                 470                 475                 480 acg act aag agc ttc tcc cgg act ccg ggt aaa tga                      1476
Thr Thr Lys Ser Phe Ser Arg Thr Pro Gly Lys
                485                 490
```

<210> SEQ ID NO 28
<211> LENGTH: 491
<212> TYPE: PRT
<213> ORGANISM: Artificial Sequence
<220> FEATURE:
<223> OTHER INFORMATION: Synthetic mouse MSP fusion protein

<400> SEQUENCE: 28

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
        35                  40                  45

Arg Gln Gly Gln His Phe Cys Gly Gly Ser Leu Val Lys Glu Gln Trp
    50                  55                  60

Val Leu Thr Ala Arg Gln Cys Ile Trp Ser Cys His Glu Pro Leu Thr
65                  70                  75                  80

Gly Tyr Glu Val Trp Leu Gly Thr Ile Asn Gln Asn Pro Gln Pro Gly
                85                  90                  95

Glu Ala Asn Leu Gln Arg Val Pro Val Ala Lys Ala Val Cys Gly Pro
            100                 105                 110

Ala Gly Ser Gln Leu Val Leu Leu Lys Leu Glu Arg Pro Val Ile Leu
        115                 120                 125

Asn His His Val Ala Leu Ile Ala Leu Pro Pro Glu Gln Tyr Val Val
    130                 135                 140

Pro Pro Gly Thr Lys Cys Glu Ile Ala Gly Trp Gly Glu Ser Ile Gly
145                 150                 155                 160
```

```
Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Pro Arg Gly Pro Thr Ile Lys Pro Cys Pro Pro Cys Lys
            260                 265                 270

Cys Pro Ala Pro Asn Leu Leu Gly Gly Pro Ser Val Phe Ile Phe Pro
        275                 280                 285

Pro Lys Ile Lys Asp Val Leu Met Ile Ser Leu Ser Pro Ile Val Thr
    290                 295                 300

Cys Val Val Val Asp Val Ser Glu Asp Pro Asp Val Gln Ile Ser
305                 310                 315                 320

Trp Phe Val Asn Asn Val Glu Val His Thr Ala Gln Thr Gln Thr His
                325                 330                 335

Arg Glu Asp Tyr Asn Ser Thr Leu Arg Val Val Ser Ala Leu Pro Ile
            340                 345                 350

Gln His Gln Asp Trp Met Ser Gly Lys Glu Phe Lys Cys Lys Val Asn
        355                 360                 365

Asn Lys Asp Leu Pro Ala Pro Ile Glu Arg Thr Ile Ser Lys Pro Lys
    370                 375                 380

Gly Ser Val Arg Ala Pro Gln Val Tyr Val Leu Pro Pro Pro Glu Glu
385                 390                 395                 400

Glu Met Thr Lys Lys Gln Val Thr Leu Thr Cys Met Val Thr Asp Phe
                405                 410                 415

Met Pro Glu Asp Ile Tyr Val Glu Trp Thr Asn Asn Gly Lys Thr Glu
            420                 425                 430

Leu Asn Tyr Lys Asn Thr Glu Pro Val Leu Asp Ser Asp Gly Ser Tyr
        435                 440                 445

Phe Met Tyr Ser Lys Leu Arg Val Glu Lys Lys Asn Trp Val Glu Arg
    450                 455                 460

Asn Ser Tyr Ser Cys Ser Val Val His Glu Gly Leu His Asn His His
465                 470                 475                 480

Thr Thr Lys Ser Phe Ser Arg Thr Pro Gly Lys
                485                 490

<210> SEQ ID NO 29
<211> LENGTH: 1488
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1488)

<400> SEQUENCE: 29 atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
```

```
         1               5                    10                   15
ctg cat ctc ctc ctg ctc ccc atc gcc atc ccc tat gca gag gga gtg        96
Leu His Leu Leu Leu Leu Pro Ile Ala Ile Pro Tyr Ala Glu Gly Val
                 20                  25                  30 gtg gga ggc cat cct ggg aac tcc cca tgg acg gtc agc ttg cgg aat       144
Val Gly Gly His Pro Gly Asn Ser Pro Trp Thr Val Ser Leu Arg Asn
                 35                  40                  45 cga cag ggc cag cat ttc tgt ggg ggc tcc cta gtg aag gag cag tgg       192
Arg Gln Gly Gln His Phe Cys Gly Gly Ser Leu Val Lys Glu Gln Trp
                 50                  55                  60 gta ctg act gcc cgg caa tgc atc tgg tca tgc cac gaa cct ctc aca       240
Val Leu Thr Ala Arg Gln Cys Ile Trp Ser Cys His Glu Pro Leu Thr
65                   70                  75                  80 gga tac gag gta tgg ttg ggt aca att aac cag aac cca cag cct gga       288
Gly Tyr Glu Val Trp Leu Gly Thr Ile Asn Gln Asn Pro Gln Pro Gly
                     85                  90                  95 gag gca aac ctg cag agg gtc cca gtg gcc aag gca gtg tgc ggc cct       336
Glu Ala Asn Leu Gln Arg Val Pro Val Ala Lys Ala Val Cys Gly Pro
                100                 105                 110 gca ggc tcc cag ctt gtt ctg ctc aag ctg gag aga cct gtg atc ctg       384
Ala Gly Ser Gln Leu Val Leu Leu Lys Leu Glu Arg Pro Val Ile Leu
                115                 120                 125 aac cat cac gtg gcc ctg att gcc ctg cct cct gaa cag tat gtg gta       432
Asn His His Val Ala Leu Ile Ala Leu Pro Pro Glu Gln Tyr Val Val
                130                 135                 140 cct cca ggg acc aag tgt gag atc gca ggc tgg ggt gaa tcc atc ggt       480
Pro Pro Gly Thr Lys Cys Glu Ile Ala Gly Trp Gly Glu Ser Ile Gly
145                 150                 155                 160 aca agc aat aac aca gtc ctt cat gtg gcc tcg atg aat gtc atc tcc       528
Thr Ser Asn Asn Thr Val Leu His Val Ala Ser Met Asn Val Ile Ser
                    165                 170                 175 aac cag gaa tgt aac acg aag tac cga gga cac ata caa gag agt gag       576
Asn Gln Glu Cys Asn Thr Lys Tyr Arg Gly His Ile Gln Glu Ser Glu
                180                 185                 190 ata tgc acc cag gga ctg gtg gtc cct gtg ggg gct tgt gag ggt gac       624
Ile Cys Thr Gln Gly Leu Val Val Pro Val Gly Ala Cys Glu Gly Asp
                195                 200                 205 tac ggg ggc cca ctt gcc tgc tat acc cat gac gca tgg gtc cta cag       672
Tyr Gly Gly Pro Leu Ala Cys Tyr Thr His Asp Ala Trp Val Leu Gln
                210                 215                 220 gga ctt atc atc ccg aac aga gtg tgt gca cgg ccc cgc tgg cca gct       720
Gly Leu Ile Ile Pro Asn Arg Val Cys Ala Arg Pro Arg Trp Pro Ala
225                 230                 235                 240 atc ttc aca cgg gtg tct gtg ttc gtg gac tgg att aac aag gtc atg       768
Ile Phe Thr Arg Val Ser Val Phe Val Asp Trp Ile Asn Lys Val Met
                    245                 250                 255 cag ctg gag aag aaa att gag ccc aga ggg ccc aca atc aag ccc tgt       816
Gln Leu Glu Lys Lys Ile Glu Pro Arg Gly Pro Thr Ile Lys Pro Cys
                260                 265                 270 cct cca tgc aaa tgc cca gca cct aac ctc ttg ggt gga cca tcc gtc       864
Pro Pro Cys Lys Cys Pro Ala Pro Asn Leu Leu Gly Gly Pro Ser Val
                275                 280                 285 ttc atc ttc cct cca aag atc aag gat gta ctc atg atc tcc ctg agc       912
Phe Ile Phe Pro Pro Lys Ile Lys Asp Val Leu Met Ile Ser Leu Ser
                290                 295                 300 ccc ata gtc aca tgt gtg gtg gtg gat gtg agc gag gat gac cca gat       960
Pro Ile Val Thr Cys Val Val Val Asp Val Ser Glu Asp Asp Pro Asp
305                 310                 315                 320 gtc cag atc agc tgg ttt gtg aac aac gtg gaa gta cac aca gct cag      1008
```

```
Val Gln Ile Ser Trp Phe Val Asn Asn Val Glu Val His Thr Ala Gln
                325                 330                 335 aca caa acc cat aga gag gat tac aac agt act cta cgc gtg gtc agt       1056
Thr Gln Thr His Arg Glu Asp Tyr Asn Ser Thr Leu Arg Val Val Ser
            340                 345                 350 gcc ctc ccc atc cag cac cag gac tgg atg agt ggc aag gag ttc aaa       1104
Ala Leu Pro Ile Gln His Gln Asp Trp Met Ser Gly Lys Glu Phe Lys
        355                 360                 365 tgc aag gtc aac aac aaa gac ctc cca gcg ccc atc gag aga acc atc       1152
Cys Lys Val Asn Asn Lys Asp Leu Pro Ala Pro Ile Glu Arg Thr Ile
    370                 375                 380 tca aaa ccc aaa ggg tca gta aga gct cca cag gta tat gtc ttg cct       1200
Ser Lys Pro Lys Gly Ser Val Arg Ala Pro Gln Val Tyr Val Leu Pro
385                 390                 395                 400 cca cca gaa gaa gag atg act aag aaa cag gtc act ctg acc tgc atg       1248
Pro Pro Glu Glu Glu Met Thr Lys Lys Gln Val Thr Leu Thr Cys Met
                405                 410                 415 gtc aca gac ttc atg cct gaa gac att tac gtg gag tgg acc aac aac       1296
Val Thr Asp Phe Met Pro Glu Asp Ile Tyr Val Glu Trp Thr Asn Asn
            420                 425                 430 ggg aaa aca gag cta aac tac aag aac act gaa cca gtc ctg gac tct       1344
Gly Lys Thr Glu Leu Asn Tyr Lys Asn Thr Glu Pro Val Leu Asp Ser
        435                 440                 445 gat ggt tct tac ttc atg tac agc aag ctg aga gtg gaa aag aag aac       1392
Asp Gly Ser Tyr Phe Met Tyr Ser Lys Leu Arg Val Glu Lys Lys Asn
    450                 455                 460 tgg gtg gaa aga aat agc tac tcc tgt tca gtg gtc cac gag ggt ctg       1440
Trp Val Glu Arg Asn Ser Tyr Ser Cys Ser Val Val His Glu Gly Leu
465                 470                 475                 480 cac aat cac cac acg act aag agc ttc tcc cgg act ccg ggt aaa tga       1488
His Asn His His Thr Thr Lys Ser Phe Ser Arg Thr Pro Gly Lys
                485                 490                 495

<210> SEQ ID NO 30
<211> LENGTH: 495
<212> TYPE: PRT
<213> ORGANISM: Artificial Sequence
<220> FEATURE:
<223> OTHER INFORMATION: Synthetic mouse MSP fusion protein

<400> SEQUENCE: 30

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
        35                  40                  45

Arg Gln Gly Gln His Phe Cys Gly Gly Ser Leu Val Lys Glu Gln Trp
    50                  55                  60

Val Leu Thr Ala Arg Gln Cys Ile Trp Ser Cys His Glu Pro Leu Thr
65                  70                  75                  80

Gly Tyr Glu Val Trp Leu Gly Thr Ile Asn Gln Asn Pro Gln Pro Gly
                85                  90                  95

Glu Ala Asn Leu Gln Arg Val Pro Val Ala Lys Ala Val Cys Gly Pro
            100                 105                 110

Ala Gly Ser Gln Leu Val Leu Leu Lys Leu Glu Arg Pro Val Ile Leu
        115                 120                 125

Asn His His Val Ala Leu Ile Ala Leu Pro Pro Glu Gln Tyr Val Val
    130                 135                 140
```

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Lys Lys Ile Glu Pro Arg Gly Pro Thr Ile Lys Pro Cys
            260                 265                 270

Pro Pro Cys Lys Cys Pro Ala Pro Asn Leu Leu Gly Gly Pro Ser Val
        275                 280                 285

Phe Ile Phe Pro Pro Lys Ile Lys Asp Val Leu Met Ile Ser Leu Ser
290                 295                 300

Pro Ile Val Thr Cys Val Val Val Asp Val Ser Glu Asp Asp Pro Asp
305                 310                 315                 320

Val Gln Ile Ser Trp Phe Val Asn Asn Val Glu Val His Thr Ala Gln
                325                 330                 335

Thr Gln Thr His Arg Glu Asp Tyr Asn Ser Thr Leu Arg Val Val Ser
            340                 345                 350

Ala Leu Pro Ile Gln His Gln Asp Trp Met Ser Gly Lys Glu Phe Lys
        355                 360                 365

Cys Lys Val Asn Asn Lys Asp Leu Pro Ala Pro Ile Glu Arg Thr Ile
370                 375                 380

Ser Lys Pro Lys Gly Ser Val Arg Ala Pro Gln Val Tyr Val Leu Pro
385                 390                 395                 400

Pro Pro Glu Glu Glu Met Thr Lys Lys Gln Val Thr Leu Thr Cys Met
                405                 410                 415

Val Thr Asp Phe Met Pro Glu Asp Ile Tyr Val Glu Trp Thr Asn Asn
            420                 425                 430

Gly Lys Thr Glu Leu Asn Tyr Lys Asn Thr Glu Pro Val Leu Asp Ser
        435                 440                 445

Asp Gly Ser Tyr Phe Met Tyr Ser Lys Leu Arg Val Glu Lys Lys Asn
450                 455                 460

Trp Val Glu Arg Asn Ser Tyr Ser Cys Ser Val Val His Glu Gly Leu
465                 470                 475                 480

His Asn His His Thr Thr Lys Ser Phe Ser Arg Thr Pro Gly Lys
                485                 490                 495

<210> SEQ ID NO 31
<211> LENGTH: 1500
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1500)

<400> SEQUENCE: 31

-continued

| | | |
|---|---|---|
| atg tgg gtg acc aaa ctc ctg cca gcc ctg ctg ctg cag cat gtc ctc<br>Met Trp Val Thr Lys Leu Leu Pro Ala Leu Leu Leu Gln His Val Leu<br>1                             5                           10                       15 | 48 |
| ctg cat ctc ctg ctc ccc atc gcc atc ccc tat gca gag gga gtg<br>Leu His Leu Leu Leu Leu Pro Ile Ala Ile Pro Tyr Ala Glu Gly Val<br>                20                         25                           30 | 96 |
| gtg gga ggc cat cct ggg aac tcc cca tgg acg gtc agc ttg cgg aat<br>Val Gly Gly His Pro Gly Asn Ser Pro Trp Thr Val Ser Leu Arg Asn<br>          35                         40                       45 | 144 |
| cga cag ggc cag cat ttc tgt ggg ggc tcc cta gtg aag gag cag tgg<br>Arg Gln Gly Gln His Phe Cys Gly Gly Ser Leu Val Lys Glu Gln Trp<br>      50                      55                      60 | 192 |
| gta ctg act gcc cgg caa tgc atc tgg tca tgc cac gaa cct ctc aca<br>Val Leu Thr Ala Arg Gln Cys Ile Trp Ser Cys His Glu Pro Leu Thr<br>65                           70                          75                       80 | 240 |
| gga tac gag gta tgg ttg ggt aca att aac cag aac cca cag cct gga<br>Gly Tyr Glu Val Trp Leu Gly Thr Ile Asn Gln Asn Pro Gln Pro Gly<br>                     85                       90                       95 | 288 |
| gag gca aac ctg cag agg gtc cca gtg gcc aag gca gtg tgc ggc cct<br>Glu Ala Asn Leu Gln Arg Val Pro Val Ala Lys Ala Val Cys Gly Pro<br>                100                      105                      110 | 336 |
| gca ggc tcc cag ctt gtt ctg ctc aag ctg gag aga cct gtg atc ctg<br>Ala Gly Ser Gln Leu Val Leu Leu Lys Leu Glu Arg Pro Val Ile Leu<br>           115                      120                      125 | 384 |
| aac cat cac gtg gcc ctg att gcc ctg cct cct gaa cag tat gtg gta<br>Asn His His Val Ala Leu Ile Ala Leu Pro Pro Glu Gln Tyr Val Val<br>     130                       135                      140 | 432 |
| cct cca ggg acc aag tgt gag atc gca ggc tgg ggt gaa tcc atc ggt<br>Pro Pro Gly Thr Lys Cys Glu Ile Ala Gly Trp Gly Glu Ser Ile Gly<br>145                       150                      155                      160 | 480 |
| aca agc aat aac aca gtc ctt cat gtg gcc tcg atg aat gtc atc tcc<br>Thr Ser Asn Asn Thr Val Leu His Val Ala Ser Met Asn Val Ile Ser<br>                165                      170                      175 | 528 |
| aac cag gaa tgt aac acg aag tac cga gga cac ata caa gag agt gag<br>Asn Gln Glu Cys Asn Thr Lys Tyr Arg Gly His Ile Gln Glu Ser Glu<br>     180                       185                      190 | 576 |
| ata tgc acc cag gga ctg gtg gtc cct gtg ggg gct tgt gag ggt gac<br>Ile Cys Thr Gln Gly Leu Val Val Pro Val Gly Ala Cys Glu Gly Asp<br>                195                      200                      205 | 624 |
| tac ggg ggc cca ctt gcc tgc tat acc cat gac gca tgg gtc cta cag<br>Tyr Gly Gly Pro Leu Ala Cys Tyr Thr His Asp Ala Trp Val Leu Gln<br>     210                       215                      220 | 672 |
| gga ctt atc atc ccg aac aga gtg tgt gca cgg ccc cgc tgg cca gct<br>Gly Leu Ile Ile Pro Asn Arg Val Cys Ala Arg Pro Arg Trp Pro Ala<br>225                       230                      235                      240 | 720 |
| atc ttc aca cgg gtg tct gtg ttc gtg gac tgg att aac aag gtc atg<br>Ile Phe Thr Arg Val Ser Val Phe Val Asp Trp Ile Asn Lys Val Met<br>                245                      250                      255 | 768 |
| cag ctg gag cag gtc acc gac aag aaa att gag ccc aga ggg ccc aca<br>Gln Leu Glu Gln Val Thr Asp Lys Lys Ile Glu Pro Arg Gly Pro Thr<br>     260                       265                      270 | 816 |
| atc aag ccc tgt cct cca tgc aaa tgc cca gca cct aac ctc ttg ggt<br>Ile Lys Pro Cys Pro Pro Cys Lys Cys Pro Ala Pro Asn Leu Leu Gly<br>                275                      280                      285 | 864 |
| gga cca tcc gtc ttc atc ttc cct cca aag atc aag gat gta ctc atg<br>Gly Pro Ser Val Phe Ile Phe Pro Pro Lys Ile Lys Asp Val Leu Met<br>     290                       295                      300 | 912 |
| atc tcc ctg agc ccc ata gtc aca tgt gtg gtg gtg gat gtg agc gag<br>Ile Ser Leu Ser Pro Ile Val Thr Cys Val Val Val Asp Val Ser Glu | 960 |

| | | |
|---|---|---|
| gat gac cca gat gtc cag atc agc tgg ttt gtg aac aac gtg gaa gta<br>Asp Asp Pro Asp Val Gln Ile Ser Trp Phe Val Asn Asn Val Glu Val<br>                         325                 330                 335 | 1008 |
| cac aca gct cag aca caa acc cat aga gag gat tac aac agt act cta<br>His Thr Ala Gln Thr Gln Thr His Arg Glu Asp Tyr Asn Ser Thr Leu<br>             340                 345                 350 | 1056 |
| cgc gtg gtc agt gcc ctc ccc atc cag cac cag gac tgg atg agt ggc<br>Arg Val Val Ser Ala Leu Pro Ile Gln His Gln Asp Trp Met Ser Gly<br>               355                 360                 365 | 1104 |
| aag gag ttc aaa tgc aag gtc aac aac aaa gac ctc cca gcg ccc atc<br>Lys Glu Phe Lys Cys Lys Val Asn Asn Lys Asp Leu Pro Ala Pro Ile<br>   370                       375                 380 | 1152 |
| gag aga acc atc tca aaa ccc aaa ggg tca gta aga gct cca cag gta<br>Glu Arg Thr Ile Ser Lys Pro Lys Gly Ser Val Arg Ala Pro Gln Val<br>385                     390                 395                 400 | 1200 |
| tat gtc ttg cct cca cca gaa gag atg act aag aaa cag gtc act<br>Tyr Val Leu Pro Pro Pro Glu Glu Glu Met Thr Lys Lys Gln Val Thr<br>                     405                 410                 415 | 1248 |
| ctg acc tgc atg gtc aca gac ttc atg cct gaa gac att tac gtg gag<br>Leu Thr Cys Met Val Thr Asp Phe Met Pro Glu Asp Ile Tyr Val Glu<br>             420                 425                 430 | 1296 |
| tgg acc aac aac ggg aaa aca gag cta aac tac aag aac act gaa cca<br>Trp Thr Asn Asn Gly Lys Thr Glu Leu Asn Tyr Lys Asn Thr Glu Pro<br>               435                 440                 445 | 1344 |
| gtc ctg gac tct gat ggt tct tac ttc atg tac agc aag ctg aga gtg<br>Val Leu Asp Ser Asp Gly Ser Tyr Phe Met Tyr Ser Lys Leu Arg Val<br>         450                 455                 460 | 1392 |
| gaa aag aag aac tgg gtg gaa aga aat agc tac tcc tgt tca gtg gtc<br>Glu Lys Lys Asn Trp Val Glu Arg Asn Ser Tyr Ser Cys Ser Val Val<br>465                     470                 475                 480 | 1440 |
| cac gag ggt ctg cac aat cac cac acg act aag agc ttc tcc cgg act<br>His Glu Gly Leu His Asn His His Thr Thr Lys Ser Phe Ser Arg Thr<br>               485                 490                 495 | 1488 |
| ccg ggt aaa tga<br>Pro Gly Lys | 1500 |

<210> SEQ ID NO 32
<211> LENGTH: 499
<212> TYPE: PRT
<213> ORGANISM: Artificial Sequence
<220> FEATURE:
<223> OTHER INFORMATION: Synthetic mouse MSP fusion protein

<400> SEQUENCE: 32

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
        50                  55                  60

Val Leu Thr Ala Arg Gln Cys Ile Trp Ser Cys His Glu Pro Leu Thr
65                  70                  75                  80

Gly Tyr Glu Val Trp Leu Gly Thr Ile Asn Gln Asn Pro Gln Pro Gly
                85                  90                  95

Glu Ala Asn Leu Gln Arg Val Pro Val Ala Lys Ala Val Cys Gly Pro
            100                 105                 110

```
Ala Gly Ser Gln Leu Val Leu Lys Leu Glu Arg Pro Val Ile Leu
        115                 120                 125

Asn His His Val Ala Leu Ile Ala Leu Pro Pro Glu Gln Tyr Val Val
    130                 135                 140

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Gln Val Thr Asp Lys Lys Ile Glu Pro Arg Gly Pro Thr
            260                 265                 270

Ile Lys Pro Cys Pro Pro Cys Lys Cys Pro Ala Pro Asn Leu Leu Gly
        275                 280                 285

Gly Pro Ser Val Phe Ile Phe Pro Pro Lys Ile Lys Asp Val Leu Met
    290                 295                 300

Ile Ser Leu Ser Pro Ile Val Thr Cys Val Val Val Asp Val Ser Glu
305                 310                 315                 320

Asp Asp Pro Asp Val Gln Ile Ser Trp Phe Val Asn Asn Val Glu Val
                325                 330                 335

His Thr Ala Gln Thr Gln Thr His Arg Glu Asp Tyr Asn Ser Thr Leu
            340                 345                 350

Arg Val Val Ser Ala Leu Pro Ile Gln His Gln Asp Trp Met Ser Gly
        355                 360                 365

Lys Glu Phe Lys Cys Lys Val Asn Asn Lys Asp Leu Pro Ala Pro Ile
    370                 375                 380

Glu Arg Thr Ile Ser Lys Pro Lys Gly Ser Val Arg Ala Pro Gln Val
385                 390                 395                 400

Tyr Val Leu Pro Pro Pro Glu Glu Met Thr Lys Lys Gln Val Thr
                405                 410                 415

Leu Thr Cys Met Val Thr Asp Phe Met Pro Glu Asp Ile Tyr Val Glu
            420                 425                 430

Trp Thr Asn Asn Gly Lys Thr Glu Leu Asn Tyr Lys Asn Thr Glu Pro
        435                 440                 445

Val Leu Asp Ser Asp Gly Ser Tyr Phe Met Tyr Ser Lys Leu Arg Val
    450                 455                 460

Glu Lys Lys Asn Trp Val Glu Arg Asn Ser Tyr Ser Cys Ser Val Val
465                 470                 475                 480

His Glu Gly Leu His Asn His His Thr Thr Lys Ser Phe Ser Arg Thr
                485                 490                 495

Pro Gly Lys

<210> SEQ ID NO 33
<211> LENGTH: 1464
<212> TYPE: DNA
```

<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1464)

<400> SEQUENCE: 33

```
atg tgg gtg acc aaa ctc ctg cca gcc ctg ctg ctg cag cat gtc ctc        48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg        96
Leu His Leu Leu Leu Leu Pro Ile Ala Ile Pro Tyr Ala Glu Gly Val
            20                  25                  30 gtg gga ggc cat cct ggg aac tcc cca tgg acg gtc agc ttg cgg aat       144
Val Gly Gly His Pro Gly Asn Ser Pro Trp Thr Val Ser Leu Arg Asn
        35                  40                  45 cga cag ggc cag cat ttc tgt ggg ggc tcc cta gtg aag gag cag tgg       192
Arg Gln Gly Gln His Phe Cys Gly Gly Ser Leu Val Lys Glu Gln Trp
    50                  55                  60 gta ctg act gcc cgg caa tgc atc tgg tca tgc cac gaa cct ctc aca       240
Val Leu Thr Ala Arg Gln Cys Ile Trp Ser Cys His Glu Pro Leu Thr
65                  70                  75                  80 gga tac gag gta tgg ttg ggt aca att aac cag aac cca cag cct gga       288
Gly Tyr Glu Val Trp Leu Gly Thr Ile Asn Gln Asn Pro Gln Pro Gly
                85                  90                  95 gag gca aac ctg cag agg gtc cca gtg gcc aag gca gtg tgc ggc cct       336
Glu Ala Asn Leu Gln Arg Val Pro Val Ala Lys Ala Val Cys Gly Pro
            100                 105                 110 gca ggc tcc cag ctt gtt ctc aag ctg gag aga cct gtg atc ctg           384
Ala Gly Ser Gln Leu Val Leu Lys Leu Glu Arg Pro Val Ile Leu
        115                 120                 125 aac cat cac gtg gcc ctg att gcc ctg cct cct gaa cag tat gtg gta       432
Asn His His Val Ala Leu Ile Ala Leu Pro Pro Glu Gln Tyr Val Val
    130                 135                 140 cct cca ggg acc aag tgt gag atc gca ggc tgg ggt gaa tcc atc ggt       480
Pro Pro Gly Thr Lys Cys Glu Ile Ala Gly Trp Gly Glu Ser Ile Gly
145                 150                 155                 160 aca agc aat aac aca gtc ctt cat gtg gcc tcg atg aat gtc atc tcc       528
Thr Ser Asn Asn Thr Val Leu His Val Ala Ser Met Asn Val Ile Ser
                165                 170                 175 aac cag gaa tgt aac acg aag tac cga gga cac ata caa gag agt gag       576
Asn Gln Glu Cys Asn Thr Lys Tyr Arg Gly His Ile Gln Glu Ser Glu
            180                 185                 190 ata tgc acc cag gga ctg gtg gtc cct gtg ggg gct tgt gag ggt gac       624
Ile Cys Thr Gln Gly Leu Val Val Pro Val Gly Ala Cys Glu Gly Asp
        195                 200                 205 tac ggg ggc cca ctt gcc tgc tat acc cat gac gca tgg gtc cta cag       672
Tyr Gly Gly Pro Leu Ala Cys Tyr Thr His Asp Ala Trp Val Leu Gln
    210                 215                 220 gga ctt atc atc ccg aac aga gtg tgt gca cgg ccc gcc tgg cca gct       720
Gly Leu Ile Ile Pro Asn Arg Val Cys Ala Arg Pro Arg Trp Pro Ala
225                 230                 235                 240 atc ttc aca cgg gtg tct gtg ttc gtg gac tgg att aac aag gtc atg       768
Ile Phe Thr Arg Val Ser Val Phe Val Asp Trp Ile Asn Lys Val Met
                245                 250                 255 cag ctg gag aca atc aag ccc tgt cct cca tgc aaa tgc cca gca cct       816
Gln Leu Glu Thr Ile Lys Pro Cys Pro Pro Cys Lys Cys Pro Ala Pro
            260                 265                 270 aac ctc ttg ggt gga cca tcc gtc ttc atc ttc cct cca aag atc aag       864
Asn Leu Leu Gly Gly Pro Ser Val Phe Ile Phe Pro Pro Lys Ile Lys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 275 |     |     |     | 280 |     |     |     | 285 |     |     |     |     |     |      |
| gat | gta | ctc | atg | atc | tcc | ctg | agc | ccc | ata | gtc | aca | tgt | gtg | gtg | gtg | 912  |
| Asp | Val | Leu | Met | Ile | Ser | Leu | Ser | Pro | Ile | Val | Thr | Cys | Val | Val | Val |      |
|     | 290 |     |     |     |     | 295 |     |     |     | 300 |     |     |     |     |     |      |
| gct | gtg | agc | gag | gat | gac | cca | gat | gtc | cag | atc | agc | tgg | ttt | gtg | aac | 960  |
| Ala | Val | Ser | Glu | Asp | Asp | Pro | Asp | Val | Gln | Ile | Ser | Trp | Phe | Val | Asn |      |
| 305 |     |     |     |     | 310 |     |     |     |     | 315 |     |     |     |     | 320 |      |
| aac | gtg | gaa | gta | cac | aca | gct | cag | aca | caa | acc | cat | aga | gag | gat | tac | 1008 |
| Asn | Val | Glu | Val | His | Thr | Ala | Gln | Thr | Gln | Thr | His | Arg | Glu | Asp | Tyr |      |
|     |     |     |     | 325 |     |     |     |     | 330 |     |     |     |     | 335 |     |      |
| gcc | agt | act | cta | cgc | gtg | gtc | agt | gcc | ctc | ccc | atc | cag | cac | cag | gac | 1056 |
| Ala | Ser | Thr | Leu | Arg | Val | Val | Ser | Ala | Leu | Pro | Ile | Gln | His | Gln | Asp |      |
|     |     |     | 340 |     |     |     |     | 345 |     |     |     |     | 350 |     |     |      |
| tgg | atg | agt | ggc | aag | gag | ttc | aaa | tgc | aag | gtc | aac | aac | aaa | gac | ctc | 1104 |
| Trp | Met | Ser | Gly | Lys | Glu | Phe | Lys | Cys | Lys | Val | Asn | Asn | Lys | Asp | Leu |      |
|     |     | 355 |     |     |     |     | 360 |     |     |     |     | 365 |     |     |     |      |
| cca | gcg | ccc | atc | gag | aga | acc | atc | tca | aaa | ccc | aaa | ggg | tca | gta | aga | 1152 |
| Pro | Ala | Pro | Ile | Glu | Arg | Thr | Ile | Ser | Lys | Pro | Lys | Gly | Ser | Val | Arg |      |
|     | 370 |     |     |     |     | 375 |     |     |     |     | 380 |     |     |     |     |      |
| gct | cca | cag | gta | tat | gtc | ttg | cct | cca | cca | gaa | gaa | gag | atg | act | aag | 1200 |
| Ala | Pro | Gln | Val | Tyr | Val | Leu | Pro | Pro | Pro | Glu | Glu | Glu | Met | Thr | Lys |      |
| 385 |     |     |     |     | 390 |     |     |     |     | 395 |     |     |     |     | 400 |      |
| aaa | cag | gtc | act | ctg | acc | tgc | atg | gtc | aca | gac | ttc | atg | cct | gaa | gac | 1248 |
| Lys | Gln | Val | Thr | Leu | Thr | Cys | Met | Val | Thr | Asp | Phe | Met | Pro | Glu | Asp |      |
|     |     |     |     | 405 |     |     |     |     | 410 |     |     |     |     | 415 |     |      |
| att | tac | gtg | gag | tgg | acc | aac | aac | ggg | aaa | aca | gag | cta | aac | tac | aag | 1296 |
| Ile | Tyr | Val | Glu | Trp | Thr | Asn | Asn | Gly | Lys | Thr | Glu | Leu | Asn | Tyr | Lys |      |
|     |     |     | 420 |     |     |     |     | 425 |     |     |     |     | 430 |     |     |      |
| aac | act | gaa | cca | gtc | ctg | gac | tct | gat | ggt | tct | tac | ttc | atg | tac | agc | 1344 |
| Asn | Thr | Glu | Pro | Val | Leu | Asp | Ser | Asp | Gly | Ser | Tyr | Phe | Met | Tyr | Ser |      |
|     |     | 435 |     |     |     |     | 440 |     |     |     |     | 445 |     |     |     |      |
| aag | ctg | aga | gtg | gaa | aag | aag | aac | tgg | gtg | gaa | aga | aat | agc | tac | tcc | 1392 |
| Lys | Leu | Arg | Val | Glu | Lys | Lys | Asn | Trp | Val | Glu | Arg | Asn | Ser | Tyr | Ser |      |
|     | 450 |     |     |     |     | 455 |     |     |     |     | 460 |     |     |     |     |      |
| tgt | tca | gtg | gtc | cac | gag | ggt | ctg | cac | aat | cac | cac | acg | act | aag | agc | 1440 |
| Cys | Ser | Val | Val | His | Glu | Gly | Leu | His | Asn | His | His | Thr | Thr | Lys | Ser |      |
| 465 |     |     |     | 470 |     |     |     |     | 475 |     |     |     |     | 480 |     |      |
| ttc | tcc | cgg | act | ccg | ggt | aaa | tga |     |     |     |     |     |     |     |     | 1464 |
| Phe | Ser | Arg | Thr | Pro | Gly | Lys |     |     |     |     |     |     |     |     |     |      |
|     |     |     |     | 485 |     |     |     |     |     |     |     |     |     |     |     |      |

<210> SEQ ID NO 34
<211> LENGTH: 487
<212> TYPE: PRT
<213> ORGANISM: Artificial Sequence
<220> FEATURE:
<223> OTHER INFORMATION: Synthetic mouse MSP fusion protein

<400> SEQUENCE: 34

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
            35                  40                  45

Arg Gln Gly Gln His Phe Cys Gly Gly Ser Leu Val Lys Glu Gln Trp
        50                  55                  60

Val Leu Thr Ala Arg Gln Cys Ile Trp Ser Cys His Glu Pro Leu Thr
65                  70                  75                  80

```
Gly Tyr Glu Val Trp Leu Gly Thr Ile Asn Gln Asn Pro Gln Pro Gly
                85                  90                  95

Glu Ala Asn Leu Gln Arg Val Pro Val Ala Lys Ala Val Cys Gly Pro
            100                 105                 110

Ala Gly Ser Gln Leu Val Leu Leu Lys Leu Glu Arg Pro Val Ile Leu
        115                 120                 125

Asn His His Val Ala Leu Ile Ala Leu Pro Pro Glu Gln Tyr Val Val
    130                 135                 140

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Thr Ile Lys Pro Cys Pro Cys Lys Cys Pro Ala Pro
            260                 265                 270

Asn Leu Leu Gly Gly Pro Ser Val Phe Ile Phe Pro Pro Lys Ile Lys
        275                 280                 285

Asp Val Leu Met Ile Ser Leu Ser Pro Ile Val Thr Cys Val Val Val
    290                 295                 300

Ala Val Ser Glu Asp Asp Pro Asp Val Gln Ile Ser Trp Phe Val Asn
305                 310                 315                 320

Asn Val Glu Val His Thr Ala Gln Thr Gln Thr His Arg Glu Asp Tyr
                325                 330                 335

Ala Ser Thr Leu Arg Val Val Ser Ala Leu Pro Ile Gln His Gln Asp
            340                 345                 350

Trp Met Ser Gly Lys Glu Phe Lys Cys Lys Val Asn Asn Lys Asp Leu
        355                 360                 365

Pro Ala Pro Ile Glu Arg Thr Ile Ser Lys Pro Lys Gly Ser Val Arg
    370                 375                 380

Ala Pro Gln Val Tyr Val Leu Pro Pro Glu Glu Glu Met Thr Lys
385                 390                 395                 400

Lys Gln Val Thr Leu Thr Cys Met Val Thr Asp Phe Met Pro Glu Asp
                405                 410                 415

Ile Tyr Val Glu Trp Thr Asn Asn Gly Lys Thr Glu Leu Asn Tyr Lys
            420                 425                 430

Asn Thr Glu Pro Val Leu Asp Ser Asp Gly Ser Tyr Phe Met Tyr Ser
        435                 440                 445

Lys Leu Arg Val Glu Lys Lys Asn Trp Val Glu Arg Asn Ser Tyr Ser
    450                 455                 460

Cys Ser Val Val His Glu Gly Leu His Asn His Thr Thr Lys Ser
465                 470                 475                 480

Phe Ser Arg Thr Pro Gly Lys
                485
```

-continued

```
<210> SEQ ID NO 35
<211> LENGTH: 1476
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1476)

<400> SEQUENCE: 35 atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga gtg      96
Leu His Leu Leu Leu Leu Pro Ile Ala Ile Pro Tyr Ala Glu Gly Val
            20                  25                  30 gtg gga ggc cat cct ggg aac tcc cca tgg acg gtc agc ttg cgg aat     144
Val Gly Gly His Pro Gly Asn Ser Pro Trp Thr Val Ser Leu Arg Asn
        35                  40                  45 cga cag ggc cag cat ttc tgt ggg ggc tcc cta gtg aag gag cag tgg     192
Arg Gln Gly Gln His Phe Cys Gly Gly Ser Leu Val Lys Glu Gln Trp
    50                  55                  60 gta ctg act gcc cgg caa tgc atc tgg tca tgc cac gaa cct ctc aca     240
Val Leu Thr Ala Arg Gln Cys Ile Trp Ser Cys His Glu Pro Leu Thr
65                  70                  75                  80 gga tac gag gta tgg ttg ggt aca att aac cag aac cca cag cct gga     288
Gly Tyr Glu Val Trp Leu Gly Thr Ile Asn Gln Asn Pro Gln Pro Gly
                85                  90                  95 gag gca aac ctg cag agg gtc cca gtg gcc aag gca gtg tgc ggc cct     336
Glu Ala Asn Leu Gln Arg Val Pro Val Ala Lys Ala Val Cys Gly Pro
            100                 105                 110 gca ggc tcc cag ctt gtt ctg ctc aag ctg gag aga cct gtg atc ctg     384
Ala Gly Ser Gln Leu Val Leu Leu Lys Leu Glu Arg Pro Val Ile Leu
        115                 120                 125 aac cat cac gtg gcc ctg att gcc ctg cct cct gaa cag tat gtg gta     432
Asn His His Val Ala Leu Ile Ala Leu Pro Pro Glu Gln Tyr Val Val
    130                 135                 140 cct cca ggg acc aag tgt gag atc gca ggc tgg ggt gaa tcc atc ggt     480
Pro Pro Gly Thr Lys Cys Glu Ile Ala Gly Trp Gly Glu Ser Ile Gly
145                 150                 155                 160 aca agc aat aac aca gtc ctt cat gtg gcc tcg atg aat gtc atc tcc     528
Thr Ser Asn Asn Thr Val Leu His Val Ala Ser Met Asn Val Ile Ser
                165                 170                 175 aac cag gaa tgt aac acg aag tac cga gga cac ata caa gag agt gag     576
Asn Gln Glu Cys Asn Thr Lys Tyr Arg Gly His Ile Gln Glu Ser Glu
            180                 185                 190 ata tgc acc cag gga ctg gtg gtc cct gtg ggg gct tgt gag ggt gac     624
Ile Cys Thr Gln Gly Leu Val Val Pro Val Gly Ala Cys Glu Gly Asp
        195                 200                 205 tac ggg ggc cca ctt gcc tgt tat acc cat gac gca tgg gtc cta cag     672
Tyr Gly Gly Pro Leu Ala Cys Tyr Thr His Asp Ala Trp Val Leu Gln
    210                 215                 220 gga ctt atc atc ccg aac aga gtg tgt gca cgg ccc cgc tgg cca gct     720
Gly Leu Ile Ile Pro Asn Arg Val Cys Ala Arg Pro Arg Trp Pro Ala
225                 230                 235                 240 atc ttc aca cgg gtg tct gtg ttc gtg gac tgg att aac aag gtc atg     768
Ile Phe Thr Arg Val Ser Val Phe Val Asp Trp Ile Asn Lys Val Met
                245                 250                 255 cag ctg gag ccc aga gga ccc aca atc aag ccc tgt cct cca tgc aaa     816
Gln Leu Glu Pro Arg Gly Pro Thr Ile Lys Pro Cys Pro Pro Cys Lys
            260                 265                 270
```

```
tgc cca gca cct aac ctc ttg ggt gga cca tcc gtc ttc atc ttc cct        864
Cys Pro Ala Pro Asn Leu Leu Gly Gly Pro Ser Val Phe Ile Phe Pro
            275                 280                 285 cca aag atc aag gat gta ctc atg atc tcc ctg agc ccc ata gtc aca        912
Pro Lys Ile Lys Asp Val Leu Met Ile Ser Leu Ser Pro Ile Val Thr
        290                 295                 300 tgt gtg gtg gtg gct gtg agc gag gat gac cca gat gtc cag atc agc        960
Cys Val Val Val Ala Val Ser Glu Asp Asp Pro Asp Val Gln Ile Ser
305                 310                 315                 320 tgg ttt gtg aac aac gtg gaa gta cac aca gct cag aca caa acc cat       1008
Trp Phe Val Asn Asn Val Glu Val His Thr Ala Gln Thr Gln Thr His
                325                 330                 335 aga gag gat tac gcc agt act cta cgc gtg gtc agt gcc ctc ccc atc       1056
Arg Glu Asp Tyr Ala Ser Thr Leu Arg Val Val Ser Ala Leu Pro Ile
            340                 345                 350 cag cac cag gac tgg atg agt ggc aag gag ttc aaa tgc aag gtc aac       1104
Gln His Gln Asp Trp Met Ser Gly Lys Glu Phe Lys Cys Lys Val Asn
        355                 360                 365 aac aaa gac ctc cca gcg ccc atc gag aga acc atc tca aaa ccc aaa       1152
Asn Lys Asp Leu Pro Ala Pro Ile Glu Arg Thr Ile Ser Lys Pro Lys
370                 375                 380 ggg tca gta aga gct cca cag gta tat gtc ttg cct cca cca gaa gaa       1200
Gly Ser Val Arg Ala Pro Gln Val Tyr Val Leu Pro Pro Pro Glu Glu
385                 390                 395                 400 gag atg act aag aaa cag gtc act ctg acc tgc atg gtc aca gac ttc       1248
Glu Met Thr Lys Lys Gln Val Thr Leu Thr Cys Met Val Thr Asp Phe
                405                 410                 415 atg cct gaa gac att tac gtg gag tgg acc aac aac ggg aaa aca gag       1296
Met Pro Glu Asp Ile Tyr Val Glu Trp Thr Asn Asn Gly Lys Thr Glu
            420                 425                 430 cta aac tac aag aac act gaa cca gtc ctg gac tct gat ggt tct tac       1344
Leu Asn Tyr Lys Asn Thr Glu Pro Val Leu Asp Ser Asp Gly Ser Tyr
        435                 440                 445 ttc atg tac agc aag ctg aga gtg gaa aag aag aac tgg gtg gaa aga       1392
Phe Met Tyr Ser Lys Leu Arg Val Glu Lys Lys Asn Trp Val Glu Arg
    450                 455                 460 aat agc tac tcc tgt tca gtg gtc cac gag ggt ctg cac aat cac cac       1440
Asn Ser Tyr Ser Cys Ser Val Val His Glu Gly Leu His Asn His His
465                 470                 475                 480 acg act aag agc ttc tcc cgg act ccg ggt aaa tga                       1476
Thr Thr Lys Ser Phe Ser Arg Thr Pro Gly Lys
                485                 490
```

<210> SEQ ID NO 36
<211> LENGTH: 491
<212> TYPE: PRT
<213> ORGANISM: Artificial Sequence
<220> FEATURE:
<223> OTHER INFORMATION: Synthetic mouse MSP fusion protein

<400> SEQUENCE: 36

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
            20                  25                  30

Val Gly Gly His Pro Gly Asn Ser Pro Trp Thr Val Ser Leu Arg Asn
        35                  40                  45

Arg Gln Gly Gln His Phe Cys Gly Gly Ser Leu Val Lys Glu Gln Trp
    50                  55                  60
```

```
Val Leu Thr Ala Arg Gln Cys Ile Trp Ser Cys His Glu Pro Leu Thr
 65                  70                  75                  80

Gly Tyr Glu Val Trp Leu Gly Thr Ile Asn Gln Asn Pro Gln Pro Gly
                 85                  90                  95

Glu Ala Asn Leu Gln Arg Val Pro Val Ala Lys Ala Val Cys Gly Pro
            100                 105                 110

Ala Gly Ser Gln Leu Val Leu Leu Lys Leu Glu Arg Pro Val Ile Leu
        115                 120                 125

Asn His His Val Ala Leu Ile Ala Leu Pro Pro Glu Gln Tyr Val Val
    130                 135                 140

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Pro Arg Gly Pro Thr Ile Lys Pro Cys Pro Pro Cys Lys
            260                 265                 270

Cys Pro Ala Pro Asn Leu Leu Gly Gly Pro Ser Val Phe Ile Phe Pro
        275                 280                 285

Pro Lys Ile Lys Asp Val Leu Met Ile Ser Leu Ser Pro Ile Val Thr
    290                 295                 300

Cys Val Val Val Ala Val Ser Glu Asp Asp Pro Asp Val Gln Ile Ser
305                 310                 315                 320

Trp Phe Val Asn Asn Val Glu Val His Thr Ala Gln Thr Gln Thr His
                325                 330                 335

Arg Glu Asp Tyr Ala Ser Thr Leu Arg Val Val Ser Ala Leu Pro Ile
            340                 345                 350

Gln His Gln Asp Trp Met Ser Gly Lys Glu Phe Lys Cys Lys Val Asn
        355                 360                 365

Asn Lys Asp Leu Pro Ala Pro Ile Glu Arg Thr Ile Ser Lys Pro Lys
    370                 375                 380

Gly Ser Val Arg Ala Pro Gln Val Tyr Val Leu Pro Pro Pro Glu Glu
385                 390                 395                 400

Glu Met Thr Lys Lys Gln Val Thr Leu Thr Cys Met Val Thr Asp Phe
                405                 410                 415

Met Pro Glu Asp Ile Tyr Val Glu Trp Thr Asn Asn Gly Lys Thr Glu
            420                 425                 430

Leu Asn Tyr Lys Asn Thr Glu Pro Val Leu Asp Ser Asp Gly Ser Tyr
        435                 440                 445

Phe Met Tyr Ser Lys Leu Arg Val Glu Lys Lys Asn Trp Val Glu Arg
    450                 455                 460

Asn Ser Tyr Ser Cys Ser Val Val His Glu Gly Leu His Asn His His
465                 470                 475                 480

Thr Thr Lys Ser Phe Ser Arg Thr Pro Gly Lys
```

<210> SEQ ID NO 37
<211> LENGTH: 1488
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1488)

<400> SEQUENCE: 37

| | | | | | | | | | | | | | | | | |
|---|---|---|---|---|---|---|---|---|---|---|---|---|---|---|---|---|
| atg | tgg | gtg | acc | aaa | ctc | ctg | cca | gcc | ctg | ctg | ctg | cag | cat | gtc | ctc | 48 |
| Met | Trp | Val | Thr | Lys | Leu | Leu | Pro | Ala | Leu | Leu | Leu | Gln | His | Val | Leu | |
| 1 | | | | 5 | | | | | 10 | | | | | 15 | | |
| ctg | cat | ctc | ctc | ctg | ctc | ccc | atc | gcc | atc | ccc | tat | gca | gag | gga | gtg | 96 |
| Leu | His | Leu | Leu | Leu | Leu | Pro | Ile | Ala | Ile | Pro | Tyr | Ala | Glu | Gly | Val | |
| | | | 20 | | | | | 25 | | | | | 30 | | | |
| gtg | gga | ggc | cat | cct | ggg | aac | tcc | cca | tgg | acg | gtc | agc | ttg | cgg | aat | 144 |
| Val | Gly | Gly | His | Pro | Gly | Asn | Ser | Pro | Trp | Thr | Val | Ser | Leu | Arg | Asn | |
| | | 35 | | | | | 40 | | | | | 45 | | | | |
| cga | cag | ggc | cag | cat | ttc | tgt | ggg | ggc | tcc | cta | gtg | aag | gag | cag | tgg | 192 |
| Arg | Gln | Gly | Gln | His | Phe | Cys | Gly | Gly | Ser | Leu | Val | Lys | Glu | Gln | Trp | |
| 50 | | | | | 55 | | | | | 60 | | | | | | |
| gta | ctg | act | gcc | cgg | caa | tgc | atc | tgg | tca | tgc | cac | gaa | cct | ctc | aca | 240 |
| Val | Leu | Thr | Ala | Arg | Gln | Cys | Ile | Trp | Ser | Cys | His | Glu | Pro | Leu | Thr | |
| 65 | | | | | 70 | | | | | 75 | | | | | 80 | |
| gga | tac | gag | gta | tgg | ttg | ggt | aca | att | aac | cag | aac | cca | cag | cct | gga | 288 |
| Gly | Tyr | Glu | Val | Trp | Leu | Gly | Thr | Ile | Asn | Gln | Asn | Pro | Gln | Pro | Gly | |
| | | | | 85 | | | | | 90 | | | | | 95 | | |
| gag | gca | aac | ctg | cag | agg | gtc | cca | gtg | gcc | aag | gca | gtg | tgc | ggc | cct | 336 |
| Glu | Ala | Asn | Leu | Gln | Arg | Val | Pro | Val | Ala | Lys | Ala | Val | Cys | Gly | Pro | |
| | | | 100 | | | | | 105 | | | | | 110 | | | |
| gca | ggc | tcc | cag | ctt | gtt | ctg | ctc | aag | ctg | gag | aga | cct | gtg | atc | ctg | 384 |
| Ala | Gly | Ser | Gln | Leu | Val | Leu | Leu | Lys | Leu | Glu | Arg | Pro | Val | Ile | Leu | |
| | | 115 | | | | | 120 | | | | | 125 | | | | |
| aac | cat | cac | gtg | gcc | ctg | att | gcc | ctg | cct | cct | gaa | cag | tat | gtg | gta | 432 |
| Asn | His | His | Val | Ala | Leu | Ile | Ala | Leu | Pro | Pro | Glu | Gln | Tyr | Val | Val | |
| 130 | | | | | 135 | | | | | 140 | | | | | | |
| cct | cca | ggg | acc | aag | tgt | gag | atc | gca | ggc | tgg | ggt | gaa | tcc | atc | ggt | 480 |
| Pro | Pro | Gly | Thr | Lys | Cys | Glu | Ile | Ala | Gly | Trp | Gly | Glu | Ser | Ile | Gly | |
| 145 | | | | 150 | | | | | 155 | | | | | 160 | | |
| aca | agc | aat | aac | aca | gtc | ctt | cat | gtg | gcc | tcg | atg | aat | gtc | atc | tcc | 528 |
| Thr | Ser | Asn | Asn | Thr | Val | Leu | His | Val | Ala | Ser | Met | Asn | Val | Ile | Ser | |
| | | | | 165 | | | | | 170 | | | | | 175 | | |
| aac | cag | gaa | tgt | aac | acg | aag | tac | cga | gga | cac | ata | caa | gag | agt | gag | 576 |
| Asn | Gln | Glu | Cys | Asn | Thr | Lys | Tyr | Arg | Gly | His | Ile | Gln | Glu | Ser | Glu | |
| | | | 180 | | | | | 185 | | | | | 190 | | | |
| ata | tgc | acc | cag | gga | ctg | gtg | gtc | cct | gtg | ggg | gct | tgt | gag | ggt | gac | 624 |
| Ile | Cys | Thr | Gln | Gly | Leu | Val | Val | Pro | Val | Gly | Ala | Cys | Glu | Gly | Asp | |
| | | 195 | | | | | 200 | | | | | 205 | | | | |
| tac | ggg | ggc | cca | ctt | gcc | tgc | tat | acc | cat | gac | gca | tgg | gtc | cta | cag | 672 |
| Tyr | Gly | Gly | Pro | Leu | Ala | Cys | Tyr | Thr | His | Asp | Ala | Trp | Val | Leu | Gln | |
| | 210 | | | | | 215 | | | | | 220 | | | | | |
| gga | ctt | atc | atc | ccg | aac | aga | gtg | tgt | gca | cgg | ccc | cgc | tgg | cca | gct | 720 |
| Gly | Leu | Ile | Ile | Pro | Asn | Arg | Val | Cys | Ala | Arg | Pro | Arg | Trp | Pro | Ala | |
| 225 | | | | | 230 | | | | | 235 | | | | | 240 | |
| atc | ttc | aca | cgg | gtg | tct | gtg | ttc | gtg | gac | tgg | att | aac | aag | gtc | atg | 768 |
| Ile | Phe | Thr | Arg | Val | Ser | Val | Phe | Val | Asp | Trp | Ile | Asn | Lys | Val | Met | |
| | | | | 245 | | | | | 250 | | | | | 255 | | |

| | | |
|---|---|---|
| cag ctg gag aag aaa att gag ccc aga gga ccc aca atc aag ccc tgt<br>Gln Leu Glu Lys Lys Ile Glu Pro Arg Gly Pro Thr Ile Lys Pro Cys<br>260 265 270 | | 816 |
| cct cca tgc aaa tgc cca gca cct aac ctc ttg ggt gga cca tcc gtc<br>Pro Pro Cys Lys Cys Pro Ala Pro Asn Leu Leu Gly Gly Pro Ser Val<br>275 280 285 | | 864 |
| ttc atc ttc cct cca aag atc aag gat gta ctc atg atc tcc ctg agc<br>Phe Ile Phe Pro Pro Lys Ile Lys Asp Val Leu Met Ile Ser Leu Ser<br>290 295 300 | | 912 |
| ccc ata gtc aca tgt gtg gtg gtg gct gtg agc gag gat gac cca gat<br>Pro Ile Val Thr Cys Val Val Val Ala Val Ser Glu Asp Asp Pro Asp<br>305 310 315 320 | | 960 |
| gtc cag atc agc tgg ttt gtg aac aac gtg gaa gta cac aca gct cag<br>Val Gln Ile Ser Trp Phe Val Asn Asn Val Glu Val His Thr Ala Gln<br>325 330 335 | | 1008 |
| aca caa acc cat aga gag gat tac gcc agt act cta cgc gtg gtc agt<br>Thr Gln Thr His Arg Glu Asp Tyr Ala Ser Thr Leu Arg Val Val Ser<br>340 345 350 | | 1056 |
| gcc ctc ccc atc cag cac cag gac tgg atg agt ggc aag gag ttc aaa<br>Ala Leu Pro Ile Gln His Gln Asp Trp Met Ser Gly Lys Glu Phe Lys<br>355 360 365 | | 1104 |
| tgc aag gtc aac aac aaa gac ctc cca gcg ccc atc gag aga acc atc<br>Cys Lys Val Asn Asn Lys Asp Leu Pro Ala Pro Ile Glu Arg Thr Ile<br>370 375 380 | | 1152 |
| tca aaa ccc aaa ggg tca gta aga gct cca cag gta tat gtc ttg cct<br>Ser Lys Pro Lys Gly Ser Val Arg Ala Pro Gln Val Tyr Val Leu Pro<br>385 390 395 400 | | 1200 |
| cca cca gaa gaa gag atg act aag aaa cag gtc act ctg acc tgc atg<br>Pro Pro Glu Glu Glu Met Thr Lys Lys Gln Val Thr Leu Thr Cys Met<br>405 410 415 | | 1248 |
| gtc aca gac ttc atg cct gaa gac att tac gtg gag tgg acc aac aac<br>Val Thr Asp Phe Met Pro Glu Asp Ile Tyr Val Glu Trp Thr Asn Asn<br>420 425 430 | | 1296 |
| ggg aaa aca gag cta aac tac aag aac act gaa cca gtc ctg gac tct<br>Gly Lys Thr Glu Leu Asn Tyr Lys Asn Thr Glu Pro Val Leu Asp Ser<br>435 440 445 | | 1344 |
| gat ggt tct tac ttc atg tac agc aag ctg aga gtg gaa aag aag aac<br>Asp Gly Ser Tyr Phe Met Tyr Ser Lys Leu Arg Val Glu Lys Lys Asn<br>450 455 460 | | 1392 |
| tgg gtg gaa aga aat agc tac tcc tgt tca gtg gtc cac gag ggt ctg<br>Trp Val Glu Arg Asn Ser Tyr Ser Cys Ser Val Val His Glu Gly Leu<br>465 470 475 480 | | 1440 |
| cac aat cac cac acg act aag agc ttc tcc cgg act ccg ggt aaa tga<br>His Asn His His Thr Thr Lys Ser Phe Ser Arg Thr Pro Gly Lys<br>485 490 495 | | 1488 |

<210> SEQ ID NO 38
<211> LENGTH: 495
<212> TYPE: PRT
<213> ORGANISM: Artificial Sequence
<220> FEATURE:
<223> OTHER INFORMATION: Synthetic mouse MSP fusion protein

<400> SEQUENCE: 38

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Val
                20                  25                  30

Val Gly Gly His Pro Gly Asn Ser Pro Trp Thr Val Ser Leu Arg Asn
        35                  40                  45

```
Arg Gln Gly Gln His Phe Cys Gly Gly Ser Leu Val Lys Glu Gln Trp
 50                  55                  60

Val Leu Thr Ala Arg Gln Cys Ile Trp Ser Cys His Glu Pro Leu Thr
 65                  70                  75                  80

Gly Tyr Glu Val Trp Leu Gly Thr Ile Asn Gln Asn Pro Gln Pro Gly
                 85                  90                  95

Glu Ala Asn Leu Gln Arg Val Pro Val Ala Lys Ala Val Cys Gly Pro
             100                 105                 110

Ala Gly Ser Gln Leu Val Leu Leu Lys Leu Glu Arg Pro Val Ile Leu
         115                 120                 125

Asn His His Val Ala Leu Ile Ala Leu Pro Pro Glu Gln Tyr Val Val
     130                 135                 140

Pro Pro Gly Thr Lys Cys Glu Ile Ala Gly Trp Gly Glu Ser Ile Gly
145                 150                 155                 160

Thr Ser Asn Asn Thr Val Leu His Val Ala Ser Met Asn Val Ile Ser
                165                 170                 175

Asn Gln Glu Cys Asn Thr Lys Tyr Arg Gly His Ile Gln Glu Ser Glu
            180                 185                 190

Ile Cys Thr Gln Gly Leu Val Val Pro Val Gly Ala Cys Glu Gly Asp
        195                 200                 205

Tyr Gly Gly Pro Leu Ala Cys Tyr Thr His Asp Ala Trp Val Leu Gln
    210                 215                 220

Gly Leu Ile Ile Pro Asn Arg Val Cys Ala Arg Pro Arg Trp Pro Ala
225                 230                 235                 240

Ile Phe Thr Arg Val Ser Val Phe Val Asp Trp Ile Asn Lys Val Met
                245                 250                 255

Gln Leu Glu Lys Lys Ile Glu Pro Arg Gly Pro Thr Ile Lys Pro Cys
            260                 265                 270

Pro Pro Cys Lys Cys Pro Ala Pro Asn Leu Leu Gly Gly Pro Ser Val
        275                 280                 285

Phe Ile Phe Pro Pro Lys Ile Lys Asp Val Leu Met Ile Ser Leu Ser
    290                 295                 300

Pro Ile Val Thr Cys Val Val Val Ala Val Ser Glu Asp Asp Pro Asp
305                 310                 315                 320

Val Gln Ile Ser Trp Phe Val Asn Asn Val Glu Val His Thr Ala Gln
                325                 330                 335

Thr Gln Thr His Arg Glu Asp Tyr Ala Ser Thr Leu Arg Val Val Ser
            340                 345                 350

Ala Leu Pro Ile Gln His Gln Asp Trp Met Ser Gly Lys Glu Phe Lys
        355                 360                 365

Cys Lys Val Asn Asn Lys Asp Leu Pro Ala Pro Ile Glu Arg Thr Ile
    370                 375                 380

Ser Lys Pro Lys Gly Ser Val Arg Ala Pro Gln Val Tyr Val Leu Pro
385                 390                 395                 400

Pro Pro Glu Glu Glu Met Thr Lys Lys Gln Val Thr Leu Thr Cys Met
                405                 410                 415

Val Thr Asp Phe Met Pro Glu Asp Ile Tyr Val Glu Trp Thr Asn Asn
            420                 425                 430

Gly Lys Thr Glu Leu Asn Tyr Lys Asn Thr Glu Pro Val Leu Asp Ser
        435                 440                 445

Asp Gly Ser Tyr Phe Met Tyr Ser Lys Leu Arg Val Glu Lys Lys Asn
    450                 455                 460

Trp Val Glu Arg Asn Ser Tyr Ser Cys Ser Val Val His Glu Gly Leu
```

His Asn His His Thr Thr Lys Ser Phe Ser Arg Thr Pro Gly Lys
              485                 490                 495

<210> SEQ ID NO 39
<211> LENGTH: 1500
<212> TYPE: DNA
<213> ORGANISM: Artificial Sequence
<220> FEATURE:
<223> OTHER INFORMATION: Synthetic mouse MSP fusion protein
<220> FEATURE:
<221> NAME/KEY: CDS
<222> LOCATION: (1)..(1500)

<400> SEQUENCE: 39

| | |
|---|---:|
| atg tgg gtg acc aaa ctc ctg cca gcc ctg ctg ctg cag cat gtc ctc<br>Met Trp Val Thr Lys Leu Leu Pro Ala Leu Leu Leu Gln His Val Leu<br>1               5                   10                  15 | 48 |
| ctg cat ctc ctc ctg ctc ccc atc gcc atc ccc tat gca gag gga gtg<br>Leu His Leu Leu Leu Leu Pro Ile Ala Ile Pro Tyr Ala Glu Gly Val<br>            20                  25                  30 | 96 |
| gtg gga ggc cat cct ggg aac tcc cca tgg acg tca agc ttg cgg aat<br>Val Gly Gly His Pro Gly Asn Ser Pro Trp Thr Val Ser Leu Arg Asn<br>        35                  40                  45 | 144 |
| cga cag ggc cag cat ttc tgt ggg ggc tcc cta gtg aag gag cag tgg<br>Arg Gln Gly Gln His Phe Cys Gly Gly Ser Leu Val Lys Glu Gln Trp<br>    50                  55                  60 | 192 |
| gta ctg act gcc cgg caa tgc atc tgg tca tgc cac gaa cct ctc aca<br>Val Leu Thr Ala Arg Gln Cys Ile Trp Ser Cys His Glu Pro Leu Thr<br>65                  70                  75                  80 | 240 |
| gga tac gag gta tgg ttg ggt aca att aac cag aac cca cag cct gga<br>Gly Tyr Glu Val Trp Leu Gly Thr Ile Asn Gln Asn Pro Gln Pro Gly<br>                85                  90                  95 | 288 |
| gag gca aac ctg cag agg gtc cca gtg gcc aag gca gtg tgc ggc cct<br>Glu Ala Asn Leu Gln Arg Val Pro Val Ala Lys Ala Val Cys Gly Pro<br>            100                 105                 110 | 336 |
| gca ggc tcc cag ctt gtt ctg ctc aag ctg gag aga cct gtg atc ctg<br>Ala Gly Ser Gln Leu Val Leu Leu Lys Leu Glu Arg Pro Val Ile Leu<br>        115                 120                 125 | 384 |
| aac cat cac gtg gcc ctg att gcc ctg cct cct gaa cag tat gtg gta<br>Asn His His Val Ala Leu Ile Ala Leu Pro Pro Glu Gln Tyr Val Val<br>    130                 135                 140 | 432 |
| cct cca ggg acc aag tgt gag atc gca ggc tgg ggt gaa tcc atc ggt<br>Pro Pro Gly Thr Lys Cys Glu Ile Ala Gly Trp Gly Glu Ser Ile Gly<br>145                 150                 155                 160 | 480 |
| aca agc aat aac aca gtc ctt cat gtg gcc tcg atg aat gtc atc tcc<br>Thr Ser Asn Asn Thr Val Leu His Val Ala Ser Met Asn Val Ile Ser<br>                165                 170                 175 | 528 |
| aac cag gaa tgt aac acg aag tac cga gga cac ata caa gag agt gag<br>Asn Gln Glu Cys Asn Thr Lys Tyr Arg Gly His Ile Gln Glu Ser Glu<br>            180                 185                 190 | 576 |
| ata tgc acc cag gga ctg gtg gtc cct gtg ggg gct tgt gag ggt gac<br>Ile Cys Thr Gln Gly Leu Val Val Pro Val Gly Ala Cys Glu Gly Asp<br>        195                 200                 205 | 624 |
| tac ggg ggc cca ctt gcc tgc tat acc cat gac gca tgg gtc cta cag<br>Tyr Gly Gly Pro Leu Ala Cys Tyr Thr His Asp Ala Trp Val Leu Gln<br>    210                 215                 220 | 672 |
| gga ctt atc atc ccg aac aga gtg tgt gca cgg ccc gc tgg cca gct<br>Gly Leu Ile Ile Pro Asn Arg Val Cys Ala Arg Pro Arg Trp Pro Ala<br>225                 230                 235                 240 | 720 |
| atc ttc aca cgg gtg tct gtg ttc gtg gac tgg att aac aag gtc atg | 768 |

| | | | | | | | | | | | | |
|---|---|---|---|---|---|---|---|---|---|---|---|---|
| Ile | Phe | Thr | Arg | Val | Ser | Val | Phe | Val | Asp | Trp | Ile | Asn | Lys | Val | Met |
| | | | | 245 | | | | 250 | | | | 255 | |

```
cag ctg gag cag gtc acc gac aag aaa att gag ccc aga gga ccc aca    816
Gln Leu Glu Gln Val Thr Asp Lys Lys Ile Glu Pro Arg Gly Pro Thr
            260                 265                 270 atc aag ccc tgt cct cca tgc aaa tgc cca gca cct aac ctc ttg ggt    864
Ile Lys Pro Cys Pro Pro Cys Lys Cys Pro Ala Pro Asn Leu Leu Gly
            275                 280                 285 gga cca tcc gtc ttc atc ttc cct cca aag atc aag gat gta ctc atg    912
Gly Pro Ser Val Phe Ile Phe Pro Pro Lys Ile Lys Asp Val Leu Met
        290                 295                 300 atc tcc ctg agc ccc ata gtc aca tgt gtg gtg gtg gct gtg agc gag    960
Ile Ser Leu Ser Pro Ile Val Thr Cys Val Val Val Ala Val Ser Glu
305                 310                 315                 320 gat gac cca gat gtc cag atc agc tgg ttt gtg aac aac gtg gaa gta   1008
Asp Asp Pro Asp Val Gln Ile Ser Trp Phe Val Asn Asn Val Glu Val
                325                 330                 335 cac aca gct cag aca caa acc cat aga gag gat tac gcc agt act cta   1056
His Thr Ala Gln Thr Gln Thr His Arg Glu Asp Tyr Ala Ser Thr Leu
            340                 345                 350 cgc gtg gtc agt gcc ctc ccc atc cag cac cag gac tgg atg agt ggc   1104
Arg Val Val Ser Ala Leu Pro Ile Gln His Gln Asp Trp Met Ser Gly
            355                 360                 365 aag gag ttc aaa tgc aag gtc aac aac aaa gac ctc cca gcg ccc atc   1152
Lys Glu Phe Lys Cys Lys Val Asn Asn Lys Asp Leu Pro Ala Pro Ile
        370                 375                 380 gag aga acc atc tca aaa ccc aaa ggg tca gta aga gct cca cag gta   1200
Glu Arg Thr Ile Ser Lys Pro Lys Gly Ser Val Arg Ala Pro Gln Val
385                 390                 395                 400 tat gtc ttg cct cca cca gaa gaa gag atg act aag aaa cag gtc act   1248
Tyr Val Leu Pro Pro Pro Glu Glu Glu Met Thr Lys Lys Gln Val Thr
                405                 410                 415 ctg acc tgc atg gtc aca gac ttc atg cct gaa gac att tac gtg gag   1296
Leu Thr Cys Met Val Thr Asp Phe Met Pro Glu Asp Ile Tyr Val Glu
            420                 425                 430 tgg acc aac aac ggg aaa aca gag cta aac tac aag aac act gaa cca   1344
Trp Thr Asn Asn Gly Lys Thr Glu Leu Asn Tyr Lys Asn Thr Glu Pro
            435                 440                 445 gtc ctg gac tct gat ggt tct tac ttc atg tac agc aag ctg aga gtg   1392
Val Leu Asp Ser Asp Gly Ser Tyr Phe Met Tyr Ser Lys Leu Arg Val
        450                 455                 460 gaa aag aag aac tgg gtg gaa aga aat agc tac tcc tgt tca gtg gtc   1440
Glu Lys Lys Asn Trp Val Glu Arg Asn Ser Tyr Ser Cys Ser Val Val
465                 470                 475                 480 cac gag ggt ctg cac aat cac cac acg act aag agc ttc tcc cgg act   1488
His Glu Gly Leu His Asn His His Thr Thr Lys Ser Phe Ser Arg Thr
                485                 490                 495 ccg ggt aaa tga                                                    1500
Pro Gly Lys
```

<210> SEQ ID NO 40
<211> LENGTH: 499
<212> TYPE: PRT
<213> ORGANISM: Artificial Sequence
<220> FEATURE:
<223> OTHER INFORMATION: Synthetic mouse MSP fusion protein

<400> SEQUENCE: 40

```
Met Trp Val Thr Lys Leu Leu Pro Ala Leu Leu Leu Gln His Val Leu
1               5                   10                  15
```

```
Leu His Leu Leu Leu Leu Pro Ile Ala Ile Pro Tyr Ala Glu Gly Val
                20                  25                  30
Val Gly Gly His Pro Gly Asn Ser Pro Trp Thr Val Ser Leu Arg Asn
         35                  40                  45
Arg Gln Gly Gln His Phe Cys Gly Gly Ser Leu Val Lys Glu Gln Trp
     50                  55                  60
Val Leu Thr Ala Arg Gln Cys Ile Trp Ser Cys His Glu Pro Leu Thr
 65                  70                  75                  80
Gly Tyr Glu Val Trp Leu Gly Thr Ile Asn Gln Asn Pro Gln Pro Gly
                 85                  90                  95
Glu Ala Asn Leu Gln Arg Val Pro Val Ala Lys Ala Val Cys Gly Pro
             100                 105                 110
Ala Gly Ser Gln Leu Val Leu Leu Lys Leu Glu Arg Pro Val Ile Leu
         115                 120                 125
Asn His His Val Ala Leu Ile Ala Leu Pro Pro Glu Gln Tyr Val Val
     130                 135                 140
Pro Pro Gly Thr Lys Cys Glu Ile Ala Gly Trp Gly Glu Ser Ile Gly
145                 150                 155                 160
Thr Ser Asn Asn Thr Val Leu His Val Ala Ser Met Asn Val Ile Ser
                 165                 170                 175
Asn Gln Glu Cys Asn Thr Lys Tyr Arg Gly His Ile Gln Glu Ser Glu
             180                 185                 190
Ile Cys Thr Gln Gly Leu Val Val Pro Val Gly Ala Cys Glu Gly Asp
         195                 200                 205
Tyr Gly Gly Pro Leu Ala Cys Tyr Thr His Asp Ala Trp Val Leu Gln
     210                 215                 220
Gly Leu Ile Ile Pro Asn Arg Val Cys Ala Arg Pro Arg Trp Pro Ala
225                 230                 235                 240
Ile Phe Thr Arg Val Ser Val Phe Val Asp Trp Ile Asn Lys Val Met
                 245                 250                 255
Gln Leu Glu Gln Val Thr Asp Lys Lys Ile Glu Pro Arg Gly Pro Thr
             260                 265                 270
Ile Lys Pro Cys Pro Pro Cys Lys Cys Pro Ala Pro Asn Leu Leu Gly
         275                 280                 285
Gly Pro Ser Val Phe Ile Phe Pro Pro Lys Ile Lys Asp Val Leu Met
     290                 295                 300
Ile Ser Leu Ser Pro Ile Val Thr Cys Val Val Ala Val Ser Glu
305                 310                 315                 320
Asp Asp Pro Asp Val Gln Ile Ser Trp Phe Val Asn Asn Val Glu Val
                 325                 330                 335
His Thr Ala Gln Thr Gln Thr His Arg Glu Asp Tyr Ala Ser Thr Leu
             340                 345                 350
Arg Val Val Ser Ala Leu Pro Ile Gln His Gln Asp Trp Met Ser Gly
         355                 360                 365
Lys Glu Phe Lys Cys Lys Val Asn Asn Lys Asp Leu Pro Ala Pro Ile
     370                 375                 380
Glu Arg Thr Ile Ser Lys Pro Lys Gly Ser Val Arg Ala Pro Gln Val
385                 390                 395                 400
Tyr Val Leu Pro Pro Pro Glu Glu Glu Met Thr Lys Lys Gln Val Thr
                 405                 410                 415
Leu Thr Cys Met Val Thr Asp Phe Met Pro Glu Asp Ile Tyr Val Glu
             420                 425                 430
Trp Thr Asn Asn Gly Lys Thr Glu Leu Asn Tyr Lys Asn Thr Glu Pro
```

```
                435              440             445
Val Leu Asp Ser Asp Gly Ser Tyr Phe Met Tyr Ser Lys Leu Arg Val
    450              455              460

Glu Lys Lys Asn Trp Val Glu Arg Asn Ser Tyr Ser Cys Ser Val Val
465              470              475              480

His Glu Gly Leu His Asn His His Thr Thr Lys Ser Phe Ser Arg Thr
                485              490              495

Pro Gly Lys

<210> SEQ ID NO 41
<211> LENGTH: 4203
<212> TYPE: DNA
<213> ORGANISM: Homo sapiens
<220> FEATURE:
<221> NAME/KEY: CDS
<222> LOCATION: (1)..(4203)

<400> SEQUENCE: 41 atg gag ctc ctc ccg ccg ctg cct cag tcc ttc ctg ttg ctg ctg ctg    48
Met Glu Leu Leu Pro Pro Leu Pro Gln Ser Phe Leu Leu Leu Leu Leu
1               5                   10                  15 ttg cct gcc aag ccc gcg gcg ggc gag gac tgg cag tgc ccg cgc acc    96
Leu Pro Ala Lys Pro Ala Ala Gly Glu Asp Trp Gln Cys Pro Arg Thr
                20                  25                  30 ccc tac gcg gcc tct cgc gac ttt gac gtg aag tac gtg gtg ccc agc    144
Pro Tyr Ala Ala Ser Arg Asp Phe Asp Val Lys Tyr Val Val Pro Ser
            35                  40                  45 ttc tcc gcc gga ggc ctg gta cag gcc atg gtg acc tac gag ggc gac    192
Phe Ser Ala Gly Gly Leu Val Gln Ala Met Val Thr Tyr Glu Gly Asp
        50                  55                  60 aga aat gag agt gct gtg ttt gta gcc ata cgc aat cgc ctg cat gtg    240
Arg Asn Glu Ser Ala Val Phe Val Ala Ile Arg Asn Arg Leu His Val
65                  70                  75                  80 ctt ggg cct gac ctg aag tct gtc cag agc ctg gcc acg ggc cct gct    288
Leu Gly Pro Asp Leu Lys Ser Val Gln Ser Leu Ala Thr Gly Pro Ala
                85                  90                  95 gga gac cct ggc tgc cag acg tgt gca gcc tgt ggc cca gga ccc cac    336
Gly Asp Pro Gly Cys Gln Thr Cys Ala Ala Cys Gly Pro Gly Pro His
                100                 105                 110 ggc cct ccc ggt gac aca gac aca aag gtg ctg gtg ctg gat ccc gcg    384
Gly Pro Pro Gly Asp Thr Asp Thr Lys Val Leu Val Leu Asp Pro Ala
            115                 120                 125 ctg cct gcg ctg gtc agt tgt ggc tcc agc ctg cag ggc cgc tgc ttc    432
Leu Pro Ala Leu Val Ser Cys Gly Ser Ser Leu Gln Gly Arg Cys Phe
        130                 135                 140 ctg cat gac cta gag ccc caa ggg aca gcc gtg cat ctg gca gcg cca    480
Leu His Asp Leu Glu Pro Gln Gly Thr Ala Val His Leu Ala Ala Pro
145                 150                 155                 160 gcc tgc ctc ttc tca gcc cac cat aac cgg ccc gat gac tgc ccc gac    528
Ala Cys Leu Phe Ser Ala His His Asn Arg Pro Asp Asp Cys Pro Asp
                165                 170                 175 tgt gtg gcc agc cca ttg ggc acc cgt gta act gtg gtt gag caa ggc    576
Cys Val Ala Ser Pro Leu Gly Thr Arg Val Thr Val Val Glu Gln Gly
            180                 185                 190 cag gcc tcc tat ttc tac gtg gca tcc tca ctg gac gca gcc gtg gct    624
Gln Ala Ser Tyr Phe Tyr Val Ala Ser Ser Leu Asp Ala Ala Val Ala
        195                 200                 205 gcc agc ttc agc cca cgc tca gtg tct atc agg cgt ctc aag gct gac    672
Ala Ser Phe Ser Pro Arg Ser Val Ser Ile Arg Arg Leu Lys Ala Asp
    210                 215                 220
```

```
gcc tcg gga ttc gca ccg ggc ttt gtg gcg ttg tca gtg ctg ccc aag    720
Ala Ser Gly Phe Ala Pro Gly Phe Val Ala Leu Ser Val Leu Pro Lys
225                 230                 235                 240 cat ctt gtc tcc tac agt att gaa tac gtg cac agc ttc cac acg gga    768
His Leu Val Ser Tyr Ser Ile Glu Tyr Val His Ser Phe His Thr Gly
                245                 250                 255 gcc ttc gta tac ttc ctg act gta cag ccg gcc agc gtg aca gat gat    816
Ala Phe Val Tyr Phe Leu Thr Val Gln Pro Ala Ser Val Thr Asp Asp
            260                 265                 270 cct agt gcc ctg cac aca cgc ctg gca cgg ctt agc gcc act gag cca    864
Pro Ser Ala Leu His Thr Arg Leu Ala Arg Leu Ser Ala Thr Glu Pro
        275                 280                 285 gag ttg ggt gac tat cgg gag ctg gtc ctc gac tgc aga ttt gct cca    912
Glu Leu Gly Asp Tyr Arg Glu Leu Val Leu Asp Cys Arg Phe Ala Pro
    290                 295                 300 aaa cgc agg cgc cgg ggg gcc cca gaa ggc gga cag ccc tac cct gtg    960
Lys Arg Arg Arg Arg Gly Ala Pro Glu Gly Gly Gln Pro Tyr Pro Val
305                 310                 315                 320 ctg cgg gtg gcc cac tcc gct cca gtg ggt gcc caa ctt gcc act gag   1008
Leu Arg Val Ala His Ser Ala Pro Val Gly Ala Gln Leu Ala Thr Glu
                325                 330                 335 ctg agc atc gcc gag ggc cag gaa gta cta ttt ggg gtc ttt gtg act   1056
Leu Ser Ile Ala Glu Gly Gln Glu Val Leu Phe Gly Val Phe Val Thr
            340                 345                 350 ggc aag gat ggt ggt cct ggc gtg ggc ccc aac tct gtc gtc tgt gcc   1104
Gly Lys Asp Gly Gly Pro Gly Val Gly Pro Asn Ser Val Val Cys Ala
        355                 360                 365 ttc ccc att gac ctg ctg gac aca cta att gat gag ggt gtg gag cgc   1152
Phe Pro Ile Asp Leu Leu Asp Thr Leu Ile Asp Glu Gly Val Glu Arg
    370                 375                 380 tgt tgt gaa tcc cca gtc cat cca ggc ctc cgg cga ggc ctc gac ttc   1200
Cys Cys Glu Ser Pro Val His Pro Gly Leu Arg Arg Gly Leu Asp Phe
385                 390                 395                 400 ttc cag tcg ccc agt ttt tgc ccc aac ccg cct ggc ctg gaa gcc ctc   1248
Phe Gln Ser Pro Ser Phe Cys Pro Asn Pro Pro Gly Leu Glu Ala Leu
                405                 410                 415 agc ccc aac acc agc tgc cgc cac ttc cct ctg ctg gtc agt agc agc   1296
Ser Pro Asn Thr Ser Cys Arg His Phe Pro Leu Leu Val Ser Ser Ser
            420                 425                 430 ttc tca cgt gtg gac cta ttc aat ggg ctg ttg gga cca gta cag gtc   1344
Phe Ser Arg Val Asp Leu Phe Asn Gly Leu Leu Gly Pro Val Gln Val
        435                 440                 445 act gca ttg tat gtg aca cgc ctt gac aac gtc aca gtg gca cac atg   1392
Thr Ala Leu Tyr Val Thr Arg Leu Asp Asn Val Thr Val Ala His Met
    450                 455                 460 ggc aca atg gat ggg cgt atc ctg cag gtg gag ctg gtc agg tca cta   1440
Gly Thr Met Asp Gly Arg Ile Leu Gln Val Glu Leu Val Arg Ser Leu
465                 470                 475                 480 aac tac ttg ctg tat gtg tcc aac ttc tca ctg ggt gac agt ggg cag   1488
Asn Tyr Leu Leu Tyr Val Ser Asn Phe Ser Leu Gly Asp Ser Gly Gln
                485                 490                 495 ccc gtg cag cgg gat gtc agt cgt ctt ggg gac cac cta ctc ttt gcc   1536
Pro Val Gln Arg Asp Val Ser Arg Leu Gly Asp His Leu Leu Phe Ala
            500                 505                 510 tct ggg gac cag gtt ttc cag gta cct atc caa ggc cct ggc tgc cgc   1584
Ser Gly Asp Gln Val Phe Gln Val Pro Ile Gln Gly Pro Gly Cys Arg
        515                 520                 525 cac ttc ctg acc tgt ggg cgt tgc cta agg gca tgg cat ttc atg ggc   1632
His Phe Leu Thr Cys Gly Arg Cys Leu Arg Ala Trp His Phe Met Gly
```

-continued

```
             530                 535                 540
tgt ggc tgg tgt ggg aac atg tgc ggc cag cag aag gag tgt cct ggc      1680
Cys Gly Trp Cys Gly Asn Met Cys Gly Gln Gln Lys Glu Cys Pro Gly
545                 550                 555                 560 tcc tgg caa cag gac cac tgc cca cct aag ctt act gag ttc cac ccc      1728
Ser Trp Gln Gln Asp His Cys Pro Pro Lys Leu Thr Glu Phe His Pro
                565                 570                 575 cac agt gga cct cta agg ggc agt aca agg ctg acc ctg tgt ggc tcc      1776
His Ser Gly Pro Leu Arg Gly Ser Thr Arg Leu Thr Leu Cys Gly Ser
            580                 585                 590 aac ttc tac ctt cac cct tct ggt ctg gtg cct gag gga acc cat cag      1824
Asn Phe Tyr Leu His Pro Ser Gly Leu Val Pro Glu Gly Thr His Gln
        595                 600                 605 gtc act gtg ggc caa agt ccc tgc cgg cca ctg ccc aag gac agc tca      1872
Val Thr Val Gly Gln Ser Pro Cys Arg Pro Leu Pro Lys Asp Ser Ser
    610                 615                 620 aaa ctc aga cca gtg ccc cgg aaa gac ttt gta gag gag ttt gag tgt      1920
Lys Leu Arg Pro Val Pro Arg Lys Asp Phe Val Glu Glu Phe Glu Cys
625                 630                 635                 640 gaa ctg gag ccc ttg ggc acc cag gca gtg ggg cct acc aac gtc agc      1968
Glu Leu Glu Pro Leu Gly Thr Gln Ala Val Gly Pro Thr Asn Val Ser
                645                 650                 655 ctc acc gtg act aac atg cca ccg ggc aag cac ttc cgg gta gac ggc      2016
Leu Thr Val Thr Asn Met Pro Pro Gly Lys His Phe Arg Val Asp Gly
            660                 665                 670 acc tcc gtg ctg aga ggc ttc tct ttc atg gag cca gtg ctg ata gca      2064
Thr Ser Val Leu Arg Gly Phe Ser Phe Met Glu Pro Val Leu Ile Ala
        675                 680                 685 gtg caa ccc ctc ttt ggc cca cgg gca gga ggc acc tgt ctc act ctt      2112
Val Gln Pro Leu Phe Gly Pro Arg Ala Gly Gly Thr Cys Leu Thr Leu
    690                 695                 700 gaa ggc cag agt ctg tct gta ggc acc agc cgg gct gtg ctg gtc aat      2160
Glu Gly Gln Ser Leu Ser Val Gly Thr Ser Arg Ala Val Leu Val Asn
705                 710                 715                 720 ggg act gag tgt ctg cta gca cgg gtc agt gag ggg cag ctt tta tgt      2208
Gly Thr Glu Cys Leu Leu Ala Arg Val Ser Glu Gly Gln Leu Leu Cys
                725                 730                 735 gcc aca ccc cct ggg gcc acg gtg gcc agt gtc ccc ctt agc ctg cag      2256
Ala Thr Pro Pro Gly Ala Thr Val Ala Ser Val Pro Leu Ser Leu Gln
            740                 745                 750 gtg ggg ggt gcc cag gta cct ggt tcc tgg acc ttc cag tac aga gaa      2304
Val Gly Gly Ala Gln Val Pro Gly Ser Trp Thr Phe Gln Tyr Arg Glu
        755                 760                 765 gac cct gtc gtg cta agc atc agc ccc aac tgt ggc tac atc aac tcc      2352
Asp Pro Val Val Leu Ser Ile Ser Pro Asn Cys Gly Tyr Ile Asn Ser
    770                 775                 780 cac atc acc atc tgt ggc cag cat cta act tca gca tgg cac tta gtg      2400
His Ile Thr Ile Cys Gly Gln His Leu Thr Ser Ala Trp His Leu Val
785                 790                 795                 800 ctg tca ttc cat gac ggg ctt agg gca gtg gaa agc agg tgt gag agg      2448
Leu Ser Phe His Asp Gly Leu Arg Ala Val Glu Ser Arg Cys Glu Arg
                805                 810                 815 cag ctt cca gag cag cag ctg tgc cgc ctt cct gaa tat gtg gtc cga      2496
Gln Leu Pro Glu Gln Gln Leu Cys Arg Leu Pro Glu Tyr Val Val Arg
            820                 825                 830 gac ccc cag gga tgg gtg gca ggg aat ctg agt gcc cga ggg gat gga      2544
Asp Pro Gln Gly Trp Val Ala Gly Asn Leu Ser Ala Arg Gly Asp Gly
        835                 840                 845 gct gct ggc ttt aca ctg cct ggc ttt cgc ttc cta ccc cca ccc cat      2592
```

-continued

```
              Ala Ala Gly Phe Thr Leu Pro Gly Phe Arg Phe Leu Pro Pro Pro His
                  850                 855                 860 cca ccc agt gcc aac cta gtt cca ctg aag cct gag gag cat gcc att         2640
Pro Pro Ser Ala Asn Leu Val Pro Leu Lys Pro Glu Glu His Ala Ile
865                 870                 875                 880 aag ttt gag tat att ggg ctg ggc gct gtg gct gac tgt gtg ggt atc         2688
Lys Phe Glu Tyr Ile Gly Leu Gly Ala Val Ala Asp Cys Val Gly Ile
                885                 890                 895 aac gtg acc gtg ggt ggt gag agc tgc cag cac gag ttc cgg ggg gac         2736
Asn Val Thr Val Gly Gly Glu Ser Cys Gln His Glu Phe Arg Gly Asp
            900                 905                 910 atg gtt gtc tgc ccc ctg ccc cca tcc ctg cag ctt ggc cag gat ggt         2784
Met Val Val Cys Pro Leu Pro Pro Ser Leu Gln Leu Gly Gln Asp Gly
        915                 920                 925 gcc cca ttg cag gtc tgc gta gat ggt gaa tgt cat atc ctg ggt aga         2832
Ala Pro Leu Gln Val Cys Val Asp Gly Glu Cys His Ile Leu Gly Arg
    930                 935                 940 gtg gtg cgg cca ggg cca gat ggg gtc cca cag agc acg ctc ctt ggt         2880
Val Val Arg Pro Gly Pro Asp Gly Val Pro Gln Ser Thr Leu Leu Gly
945                 950                 955                 960 atc ctg ctg cct ttg ctg ctg ctt gtg gct gca ctg gcg act gca ctg         2928
Ile Leu Leu Pro Leu Leu Leu Leu Val Ala Ala Leu Ala Thr Ala Leu
                965                 970                 975 gtc ttc agc tac tgg tgg cgg agg aag cag cta gtt ctt cct ccc aac         2976
Val Phe Ser Tyr Trp Trp Arg Arg Lys Gln Leu Val Leu Pro Pro Asn
                980                 985                 990 ctg aat gac ctg gca tcc ctg gac cag act gct gga gcc aca ccc ctg         3024
Leu Asn Asp Leu Ala Ser Leu Asp Gln Thr Ala Gly Ala Thr Pro Leu
            995                 1000                1005 cct att ctg tac tcg ggc tct gac tac aga agt ggc ctt gca ctc             3069
Pro Ile Leu Tyr Ser Gly Ser Asp Tyr Arg Ser Gly Leu Ala Leu
        1010                1015                1020 cct gcc att gat ggt ctg gat tcc acc act tgt gtc cat gga gca             3114
Pro Ala Ile Asp Gly Leu Asp Ser Thr Thr Cys Val His Gly Ala
    1025                1030                1035 tcc ttc tcc gat agt gaa gat gaa tcc tgt gtg cca ctg ctg cgg             3159
Ser Phe Ser Asp Ser Glu Asp Glu Ser Cys Val Pro Leu Leu Arg
1040                1045                1050 aaa gag tcc atc cag cta agg gac ctg gac tct gcg ctc ttg gct             3204
Lys Glu Ser Ile Gln Leu Arg Asp Leu Asp Ser Ala Leu Leu Ala
        1055                1060                1065 gag gtc aag gat gtg ctg att ccc cat gag cgg gtg gtc acc cac             3249
Glu Val Lys Asp Val Leu Ile Pro His Glu Arg Val Val Thr His
    1070                1075                1080 agt gac cga gtc att ggc aaa ggc cac ttt gga gtt gtc tac cac             3294
Ser Asp Arg Val Ile Gly Lys Gly His Phe Gly Val Val Tyr His
1085                1090                1095 gga gaa tac ata gac cag gcc cag aat cga atc caa tgt gcc atc             3339
Gly Glu Tyr Ile Asp Gln Ala Gln Asn Arg Ile Gln Cys Ala Ile
        1100                1105                1110 aag tca cta agt cgc atc aca gag atg cag cag gtg gag gcc ttc             3384
Lys Ser Leu Ser Arg Ile Thr Glu Met Gln Gln Val Glu Ala Phe
    1115                1120                1125 ctg cga gag ggg ctg ctc atg cgt ggc ctg aac cac ccg aat gtg             3429
Leu Arg Glu Gly Leu Leu Met Arg Gly Leu Asn His Pro Asn Val
1130                1135                1140 ctg gct ctc att ggt atc atg ttg cca cct gag ggc ctg ccc cat             3474
Leu Ala Leu Ile Gly Ile Met Leu Pro Pro Glu Gly Leu Pro His
        1145                1150                1155
```

| | | | | | | | | | | | | | | |
|---|---|---|---|---|---|---|---|---|---|---|---|---|---|---|
| gtg | ctg | ctg | ccc | tat | atg | tgc | cac | ggt | gac | ctg | ctc | cag | ttc | atc | 3519 |
| Val | Leu | Leu | Pro | Tyr | Met | Cys | His | Gly | Asp | Leu | Leu | Gln | Phe | Ile | |
| | 1160 | | | | 1165 | | | | | 1170 | | | | | |
| cgc | tca | cct | cag | cgg | aac | ccc | acc | gtg | aag | gac | ctc | atc | agc | ttt | 3564 |
| Arg | Ser | Pro | Gln | Arg | Asn | Pro | Thr | Val | Lys | Asp | Leu | Ile | Ser | Phe | |
| | 1175 | | | | 1180 | | | | | 1185 | | | | | |
| ggc | ctg | cag | gta | gcc | cgc | ggc | atg | gag | tac | ctg | gca | gag | cag | aag | 3609 |
| Gly | Leu | Gln | Val | Ala | Arg | Gly | Met | Glu | Tyr | Leu | Ala | Glu | Gln | Lys | |
| | 1190 | | | | 1195 | | | | | 1200 | | | | | |
| ttt | gtg | cac | agg | gac | ctg | gct | gcg | cgg | aac | tgc | atg | ctg | gac | gag | 3654 |
| Phe | Val | His | Arg | Asp | Leu | Ala | Ala | Arg | Asn | Cys | Met | Leu | Asp | Glu | |
| | 1205 | | | | 1210 | | | | | 1215 | | | | | |
| tca | ttc | aca | gtc | aag | gtg | gct | gac | ttt | ggt | ttg | gcc | cgc | gac | atc | 3699 |
| Ser | Phe | Thr | Val | Lys | Val | Ala | Asp | Phe | Gly | Leu | Ala | Arg | Asp | Ile | |
| | 1220 | | | | 1225 | | | | | 1230 | | | | | |
| ctg | gac | agg | gag | tac | tat | agt | gtt | caa | cag | cat | cgc | cac | gct | cgc | 3744 |
| Leu | Asp | Arg | Glu | Tyr | Tyr | Ser | Val | Gln | Gln | His | Arg | His | Ala | Arg | |
| | 1235 | | | | 1240 | | | | | 1245 | | | | | |
| cta | cct | gtg | aag | tgg | atg | gcg | ctg | gag | agc | ctg | cag | acc | tat | aga | 3789 |
| Leu | Pro | Val | Lys | Trp | Met | Ala | Leu | Glu | Ser | Leu | Gln | Thr | Tyr | Arg | |
| | 1250 | | | | 1255 | | | | | 1260 | | | | | |
| ttt | acc | acc | aag | tct | gat | gtg | tgg | tca | ttt | ggt | gtg | ctg | ctg | tgg | 3834 |
| Phe | Thr | Thr | Lys | Ser | Asp | Val | Trp | Ser | Phe | Gly | Val | Leu | Leu | Trp | |
| | 1265 | | | | 1270 | | | | | 1275 | | | | | |
| gaa | ctg | ctg | aca | cgg | ggt | gcc | cca | cca | tac | cgc | cac | att | gac | cct | 3879 |
| Glu | Leu | Leu | Thr | Arg | Gly | Ala | Pro | Pro | Tyr | Arg | His | Ile | Asp | Pro | |
| | 1280 | | | | 1285 | | | | | 1290 | | | | | |
| ttt | gac | ctt | acc | cac | ttc | ctg | gcc | cag | ggt | cgg | cgc | ctg | ccc | cag | 3924 |
| Phe | Asp | Leu | Thr | His | Phe | Leu | Ala | Gln | Gly | Arg | Arg | Leu | Pro | Gln | |
| | 1295 | | | | 1300 | | | | | 1305 | | | | | |
| cct | gag | tat | tgc | cct | gat | tct | ctg | tac | caa | gtg | atg | cag | caa | tgc | 3969 |
| Pro | Glu | Tyr | Cys | Pro | Asp | Ser | Leu | Tyr | Gln | Val | Met | Gln | Gln | Cys | |
| | 1310 | | | | 1315 | | | | | 1320 | | | | | |
| tgg | gag | gca | gac | cca | gca | gtg | cga | ccc | acc | ttc | aga | gta | cta | gtg | 4014 |
| Trp | Glu | Ala | Asp | Pro | Ala | Val | Arg | Pro | Thr | Phe | Arg | Val | Leu | Val | |
| | 1325 | | | | 1330 | | | | | 1335 | | | | | |
| ggg | gag | gtg | gag | cag | ata | gtg | tct | gca | ctg | ctt | ggg | gac | cat | tat | 4059 |
| Gly | Glu | Val | Glu | Gln | Ile | Val | Ser | Ala | Leu | Leu | Gly | Asp | His | Tyr | |
| | 1340 | | | | 1345 | | | | | 1350 | | | | | |
| gtg | cag | ctg | cca | gca | acc | tac | atg | aac | ttg | ggc | ccc | agc | acc | tcg | 4104 |
| Val | Gln | Leu | Pro | Ala | Thr | Tyr | Met | Asn | Leu | Gly | Pro | Ser | Thr | Ser | |
| | 1355 | | | | 1360 | | | | | 1365 | | | | | |
| cat | gag | atg | aat | gtg | cgt | cca | gaa | cag | ccg | cag | ttc | tca | ccc | atg | 4149 |
| His | Glu | Met | Asn | Val | Arg | Pro | Glu | Gln | Pro | Gln | Phe | Ser | Pro | Met | |
| | 1370 | | | | 1375 | | | | | 1380 | | | | | |
| cca | ggg | aat | gta | cgc | cgg | ccc | cgg | cca | ctc | tca | gag | cct | cct | cgg | 4194 |
| Pro | Gly | Asn | Val | Arg | Arg | Pro | Arg | Pro | Leu | Ser | Glu | Pro | Pro | Arg | |
| | 1385 | | | | 1390 | | | | | 1395 | | | | | |
| ccc | act | tga | | | | | | | | | | | | | 4203 |
| Pro | Thr | | | | | | | | | | | | | | |
| | 1400 | | | | | | | | | | | | | | |

<210> SEQ ID NO 42
<211> LENGTH: 1400
<212> TYPE: PRT
<213> ORGANISM: Homo sapiens

<400> SEQUENCE: 42

Met Glu Leu Leu Pro Pro Leu Pro Gln Ser Phe Leu Leu Leu Leu
1               5                   10                  15

```
Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
                35                  40                  45

Phe Ser Ala Gly Gly Leu Val Gln Ala Met Val Thr Tyr Glu Gly Asp
 50                      55                  60

Arg Asn Glu Ser Ala Val Phe Val Ala Ile Arg Asn Arg Leu His Val
 65                  70                  75                  80

Leu Gly Pro Asp Leu Lys Ser Val Gln Ser Leu Ala Thr Gly Pro Ala
                 85                  90                  95

Gly Asp Pro Gly Cys Gln Thr Cys Ala Ala Cys Gly Pro Gly Pro His
                100                 105                 110

Gly Pro Pro Gly Asp Thr Asp Thr Lys Val Leu Val Leu Asp Pro Ala
            115                 120                 125

Leu Pro Ala Leu Val Ser Cys Gly Ser Ser Leu Gln Gly Arg Cys Phe
130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Ala Ser Phe Ser Pro Arg Ser Val Ser Ile Arg Arg Leu Lys Ala Asp
210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
290                 295                 300

Lys Arg Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
```

```
                435                 440                 445
Thr Ala Leu Tyr Val Thr Arg Leu Asp Asn Val Thr Val Ala His Met
    450                 455                 460
Gly Thr Met Asp Gly Arg Ile Leu Gln Val Glu Leu Val Arg Ser Leu
465                 470                 475                 480
Asn Tyr Leu Leu Tyr Val Ser Asn Phe Ser Leu Gly Asp Ser Gly Gln
                485                 490                 495
Pro Val Gln Arg Asp Val Ser Arg Leu Gly Asp His Leu Leu Phe Ala
                500                 505                 510
Ser Gly Asp Gln Val Phe Gln Val Pro Ile Gln Gly Pro Gly Cys Arg
            515                 520                 525
His Phe Leu Thr Cys Gly Arg Cys Leu Arg Ala Trp His Phe Met Gly
        530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
        595                 600                 605
Val Thr Val Gly Gln Ser Pro Cys Arg Pro Leu Pro Lys Asp Ser Ser
610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
                660                 665                 670
Thr Ser Val Leu Arg Gly Phe Ser Phe Met Glu Pro Val Leu Ile Ala
            675                 680                 685
Val Gln Pro Leu Phe Gly Pro Arg Ala Gly Gly Thr Cys Leu Thr Leu
        690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
                740                 745                 750
Val Gly Gly Ala Gln Val Pro Gly Ser Trp Thr Phe Gln Tyr Arg Glu
            755                 760                 765
Asp Pro Val Val Leu Ser Ile Ser Pro Asn Cys Gly Tyr Ile Asn Ser
        770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
Asp Pro Gln Gly Trp Val Ala Gly Asn Leu Ser Ala Arg Gly Asp Gly
        835                 840                 845
Ala Ala Gly Phe Thr Leu Pro Gly Phe Arg Phe Leu Pro Pro Pro His
    850                 855                 860
```

```
Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
            885                 890                 895

Asn Val Thr Val Gly Gly Glu Ser Cys Gln His Glu Phe Arg Gly Asp
        900                 905                 910

Met Val Val Cys Pro Leu Pro Pro Ser Leu Gln Leu Gly Gln Asp Gly
    915                 920                 925

Ala Pro Leu Gln Val Cys Val Asp Gly Glu Cys His Ile Leu Gly Arg
930                 935                 940

Val Val Arg Pro Gly Pro Asp Gly Val Pro Gln Ser Thr Leu Leu Gly
945                 950                 955                 960

Ile Leu Leu Pro Leu Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
            980                 985                 990

Leu Asn Asp Leu Ala Ser Leu Asp Gln Thr Ala Gly Ala Thr Pro Leu
            995                 1000                1005

Pro Ile Leu Tyr Ser Gly Ser Asp Tyr Arg Ser Gly Leu Ala Leu
    1010                1015                1020

Pro Ala Ile Asp Gly Leu Asp Ser Thr Thr Cys Val His Gly Ala
    1025                1030                1035

Ser Phe Ser Asp Ser Glu Asp Glu Ser Cys Val Pro Leu Leu Arg
    1040                1045                1050

Lys Glu Ser Ile Gln Leu Arg Asp Leu Asp Ser Ala Leu Leu Ala
    1055                1060                1065

Glu Val Lys Asp Val Leu Ile Pro His Glu Arg Val Val Thr His
    1070                1075                1080

Ser Asp Arg Val Ile Gly Lys Gly His Phe Gly Val Val Tyr His
    1085                1090                1095

Gly Glu Tyr Ile Asp Gln Ala Gln Asn Arg Ile Gln Cys Ala Ile
    1100                1105                1110

Lys Ser Leu Ser Arg Ile Thr Glu Met Gln Gln Val Glu Ala Phe
    1115                1120                1125

Leu Arg Glu Gly Leu Leu Met Arg Gly Leu Asn His Pro Asn Val
    1130                1135                1140

Leu Ala Leu Ile Gly Ile Met Leu Pro Pro Glu Gly Leu Pro His
    1145                1150                1155

Val Leu Leu Pro Tyr Met Cys His Gly Asp Leu Leu Gln Phe Ile
    1160                1165                1170

Arg Ser Pro Gln Arg Asn Pro Thr Val Lys Asp Leu Ile Ser Phe
    1175                1180                1185

Gly Leu Gln Val Ala Arg Gly Met Glu Tyr Leu Ala Glu Gln Lys
    1190                1195                1200

Phe Val His Arg Asp Leu Ala Ala Arg Asn Cys Met Leu Asp Glu
    1205                1210                1215

Ser Phe Thr Val Lys Val Ala Asp Phe Gly Leu Ala Arg Asp Ile
    1220                1225                1230

Leu Asp Arg Glu Tyr Tyr Ser Val Gln Gln His Arg His Ala Arg
    1235                1240                1245

Leu Pro Val Lys Trp Met Ala Leu Glu Ser Leu Gln Thr Tyr Arg
    1250                1255                1260
```

```
Phe Thr Thr Lys Ser Asp Val Trp Ser Phe Gly Val Leu Leu Trp
1265                1270                1275

Glu Leu Leu Thr Arg Gly Ala Pro Pro Tyr Arg His Ile Asp Pro
1280                1285                1290

Phe Asp Leu Thr His Phe Leu Ala Gln Gly Arg Arg Leu Pro Gln
1295                1300                1305

Pro Glu Tyr Cys Pro Asp Ser Leu Tyr Gln Val Met Gln Gln Cys
1310                1315                1320

Trp Glu Ala Asp Pro Ala Val Arg Pro Thr Phe Arg Val Leu Val
1325                1330                1335

Gly Glu Val Glu Gln Ile Val Ser Ala Leu Leu Gly Asp His Tyr
1340                1345                1350

Val Gln Leu Pro Ala Thr Tyr Met Asn Leu Gly Pro Ser Thr Ser
1355                1360                1365

His Glu Met Asn Val Arg Pro Glu Gln Pro Gln Phe Ser Pro Met
1370                1375                1380

Pro Gly Asn Val Arg Arg Pro Arg Pro Leu Ser Glu Pro Pro Arg
1385                1390                1395

Pro Thr
1400

<210> SEQ ID NO 43
<211> LENGTH: 2745
<212> TYPE: DNA
<213> ORGANISM: Artificial Sequence
<220> FEATURE:
<223> OTHER INFORMATION: Synthetic human RON fusion protein
<220> FEATURE:
<221> NAME/KEY: CDS
<222> LOCATION: (1)..(2745)

<400> SEQUENCE: 43 atg gag ctc ctc ccg ccg ctg cct cag tcc ttc ctg ttg ctg ctg ctg      48
Met Glu Leu Leu Pro Pro Leu Pro Gln Ser Phe Leu Leu Leu Leu Leu
1               5                   10                  15 ttg cct gcc aag ccc gcg gcg ggc gag gac tgg cag tgc ccg cgc acc      96
Leu Pro Ala Lys Pro Ala Ala Gly Glu Asp Trp Gln Cys Pro Arg Thr
            20                  25                  30 ccc tac gcg gcc tct cgc gac ttt gac gtg aag tac gtg gtg ccc agc     144
Pro Tyr Ala Ala Ser Arg Asp Phe Asp Val Lys Tyr Val Val Pro Ser
        35                  40                  45 ttc tcc gcc gga ggc ctg gta cag gcc atg gtg acc tac gag ggc gac     192
Phe Ser Ala Gly Gly Leu Val Gln Ala Met Val Thr Tyr Glu Gly Asp
    50                  55                  60 aga aat gag agt gct gtg ttt gta gcc ata cgc aat cgc ctg cat gtg     240
Arg Asn Glu Ser Ala Val Phe Val Ala Ile Arg Asn Arg Leu His Val
65                  70                  75                  80 ctt ggg cct gac ctg aag tct gtc cag agc ctg gcc acg ggc cct gct     288
Leu Gly Pro Asp Leu Lys Ser Val Gln Ser Leu Ala Thr Gly Pro Ala
                85                  90                  95 gga gac cct ggc tgc cag acg tgt gca gcc tgt ggc cca gga ccc cac     336
Gly Asp Pro Gly Cys Gln Thr Cys Ala Ala Cys Gly Pro Gly Pro His
            100                 105                 110 ggc cct ccc ggt gac aca gac aca aag gtg ctg gtg ctg gat ccc gcg     384
Gly Pro Pro Gly Asp Thr Asp Thr Lys Val Leu Val Leu Asp Pro Ala
        115                 120                 125 ctg cct gcg ctg gtc agt tgt ggc tcc agc ctg cag ggc cgc tgc ttc     432
Leu Pro Ala Leu Val Ser Cys Gly Ser Ser Leu Gln Gly Arg Cys Phe
    130                 135                 140
```

-continued

| | | |
|---|---|---|
| ctg cat gac cta gag ccc caa ggg aca gcc gtg cat ctg gca gcg cca<br>Leu His Asp Leu Glu Pro Gln Gly Thr Ala Val His Leu Ala Ala Pro<br>145                              150                       155                   160 | 480 |
| gcc tgc ctc ttc tca gcc cac cat aac cgg ccc gat gac tgc ccc gac<br>Ala Cys Leu Phe Ser Ala His His Asn Arg Pro Asp Asp Cys Pro Asp<br>                 165                     170                     175 | 528 |
| tgt gtg gcc agc cca ttg ggc acc cgt gta act gtg gtt gag caa ggc<br>Cys Val Ala Ser Pro Leu Gly Thr Arg Val Thr Val Val Glu Gln Gly<br>              180                     185                  190 | 576 |
| cag gcc tcc tat ttc tac gtg gca tcc tca ctg gac gca gcc gtg gct<br>Gln Ala Ser Tyr Phe Tyr Val Ala Ser Ser Leu Asp Ala Ala Val Ala<br>       195                     200                     205 | 624 |
| gcc agc ttc agc cca cgc tca gtg tct atc agg cgt ctc aag gct gac<br>Ala Ser Phe Ser Pro Arg Ser Val Ser Ile Arg Arg Leu Lys Ala Asp<br>210                              215                     220 | 672 |
| gcc tcg gga ttc gca ccg ggc ttt gtg gcg ttg tca gtg ctg ccc aag<br>Ala Ser Gly Phe Ala Pro Gly Phe Val Ala Leu Ser Val Leu Pro Lys<br>225                            230                     235                  240 | 720 |
| cat ctt gtc tcc tac agt att gaa tac gtg cac agc ttc cac acg gga<br>His Leu Val Ser Tyr Ser Ile Glu Tyr Val His Ser Phe His Thr Gly<br>                          245                     250                  255 | 768 |
| gcc ttc gta tac ttc ctg act gta cag ccg gcc agc gtg aca gat gat<br>Ala Phe Val Tyr Phe Leu Thr Val Gln Pro Ala Ser Val Thr Asp Asp<br>                 260                     265                     270 | 816 |
| cct agt gcc ctg cac aca cgc ctg gca cgg ctt agc gcc act gag cca<br>Pro Ser Ala Leu His Thr Arg Leu Ala Arg Leu Ser Ala Thr Glu Pro<br>      275                     280                     285 | 864 |
| gag ttg ggt gac tat cgg gag ctg gtc ctc gac tgc aga ttt gct cca<br>Glu Leu Gly Asp Tyr Arg Glu Leu Val Leu Asp Cys Arg Phe Ala Pro<br>290                              295                     300 | 912 |
| aaa cgc agg cgc cgg ggg gcc cca gaa ggc gga cag ccc tac cct gtg<br>Lys Arg Arg Arg Arg Gly Ala Pro Glu Gly Gly Gln Pro Tyr Pro Val<br>305                              310                     315                  320 | 960 |
| ctg cgg gtg gcc cac tcc gct cca gtg ggt gcc caa ctt gcc act gag<br>Leu Arg Val Ala His Ser Ala Pro Val Gly Ala Gln Leu Ala Thr Glu<br>                       325                     330                  335 | 1008 |
| ctg agc atc gcc gag ggc cag gaa gta cta ttt ggg gtc ttt gtg act<br>Leu Ser Ile Ala Glu Gly Gln Glu Val Leu Phe Gly Val Phe Val Thr<br>               340                     345                  350 | 1056 |
| ggc aag gat ggt ggt cct ggc gtg ggc ccc aac tct gtc gtc tgt gcc<br>Gly Lys Asp Gly Gly Pro Gly Val Gly Pro Asn Ser Val Val Cys Ala<br>      355                     360                     365 | 1104 |
| ttc ccc att gac ctg ctg gac aca cta att gat gag ggt gtg gag cgc<br>Phe Pro Ile Asp Leu Leu Asp Thr Leu Ile Asp Glu Gly Val Glu Arg<br>370                              375                     380 | 1152 |
| tgt tgt gaa tcc cca gtc cat cca ggc ctc cgg cga ggc ctc gac ttc<br>Cys Cys Glu Ser Pro Val His Pro Gly Leu Arg Arg Gly Leu Asp Phe<br>385                              390                     395                  400 | 1200 |
| ttc cag tcg ccc agt ttt tgc ccc aac ccg cct ggc ctg gaa gcc ctc<br>Phe Gln Ser Pro Ser Phe Cys Pro Asn Pro Pro Gly Leu Glu Ala Leu<br>               405                     410                  415 | 1248 |
| agc ccc aac acc agc tgc cgc cac ttc cct ctg ctg gtc agt agc agc<br>Ser Pro Asn Thr Ser Cys Arg His Phe Pro Leu Leu Val Ser Ser Ser<br>                 420                     425                     430 | 1296 |
| ttc tca cgt gtg gac cta ttc aat ggg ctg ttg gga cca gta cag gtc<br>Phe Ser Arg Val Asp Leu Phe Asn Gly Leu Leu Gly Pro Val Gln Val<br>               435                     440                  445 | 1344 |
| act gca ttg tat gtg aca cgc ctt gac aac gtc aca gtg gca cac atg<br>Thr Ala Leu Tyr Val Thr Arg Leu Asp Asn Val Thr Val Ala His Met<br>450                              455                     460 | 1392 |

```
ggc aca atg gat ggg cgt atc ctg cag gtg gag ctg tcc agg tca cta      1440
Gly Thr Met Asp Gly Arg Ile Leu Gln Val Glu Leu Val Arg Ser Leu
465             470                 475                 480 aac tac ttg ctg tat gtg tcc aac ttc tca ctg ggt gac agt ggg cag      1488
Asn Tyr Leu Leu Tyr Val Ser Asn Phe Ser Leu Gly Asp Ser Gly Gln
                485                 490                 495 ccc gtg cag cgg gat gtc agt cgt ctt ggg gac cac cta ctc ttt gcc      1536
Pro Val Gln Arg Asp Val Ser Arg Leu Gly Asp His Leu Leu Phe Ala
            500                 505                 510 tct ggg gac cag gtt ttc cag gta cct atc caa ggc cct ggc tgc cgc      1584
Ser Gly Asp Gln Val Phe Gln Val Pro Ile Gln Gly Pro Gly Cys Arg
        515                 520                 525 cac ttc ctg acc tgt ggg cgt tgc cta agg gca tgg cat ttc atg ggc      1632
His Phe Leu Thr Cys Gly Arg Cys Leu Arg Ala Trp His Phe Met Gly
    530                 535                 540 tgt ggc tgg tgt ggg aac atg tgc ggc cag cag aag gag tgt cct ggc      1680
Cys Gly Trp Cys Gly Asn Met Cys Gly Gln Gln Lys Glu Cys Pro Gly
545                 550                 555                 560 tcc tgg caa cag gac cac tgc cca cct aag ctt act gag ttc cac ccc      1728
Ser Trp Gln Gln Asp His Cys Pro Pro Lys Leu Thr Glu Phe His Pro
                565                 570                 575 cac agt gga cct cta agg ggc agt aca agg ctg acc ctg tgt ggc tcc      1776
His Ser Gly Pro Leu Arg Gly Ser Thr Arg Leu Thr Leu Cys Gly Ser
            580                 585                 590 aac ttc tac ctt cac cct tct ggt ctg gtg cct gag gga acc cat cag      1824
Asn Phe Tyr Leu His Pro Ser Gly Leu Val Pro Glu Gly Thr His Gln
        595                 600                 605 gtc act gtg ggc caa agt ccc tgc cgg cca ctg ccc aag gac agc tca      1872
Val Thr Val Gly Gln Ser Pro Cys Arg Pro Leu Pro Lys Asp Ser Ser
    610                 615                 620 aaa ctc aga cca gtg ccc cgg aaa gac ttt gta gag gag ttt gag tgt      1920
Lys Leu Arg Pro Val Pro Arg Lys Asp Phe Val Glu Glu Phe Glu Cys
625                 630                 635                 640 gaa ctg gag ccc ttg ggc acc cag gca gtg ggg cct acc aac gtc agc      1968
Glu Leu Glu Pro Leu Gly Thr Gln Ala Val Gly Pro Thr Asn Val Ser
                645                 650                 655 ctc acc gtg act aac atg cca ccg ggc aag cac ttc cgg gta gac ggc      2016
Leu Thr Val Thr Asn Met Pro Pro Gly Lys His Phe Arg Val Asp Gly
            660                 665                 670 acc tcc gtg ctg aga ggc ttc tct ttc atg acc ggt acg gtc acc gac      2064
Thr Ser Val Leu Arg Gly Phe Ser Phe Met Thr Gly Thr Val Thr Asp
        675                 680                 685 aaa act cac aca tgc cca ccg tgc cca gca cct gaa ctc ctg ggg gga      2112
Lys Thr His Thr Cys Pro Pro Cys Pro Ala Pro Glu Leu Leu Gly Gly
    690                 695                 700 ccg tca gtc ttc ctc ttc ccc cca aaa ccc aag gac acc ctc atg atc      2160
Pro Ser Val Phe Leu Phe Pro Pro Lys Pro Lys Asp Thr Leu Met Ile
705                 710                 715                 720 tcc cgg acc cct gag gtc aca tgc gtg gtg gtg gac gtg agc cac gaa      2208
Ser Arg Thr Pro Glu Val Thr Cys Val Val Val Asp Val Ser His Glu
                725                 730                 735 gac cct gag gtc aag ttc aac tgg tac gtg gac ggc gtg gag gtg cat      2256
Asp Pro Glu Val Lys Phe Asn Trp Tyr Val Asp Gly Val Glu Val His
            740                 745                 750 aat gcc aag aca aag ccg cgg gag gag cag tac aac agc acg tac cgt      2304
Asn Ala Lys Thr Lys Pro Arg Glu Glu Gln Tyr Asn Ser Thr Tyr Arg
        755                 760                 765 gtg gtc agc gtc ctc acc gtc ctg cac cag gac tgg ctg aat ggc aag      2352
Val Val Ser Val Leu Thr Val Leu His Gln Asp Trp Leu Asn Gly Lys
```

```
                770                 775                 780
gag tac aag tgc aag gtc tcc aac aaa gcc ctc cca gcc ccc atc gag      2400
Glu Tyr Lys Cys Lys Val Ser Asn Lys Ala Leu Pro Ala Pro Ile Glu
785                 790                 795                 800 aaa acc atc tcc aaa gcc aaa ggg cag ccc cga gaa cca cag gtg tac      2448
Lys Thr Ile Ser Lys Ala Lys Gly Gln Pro Arg Glu Pro Gln Val Tyr
            805                 810                 815 acc ctg ccc cca tcc cgg gaa gag atg acc aag aac cag gtc agc ctg      2496
Thr Leu Pro Pro Ser Arg Glu Glu Met Thr Lys Asn Gln Val Ser Leu
        820                 825                 830 acc tgc ctg gtc aaa ggc ttc tat ccc agc gac atc gcc gtg gag tgg      2544
Thr Cys Leu Val Lys Gly Phe Tyr Pro Ser Asp Ile Ala Val Glu Trp
    835                 840                 845 gag agc aat ggg cag ccg gag aac aac tac aag acc acg cct ccc gtg      2592
Glu Ser Asn Gly Gln Pro Glu Asn Asn Tyr Lys Thr Thr Pro Pro Val
850                 855                 860 ctg gac tcc gac ggc tcc ttc ttc ctc tac agc aag ctc acc gtg gac      2640
Leu Asp Ser Asp Gly Ser Phe Phe Leu Tyr Ser Lys Leu Thr Val Asp
865                 870                 875                 880 aag agc agg tgg cag cag ggg aac gtc ttc tca tgc tcc gtg atg cat      2688
Lys Ser Arg Trp Gln Gln Gly Asn Val Phe Ser Cys Ser Val Met His
            885                 890                 895 gag gct ctg cac aac cac tac acg cag aag agc ctc tcc ctg tct ccg      2736
Glu Ala Leu His Asn His Tyr Thr Gln Lys Ser Leu Ser Leu Ser Pro
        900                 905                 910 ggt aaa tga                                                          2745
Gly Lys
```

<210> SEQ ID NO 44
<211> LENGTH: 914
<212> TYPE: PRT
<213> ORGANISM: Artificial Sequence
<220> FEATURE:
<223> OTHER INFORMATION: Synthetic human RON fusion protein

<400> SEQUENCE: 44

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175
```

```
Cys Val Ala Ser Pro Leu Gly Thr Arg Val Thr Val Glu Gln Gly
                180                 185                 190

Gln Ala Ser Tyr Phe Tyr Val Ala Ser Ser Leu Asp Ala Ala Val Ala
        195                 200                 205

Ala Ser Phe Ser Pro Arg Ser Val Ser Ile Arg Arg Leu Lys Ala Asp
210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
                260                 265                 270

Pro Ser Ala Leu His Thr Arg Leu Ala Arg Leu Ser Ala Thr Glu Pro
                275                 280                 285

Glu Leu Gly Asp Tyr Arg Glu Leu Val Leu Asp Cys Arg Phe Ala Pro
            290                 295                 300

Lys Arg Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
                340                 345                 350

Gly Lys Asp Gly Gly Pro Gly Val Gly Pro Asn Ser Val Val Cys Ala
            355                 360                 365

Phe Pro Ile Asp Leu Leu Asp Thr Leu Ile Asp Glu Gly Val Glu Arg
            370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
                420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Gln Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590
```

```
Asn Phe Tyr Leu His Pro Ser Gly Leu Val Pro Glu Gly Thr His Gln
            595                 600                 605

Val Thr Val Gly Gln Ser Pro Cys Arg Pro Leu Pro Lys Asp Ser Ser
610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
            645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Thr Gly Thr Val Thr Asp
            675                 680                 685

Lys Thr His Thr Cys Pro Pro Cys Pro Ala Pro Glu Leu Leu Gly Gly
            690                 695                 700

Pro Ser Val Phe Leu Phe Pro Pro Lys Pro Lys Asp Thr Leu Met Ile
705                 710                 715                 720

Ser Arg Thr Pro Glu Val Thr Cys Val Val Asp Val Ser His Glu
                725                 730                 735

Asp Pro Glu Val Lys Phe Asn Trp Tyr Val Asp Gly Val Glu Val His
            740                 745                 750

Asn Ala Lys Thr Lys Pro Arg Glu Glu Gln Tyr Asn Ser Thr Tyr Arg
            755                 760                 765

Val Val Ser Val Leu Thr Val Leu His Gln Asp Trp Leu Asn Gly Lys
770                 775                 780

Glu Tyr Lys Cys Lys Val Ser Asn Lys Ala Leu Pro Ala Pro Ile Glu
785                 790                 795                 800

Lys Thr Ile Ser Lys Ala Lys Gly Gln Pro Arg Glu Pro Gln Val Tyr
            805                 810                 815

Thr Leu Pro Pro Ser Arg Glu Glu Met Thr Lys Asn Gln Val Ser Leu
            820                 825                 830

Thr Cys Leu Val Lys Gly Phe Tyr Pro Ser Asp Ile Ala Val Glu Trp
            835                 840                 845

Glu Ser Asn Gly Gln Pro Glu Asn Asn Tyr Lys Thr Thr Pro Pro Val
850                 855                 860

Leu Asp Ser Asp Gly Ser Phe Phe Leu Tyr Ser Lys Leu Thr Val Asp
865                 870                 875                 880

Lys Ser Arg Trp Gln Gln Gly Asn Val Phe Ser Cys Ser Val Met His
            885                 890                 895

Glu Ala Leu His Asn His Tyr Thr Gln Lys Ser Leu Ser Leu Ser Pro
            900                 905                 910

Gly Lys

<210> SEQ ID NO 45
<211> LENGTH: 2079
<212> TYPE: DNA
<213> ORGANISM: Artificial Sequence
<220> FEATURE:
<223> OTHER INFORMATION: Synthetic human RON polypeptide
<220> FEATURE:
<221> NAME/KEY: CDS
<222> LOCATION: (1)..(2079)

<400> SEQUENCE: 45 atg gag ctc ctc ccg ccg ctg cct cag tcc ttc ctg ttg ctg ctg        48
Met Glu Leu Leu Pro Pro Leu Pro Gln Ser Phe Leu Leu Leu Leu
1               5                   10                  15
```

-continued

| | |
|---|---|
| ttg cct gcc aag ccc gcg gcg ggc gag gac tgg cag tgc ccg cgc acc<br>Leu Pro Ala Lys Pro Ala Ala Gly Glu Asp Trp Gln Cys Pro Arg Thr<br>            20                    25                   30 | 96 |
| ccc tac gcg gcc tct cgc gac ttt gac gtg aag tac gtg gtg ccc agc<br>Pro Tyr Ala Ala Ser Arg Asp Phe Asp Val Lys Tyr Val Val Pro Ser<br>            35                    40                   45 | 144 |
| ttc tcc gcc gga ggc ctg gta cag gcc atg gtg acc tac gag ggc gac<br>Phe Ser Ala Gly Gly Leu Val Gln Ala Met Val Thr Tyr Glu Gly Asp<br>      50                    55                   60 | 192 |
| aga aat gag agt gct gtg ttt gta gcc ata cgc aat cgc ctg cat gtg<br>Arg Asn Glu Ser Ala Val Phe Val Ala Ile Arg Asn Arg Leu His Val<br>65                   70                    75                   80 | 240 |
| ctt ggg cct gac ctg aag tct gtc cag agc ctg gcc acg ggc cct gct<br>Leu Gly Pro Asp Leu Lys Ser Val Gln Ser Leu Ala Thr Gly Pro Ala<br>                  85                    90                   95 | 288 |
| gga gac cct ggc tgc cag acg tgt gca gcc tgt ggc cca gga ccc cac<br>Gly Asp Pro Gly Cys Gln Thr Cys Ala Ala Cys Gly Pro Gly Pro His<br>                100                   105               110 | 336 |
| ggc cct ccc ggt gac aca gac aca aag gtg ctg gtg ctg gat ccc gcg<br>Gly Pro Pro Gly Asp Thr Asp Thr Lys Val Leu Val Leu Asp Pro Ala<br>            115                   120               125 | 384 |
| ctg cct gcg ctg gtc agt tgt ggc tcc agc ctg cag ggc cgc tgc ttc<br>Leu Pro Ala Leu Val Ser Cys Gly Ser Ser Leu Gln Gly Arg Cys Phe<br>130                   135                   140 | 432 |
| ctg cat gac cta gag ccc caa ggg aca gcc gtg cat ctg gca gcg cca<br>Leu His Asp Leu Glu Pro Gln Gly Thr Ala Val His Leu Ala Ala Pro<br>145                   150                   155               160 | 480 |
| gcc tgc ctc ttc tca gcc cac cat aac cgg ccc gat gac tgc ccc gac<br>Ala Cys Leu Phe Ser Ala His His Asn Arg Pro Asp Asp Cys Pro Asp<br>                       165                   170               175 | 528 |
| tgt gtg gcc agc cca ttg ggc acc cgt gta act gtg gtt gag caa ggc<br>Cys Val Ala Ser Pro Leu Gly Thr Arg Val Thr Val Val Glu Gln Gly<br>            180                   185               190 | 576 |
| cag gcc tcc tat ttc tac gtg gca tcc tca ctg gac gca gcc gtg gct<br>Gln Ala Ser Tyr Phe Tyr Val Ala Ser Ser Leu Asp Ala Ala Val Ala<br>                 195                   200               205 | 624 |
| gcc agc ttc agc cca cgc tca gtg tct atc agg cgt ctc aag gct gac<br>Ala Ser Phe Ser Pro Arg Ser Val Ser Ile Arg Arg Leu Lys Ala Asp<br>      210                    215                   220 | 672 |
| gcc tcg gga ttc gca ccg ggc ttt gtg gcg ttg tca gtg ctg ccc aag<br>Ala Ser Gly Phe Ala Pro Gly Phe Val Ala Leu Ser Val Leu Pro Lys<br>225                   230                   235               240 | 720 |
| cat ctt gtc tcc tac agt att gaa tac gtg cac agc ttc cac acg gga<br>His Leu Val Ser Tyr Ser Ile Glu Tyr Val His Ser Phe His Thr Gly<br>                     245                   250               255 | 768 |
| gcc ttc gta tac ttc ctg act gta cag ccg gcc agc gtg aca gat gat<br>Ala Phe Val Tyr Phe Leu Thr Val Gln Pro Ala Ser Val Thr Asp Asp<br>              260                   265               270 | 816 |
| cct agt gcc ctg cac aca cgc ctg gca cgg ctt agc gcc act gag cca<br>Pro Ser Ala Leu His Thr Arg Leu Ala Arg Leu Ser Ala Thr Glu Pro<br>            275                   280               285 | 864 |
| gag ttg ggt gac tat cgg gag ctg gtc ctc gac tgc aga ttt gct cca<br>Glu Leu Gly Asp Tyr Arg Glu Leu Val Leu Asp Cys Arg Phe Ala Pro<br>290                   295                   300 | 912 |
| aaa cgc agg cgc cgg ggg gcc cca gaa ggc gga cag ccc tac cct gtg<br>Lys Arg Arg Arg Arg Gly Ala Pro Glu Gly Gly Gln Pro Tyr Pro Val<br>305                   310                   315               320 | 960 |
| ctg cgg gtg gcc cac tcc gct cca gtg ggt gcc caa ctt gcc act gag<br>Leu Arg Val Ala His Ser Ala Pro Val Gly Ala Gln Leu Ala Thr Glu<br>              325                   330               335 | 1008 |

```
ctg agc atc gcc gag ggc cag gaa gta cta ttt ggg gtc ttt gtg act    1056
Leu Ser Ile Ala Glu Gly Gln Glu Val Leu Phe Gly Val Phe Val Thr
            340                 345                 350 ggc aag gat ggt ggt cct ggc gtg ggc ccc aac tct gtc gtc tgt gcc    1104
Gly Lys Asp Gly Gly Pro Gly Val Gly Pro Asn Ser Val Val Cys Ala
                355                 360                 365 ttc ccc att gac ctg ctg gac aca cta att gat gag ggt gtg gag cgc    1152
Phe Pro Ile Asp Leu Leu Asp Thr Leu Ile Asp Glu Gly Val Glu Arg
    370                 375                 380 tgt tgt gaa tcc cca gtc cat cca ggc ctc cgg cga ggc ctc gac ttc    1200
Cys Cys Glu Ser Pro Val His Pro Gly Leu Arg Arg Gly Leu Asp Phe
385                 390                 395                 400 ttc cag tcg ccc agt ttt tgc ccc aac ccg cct ggc ctg gaa gcc ctc    1248
Phe Gln Ser Pro Ser Phe Cys Pro Asn Pro Pro Gly Leu Glu Ala Leu
                405                 410                 415 agc ccc aac acc agc tgc cgc cac ttc cct ctg ctc gtc agt agc agc    1296
Ser Pro Asn Thr Ser Cys Arg His Phe Pro Leu Leu Val Ser Ser Ser
            420                 425                 430 ttc tca cgt gtg gac cta ttc aat ggg ctg ttg gga cca gta cag gtc    1344
Phe Ser Arg Val Asp Leu Phe Asn Gly Leu Leu Gly Pro Val Gln Val
        435                 440                 445 act gca ttg tat gtg aca cgc ctt gac aac gtc aca gtg gca cac atg    1392
Thr Ala Leu Tyr Val Thr Arg Leu Asp Asn Val Thr Val Ala His Met
450                 455                 460 ggc aca atg gat ggg cgt atc ctg cag gtg gag ctg gtc agg tca cta    1440
Gly Thr Met Asp Gly Arg Ile Leu Gln Val Glu Leu Val Arg Ser Leu
465                 470                 475                 480 aac tac ttg ctg tat gtg tcc aac ttc tca ctg ggt gac agt ggg cag    1488
Asn Tyr Leu Leu Tyr Val Ser Asn Phe Ser Leu Gly Asp Ser Gly Gln
                485                 490                 495 ccc gtg cag cgg gat gtc agt cgt ctt ggg gac cac cta ctc ttt gcc    1536
Pro Val Gln Arg Asp Val Ser Arg Leu Gly Asp His Leu Leu Phe Ala
            500                 505                 510 tct ggg gac cag gtt ttc cag gta cct atc caa ggc cct ggc tgc cgc    1584
Ser Gly Asp Gln Val Phe Gln Val Pro Ile Gln Gly Pro Gly Cys Arg
        515                 520                 525 cac ttc ctg acc tgt ggg cgt tgc cta agg gca tgg cat ttc atg ggc    1632
His Phe Leu Thr Cys Gly Arg Cys Leu Arg Ala Trp His Phe Met Gly
530                 535                 540 tgt ggc tgg tgt ggg aac atg tgc ggc cag cag aag gag tgt cct ggc    1680
Cys Gly Trp Cys Gly Asn Met Cys Gly Gln Gln Lys Glu Cys Pro Gly
545                 550                 555                 560 tcc tgg caa cag gac cac tgc cca cct aag ctt act gag ttc cac ccc    1728
Ser Trp Gln Gln Asp His Cys Pro Pro Lys Leu Thr Glu Phe His Pro
                565                 570                 575 cac agt gga cct cta agg ggc agt aca agg ctg acc ctg tgt ggc tcc    1776
His Ser Gly Pro Leu Arg Gly Ser Thr Arg Leu Thr Leu Cys Gly Ser
            580                 585                 590 aac ttc tac ctt cac cct tct ggt ctg gtg cct gag gga acc cat cag    1824
Asn Phe Tyr Leu His Pro Ser Gly Leu Val Pro Glu Gly Thr His Gln
        595                 600                 605 gtc act gtg ggc caa agt ccc tgc cgg cca ctg ccc aag gac agc tca    1872
Val Thr Val Gly Gln Ser Pro Cys Arg Pro Leu Pro Lys Asp Ser Ser
610                 615                 620 aaa ctc aga cca gtg ccc cgg aaa gac ttt gta gag gag ttt gag tgt    1920
Lys Leu Arg Pro Val Pro Arg Lys Asp Phe Val Glu Glu Phe Glu Cys
625                 630                 635                 640 gaa ctg gag ccc ttg ggc acc cag gca gtg ggg cct acc aac gtc agc    1968
Glu Leu Glu Pro Leu Gly Thr Gln Ala Val Gly Pro Thr Asn Val Ser
```

```
                     645                 650                 655
ctc acc gtg act aac atg cca ccg ggc aag cac ttc cgg gta gac ggc    2016
Leu Thr Val Thr Asn Met Pro Pro Gly Lys His Phe Arg Val Asp Gly
            660                 665                 670 acc tcc gtg ctg aga ggc ttc tct ttc atg acc ggt cat cat cat cat    2064
Thr Ser Val Leu Arg Gly Phe Ser Phe Met Thr Gly His His His His
        675                 680                 685 cat cat cat cat tga                                                2079
His His His His
    690

<210> SEQ ID NO 46
<211> LENGTH: 692
<212> TYPE: PRT
<213> ORGANISM: Artificial Sequence
<220> FEATURE:
<223> OTHER INFORMATION: Synthetic human RON polypeptide

<400> SEQUENCE: 46
```

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Ala Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro

```
             290                 295                 300
Lys Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
                340                 345                 350

Gly Lys Asp Gly Gly Pro Gly Val Gly Pro Asn Ser Val Val Cys Ala
                355                 360                 365

Phe Pro Ile Asp Leu Leu Asp Thr Leu Ile Asp Glu Gly Val Glu Arg
            370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
                420                 425                 430

Phe Ser Arg Val Asp Leu Phe Asn Gly Leu Leu Gly Pro Val Gln Val
                435                 440                 445

Thr Ala Leu Tyr Val Thr Arg Leu Asp Asn Val Thr Val Ala His Met
            450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
                500                 505                 510

Ser Gly Asp Gln Val Phe Gln Val Pro Ile Gln Gly Pro Gly Cys Arg
                515                 520                 525

His Phe Leu Thr Cys Gly Arg Cys Leu Arg Ala Trp His Phe Met Gly
                530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
                580                 585                 590

Asn Phe Tyr Leu His Pro Ser Gly Leu Val Pro Glu Gly Thr His Gln
                595                 600                 605

Val Thr Val Gly Gln Ser Pro Cys Arg Pro Leu Pro Lys Asp Ser Ser
            610                 615                 620

Lys Leu Arg Pro Val Pro Arg Lys Asp Phe Val Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
                660                 665                 670

Thr Ser Val Leu Arg Gly Phe Ser Phe Met Thr Gly His His His
            675                 680                 685

His His His His
    690

<210> SEQ ID NO 47
```

```
<211> LENGTH: 4137
<212> TYPE: DNA
<213> ORGANISM: Mus musculus
<220> FEATURE:
<221> NAME/KEY: CDS
<222> LOCATION: (1)..(4137)

<400> SEQUENCE: 47
```

| | | | | | | | | | | | | | | | | |
|---|---|---|---|---|---|---|---|---|---|---|---|---|---|---|---|---|
| atg | ggg | ctg | cct | ctg | ccg | ctg | ctt | caa | tcc | tct | ctt | ctg | cta | atg | ctt | 48 |
| Met | Gly | Leu | Pro | Leu | Pro | Leu | Leu | Gln | Ser | Ser | Leu | Leu | Leu | Met | Leu | |
| 1 | | | | 5 | | | | | 10 | | | | | 15 | | |
| ctt | ttg | cgg | ctg | tcg | gcg | gcg | tcc | acc | aac | ctg | aac | tgg | cag | tgc | cca | 96 |
| Leu | Leu | Arg | Leu | Ser | Ala | Ala | Ser | Thr | Asn | Leu | Asn | Trp | Gln | Cys | Pro | |
| | | | 20 | | | | | 25 | | | | | 30 | | | |
| cga | ata | ccc | tac | gca | gcc | tcc | cga | gac | ttc | agt | gtc | aag | tac | gtg | gtc | 144 |
| Arg | Ile | Pro | Tyr | Ala | Ala | Ser | Arg | Asp | Phe | Ser | Val | Lys | Tyr | Val | Val | |
| | | 35 | | | | | 40 | | | | | 45 | | | | |
| ccc | agc | ttc | tcc | gcg | ggg | ggc | cgg | gta | cag | gcc | acc | gca | gcc | tac | gag | 192 |
| Pro | Ser | Phe | Ser | Ala | Gly | Gly | Arg | Val | Gln | Ala | Thr | Ala | Ala | Tyr | Glu | |
| | 50 | | | | | 55 | | | | | 60 | | | | | |
| gac | agt | aca | aat | agt | gcg | gtg | ttt | gtg | gcc | aca | cgc | aat | cac | ctg | cac | 240 |
| Asp | Ser | Thr | Asn | Ser | Ala | Val | Phe | Val | Ala | Thr | Arg | Asn | His | Leu | His | |
| 65 | | | | | 70 | | | | | 75 | | | | | 80 | |
| gtg | ctt | ggg | cct | gac | ctg | cag | ttc | ata | gag | aac | ctg | acc | act | ggc | cct | 288 |
| Val | Leu | Gly | Pro | Asp | Leu | Gln | Phe | Ile | Glu | Asn | Leu | Thr | Thr | Gly | Pro | |
| | | | | 85 | | | | | 90 | | | | | 95 | | |
| atc | ggg | aac | cct | ggc | tgc | cag | act | tgt | gcg | agc | tgt | ggt | cca | ggc | cct | 336 |
| Ile | Gly | Asn | Pro | Gly | Cys | Gln | Thr | Cys | Ala | Ser | Cys | Gly | Pro | Gly | Pro | |
| | | | 100 | | | | | 105 | | | | | 110 | | | |
| cat | gga | cca | cca | aag | gac | aca | gac | aca | ctg | gtg | cta | gtg | atg | gag | cca | 384 |
| His | Gly | Pro | Pro | Lys | Asp | Thr | Asp | Thr | Leu | Val | Leu | Val | Met | Glu | Pro | |
| | | 115 | | | | | 120 | | | | | 125 | | | | |
| ggt | ttg | cca | gcc | ctg | gtc | agc | tgt | ggc | tca | acc | cta | cag | ggc | cgc | tgc | 432 |
| Gly | Leu | Pro | Ala | Leu | Val | Ser | Cys | Gly | Ser | Thr | Leu | Gln | Gly | Arg | Cys | |
| | 130 | | | | | 135 | | | | | 140 | | | | | |
| ttc | ctg | cat | gag | ctg | gag | cct | cgg | ggg | aaa | gcc | ctg | cac | tta | gca | gct | 480 |
| Phe | Leu | His | Glu | Leu | Glu | Pro | Arg | Gly | Lys | Ala | Leu | His | Leu | Ala | Ala | |
| 145 | | | | | 150 | | | | | 155 | | | | | 160 | |
| cca | gcc | tgc | cta | ttc | tca | gca | aac | aat | aac | aag | cct | gag | gcc | tgc | acg | 528 |
| Pro | Ala | Cys | Leu | Phe | Ser | Ala | Asn | Asn | Asn | Lys | Pro | Glu | Ala | Cys | Thr | |
| | | | | 165 | | | | | 170 | | | | | 175 | | |
| gac | tgt | gtg | gct | agc | ccc | ctg | ggc | act | cgt | gtg | act | gtg | gtg | gag | cag | 576 |
| Asp | Cys | Val | Ala | Ser | Pro | Leu | Gly | Thr | Arg | Val | Thr | Val | Val | Glu | Gln | |
| | | | 180 | | | | | 185 | | | | | 190 | | | |
| ggg | cat | gct | tcc | tac | ttc | tat | gtg | gca | tct | tcg | cta | gac | cca | gag | ttg | 624 |
| Gly | His | Ala | Ser | Tyr | Phe | Tyr | Val | Ala | Ser | Ser | Leu | Asp | Pro | Glu | Leu | |
| | | 195 | | | | | 200 | | | | | 205 | | | | |
| gcc | gct | agc | ttt | agc | ccc | cgc | tcg | gtg | tcc | atc | cgt | cgt | cta | aag | tct | 672 |
| Ala | Ala | Ser | Phe | Ser | Pro | Arg | Ser | Val | Ser | Ile | Arg | Arg | Leu | Lys | Ser | |
| | 210 | | | | | 215 | | | | | 220 | | | | | |
| gat | act | tct | gga | ttc | caa | cca | ggt | ttt | ccg | tcg | ctg | tcg | gtg | ctg | ccc | 720 |
| Asp | Thr | Ser | Gly | Phe | Gln | Pro | Gly | Phe | Pro | Ser | Leu | Ser | Val | Leu | Pro | |
| 225 | | | | | 230 | | | | | 235 | | | | | 240 | |
| aaa | tat | ttg | gcc | tcc | tac | ctc | atc | aaa | tat | gtg | tac | agc | ttc | cac | tcg | 768 |
| Lys | Tyr | Leu | Ala | Ser | Tyr | Leu | Ile | Lys | Tyr | Val | Tyr | Ser | Phe | His | Ser | |
| | | | | 245 | | | | | 250 | | | | | 255 | | |
| ggg | gat | ttt | gtc | tac | ttt | ctg | act | gtc | cag | ccc | atc | agt | gtc | aca | agc | 816 |
| Gly | Asp | Phe | Val | Tyr | Phe | Leu | Thr | Val | Gln | Pro | Ile | Ser | Val | Thr | Ser | |
| | | | 260 | | | | | 265 | | | | | 270 | | | |
| cct | ccc | agt | gcc | ttg | cat | aca | cgt | ctg | gtc | cgg | ctc | aat | gct | gta | gag | 864 |
| Pro | Pro | Ser | Ala | Leu | His | Thr | Arg | Leu | Val | Arg | Leu | Asn | Ala | Val | Glu | |

-continued

|     |     | 275 |     |     |     | 280 |     |     |     | 285 |     |     |     |      |
|-----|-----|-----|-----|-----|-----|-----|-----|-----|-----|-----|-----|-----|-----|------|
| cca | gag | att | ggt | gac | tac | cgg | gag | ctg | gtc | ttg | gac | tgt | cat | ttt  gca | 912 |
| Pro | Glu | Ile | Gly | Asp | Tyr | Arg | Glu | Leu | Val | Leu | Asp | Cys | His | Phe Ala |
|     | 290 |     |     |     | 295 |     |     |     |     | 300 |     |     |     |      |

| cct | aaa | cgc | cgg | cgc | cgt | gga | gcc | ccg | gag | ggc | aca | cag | ccc | tac cca | 960 |
| Pro | Lys | Arg | Arg | Arg | Arg | Gly | Ala | Pro | Glu | Gly | Thr | Gln | Pro | Tyr Pro |
| 305 |     |     |     | 310 |     |     |     |     | 315 |     |     |     |     | 320  |

| gtg | ctt | cag | gca | gcc | cac | tct | gct | cca | gtg | gat | gcc | aaa | ctg | gct gtg | 1008 |
| Val | Leu | Gln | Ala | Ala | His | Ser | Ala | Pro | Val | Asp | Ala | Lys | Leu | Ala Val |
|     |     |     |     | 325 |     |     |     |     | 330 |     |     |     |     | 335  |

| gaa | ctg | agc | att | tca | gag | ggc | cag | gaa | gtg | ctt | ttt | ggg | gtc | ttt gtg | 1056 |
| Glu | Leu | Ser | Ile | Ser | Glu | Gly | Gln | Glu | Val | Leu | Phe | Gly | Val | Phe Val |
|     |     |     | 340 |     |     |     |     | 345 |     |     |     |     | 350 |      |

| acc | gtc | aag | gat | ggt | ggc | tct | ggc | atg | ggt | ccc | aac | tct | gtt | gta tgt | 1104 |
| Thr | Val | Lys | Asp | Gly | Gly | Ser | Gly | Met | Gly | Pro | Asn | Ser | Val | Val Cys |
|     |     | 355 |     |     |     |     | 360 |     |     |     |     | 365 |     |      |

| gcc | ttc | ccc | att | tac | cac | ctg | aac | atc | ctg | att | gaa | gag | ggt | gtc gaa | 1152 |
| Ala | Phe | Pro | Ile | Tyr | His | Leu | Asn | Ile | Leu | Ile | Glu | Glu | Gly | Val Glu |
| 370 |     |     |     |     | 375 |     |     |     |     | 380 |     |     |     |      |

| tat | tgc | tgt | cac | tct | tca | aat | tct | tct | tcc | ctg | ttg | tcg | aga | ggc ctt | 1200 |
| Tyr | Cys | Cys | His | Ser | Ser | Asn | Ser | Ser | Ser | Leu | Leu | Ser | Arg | Gly Leu |
| 385 |     |     |     |     | 390 |     |     |     |     | 395 |     |     |     | 400  |

| gac | ttc | ttc | cag | acg | ccc | agt | ttt | tgt | cct | aat | ccg | cct | ggt | gga gag | 1248 |
| Asp | Phe | Phe | Gln | Thr | Pro | Ser | Phe | Cys | Pro | Asn | Pro | Pro | Gly | Gly Glu |
|     |     |     |     | 405 |     |     |     |     | 410 |     |     |     |     | 415  |

| gcc | tcc | ggc | ccc | agc | tcc | cgt | tgc | cac | tac | ttc | cct | ttg | atg | gtc cac | 1296 |
| Ala | Ser | Gly | Pro | Ser | Ser | Arg | Cys | His | Tyr | Phe | Pro | Leu | Met | Val His |
|     |     |     | 420 |     |     |     |     | 425 |     |     |     |     | 430 |      |

| gct | agc | ttc | acc | cgt | gtg | gac | ctc | ttc | aat | gga | ctg | tta | gga | tca gtg | 1344 |
| Ala | Ser | Phe | Thr | Arg | Val | Asp | Leu | Phe | Asn | Gly | Leu | Leu | Gly | Ser Val |
|     |     | 435 |     |     |     |     | 440 |     |     |     |     | 445 |     |      |

| aag | gtc | acc | gca | ctg | cat | gtg | aca | cgt | ctt | ggc | aat | gtt | aca | gtg gcc | 1392 |
| Lys | Val | Thr | Ala | Leu | His | Val | Thr | Arg | Leu | Gly | Asn | Val | Thr | Val Ala |
|     | 450 |     |     |     |     | 455 |     |     |     |     | 460 |     |     |      |

| cac | atg | ggc | act | gtg | gat | ggg | cgt | gtc | cta | cag | gtg | gag | ata | gcc agg | 1440 |
| His | Met | Gly | Thr | Val | Asp | Gly | Arg | Val | Leu | Gln | Val | Glu | Ile | Ala Arg |
| 465 |     |     |     |     | 470 |     |     |     |     | 475 |     |     |     | 480  |

| tca | ctc | aac | tac | ctg | ctg | tat | gtg | tcc | aac | ttc | tcc | ctg | ggc | agc agt | 1488 |
| Ser | Leu | Asn | Tyr | Leu | Leu | Tyr | Val | Ser | Asn | Phe | Ser | Leu | Gly | Ser Ser |
|     |     |     |     | 485 |     |     |     |     | 490 |     |     |     |     | 495  |

| gga | cag | cct | gtt | cat | cgg | gat | gtc | agc | cgc | ctc | ggg | aat | gac | cta ctc | 1536 |
| Gly | Gln | Pro | Val | His | Arg | Asp | Val | Ser | Arg | Leu | Gly | Asn | Asp | Leu Leu |
|     |     |     | 500 |     |     |     |     | 505 |     |     |     |     | 510 |      |

| ttt | gcc | tct | ggg | gac | cag | gtc | ttc | aag | gtg | ccc | atc | cag | ggc | cct ggc | 1584 |
| Phe | Ala | Ser | Gly | Asp | Gln | Val | Phe | Lys | Val | Pro | Ile | Gln | Gly | Pro Gly |
|     |     | 515 |     |     |     |     | 520 |     |     |     |     | 525 |     |      |

| tgt | cgt | cat | ttt | ctc | acc | tgt | tgg | cgt | tgc | ctg | aga | gca | cag | cgc ttc | 1632 |
| Cys | Arg | His | Phe | Leu | Thr | Cys | Trp | Arg | Cys | Leu | Arg | Ala | Gln | Arg Phe |
|     | 530 |     |     |     |     | 535 |     |     |     |     | 540 |     |     |      |

| atg | gga | tgt | ggc | tgg | tgt | ggg | gac | cgg | tgt | gac | cgg | cag | aag | gag tgt | 1680 |
| Met | Gly | Cys | Gly | Trp | Cys | Gly | Asp | Arg | Cys | Asp | Arg | Gln | Lys | Glu Cys |
| 545 |     |     |     |     | 550 |     |     |     |     | 555 |     |     |     | 560  |

| cct | ggc | tcc | tgg | caa | cag | gac | cac | tgt | ccg | cct | gag | atc | agt | gag ttc | 1728 |
| Pro | Gly | Ser | Trp | Gln | Gln | Asp | His | Cys | Pro | Pro | Glu | Ile | Ser | Glu Phe |
|     |     |     |     | 565 |     |     |     |     | 570 |     |     |     |     | 575  |

| tat | cct | cac | agc | ggg | cct | cta | agg | ggc | act | acg | agg | ctc | acc | ctt tgt | 1776 |
| Tyr | Pro | His | Ser | Gly | Pro | Leu | Arg | Gly | Thr | Thr | Arg | Leu | Thr | Leu Cys |
|     |     |     | 580 |     |     |     |     | 585 |     |     |     |     | 590 |      |

| ggc | tcc | aac | ttc | tac | ctg | cga | cct | gat | gat | gtc | gta | cct | gag | gga aca | 1824 |

-continued

```
                Gly Ser Asn Phe Tyr Leu Arg Pro Asp Asp Val Val Pro Glu Gly Thr
                        595                 600                 605 cac cag atc acc gtg ggc caa agt ccc tgc cga ctg ctg cct aag gac      1872
His Gln Ile Thr Val Gly Gln Ser Pro Cys Arg Leu Leu Pro Lys Asp
610                 615                 620 tct tca agc cct agg cca ggg tcc ctc aag gaa ttc ata cag gaa ctt      1920
Ser Ser Ser Pro Arg Pro Gly Ser Leu Lys Glu Phe Ile Gln Glu Leu
625                 630                 635                 640 gaa tgt gag ctg gag ccc ctg gtc acc cag gca gtg ggg act aca aac      1968
Glu Cys Glu Leu Glu Pro Leu Val Thr Gln Ala Val Gly Thr Thr Asn
                645                 650                 655 atc agc ctt gtc atc acc aac atg cca gca ggc aag cac ttc cga gtg      2016
Ile Ser Leu Val Ile Thr Asn Met Pro Ala Gly Lys His Phe Arg Val
            660                 665                 670 gaa ggc atc tct gta cag gaa ggc ttc tct ttc gtg gag cca gtg ctg      2064
Glu Gly Ile Ser Val Gln Glu Gly Phe Ser Phe Val Glu Pro Val Leu
        675                 680                 685 aca tca ata aaa cct gac ttt ggc ccg cgg gct ggg ggt act tat ctc      2112
Thr Ser Ile Lys Pro Asp Phe Gly Pro Arg Ala Gly Gly Thr Tyr Leu
    690                 695                 700 acc ctt gaa ggc cag agc ctg tct gtc ggc acc agc cgg gct gtg ctg      2160
Thr Leu Glu Gly Gln Ser Leu Ser Val Gly Thr Ser Arg Ala Val Leu
705                 710                 715                 720 gtc aat gga acc cag tgc cgg ctg gaa cag gtc aat gag gag cag atc      2208
Val Asn Gly Thr Gln Cys Arg Leu Glu Gln Val Asn Glu Glu Gln Ile
                725                 730                 735 tta tgt gtc acg cct cct gga gct ggc acg gcc agg gtc ccc ctt cat      2256
Leu Cys Val Thr Pro Pro Gly Ala Gly Thr Ala Arg Val Pro Leu His
            740                 745                 750 ctg cag ata ggg ggt gct gag gtg cct ggc tcc tgg acc ttt cac tac      2304
Leu Gln Ile Gly Gly Ala Glu Val Pro Gly Ser Trp Thr Phe His Tyr
        755                 760                 765 aag gaa gac cct att gtg ttg gac atc agt ccc aag tgt ggc tac agt      2352
Lys Glu Asp Pro Ile Val Leu Asp Ile Ser Pro Lys Cys Gly Tyr Ser
    770                 775                 780 ggc tcc cac atc atg atc cat ggc cag cat ctg act tca gca tgg cac      2400
Gly Ser His Ile Met Ile His Gly Gln His Leu Thr Ser Ala Trp His
785                 790                 795                 800 ttc acg cta tca ttc cat gat gga caa agt aca gtg gag agc agg tgt      2448
Phe Thr Leu Ser Phe His Asp Gly Gln Ser Thr Val Glu Ser Arg Cys
                805                 810                 815 gcg ggg cag ttt gtg gaa caa cag cag cgt cga tgt cgc ctg cct gaa      2496
Ala Gly Gln Phe Val Glu Gln Gln Gln Arg Arg Cys Arg Leu Pro Glu
            820                 825                 830 tat gtg gtc cga aac cct cag ggg tgg gca aca ggg aat ctg agc gtc      2544
Tyr Val Val Arg Asn Pro Gln Gly Trp Ala Thr Gly Asn Leu Ser Val
        835                 840                 845 tgg ggt gat gga gca gct ggc ttc acg ctg cct ggt ttt cgc ttc ctg      2592
Trp Gly Asp Gly Ala Ala Gly Phe Thr Leu Pro Gly Phe Arg Phe Leu
    850                 855                 860 ccc cca ccc agt cca ctc aga gct ggc ctg gtt gag ttg aaa cct gaa      2640
Pro Pro Pro Ser Pro Leu Arg Ala Gly Leu Val Glu Leu Lys Pro Glu
865                 870                 875                 880 gaa cat tca gtt aaa gtt gag tat gtc ggg ctg ggc gct gtg gca gac      2688
Glu His Ser Val Lys Val Glu Tyr Val Gly Leu Gly Ala Val Ala Asp
                885                 890                 895 tgt gtg act gtg aac atg acc gtg ggt ggt gag gtc tgc caa cat gag      2736
Cys Val Thr Val Asn Met Thr Val Gly Gly Glu Val Cys Gln His Glu
            900                 905                 910
```

-continued

| | |
|---|---|
| ctc cgg ggg gat gtg gtg atc tgc ccc ctg ccc cct tcc ctg caa ctt<br>Leu Arg Gly Asp Val Val Ile Cys Pro Leu Pro Pro Ser Leu Gln Leu<br>     915                   920               925 | 2784 |
| ggc aag gat ggt gtc cca ttg cag gtc tgt gta gac ggt ggg tgt cac<br>Gly Lys Asp Gly Val Pro Leu Gln Val Cys Val Asp Gly Gly Cys His<br>     930                   935               940 | 2832 |
| atc ctg agc caa gtg gtt cgc tca agc cca ggc agg gcc tca cag agg<br>Ile Leu Ser Gln Val Val Arg Ser Ser Pro Gly Arg Ala Ser Gln Arg<br>945                   950               955               960 | 2880 |
| ata ctc ctt att gct ctt ctg gtc ttg atc ctg ctt gtg gct gtg ctg<br>Ile Leu Leu Ile Ala Leu Leu Val Leu Ile Leu Leu Val Ala Val Leu<br>             965                   970               975 | 2928 |
| gcc gtt gcc ctg atc ttt aac tcc cga aga cgg aaa aag cag cta ggt<br>Ala Val Ala Leu Ile Phe Asn Ser Arg Arg Arg Lys Lys Gln Leu Gly<br>     980                   985               990 | 2976 |
| gct cac tcc ctc tcc cca aca aca ctc tct gac atc aac gat aca gct<br>Ala His Ser Leu Ser Pro Thr Thr Leu Ser Asp Ile Asn Asp Thr Ala<br>            995                1000            1005 | 3024 |
| tcc ggg gct ccg aac cat gaa gaa tcg tca gag agt agg gat ggg<br>Ser Gly Ala Pro Asn His Glu Glu Ser Ser Glu Ser Arg Asp Gly<br>1010                   1015               1020 | 3069 |
| aca agt gtc cca ctg ctg cgg aca gag tct atc cgg ctc cag gat<br>Thr Ser Val Pro Leu Leu Arg Thr Glu Ser Ile Arg Leu Gln Asp<br>1025                 1030               1035 | 3114 |
| ctg gac agg atg ctc cta gct gag gtc aag gat gta ctg att ccc<br>Leu Asp Arg Met Leu Leu Ala Glu Val Lys Asp Val Leu Ile Pro<br>1040                 1045               1050 | 3159 |
| cat gaa caa gtg gtc atc cat act gac caa gtc att ggc aaa ggc<br>His Glu Gln Val Val Ile His Thr Asp Gln Val Ile Gly Lys Gly<br>1055                 1060               1065 | 3204 |
| cac ttt ggt gtt gtc tac cac gga gaa tat aca gac gga gca cag<br>His Phe Gly Val Val Tyr His Gly Glu Tyr Thr Asp Gly Ala Gln<br>1070                 1075               1080 | 3249 |
| aat cag acc cac tgt gcc atc aag tct ctg agt cgc att aca gag<br>Asn Gln Thr His Cys Ala Ile Lys Ser Leu Ser Arg Ile Thr Glu<br>1085                 1090               1095 | 3294 |
| gtg cag gag gtg gag gct ttc ctg cgg gag ggg ctg ctc atg cgt<br>Val Gln Glu Val Glu Ala Phe Leu Arg Glu Gly Leu Leu Met Arg<br>1100                 1105               1110 | 3339 |
| ggc cta cat cac cca aac atc ctg gct ctc atc ggt atc atg ctg<br>Gly Leu His His Pro Asn Ile Leu Ala Leu Ile Gly Ile Met Leu<br>1115                 1120               1125 | 3384 |
| ccc ccg gag ggg ctt ccc cgg gtg ctg ttg ccc tat atg cgc cac<br>Pro Pro Glu Gly Leu Pro Arg Val Leu Leu Pro Tyr Met Arg His<br>1130                 1135               1140 | 3429 |
| gga gac ctg ctt cat ttc att cgc tcc cct cag agg aac ccc act<br>Gly Asp Leu Leu His Phe Ile Arg Ser Pro Gln Arg Asn Pro Thr<br>1145                 1150               1155 | 3474 |
| gtg aag gat ctt gtc agc ttt ggc ctg cag gta gcc tgt ggt atg<br>Val Lys Asp Leu Val Ser Phe Gly Leu Gln Val Ala Cys Gly Met<br>1160                 1165               1170 | 3519 |
| gag tac ctg gca gag cag aag ttc gtg cac aga gac ctg gct gct<br>Glu Tyr Leu Ala Glu Gln Lys Phe Val His Arg Asp Leu Ala Ala<br>1175                 1180               1185 | 3564 |
| agg aac tgc atg ctg gac gag tca ttc aca gtc aag gtg gct gac<br>Arg Asn Cys Met Leu Asp Glu Ser Phe Thr Val Lys Val Ala Asp<br>1190                 1195               1200 | 3609 |
| ttt ggt ctg gca cgg ggc gtc cta gac aag gaa tac tac agt gtt<br>Phe Gly Leu Ala Arg Gly Val Leu Asp Lys Glu Tyr Tyr Ser Val<br>1205                 1210               1215 | 3654 |

```
cgc cag cat cgc cat gct cgc ctg cca gtc aaa tgg atg gca ctg     3699
Arg Gln His Arg His Ala Arg Leu Pro Val Lys Trp Met Ala Leu
    1220            1225                1230 gag agc ctg cag acc tac agg ttc acc acc aag tcc gat gtg tgg     3744
Glu Ser Leu Gln Thr Tyr Arg Phe Thr Thr Lys Ser Asp Val Trp
1235                1240                1245 tca ttc ggg gtg ctg ctc tgg gag cta cta aca cgg ggt gct cca     3789
Ser Phe Gly Val Leu Leu Trp Glu Leu Leu Thr Arg Gly Ala Pro
    1250            1255                1260 ccc tac ccc cat atc gat ccc ttc gac ctc tct cac ttc ctg gct     3834
Pro Tyr Pro His Ile Asp Pro Phe Asp Leu Ser His Phe Leu Ala
1265                1270                1275 cag ggc cgt cgc ctg cct cag cct gag tac tgt cct gat tca ctg     3879
Gln Gly Arg Arg Leu Pro Gln Pro Glu Tyr Cys Pro Asp Ser Leu
    1280            1285                1290 tat cac gtg atg ctt cga tgc tgg gag gct gac cca gcg gca cga     3924
Tyr His Val Met Leu Arg Cys Trp Glu Ala Asp Pro Ala Ala Arg
1295                1300                1305 ccc acc ttc aga gcc cta gtg ctg gaa gta aag cag gta gtg gcc     3969
Pro Thr Phe Arg Ala Leu Val Leu Glu Val Lys Gln Val Val Ala
    1310            1315                1320 tca ctg ctt ggg gac cac tat gtg cag ctg aca gca gct tat gtg     4014
Ser Leu Leu Gly Asp His Tyr Val Gln Leu Thr Ala Ala Tyr Val
1325                1330                1335 aac gta ggc ccc aga gcg gtg gat gat ggg agt gtg cct ccg gag     4059
Asn Val Gly Pro Arg Ala Val Asp Asp Gly Ser Val Pro Pro Glu
    1340            1345                1350 cag gta cag ccc tcg cct cag cat tgc agg agc acg tca aag ccc     4104
Gln Val Gln Pro Ser Pro Gln His Cys Arg Ser Thr Ser Lys Pro
1355                1360                1365 cgg cct ctc tca gag cca ccc ctg ccc act tga                     4137
Arg Pro Leu Ser Glu Pro Pro Leu Pro Thr
    1370            1375
```

<210> SEQ ID NO 48
<211> LENGTH: 1378
<212> TYPE: PRT
<213> ORGANISM: Mus musculus

<400> SEQUENCE: 48

```
Met Gly Leu Pro Leu Pro Leu Leu Gln Ser Ser Leu Leu Met Leu
1               5                   10                  15

Leu Leu Arg Leu Ser Ala Ala Ser Thr Asn Leu Asn Trp Gln Cys Pro
            20                  25                  30

Arg Ile Pro Tyr Ala Ala Ser Arg Asp Phe Ser Val Lys Tyr Val Val
        35                  40                  45

Pro Ser Phe Ser Ala Gly Gly Arg Val Gln Ala Thr Ala Ala Tyr Glu
    50                  55                  60

Asp Ser Thr Asn Ser Ala Val Phe Val Ala Thr Arg Asn His Leu His
65                  70                  75                  80

Val Leu Gly Pro Asp Leu Gln Phe Ile Glu Asn Leu Thr Thr Gly Pro
                85                  90                  95

Ile Gly Asn Pro Gly Cys Gln Thr Cys Ala Ser Cys Gly Pro Gly Pro
            100                 105                 110

His Gly Pro Pro Lys Asp Thr Asp Thr Leu Val Leu Val Met Glu Pro
        115                 120                 125

Gly Leu Pro Ala Leu Val Ser Cys Gly Ser Thr Leu Gln Gly Arg Cys
    130                 135                 140
```

```
Phe Leu His Glu Leu Glu Pro Arg Gly Lys Ala Leu His Leu Ala Ala
145                 150                 155                 160

Pro Ala Cys Leu Phe Ser Ala Asn Asn Lys Pro Glu Ala Cys Thr
        165                 170                 175

Asp Cys Val Ala Ser Pro Leu Gly Thr Arg Val Thr Val Glu Gln
            180                 185                 190

Gly His Ala Ser Tyr Phe Tyr Val Ala Ser Ser Leu Asp Pro Glu Leu
                195                 200                 205

Ala Ala Ser Phe Ser Pro Arg Ser Val Ser Ile Arg Arg Leu Lys Ser
210                 215                 220

Asp Thr Ser Gly Phe Gln Pro Gly Phe Pro Ser Leu Ser Val Leu Pro
225                 230                 235                 240

Lys Tyr Leu Ala Ser Tyr Leu Ile Lys Tyr Val Tyr Ser Phe His Ser
                245                 250                 255

Gly Asp Phe Val Tyr Phe Leu Thr Val Gln Pro Ile Ser Val Thr Ser
                260                 265                 270

Pro Pro Ser Ala Leu His Thr Arg Leu Val Arg Leu Asn Ala Val Glu
        275                 280                 285

Pro Glu Ile Gly Asp Tyr Arg Glu Leu Val Leu Asp Cys His Phe Ala
        290                 295                 300

Pro Lys Arg Arg Arg Gly Ala Pro Glu Gly Thr Gln Pro Tyr Pro
305                 310                 315                 320

Val Leu Gln Ala Ala His Ser Ala Pro Val Asp Ala Lys Leu Ala Val
                325                 330                 335

Glu Leu Ser Ile Ser Glu Gly Gln Glu Val Leu Phe Gly Val Phe Val
                340                 345                 350

Thr Val Lys Asp Gly Gly Ser Gly Met Gly Pro Asn Ser Val Val Cys
                355                 360                 365

Ala Phe Pro Ile Tyr His Leu Asn Ile Leu Ile Glu Glu Gly Val Glu
370                 375                 380

Tyr Cys Cys His Ser Ser Asn Ser Ser Ser Leu Leu Ser Arg Gly Leu
385                 390                 395                 400

Asp Phe Phe Gln Thr Pro Ser Phe Cys Pro Asn Pro Pro Gly Gly Glu
                405                 410                 415

Ala Ser Gly Pro Ser Ser Arg Cys His Tyr Phe Pro Leu Met Val His
                420                 425                 430

Ala Ser Phe Thr Arg Val Asp Leu Phe Asn Gly Leu Leu Gly Ser Val
            435                 440                 445

Lys Val Thr Ala Leu His Val Thr Arg Leu Gly Asn Val Thr Val Ala
450                 455                 460

His Met Gly Thr Val Asp Gly Arg Val Leu Gln Val Glu Ile Ala Arg
465                 470                 475                 480

Ser Leu Asn Tyr Leu Leu Tyr Val Ser Asn Phe Ser Leu Gly Ser Ser
                485                 490                 495

Gly Gln Pro Val His Arg Asp Val Ser Arg Leu Gly Asn Asp Leu Leu
            500                 505                 510

Phe Ala Ser Gly Asp Gln Val Phe Lys Val Pro Ile Gln Gly Pro Gly
            515                 520                 525

Cys Arg His Phe Leu Thr Cys Trp Arg Cys Leu Arg Ala Gln Arg Phe
    530                 535                 540

Met Gly Cys Gly Trp Cys Gly Asp Arg Cys Asp Arg Gln Lys Glu Cys
545                 550                 555                 560
```

-continued

```
Pro Gly Ser Trp Gln Gln Asp His Cys Pro Pro Glu Ile Ser Glu Phe
            565                 570                 575

Tyr Pro His Ser Gly Pro Leu Arg Gly Thr Thr Arg Leu Thr Leu Cys
            580                 585                 590

Gly Ser Asn Phe Tyr Leu Arg Pro Asp Asp Val Val Pro Glu Gly Thr
            595                 600                 605

His Gln Ile Thr Val Gly Gln Ser Pro Cys Arg Leu Leu Pro Lys Asp
            610                 615                 620

Ser Ser Ser Pro Arg Pro Gly Ser Leu Lys Glu Phe Ile Gln Glu Leu
625                 630                 635                 640

Glu Cys Glu Leu Glu Pro Leu Val Thr Gln Ala Val Gly Thr Thr Asn
            645                 650                 655

Ile Ser Leu Val Ile Thr Asn Met Pro Ala Gly Lys His Phe Arg Val
            660                 665                 670

Glu Gly Ile Ser Val Gln Gly Phe Ser Phe Val Glu Pro Val Leu
            675                 680                 685

Thr Ser Ile Lys Pro Asp Phe Gly Pro Arg Ala Gly Thr Tyr Leu
            690                 695                 700

Thr Leu Glu Gly Gln Ser Leu Ser Val Gly Thr Ser Arg Ala Val Leu
705                 710                 715                 720

Val Asn Gly Thr Gln Cys Arg Leu Glu Gln Val Asn Glu Glu Gln Ile
            725                 730                 735

Leu Cys Val Thr Pro Pro Gly Ala Gly Thr Ala Arg Val Pro Leu His
            740                 745                 750

Leu Gln Ile Gly Gly Ala Glu Val Pro Gly Ser Trp Thr Phe His Tyr
            755                 760                 765

Lys Glu Asp Pro Ile Val Leu Asp Ile Ser Pro Lys Cys Gly Tyr Ser
            770                 775                 780

Gly Ser His Ile Met Ile His Gly Gln His Leu Thr Ser Ala Trp His
785                 790                 795                 800

Phe Thr Leu Ser Phe His Asp Gly Gln Ser Thr Val Glu Ser Arg Cys
            805                 810                 815

Ala Gly Gln Phe Val Glu Gln Gln Gln Arg Arg Cys Arg Leu Pro Glu
            820                 825                 830

Tyr Val Val Arg Asn Pro Gln Gly Trp Ala Thr Gly Asn Leu Ser Val
            835                 840                 845

Trp Gly Asp Gly Ala Ala Gly Phe Thr Leu Pro Gly Phe Arg Phe Leu
850                 855                 860

Pro Pro Pro Ser Pro Leu Arg Ala Gly Leu Val Glu Leu Lys Pro Glu
865                 870                 875                 880

Glu His Ser Val Lys Val Glu Tyr Val Gly Leu Gly Ala Val Ala Asp
            885                 890                 895

Cys Val Thr Val Asn Met Thr Val Gly Gly Glu Val Cys Gln His Glu
            900                 905                 910

Leu Arg Gly Asp Val Val Ile Cys Pro Leu Pro Ser Leu Gln Leu
            915                 920                 925

Gly Lys Asp Gly Val Pro Leu Gln Val Cys Val Asp Gly Gly Cys His
            930                 935                 940

Ile Leu Ser Gln Val Val Arg Ser Ser Pro Gly Arg Ala Ser Gln Arg
945                 950                 955                 960

Ile Leu Leu Ile Ala Leu Leu Val Leu Leu Val Ala Val Leu
            965                 970                 975

Ala Val Ala Leu Ile Phe Asn Ser Arg Arg Arg Lys Lys Gln Leu Gly
```

```
              980             985              990
Ala His Ser Leu Ser Pro Thr Thr Leu Ser Asp Ile Asn Asp Thr Ala
              995            1000             1005

Ser Gly Ala Pro Asn His Glu Glu Ser Glu Ser Arg Asp Gly
        1010         1015             1020

Thr Ser Val Pro Leu Leu Arg Thr Glu Ser Ile Arg Leu Gln Asp
        1025             1030             1035

Leu Asp Arg Met Leu Leu Ala Glu Val Lys Asp Val Leu Ile Pro
        1040             1045             1050

His Glu Gln Val Val Ile His Thr Asp Gln Val Ile Gly Lys Gly
        1055             1060             1065

His Phe Gly Val Val Tyr His Gly Glu Tyr Thr Asp Gly Ala Gln
        1070             1075             1080

Asn Gln Thr His Cys Ala Ile Lys Ser Leu Ser Arg Ile Thr Glu
        1085             1090             1095

Val Gln Glu Val Glu Ala Phe Leu Arg Glu Gly Leu Leu Met Arg
        1100             1105             1110

Gly Leu His His Pro Asn Ile Leu Ala Leu Ile Gly Ile Met Leu
        1115             1120             1125

Pro Pro Glu Gly Leu Pro Arg Val Leu Leu Pro Tyr Met Arg His
        1130             1135             1140

Gly Asp Leu Leu His Phe Ile Arg Ser Pro Gln Arg Asn Pro Thr
        1145             1150             1155

Val Lys Asp Leu Val Ser Phe Gly Leu Gln Val Ala Cys Gly Met
        1160             1165             1170

Glu Tyr Leu Ala Glu Gln Lys Phe Val His Arg Asp Leu Ala Ala
        1175             1180             1185

Arg Asn Cys Met Leu Asp Glu Ser Phe Thr Val Lys Val Ala Asp
        1190             1195             1200

Phe Gly Leu Ala Arg Gly Val Leu Asp Lys Glu Tyr Tyr Ser Val
        1205             1210             1215

Arg Gln His Arg His Ala Arg Leu Pro Val Lys Trp Met Ala Leu
        1220             1225             1230

Glu Ser Leu Gln Thr Tyr Arg Phe Thr Thr Lys Ser Asp Val Trp
        1235             1240             1245

Ser Phe Gly Val Leu Leu Trp Glu Leu Leu Thr Arg Gly Ala Pro
        1250             1255             1260

Pro Tyr Pro His Ile Asp Pro Phe Asp Leu Ser His Phe Leu Ala
        1265             1270             1275

Gln Gly Arg Arg Leu Pro Gln Pro Glu Tyr Cys Pro Asp Ser Leu
        1280             1285             1290

Tyr His Val Met Leu Arg Cys Trp Glu Ala Asp Pro Ala Ala Arg
        1295             1300             1305

Pro Thr Phe Arg Ala Leu Val Leu Glu Val Lys Gln Val Val Ala
        1310             1315             1320

Ser Leu Leu Gly Asp His Tyr Val Gln Leu Thr Ala Ala Tyr Val
        1325             1330             1335

Asn Val Gly Pro Arg Ala Val Asp Asp Gly Ser Val Pro Pro Glu
        1340             1345             1350

Gln Val Gln Pro Ser Pro Gln His Cys Arg Ser Thr Ser Lys Pro
        1355             1360             1365

Arg Pro Leu Ser Glu Pro Pro Leu Pro Thr
        1370             1375
```

<210> SEQ ID NO 49
<211> LENGTH: 2751
<212> TYPE: DNA
<213> ORGANISM: Artificial Sequence
<220> FEATURE:
<223> OTHER INFORMATION: Synthetic mouse RON fusion protein
<220> FEATURE:
<221> NAME/KEY: CDS
<222> LOCATION: (1)..(2751)

<400> SEQUENCE: 49

| | | | | | | | | | | | | | | | | |
|---|---|---|---|---|---|---|---|---|---|---|---|---|---|---|---|---|
| atg | ggg | ctg | cct | ctg | ccg | ctg | ctt | caa | tcc | tct | ctt | ctg | cta | atg | ctt | 48 |
| Met | Gly | Leu | Pro | Leu | Pro | Leu | Leu | Gln | Ser | Ser | Leu | Leu | Leu | Met | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctt | ttg | cgg | ctg | tcg | gcg | gcg | tcc | acc | aac | ctg | aac | tgg | cag | tgc | cca | 96 |
| Leu | Leu | Arg | Leu | Ser | Ala | Ala | Ser | Thr | Asn | Leu | Asn | Trp | Gln | Cys | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| cga | ata | ccc | tac | gca | gcc | tcc | cga | gac | ttc | agt | gtc | aag | tac | gtg | gtc | 144 |
| Arg | Ile | Pro | Tyr | Ala | Ala | Ser | Arg | Asp | Phe | Ser | Val | Lys | Tyr | Val | Val | |
| | | | | 35 | | | | | 40 | | | | | 45 | | |

| | | | | | | | | | | | | | | | | |
|---|---|---|---|---|---|---|---|---|---|---|---|---|---|---|---|---|
| ccc | agc | ttc | tcc | gcg | ggg | ggc | cgg | gta | cag | gcc | acc | gca | gcc | tac | gag | 192 |
| Pro | Ser | Phe | Ser | Ala | Gly | Gly | Arg | Val | Gln | Ala | Thr | Ala | Ala | Tyr | Glu | |
| | | 50 | | | | | 55 | | | | | 60 | | | | |

| | | | | | | | | | | | | | | | | |
|---|---|---|---|---|---|---|---|---|---|---|---|---|---|---|---|---|
| gac | agt | aca | aat | agt | gcg | gtg | ttt | gtg | gcc | aca | cgc | aat | cac | ctg | cac | 240 |
| Asp | Ser | Thr | Asn | Ser | Ala | Val | Phe | Val | Ala | Thr | Arg | Asn | His | Leu | His | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtg | ctt | ggg | cct | gac | ctg | cag | ttc | ata | gag | aac | ctg | acc | act | ggc | cct | 288 |
| Val | Leu | Gly | Pro | Asp | Leu | Gln | Phe | Ile | Glu | Asn | Leu | Thr | Thr | Gly | Pro | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | ggg | aac | cct | ggc | tgc | cag | act | tgt | gcg | agc | tgt | ggt | cca | ggc | cct | 336 |
| Ile | Gly | Asn | Pro | Gly | Cys | Gln | Thr | Cys | Ala | Ser | Cys | Gly | Pro | Gly | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| cat | gga | cca | cca | aag | gac | aca | gac | aca | ctg | gtg | cta | gtg | atg | gag | cca | 384 |
| His | Gly | Pro | Pro | Lys | Asp | Thr | Asp | Thr | Leu | Val | Leu | Val | Met | Glu | Pro | |
| | | | 115 | | | | | 120 | | | | | 125 | | | |

| | | | | | | | | | | | | | | | | |
|---|---|---|---|---|---|---|---|---|---|---|---|---|---|---|---|---|
| ggt | ttg | cca | gcc | ctg | gtc | agc | tgt | ggc | tca | acc | cta | cag | ggc | cgc | tgc | 432 |
| Gly | Leu | Pro | Ala | Leu | Val | Ser | Cys | Gly | Ser | Thr | Leu | Gln | Gly | Arg | Cys | |
| | | 130 | | | | | 135 | | | | | 140 | | | | |

| | | | | | | | | | | | | | | | | |
|---|---|---|---|---|---|---|---|---|---|---|---|---|---|---|---|---|
| ttc | ctg | cat | gag | ctg | gag | cct | cgg | ggg | aaa | gcc | ctg | cac | tta | gca | gct | 480 |
| Phe | Leu | His | Glu | Leu | Glu | Pro | Arg | Gly | Lys | Ala | Leu | His | Leu | Ala | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cca | gcc | tgc | cta | ttc | tca | gca | aac | aat | aac | aag | cct | gag | gcc | tgc | acg | 528 |
| Pro | Ala | Cys | Leu | Phe | Ser | Ala | Asn | Asn | Asn | Lys | Pro | Glu | Ala | Cys | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | tgt | gtg | gct | agc | ccc | ctg | ggc | act | cgt | gtg | act | gtg | gtg | gag | cag | 576 |
| Asp | Cys | Val | Ala | Ser | Pro | Leu | Gly | Thr | Arg | Val | Thr | Val | Val | Glu | Gln | |
| | | | 180 | | | | | 185 | | | | | 190 | | | |

| | | | | | | | | | | | | | | | | |
|---|---|---|---|---|---|---|---|---|---|---|---|---|---|---|---|---|
| ggg | cat | gct | tcc | tac | ttc | tat | gtg | gca | tct | tcg | cta | gac | cca | gag | ttg | 624 |
| Gly | His | Ala | Ser | Tyr | Phe | Tyr | Val | Ala | Ser | Ser | Leu | Asp | Pro | Glu | Leu | |
| | | | 195 | | | | | 200 | | | | | 205 | | | |

| | | | | | | | | | | | | | | | | |
|---|---|---|---|---|---|---|---|---|---|---|---|---|---|---|---|---|
| gcc | gct | agc | ttt | agc | ccc | cgc | tcg | gtg | tcc | atc | cgt | cgt | cta | aag | tct | 672 |
| Ala | Ala | Ser | Phe | Ser | Pro | Arg | Ser | Val | Ser | Ile | Arg | Arg | Leu | Lys | Ser | |
| | | 210 | | | | | 215 | | | | | 220 | | | | |

| | | | | | | | | | | | | | | | | |
|---|---|---|---|---|---|---|---|---|---|---|---|---|---|---|---|---|
| gat | act | tct | gga | ttc | caa | cca | ggt | ttt | ccg | tcg | ctg | tcg | gtg | ctg | ccc | 720 |
| Asp | Thr | Ser | Gly | Phe | Gln | Pro | Gly | Phe | Pro | Ser | Leu | Ser | Val | Leu | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aaa | tat | ttg | gcc | tcc | tac | ctc | atc | aaa | tat | gtg | tac | agc | ttc | cac | tcg | 768 |
| Lys | Tyr | Leu | Ala | Ser | Tyr | Leu | Ile | Lys | Tyr | Val | Tyr | Ser | Phe | His | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| ggg | gat | ttt | gtc | tac | ttt | ctg | act | gtc | cag | ccc | atc | agt | gtc | aca | agc | 816 |

```
                Gly Asp Phe Val Tyr Phe Leu Thr Val Gln Pro Ile Ser Val Thr Ser
                            260                 265                 270 cct ccc agt gcc ttg cat aca cgt ctg gtc cgg ctc aat gct gta gag              864
Pro Pro Ser Ala Leu His Thr Arg Leu Val Arg Leu Asn Ala Val Glu
            275                 280                 285 cca gag att ggt gac tac cgg gag ctg gtc ttg gac tgt cat ttt gca              912
Pro Glu Ile Gly Asp Tyr Arg Glu Leu Val Leu Asp Cys His Phe Ala
            290                 295                 300 cct aaa cgc cgg cgc cgt gga gcc ccg gag ggc aca cag ccc tac cca              960
Pro Lys Arg Arg Arg Arg Gly Ala Pro Glu Gly Thr Gln Pro Tyr Pro
305                 310                 315                 320 gtg ctt cag gca gcc cac tct gct cca gtg gat gcc aaa ctg gct gtg             1008
Val Leu Gln Ala Ala His Ser Ala Pro Val Asp Ala Lys Leu Ala Val
            325                 330                 335 gaa ctg agc att tca gag ggc cag gaa gtg ctt ttt ggg gtc ttt gtg             1056
Glu Leu Ser Ile Ser Glu Gly Gln Glu Val Leu Phe Gly Val Phe Val
            340                 345                 350 acc gtc aag gat ggt ggc tct ggc atg ggt ccc aac tct gtt gta tgt             1104
Thr Val Lys Asp Gly Gly Ser Gly Met Gly Pro Asn Ser Val Val Cys
            355                 360                 365 gcc ttc ccc att tac cac ctg aac atc ctg att gaa gag ggt gtc gaa             1152
Ala Phe Pro Ile Tyr His Leu Asn Ile Leu Ile Glu Glu Gly Val Glu
370                 375                 380 tat tgc tgt cac tct tca aat tct tct tcc ctg ttg tcg aga ggc ctt             1200
Tyr Cys Cys His Ser Ser Asn Ser Ser Ser Leu Leu Ser Arg Gly Leu
385                 390                 395                 400 gac ttc ttc cag acg ccc agt ttt tgt cct aat ccg cct ggt gga gag             1248
Asp Phe Phe Gln Thr Pro Ser Phe Cys Pro Asn Pro Pro Gly Gly Glu
            405                 410                 415 gcc tcc ggc ccc agc tcc cgt tgc cac tac ttc cct ttg atg gtc cac             1296
Ala Ser Gly Pro Ser Ser Arg Cys His Tyr Phe Pro Leu Met Val His
            420                 425                 430 gct agc ttc acc cgt gtg gac ctc ttc aat gga ctg tta gga tca gtg             1344
Ala Ser Phe Thr Arg Val Asp Leu Phe Asn Gly Leu Leu Gly Ser Val
            435                 440                 445 aag gtc acc gca ctg cat gtg aca cgt ctt ggc aat gtt aca gtg gcc             1392
Lys Val Thr Ala Leu His Val Thr Arg Leu Gly Asn Val Thr Val Ala
450                 455                 460 cac atg ggc act gtg gat ggg cgt gtc cta cag gtg gag ata gcc agg             1440
His Met Gly Thr Val Asp Gly Arg Val Leu Gln Val Glu Ile Ala Arg
465                 470                 475                 480 tca ctc aac tac ctg ctg tat gtg tcc aac ttc tcc ctg ggc agc agt             1488
Ser Leu Asn Tyr Leu Leu Tyr Val Ser Asn Phe Ser Leu Gly Ser Ser
            485                 490                 495 gga cag cct gtt cat cgg gat gtc agc cgc ctc ggg aat gac cta ctc             1536
Gly Gln Pro Val His Arg Asp Val Ser Arg Leu Gly Asn Asp Leu Leu
            500                 505                 510 ttt gcc tct ggg gac cag gtc ttc aag gtg ccc atc cag ggc cct ggc             1584
Phe Ala Ser Gly Asp Gln Val Phe Lys Val Pro Ile Gln Gly Pro Gly
            515                 520                 525 tgt cgt cat ttt ctc acc tgt tgg cgt tgc ctg aga gca cag cgc ttc             1632
Cys Arg His Phe Leu Thr Cys Trp Arg Cys Leu Arg Ala Gln Arg Phe
530                 535                 540 atg gga tgt ggc tgg tgt ggg gac cgg tgt gac cgg cag aag gag tgt             1680
Met Gly Cys Gly Trp Cys Gly Asp Arg Cys Asp Arg Gln Lys Glu Cys
545                 550                 555                 560 cct ggc tcc tgg caa cag gac cac tgt ccg cct gag atc agt gag ttc             1728
Pro Gly Ser Trp Gln Gln Asp His Cys Pro Pro Glu Ile Ser Glu Phe
            565                 570                 575
```

```
tat cct cac agc ggg cct cta agg ggc act acg agg ctc acc ctt tgt     1776
Tyr Pro His Ser Gly Pro Leu Arg Gly Thr Thr Arg Leu Thr Leu Cys
            580                 585                 590 ggc tcc aac ttc tac ctg cga cct gat gat gtc gta cct gag gga aca     1824
Gly Ser Asn Phe Tyr Leu Arg Pro Asp Asp Val Val Pro Glu Gly Thr
        595                 600                 605 cac cag atc acc gtg ggc caa agt ccc tgc cga ctg ctg cct aag gac     1872
His Gln Ile Thr Val Gly Gln Ser Pro Cys Arg Leu Leu Pro Lys Asp
    610                 615                 620 tct tca agc cct agg cca ggg tcc ctc aag gaa ttc ata cag gaa ctt     1920
Ser Ser Ser Pro Arg Pro Gly Ser Leu Lys Glu Phe Ile Gln Glu Leu
625                 630                 635                 640 gaa tgt gag ctg gag ccc ctg gtc acc cag gca gtg ggg act aca aac     1968
Glu Cys Glu Leu Glu Pro Leu Val Thr Gln Ala Val Gly Thr Thr Asn
            645                 650                 655 atc agc ctt gtc atc acc aac atg cca gca ggc aag cac ttc cga gtg     2016
Ile Ser Leu Val Ile Thr Asn Met Pro Ala Gly Lys His Phe Arg Val
        660                 665                 670 gaa ggc atc tct gta cag gaa ggc ttc tct ttc ggg cgc gcc cag gtc     2064
Glu Gly Ile Ser Val Gln Glu Gly Phe Ser Phe Gly Arg Ala Gln Val
    675                 680                 685 acc gac aaa act cac aca tgc cca ccg tgc cca gca cct gaa ctc ctg     2112
Thr Asp Lys Thr His Thr Cys Pro Pro Cys Pro Ala Pro Glu Leu Leu
690                 695                 700 ggg gga ccg tca gtc ttc ctc ttc ccc cca aaa ccc aag gac acc ctc     2160
Gly Gly Pro Ser Val Phe Leu Phe Pro Pro Lys Pro Lys Asp Thr Leu
705                 710                 715                 720 atg atc tcc cgg acc cct gag gtc aca tgc gtg gtg gtg gac gtg agc     2208
Met Ile Ser Arg Thr Pro Glu Val Thr Cys Val Val Val Asp Val Ser
            725                 730                 735 cac gaa gac cct gag gtc aag ttc aac tgg tac gtg gac ggc gtg gag     2256
His Glu Asp Pro Glu Val Lys Phe Asn Trp Tyr Val Asp Gly Val Glu
        740                 745                 750 gtg cat aat gcc aag aca aag ccg cgg gag gag cag tac aac agc acg     2304
Val His Asn Ala Lys Thr Lys Pro Arg Glu Glu Gln Tyr Asn Ser Thr
    755                 760                 765 tac cgt gtg gtc agc gtc ctc acc gtc ctg cac cag gac tgg ctg aat     2352
Tyr Arg Val Val Ser Val Leu Thr Val Leu His Gln Asp Trp Leu Asn
770                 775                 780 ggc aag gag tac aag tgc aag gtc tcc aac aaa gcc ctc cca gcc ccc     2400
Gly Lys Glu Tyr Lys Cys Lys Val Ser Asn Lys Ala Leu Pro Ala Pro
            785                 790                 795                 800 atc gag aaa acc atc tcc aaa gcc aaa ggg cag ccc cga gaa cca cag     2448
Ile Glu Lys Thr Ile Ser Lys Ala Lys Gly Gln Pro Arg Glu Pro Gln
        805                 810                 815 gtg tac acc ctg ccc cca tcc cgg gaa gag atg acc aag aac cag gtc     2496
Val Tyr Thr Leu Pro Pro Ser Arg Glu Glu Met Thr Lys Asn Gln Val
    820                 825                 830 agc ctg acc tgc ctg gtc aaa ggc ttc tat ccc agc gac atc gcc gtg     2544
Ser Leu Thr Cys Leu Val Lys Gly Phe Tyr Pro Ser Asp Ile Ala Val
835                 840                 845 gag tgg gag agc aat ggg cag ccg gag aac aac tac aag acc acg cct     2592
Glu Trp Glu Ser Asn Gly Gln Pro Glu Asn Asn Tyr Lys Thr Thr Pro
            850                 855                 860 ccc gtg ctg gac tcc gac ggc tcc ttc ttc ctc tac agc aag ctc acc     2640
Pro Val Leu Asp Ser Asp Gly Ser Phe Phe Leu Tyr Ser Lys Leu Thr
865                 870                 875                 880 gtg gac aag agc agg tgg cag cag ggg aac gtc ttc tca tgc tcc gtg     2688
Val Asp Lys Ser Arg Trp Gln Gln Gly Asn Val Phe Ser Cys Ser Val
                885                 890                 895
```

```
atg cat gag gct ctg cac aac cac tac acg cag aag agc ctc tcc ctg   2736
Met His Glu Ala Leu His Asn His Tyr Thr Gln Lys Ser Leu Ser Leu
        900                 905                 910 tct ccg ggt aaa tga                                              2751
Ser Pro Gly Lys
        915

<210> SEQ ID NO 50
<211> LENGTH: 916
<212> TYPE: PRT
<213> ORGANISM: Artificial Sequence
<220> FEATURE:
<223> OTHER INFORMATION: Synthetic mouse RON fusion protein

<400> SEQUENCE: 50

Met Gly Leu Pro Leu Pro Leu Leu Gln Ser Ser Leu Leu Met Leu
1               5                   10                  15

Leu Leu Arg Leu Ser Ala Ala Ser Thr Asn Leu Asn Trp Gln Cys Pro
            20                  25                  30

Arg Ile Pro Tyr Ala Ala Ser Arg Asp Phe Ser Val Lys Tyr Val Val
                35                  40                  45

Pro Ser Phe Ser Ala Gly Gly Arg Val Gln Ala Thr Ala Ala Tyr Glu
    50                  55                  60

Asp Ser Thr Asn Ser Ala Val Phe Val Ala Thr Arg Asn His Leu His
65                  70                  75                  80

Val Leu Gly Pro Asp Leu Gln Phe Ile Glu Asn Leu Thr Thr Gly Pro
                85                  90                  95

Ile Gly Asn Pro Gly Cys Gln Thr Cys Ala Ser Cys Gly Pro Gly Pro
                100                 105                 110

His Gly Pro Pro Lys Asp Thr Asp Thr Leu Val Leu Val Met Glu Pro
            115                 120                 125

Gly Leu Pro Ala Leu Val Ser Cys Gly Ser Thr Leu Gln Gly Arg Cys
    130                 135                 140

Phe Leu His Glu Leu Glu Pro Arg Gly Lys Ala Leu His Leu Ala Ala
145                 150                 155                 160

Pro Ala Cys Leu Phe Ser Ala Asn Asn Asn Lys Pro Glu Ala Cys Thr
                165                 170                 175

Asp Cys Val Ala Ser Pro Leu Gly Thr Arg Val Thr Val Val Glu Gln
            180                 185                 190

Gly His Ala Ser Tyr Phe Tyr Val Ala Ser Ser Leu Asp Pro Glu Leu
        195                 200                 205

Ala Ala Ser Phe Ser Pro Arg Ser Val Ser Ile Arg Arg Leu Lys Ser
    210                 215                 220

Asp Thr Ser Gly Phe Gln Pro Gly Phe Pro Ser Leu Ser Val Leu Pro
225                 230                 235                 240

Lys Tyr Leu Ala Ser Tyr Leu Ile Lys Tyr Val Tyr Ser Phe His Ser
                245                 250                 255

Gly Asp Phe Val Tyr Phe Leu Thr Val Gln Pro Ile Ser Val Thr Ser
            260                 265                 270

Pro Pro Ser Ala Leu His Thr Arg Leu Val Arg Leu Asn Ala Val Glu
        275                 280                 285

Pro Glu Ile Gly Asp Tyr Arg Glu Leu Val Leu Asp Cys His Phe Ala
    290                 295                 300

Pro Lys Arg Arg Arg Arg Gly Ala Pro Glu Gly Thr Gln Pro Tyr Pro
305                 310                 315                 320
```

-continued

Val Leu Gln Ala Ala His Ser Ala Pro Val Asp Ala Lys Leu Ala Val
              325                 330                 335

Glu Leu Ser Ile Ser Glu Gly Gln Glu Val Leu Phe Gly Val Phe Val
              340                 345                 350

Thr Val Lys Asp Gly Gly Ser Gly Met Gly Pro Asn Ser Val Val Cys
              355                 360                 365

Ala Phe Pro Ile Tyr His Leu Asn Ile Leu Glu Glu Gly Val Glu
370                 375                 380

Tyr Cys Cys His Ser Ser Asn Ser Ser Ser Leu Ser Arg Gly Leu
385                 390                 395                 400

Asp Phe Phe Gln Thr Pro Ser Phe Cys Pro Asn Pro Pro Gly Gly Glu
              405                 410                 415

Ala Ser Gly Pro Ser Ser Arg Cys His Tyr Phe Pro Leu Met Val His
              420                 425                 430

Ala Ser Phe Thr Arg Val Asp Leu Phe Asn Gly Leu Leu Gly Ser Val
              435                 440                 445

Lys Val Thr Ala Leu His Val Thr Arg Leu Gly Asn Val Thr Val Ala
              450                 455                 460

His Met Gly Thr Val Asp Gly Arg Val Leu Gln Val Glu Ile Ala Arg
465                 470                 475                 480

Ser Leu Asn Tyr Leu Leu Tyr Val Ser Asn Phe Ser Leu Gly Ser Ser
              485                 490                 495

Gly Gln Pro Val His Arg Asp Val Ser Arg Leu Gly Asn Asp Leu Leu
              500                 505                 510

Phe Ala Ser Gly Asp Gln Val Phe Lys Val Pro Ile Gln Gly Pro Gly
              515                 520                 525

Cys Arg His Phe Leu Thr Cys Trp Arg Cys Leu Arg Ala Gln Arg Phe
              530                 535                 540

Met Gly Cys Gly Trp Cys Gly Asp Arg Cys Asp Arg Gln Lys Glu Cys
545                 550                 555                 560

Pro Gly Ser Trp Gln Gln Asp His Cys Pro Pro Glu Ile Ser Glu Phe
              565                 570                 575

Tyr Pro His Ser Gly Pro Leu Arg Gly Thr Thr Arg Leu Thr Leu Cys
              580                 585                 590

Gly Ser Asn Phe Tyr Leu Arg Pro Asp Asp Val Val Pro Glu Gly Thr
              595                 600                 605

His Gln Ile Thr Val Gly Gln Ser Pro Cys Arg Leu Leu Pro Lys Asp
              610                 615                 620

Ser Ser Ser Pro Arg Pro Gly Ser Leu Lys Glu Phe Ile Gln Glu Leu
625                 630                 635                 640

Glu Cys Glu Leu Glu Pro Leu Val Thr Gln Ala Val Gly Thr Thr Asn
              645                 650                 655

Ile Ser Leu Val Ile Thr Asn Met Pro Ala Gly Lys His Phe Arg Val
              660                 665                 670

Glu Gly Ile Ser Val Gln Glu Gly Phe Ser Phe Gly Arg Ala Gln Val
              675                 680                 685

Thr Asp Lys Thr His Thr Cys Pro Cys Pro Ala Pro Glu Leu Leu
              690                 695                 700

Gly Gly Pro Ser Val Phe Leu Phe Pro Pro Lys Pro Lys Asp Thr Leu
705                 710                 715                 720

Met Ile Ser Arg Thr Pro Glu Val Thr Cys Val Val Val Asp Val Ser
              725                 730                 735

His Glu Asp Pro Glu Val Lys Phe Asn Trp Tyr Val Asp Gly Val Glu

```
                    740                 745                 750
Val His Asn Ala Lys Thr Lys Pro Arg Glu Glu Gln Tyr Asn Ser Thr
                755                 760                 765

Tyr Arg Val Val Ser Val Leu Thr Val Leu His Gln Asp Trp Leu Asn
            770                 775                 780

Gly Lys Glu Tyr Lys Cys Lys Val Ser Asn Lys Ala Leu Pro Ala Pro
785                 790                 795                 800

Ile Glu Lys Thr Ile Ser Lys Ala Lys Gly Gln Pro Arg Glu Pro Gln
                805                 810                 815

Val Tyr Thr Leu Pro Pro Ser Arg Glu Glu Met Thr Lys Asn Gln Val
            820                 825                 830

Ser Leu Thr Cys Leu Val Lys Gly Phe Tyr Pro Ser Asp Ile Ala Val
            835                 840                 845

Glu Trp Glu Ser Asn Gly Gln Pro Glu Asn Asn Tyr Lys Thr Thr Pro
        850                 855                 860

Pro Val Leu Asp Ser Asp Gly Ser Phe Phe Leu Tyr Ser Lys Leu Thr
865                 870                 875                 880

Val Asp Lys Ser Arg Trp Gln Gln Gly Asn Val Phe Ser Cys Ser Val
                885                 890                 895

Met His Glu Ala Leu His Asn His Tyr Thr Gln Lys Ser Leu Ser Leu
            900                 905                 910

Ser Pro Gly Lys
        915

<210> SEQ ID NO 51
<211> LENGTH: 2079
<212> TYPE: DNA
<213> ORGANISM: Artificial Sequence
<220> FEATURE:
<223> OTHER INFORMATION: Synthetic mouse RON polypeptide
<220> FEATURE:
<221> NAME/KEY: CDS
<222> LOCATION: (1)..(2079)

<400> SEQUENCE: 51 atg ggg ctg cct ctg ccg ctg ctt caa tcc tct ctt ctg cta atg ctt      48
Met Gly Leu Pro Leu Pro Leu Leu Gln Ser Ser Leu Leu Leu Met Leu
1               5                  10                  15 ctt ttg cgg ctg tcg gcg gcg tcc acc aac ctg aac tgg cag tgc cca      96
Leu Leu Arg Leu Ser Ala Ala Ser Thr Asn Leu Asn Trp Gln Cys Pro
            20                  25                  30 cga ata ccc tac gca gcc tcc cga gac ttc agt gtc aag tac gtg gtc     144
Arg Ile Pro Tyr Ala Ala Ser Arg Asp Phe Ser Val Lys Tyr Val Val
        35                  40                  45 ccc agc ttc tcc gcg ggg ggc cgg gta cag gcc acc gca gcc tac gag     192
Pro Ser Phe Ser Ala Gly Gly Arg Val Gln Ala Thr Ala Ala Tyr Glu
    50                  55                  60 gac agt aca aat agt gcg gtg ttt gtg gcc aca cgc aat cac ctg cac     240
Asp Ser Thr Asn Ser Ala Val Phe Val Ala Thr Arg Asn His Leu His
65                  70                  75                  80 gtg ctt ggg cct gac ctg cag ttc ata gag aac ctg acc act ggc cct     288
Val Leu Gly Pro Asp Leu Gln Phe Ile Glu Asn Leu Thr Thr Gly Pro
                85                  90                  95 atc ggg aac cct ggc tgc cag act tgt gcg agc tgt ggt cca ggc cct     336
Ile Gly Asn Pro Gly Cys Gln Thr Cys Ala Ser Cys Gly Pro Gly Pro
            100                 105                 110 cat gga cca cca aag gac aca gac aca ctg gtg cta gtg atg gag cca     384
His Gly Pro Pro Lys Asp Thr Asp Thr Leu Val Leu Val Met Glu Pro
        115                 120                 125
```

```
ggt ttg cca gcc ctg gtc agc tgt ggc tca acc cta cag ggc cgc tgc      432
Gly Leu Pro Ala Leu Val Ser Cys Gly Ser Thr Leu Gln Gly Arg Cys
    130                 135                 140 ttc ctg cat gag ctg gag cct cgg ggg aaa gcc ctg cac tta gca gct      480
Phe Leu His Glu Leu Glu Pro Arg Gly Lys Ala Leu His Leu Ala Ala
145                 150                 155                 160 cca gcc tgc cta ttc tca gca aac aat aac aag cct gag gcc tgc acg      528
Pro Ala Cys Leu Phe Ser Ala Asn Asn Asn Lys Pro Glu Ala Cys Thr
                165                 170                 175 gac tgt gtg gct agc ccc ctg ggc act cgt gtg act gtg gtg gag cag      576
Asp Cys Val Ala Ser Pro Leu Gly Thr Arg Val Thr Val Val Glu Gln
            180                 185                 190 ggg cat gct tcc tac ttc tat gtg gca tct tcg cta gac cca gag ttg      624
Gly His Ala Ser Tyr Phe Tyr Val Ala Ser Ser Leu Asp Pro Glu Leu
        195                 200                 205 gcc gct agc ttt agc ccc cgc tcg gtg tcc atc cgt cgt cta aag tct      672
Ala Ala Ser Phe Ser Pro Arg Ser Val Ser Ile Arg Arg Leu Lys Ser
    210                 215                 220 gat act tct gga ttc caa cca ggt ttt ccg tcg ctg tcg gtg ctg ccc      720
Asp Thr Ser Gly Phe Gln Pro Gly Phe Pro Ser Leu Ser Val Leu Pro
225                 230                 235                 240 aaa tat ttg gcc tcc tac ctc atc aaa tat gtg tac agc ttc cac tcg      768
Lys Tyr Leu Ala Ser Tyr Leu Ile Lys Tyr Val Tyr Ser Phe His Ser
                245                 250                 255 ggg gat ttt gtc tac ttt ctg act gtc cag ccc atc agt gtc aca agc      816
Gly Asp Phe Val Tyr Phe Leu Thr Val Gln Pro Ile Ser Val Thr Ser
            260                 265                 270 cct ccc agt gcc ttg cat aca cgt ctg gtc cgg ctc aat gct gta gag      864
Pro Pro Ser Ala Leu His Thr Arg Leu Val Arg Leu Asn Ala Val Glu
        275                 280                 285 cca gag att ggt gac tac cgg gag ctg gtc ttg gac tgt cat ttt gca      912
Pro Glu Ile Gly Asp Tyr Arg Glu Leu Val Leu Asp Cys His Phe Ala
    290                 295                 300 cct aaa cgc cgg cgc cgt gga gcc ccg gag ggc aca cag ccc tac cca      960
Pro Lys Arg Arg Arg Arg Gly Ala Pro Glu Gly Thr Gln Pro Tyr Pro
305                 310                 315                 320 gtg ctt cag gca gcc cac tct gct cca gtg gat gcc aaa ctg gct gtg     1008
Val Leu Gln Ala Ala His Ser Ala Pro Val Asp Ala Lys Leu Ala Val
                325                 330                 335 gaa ctg agc att tca gag ggc cag gaa gtg ctt ttt ggg gtc ttt gtg     1056
Glu Leu Ser Ile Ser Glu Gly Gln Glu Val Leu Phe Gly Val Phe Val
            340                 345                 350 acc gtc aag gat ggt ggc tct ggc atg ggt ccc aac tct gtt gta tgt     1104
Thr Val Lys Asp Gly Gly Ser Gly Met Gly Pro Asn Ser Val Val Cys
        355                 360                 365 gcc ttc ccc att tac cac ctg aac atc ctg att gaa gag ggt gtc gaa     1152
Ala Phe Pro Ile Tyr His Leu Asn Ile Leu Ile Glu Glu Gly Val Glu
    370                 375                 380 tat tgc tgt cac tct tca aat tct tct tcc ctg ttg tcg aga ggc ctt     1200
Tyr Cys Cys His Ser Ser Asn Ser Ser Ser Leu Leu Ser Arg Gly Leu
385                 390                 395                 400 gac ttc ttc cag acg ccc agt ttt tgt cct aat ccg cct ggt gga gag     1248
Asp Phe Phe Gln Thr Pro Ser Phe Cys Pro Asn Pro Pro Gly Gly Glu
                405                 410                 415 gcc tcc ggc ccc agc tcc cgt tgc cac tac ttc cct ttg atg gtc cac     1296
Ala Ser Gly Pro Ser Ser Arg Cys His Tyr Phe Pro Leu Met Val His
            420                 425                 430 gct agc ttc acc cgt gtg gac ctc ttc aat gga ctg tta gga tca gtg     1344
Ala Ser Phe Thr Arg Val Asp Leu Phe Asn Gly Leu Leu Gly Ser Val
```

```
                435                 440                 445
aag gtc acc gca ctg cat gtg aca cgt ctt ggc aat gtt aca gtg gcc      1392
Lys Val Thr Ala Leu His Val Thr Arg Leu Gly Asn Val Thr Val Ala
    450                 455                 460 cac atg ggc act gtg gat ggg cgt gtc cta cag gtg gag ata gcc agg      1440
His Met Gly Thr Val Asp Gly Arg Val Leu Gln Val Glu Ile Ala Arg
465                 470                 475                 480 tca ctc aac tac ctg ctg tat gtg tcc aac ttc tcc ctg ggc agc agt      1488
Ser Leu Asn Tyr Leu Leu Tyr Val Ser Asn Phe Ser Leu Gly Ser Ser
                485                 490                 495 gga cag cct gtt cat cgg gat gtc agc cgc ctc ggg aat gac cta ctc      1536
Gly Gln Pro Val His Arg Asp Val Ser Arg Leu Gly Asn Asp Leu Leu
            500                 505                 510 ttt gcc tct ggg gac cag gtc ttc aag gtg ccc atc cag ggc cct ggc      1584
Phe Ala Ser Gly Asp Gln Val Phe Lys Val Pro Ile Gln Gly Pro Gly
        515                 520                 525 tgt cgt cat ttt ctc acc tgt tgg cgt tgc ctg aga gca cag cgc ttc      1632
Cys Arg His Phe Leu Thr Cys Trp Arg Cys Leu Arg Ala Gln Arg Phe
    530                 535                 540 atg gga tgt ggc tgg tgt ggg gac cgg tgt gac cgg cag aag gag tgt      1680
Met Gly Cys Gly Trp Cys Gly Asp Arg Cys Asp Arg Gln Lys Glu Cys
545                 550                 555                 560 cct ggc tcc tgg caa cag gac cac tgt ccg cct gag atc agt gag ttc      1728
Pro Gly Ser Trp Gln Gln Asp His Cys Pro Pro Glu Ile Ser Glu Phe
                565                 570                 575 tat cct cac agc ggg cct cta agg ggc act acg agg ctc acc ctt tgt      1776
Tyr Pro His Ser Gly Pro Leu Arg Gly Thr Thr Arg Leu Thr Leu Cys
            580                 585                 590 ggc tcc aac ttc tac ctg cga cct gat gat gtc gta cct gag gga aca      1824
Gly Ser Asn Phe Tyr Leu Arg Pro Asp Asp Val Val Pro Glu Gly Thr
        595                 600                 605 cac cag atc acc gtg ggc caa agt ccc tgc cga ctg ctg cct aag gac      1872
His Gln Ile Thr Val Gly Gln Ser Pro Cys Arg Leu Leu Pro Lys Asp
    610                 615                 620 tct tca agc cct agg cca ggg tcc ctc aag gaa ttc ata cag gaa ctt      1920
Ser Ser Ser Pro Arg Pro Gly Ser Leu Lys Glu Phe Ile Gln Glu Leu
625                 630                 635                 640 gaa tgt gag ctg gag ccc ctg gtc acc cag gca gtg ggg act aca aac      1968
Glu Cys Glu Leu Glu Pro Leu Val Thr Gln Ala Val Gly Thr Thr Asn
                645                 650                 655 atc agc ctt gtc atc acc aac atg cca gca ggc aag cac ttc cga gtg      2016
Ile Ser Leu Val Ile Thr Asn Met Pro Ala Gly Lys His Phe Arg Val
            660                 665                 670 gaa ggc atc tct gta cag gaa ggc ttc tct ttc gtg cat cat cat cat      2064
Glu Gly Ile Ser Val Gln Glu Gly Phe Ser Phe Val His His His His
        675                 680                 685 cat cat cat cat tga                                                  2079
His His His His
    690

<210> SEQ ID NO 52
<211> LENGTH: 692
<212> TYPE: PRT
<213> ORGANISM: Artificial Sequence
<220> FEATURE:
<223> OTHER INFORMATION: Synthetic mouse RON polypeptide

<400> SEQUENCE: 52

Met Gly Leu Pro Leu Pro Leu Leu Gln Ser Ser Leu Leu Leu Met Leu
1               5                   10                  15
```

```
Leu Leu Arg Leu Ser Ala Ala Ser Thr Asn Leu Asn Trp Gln Cys Pro
            20                  25                  30

Arg Ile Pro Tyr Ala Ala Ser Arg Asp Phe Ser Val Lys Tyr Val Val
            35                  40                  45

Pro Ser Phe Ser Ala Gly Gly Arg Val Gln Ala Thr Ala Ala Tyr Glu
50                  55                  60

Asp Ser Thr Asn Ser Ala Val Phe Val Ala Thr Arg Asn His Leu His
65                  70                  75                  80

Val Leu Gly Pro Asp Leu Gln Phe Ile Glu Asn Leu Thr Thr Gly Pro
            85                  90                  95

Ile Gly Asn Pro Gly Cys Gln Thr Cys Ala Ser Cys Gly Pro Gly Pro
            100                 105                 110

His Gly Pro Pro Lys Asp Thr Asp Thr Leu Val Leu Val Met Glu Pro
            115                 120                 125

Gly Leu Pro Ala Leu Val Ser Cys Gly Ser Thr Leu Gln Gly Arg Cys
            130                 135                 140

Phe Leu His Glu Leu Glu Pro Arg Gly Lys Ala Leu His Leu Ala Ala
145                 150                 155                 160

Pro Ala Cys Leu Phe Ser Ala Asn Asn Asn Lys Pro Glu Ala Cys Thr
            165                 170                 175

Asp Cys Val Ala Ser Pro Leu Gly Thr Arg Val Thr Val Val Glu Gln
            180                 185                 190

Gly His Ala Ser Tyr Phe Tyr Val Ala Ser Ser Leu Asp Pro Glu Leu
            195                 200                 205

Ala Ala Ser Phe Ser Pro Arg Ser Val Ser Ile Arg Arg Leu Lys Ser
            210                 215                 220

Asp Thr Ser Gly Phe Gln Pro Gly Phe Pro Ser Leu Ser Val Leu Pro
225                 230                 235                 240

Lys Tyr Leu Ala Ser Tyr Leu Ile Lys Tyr Val Tyr Ser Phe His Ser
            245                 250                 255

Gly Asp Phe Val Tyr Phe Leu Thr Val Gln Pro Ile Ser Val Thr Ser
            260                 265                 270

Pro Pro Ser Ala Leu His Thr Arg Leu Val Arg Leu Asn Ala Val Glu
            275                 280                 285

Pro Glu Ile Gly Asp Tyr Arg Glu Leu Val Leu Asp Cys His Phe Ala
            290                 295                 300

Pro Lys Arg Arg Arg Gly Ala Pro Glu Gly Thr Gln Pro Tyr Pro
305                 310                 315                 320

Val Leu Gln Ala Ala His Ser Ala Pro Val Asp Ala Lys Leu Ala Val
            325                 330                 335

Glu Leu Ser Ile Ser Glu Gly Gln Glu Val Leu Phe Gly Val Phe Val
            340                 345                 350

Thr Val Lys Asp Gly Gly Ser Gly Met Gly Pro Asn Ser Val Val Cys
            355                 360                 365

Ala Phe Pro Ile Tyr His Leu Asn Ile Leu Ile Glu Glu Gly Val Glu
            370                 375                 380

Tyr Cys Cys His Ser Ser Asn Ser Ser Ser Leu Leu Ser Arg Gly Leu
385                 390                 395                 400

Asp Phe Phe Gln Thr Pro Ser Phe Cys Pro Asn Pro Gly Gly Glu
            405                 410                 415

Ala Ser Gly Pro Ser Ser Arg Cys His Tyr Phe Pro Leu Met Val His
            420                 425                 430

Ala Ser Phe Thr Arg Val Asp Leu Phe Asn Gly Leu Leu Gly Ser Val
```

-continued

```
                435                 440                 445
Lys Val Thr Ala Leu His Val Thr Arg Leu Gly Asn Val Thr Val Ala
    450                 455                 460
His Met Gly Thr Val Asp Gly Arg Val Leu Gln Val Glu Ile Ala Arg
465                 470                 475                 480
Ser Leu Asn Tyr Leu Tyr Val Ser Asn Phe Ser Leu Gly Ser Ser
                485                 490                 495
Gly Gln Pro Val His Arg Asp Val Ser Arg Leu Gly Asn Asp Leu Leu
            500                 505                 510
Phe Ala Ser Gly Asp Gln Val Phe Lys Val Pro Ile Gln Gly Pro Gly
        515                 520                 525
Cys Arg His Phe Leu Thr Cys Trp Arg Cys Leu Arg Ala Gln Arg Phe
    530                 535                 540
Met Gly Cys Gly Trp Cys Gly Asp Arg Cys Asp Arg Gln Lys Glu Cys
545                 550                 555                 560
Pro Gly Ser Trp Gln Gln Asp His Cys Pro Pro Glu Ile Ser Glu Phe
                565                 570                 575
Tyr Pro His Ser Gly Pro Leu Arg Gly Thr Thr Arg Leu Thr Leu Cys
            580                 585                 590
Gly Ser Asn Phe Tyr Leu Arg Pro Asp Asp Val Val Pro Glu Gly Thr
        595                 600                 605
His Gln Ile Thr Val Gly Gln Ser Pro Cys Arg Leu Leu Pro Lys Asp
    610                 615                 620
Ser Ser Ser Pro Arg Pro Gly Ser Leu Lys Glu Phe Ile Gln Glu Leu
625                 630                 635                 640
Glu Cys Glu Leu Glu Pro Leu Val Thr Gln Ala Val Gly Thr Thr Asn
                645                 650                 655
Ile Ser Leu Val Ile Thr Asn Met Pro Ala Gly Lys His Phe Arg Val
            660                 665                 670
Glu Gly Ile Ser Val Gln Glu Gly Phe Ser Phe Val His His His His
        675                 680                 685
His His His His
    690

<210> SEQ ID NO 53
<211> LENGTH: 1248
<212> TYPE: DNA
<213> ORGANISM: Artificial Sequence
<220> FEATURE:
<223> OTHER INFORMATION: Synthetic sHepsin
<220> FEATURE:
<221> NAME/KEY: CDS
<222> LOCATION: (1)..(1248)

<400> SEQUENCE: 53 atg tgg gtg acc aaa ctc ctg cca gcc ctg ctg ctg cag cat gtc ctc        48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga agg        96
Leu His Leu Leu Leu Leu Pro Ile Ala Ile Pro Tyr Ala Glu Gly Arg
                20                  25                  30 agt gac cag gag ccg ctg tac cca gtg cag gtc agc tct gcg gac gct       144
Ser Asp Gln Glu Pro Leu Tyr Pro Val Gln Val Ser Ser Ala Asp Ala
            35                  40                  45 cgg ctc atg gtc ttt gac aag acg gaa ggg acg tgg cgg ctg ctg tgc       192
Arg Leu Met Val Phe Asp Lys Thr Glu Gly Thr Trp Arg Leu Leu Cys
        50                  55                  60
```

| | | |
|---|---|---|
| tcc tcg cgc tcc aac gcc agg gta gcc gga ctc agc tgc gag gag atg<br>Ser Ser Arg Ser Asn Ala Arg Val Ala Gly Leu Ser Cys Glu Glu Met<br>65                    70                    75                    80 | 240 |
| ggc ttc ctc agg gca ctg acc cac tcc gag ctg gac gtc cga acg gcg<br>Gly Phe Leu Arg Ala Leu Thr His Ser Glu Leu Asp Val Arg Thr Ala<br>                  85                    90                    95 | 288 |
| ggc gcc aat ggc acg tcg ggc ttc ttc tgt gtg gac gag ggg agg ctg<br>Gly Ala Asn Gly Thr Ser Gly Phe Phe Cys Val Asp Glu Gly Arg Leu<br>                    100                   105                  110 | 336 |
| ccc cac acc cag agg ctg ctg gag gtc atc tcc gtg tgt gat tgc ccc<br>Pro His Thr Gln Arg Leu Leu Glu Val Ile Ser Val Cys Asp Cys Pro<br>            115                   120                   125 | 384 |
| aga ggc cgt ttc ttg gcc gcc atc tgc caa gac tgt ggc cgc agg aag<br>Arg Gly Arg Phe Leu Ala Ala Ile Cys Gln Asp Cys Gly Arg Arg Lys<br>130                    135                   140 | 432 |
| ctg ccc gtg gac gat gac gat aag atc gtg gga ggc cgg gac acc agc<br>Leu Pro Val Asp Asp Asp Asp Lys Ile Val Gly Gly Arg Asp Thr Ser<br>145                    150                   155                   160 | 480 |
| ttg ggc cgg tgg ccg tgg caa gtc agc ctt cgc tat gat gga gca cac<br>Leu Gly Arg Trp Pro Trp Gln Val Ser Leu Arg Tyr Asp Gly Ala His<br>                      165                   170                  175 | 528 |
| ctc tgt ggg gga tcc ctg ctc tcc ggg gac tgg gtg ctg aca gcc gcc<br>Leu Cys Gly Gly Ser Leu Leu Ser Gly Asp Trp Val Leu Thr Ala Ala<br>                  180                   185                  190 | 576 |
| cac tgc ttc ccg gag cgg aac cgg gtc ctg tcc cga tgg cga gtg ttt<br>His Cys Phe Pro Glu Arg Asn Arg Val Leu Ser Arg Trp Arg Val Phe<br>         195                   200                   205 | 624 |
| gcc ggt gcc gtg gcc cag gcc tct ccc cac ggt ctg cag ctg ggg gtg<br>Ala Gly Ala Val Ala Gln Ala Ser Pro His Gly Leu Gln Leu Gly Val<br>210                    215                   220 | 672 |
| cag gct gtg gtc tac cac ggg ggc tat ctt ccc ttt cgg gac ccc aac<br>Gln Ala Val Val Tyr His Gly Gly Tyr Leu Pro Phe Arg Asp Pro Asn<br>225                    230                   235                   240 | 720 |
| agc gag gag aac agc aac gat att gcc ctg gtc cac ctc tcc agt ccc<br>Ser Glu Glu Asn Ser Asn Asp Ile Ala Leu Val His Leu Ser Ser Pro<br>                      245                   250                  255 | 768 |
| ctg ccc ctc aca gaa tac atc cag cct gtg tgc ctc cca gct gcc ggc<br>Leu Pro Leu Thr Glu Tyr Ile Gln Pro Val Cys Leu Pro Ala Ala Gly<br>            260                   265                   270 | 816 |
| cag gcc ctg gtg gat ggc aag atc tgt acc gtg acg ggc tgg ggc aac<br>Gln Ala Leu Val Asp Gly Lys Ile Cys Thr Val Thr Gly Trp Gly Asn<br>                  275                   280                  285 | 864 |
| acg cag tac tat ggc caa cag gcc ggg gta ctc cag gag gct cga gtc<br>Thr Gln Tyr Tyr Gly Gln Gln Ala Gly Val Leu Gln Glu Ala Arg Val<br>290                    295                   300 | 912 |
| ccc ata atc agc aat gat gtc tgc aat ggc gct gac ttc tat gga aac<br>Pro Ile Ile Ser Asn Asp Val Cys Asn Gly Ala Asp Phe Tyr Gly Asn<br>305                    310                   315                   320 | 960 |
| cag atc aag ccc aag atg ttc tgt gct ggc tac ccc gag ggt ggc att<br>Gln Ile Lys Pro Lys Met Phe Cys Ala Gly Tyr Pro Glu Gly Gly Ile<br>                      325                   330                  335 | 1008 |
| gat gcc tgc cag ggc gac agc ggt ggt ccc ttt gtg tgt gag gac agc<br>Asp Ala Cys Gln Gly Asp Ser Gly Gly Pro Phe Val Cys Glu Asp Ser<br>            340                   345                   350 | 1056 |
| atc tct cgg acg cca cgt tgg cgg ctg tgt ggc att gtg agt tgg ggc<br>Ile Ser Arg Thr Pro Arg Trp Arg Leu Cys Gly Ile Val Ser Trp Gly<br>                  355                   360                  365 | 1104 |
| act ggc tgt gcc ctg gcc cag aag cca ggc gtc tac acc aaa gtc agt<br>Thr Gly Cys Ala Leu Ala Gln Lys Pro Gly Val Tyr Thr Lys Val Ser<br>370                      375                   380 | 1152 |

```
gac ttc cgg gag tgg atc ttc cag gcc ata aag act cac tcc gaa gcc      1200
Asp Phe Arg Glu Trp Ile Phe Gln Ala Ile Lys Thr His Ser Glu Ala
385                 390                 395                 400 agc ggc atg gtg acc cag ctc cac cat cac cat cac cat taa              1248
Ser Gly Met Val Thr Gln Leu His His His His His His
                405                 410                 415
```

<210> SEQ ID NO 54
<211> LENGTH: 415
<212> TYPE: PRT
<213> ORGANISM: Artificial Sequence
<220> FEATURE:
<223> OTHER INFORMATION: Synthetic sHepsin polypeptide

<400> SEQUENCE: 54

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Arg
            20                  25                  30

Ser Asp Gln Glu Pro Leu Tyr Pro Val Gln Val Ser Ser Ala Asp Ala
            35                  40                  45

Arg Leu Met Val Phe Asp Lys Thr Glu Gly Thr Trp Arg Leu Leu Cys
    50                  55                  60

Ser Ser Arg Ser Asn Ala Arg Val Ala Gly Leu Ser Cys Glu Met
65                  70                  75                  80

Gly Phe Leu Arg Ala Leu Thr His Ser Glu Leu Asp Val Arg Thr Ala
                85                  90                  95

Gly Ala Asn Gly Thr Ser Gly Phe Phe Cys Val Asp Glu Gly Arg Leu
            100                 105                 110

Pro His Thr Gln Arg Leu Leu Glu Val Ile Ser Val Cys Asp Cys Pro
        115                 120                 125

Arg Gly Arg Phe Leu Ala Ala Ile Cys Gln Asp Cys Gly Arg Arg Lys
    130                 135                 140

Leu Pro Val Asp Asp Asp Lys Ile Val Gly Gly Arg Asp Thr Ser
145                 150                 155                 160

Leu Gly Arg Trp Pro Trp Gln Val Ser Leu Arg Tyr Asp Gly Ala His
                165                 170                 175

Leu Cys Gly Gly Ser Leu Leu Ser Gly Asp Trp Val Leu Thr Ala Ala
            180                 185                 190

His Cys Phe Pro Glu Arg Asn Arg Val Leu Ser Arg Trp Arg Val Phe
        195                 200                 205

Ala Gly Ala Val Ala Gln Ala Ser Pro His Gly Leu Gln Leu Gly Val
    210                 215                 220

Gln Ala Val Val Tyr His Gly Gly Tyr Leu Pro Phe Arg Asp Pro Asn
225                 230                 235                 240

Ser Glu Glu Asn Ser Asn Asp Ile Ala Leu Val His Leu Ser Ser Pro
                245                 250                 255

Leu Pro Leu Thr Glu Tyr Ile Gln Pro Val Cys Leu Pro Ala Ala Gly
            260                 265                 270

Gln Ala Leu Val Asp Gly Lys Ile Cys Thr Val Thr Gly Trp Gly Asn
        275                 280                 285

Thr Gln Tyr Tyr Gly Gln Gln Ala Gly Val Leu Gln Glu Ala Arg Val
    290                 295                 300

Pro Ile Ile Ser Asn Asp Val Cys Asn Gly Ala Asp Phe Tyr Gly Asn
305                 310                 315                 320
```

```
Gln Ile Lys Pro Lys Met Phe Cys Ala Gly Tyr Pro Glu Gly Gly Ile
            325                 330                 335

Asp Ala Cys Gln Gly Asp Ser Gly Gly Pro Phe Val Cys Glu Asp Ser
        340                 345                 350

Ile Ser Arg Thr Pro Arg Trp Arg Leu Cys Gly Ile Val Ser Trp Gly
    355                 360                 365

Thr Gly Cys Ala Leu Ala Gln Lys Pro Gly Val Tyr Thr Lys Val Ser
370                 375                 380

Asp Phe Arg Glu Trp Ile Phe Gln Ala Ile Lys Thr His Ser Glu Ala
385                 390                 395                 400

Ser Gly Met Val Thr Gln Leu His His His His His His His
            405                 410                 415

<210> SEQ ID NO 55
<211> LENGTH: 31
<212> TYPE: PRT
<213> ORGANISM: Artificial Sequence
<220> FEATURE:
<223> OTHER INFORMATION: Synthetic peptide, HGF leader sequence

<400> SEQUENCE: 55

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly
            20                  25                  30

<210> SEQ ID NO 56
<211> LENGTH: 21
<212> TYPE: DNA
<213> ORGANISM: Artificial Sequence
<220> FEATURE:
<223> OTHER INFORMATION: PCR primer

<400> SEQUENCE: 56
ccactgctta ctggcttatc g                                            21

<210> SEQ ID NO 57
<211> LENGTH: 20
<212> TYPE: DNA
<213> ORGANISM: Artificial Sequence
<220> FEATURE:
<223> OTHER INFORMATION: PCR primer

<400> SEQUENCE: 57
tcttcagcat ctgccacatc                                              20

<210> SEQ ID NO 58
<211> LENGTH: 20
<212> TYPE: DNA
<213> ORGANISM: Artificial Sequence
<220> FEATURE:
<223> OTHER INFORMATION: snthetic polynucleotide

<400> SEQUENCE: 58
tagcgctacc ggactcagat                                              20

<210> SEQ ID NO 59
<211> LENGTH: 18
<212> TYPE: DNA
<213> ORGANISM: Artificial Sequence
<220> FEATURE:
<223> OTHER INFORMATION: PCR primer

<400> SEQUENCE: 59
```
agggcagtcc tgcaacat                                                   18

<210> SEQ ID NO 60
<211> LENGTH: 19
<212> TYPE: DNA
<213> ORGANISM: Artificial Sequence
<220> FEATURE:
<223> OTHER INFORMATION: PCR primer

<400> SEQUENCE: 60
gagtccactg tgcccagaa                                                  19

<210> SEQ ID NO 61
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 61
acagggtcca cagcaggcac tc                                              22

<210> SEQ ID NO 62
<211> LENGTH: 19
<212> TYPE: DNA
<213> ORGANISM: Artificial Sequence
<220> FEATURE:
<223> OTHER INFORMATION: PCR primer

<400> SEQUENCE: 62
caatgccaac tcccgtcag                                                  19

<210> SEQ ID NO 63
<211> LENGTH: 19
<212> TYPE: DNA
<213> ORGANISM: Artificial Sequence
<220> FEATURE:
<223> OTHER INFORMATION: PCR primer

<400> SEQUENCE: 63
gtcacaggct tgcggatga                                                  19

<210> SEQ ID NO 64
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 64
agatccggaa gctcatcaaa gatgggct                                        28

<210> SEQ ID NO 65
<211> LENGTH: 30
<212> TYPE: DNA
<213> ORGANISM: Mesocricetus Auratus
<220> FEATURE:
<221> NAME/KEY: CDS
<222> LOCATION: (1)..(30)

<400> SEQUENCE: 65 gga ttc atc ttc agt gaa tat ggc atg aac                               30
Gly Phe Ile Phe Ser Glu Tyr Gly Met Asn
1               5                   10

```
<210> SEQ ID NO 66
<211> LENGTH: 10
<212> TYPE: PRT
<213> ORGANISM: Mesocricetus Auratus

<400> SEQUENCE: 66

Gly Phe Ile Phe Ser Glu Tyr Gly Met Asn
1               5                   10

<210> SEQ ID NO 67
<211> LENGTH: 60
<212> TYPE: DNA
<213> ORGANISM: Mesocricetus Auratus
<220> FEATURE:
<221> NAME/KEY: CDS
<222> LOCATION: (1)..(60)

<400> SEQUENCE: 67 gct cgc ata cga cct aaa cct aat aat tat gca acc tat tac gcg gat       48
Ala Arg Ile Arg Pro Lys Pro Asn Asn Tyr Ala Thr Tyr Tyr Ala Asp
1               5                   10                  15 tcg gtg aag ggc                                                        60
Ser Val Lys Gly
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic Construct

<400> SEQUENCE: 68

Ala Arg Ile Arg Pro Lys Pro Asn Asn Tyr Ala Thr Tyr Tyr Ala Asp
1               5                   10                  15

Ser Val Lys Gly
            20

<210> SEQ ID NO 69
<211> LENGTH: 39
<212> TYPE: DNA
<213> ORGANISM: Artificial Sequence
<220> FEATURE:
<223> OTHER INFORMATION: Artificial Sequence
<220> FEATURE:
<221> NAME/KEY: CDS
<222> LOCATION: (1)..(39)

<400> SEQUENCE: 69 aca aga gac tat agc gga tac cac aat gct ttt gat tcc                   39
Thr Arg Asp Tyr Ser Gly Tyr His Asn Ala Phe Asp Ser
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic Construct

<400> SEQUENCE: 70

Thr Arg Asp Tyr Ser Gly Tyr His Asn Ala Phe Asp Ser
1               5                   10

<210> SEQ ID NO 71
<211> LENGTH: 33
<212> TYPE: DNA
```

```
<213> ORGANISM: Artificial Sequence
<220> FEATURE:
<223> OTHER INFORMATION: Artificial Sequence
<220> FEATURE:
<221> NAME/KEY: CDS
<222> LOCATION: (1)..(33)

<400> SEQUENCE: 71 aag gct agt cag aac att aac cag tac tta cac                    33
Lys Ala Ser Gln Asn Ile Asn Gln Tyr Leu His
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Lys Ala Ser Gln Asn Ile Asn Gln Tyr Leu His
1               5                   10

<210> SEQ ID NO 73
<211> LENGTH: 21
<212> TYPE: DNA
<213> ORGANISM: Artificial Sequence
<220> FEATURE:
<223> OTHER INFORMATION: Artificial Sequence
<220> FEATURE:
<221> NAME/KEY: CDS
<222> LOCATION: (1)..(21)

<400> SEQUENCE: 73 agt gcg tcc aat ctg cag gca                                    21
Ser Ala Ser Asn Leu Gln Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Construct

<400> SEQUENCE: 74

Ser Ala Ser Asn Leu Gln Ala
1               5

<210> SEQ ID NO 75
<211> LENGTH: 24
<212> TYPE: DNA
<213> ORGANISM: Artificial Sequence
<220> FEATURE:
<223> OTHER INFORMATION: Artificial Sequence
<220> FEATURE:
<221> NAME/KEY: CDS
<222> LOCATION: (1)..(24)

<400> SEQUENCE: 75 caa caa ggt tat aca cct cgc acg                                24
Gln Gln Gly Tyr Thr Pro Arg Thr
1               5

<210> SEQ ID NO 76
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 76

Gln Gln Gly Tyr Thr Pro Arg Thr
1               5

<210> SEQ ID NO 77
<211> LENGTH: 30
<212> TYPE: DNA
<213> ORGANISM: Artificial Sequence
<220> FEATURE:
<223> OTHER INFORMATION: Synthetic polypeptide
<220> FEATURE:
<221> NAME/KEY: CDS
<222> LOCATION: (1)..(30)

<400> SEQUENCE: 77 ggc ttc acc ttc agc agc tac gct atg agc                           30
Gly Phe Thr Phe Ser Ser Tyr Ala Met Ser
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 78

Gly Phe Thr Phe Ser Ser Tyr Ala Met Ser
1               5                   10

<210> SEQ ID NO 79
<211> LENGTH: 51
<212> TYPE: DNA
<213> ORGANISM: Artificial Sequence
<220> FEATURE:
<223> OTHER INFORMATION: Synthetic polypeptide
<220> FEATURE:
<221> NAME/KEY: CDS
<222> LOCATION: (1)..(51)

<400> SEQUENCE: 79 gcc att agc agc agc ggc agc agc act tac tat gcc gat agc gtc aag     48
Ala Ile Ser Ser Ser Gly Ser Ser Thr Tyr Tyr Ala Asp Ser Val Lys
1               5                   10                  15 ggc                                                                 51
Gly

<210> SEQ ID NO 80
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 80

Ala Ile Ser Ser Ser Gly Ser Ser Thr Tyr Tyr Ala Asp Ser Val Lys
1               5                   10                  15

Gly

<210> SEQ ID NO 81
<211> LENGTH: 45
<212> TYPE: DNA
<213> ORGANISM: Artificial Sequence
<220> FEATURE:
<223> OTHER INFORMATION: Synthetic polypeptide

```
<220> FEATURE:
<221> NAME/KEY: CDS
<222> LOCATION: (1)..(45)

<400> SEQUENCE: 81 gac atg tac act tac ggt cgt tac ccg gaa ccg cgt ttc gac tac      45
Asp Met Tyr Thr Tyr Gly Arg Tyr Pro Glu Pro Arg Phe Asp Tyr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 82

Asp Met Tyr Thr Tyr Gly Arg Tyr Pro Glu Pro Arg Phe Asp Tyr
1               5                   10                  15

<210> SEQ ID NO 83
<211> LENGTH: 51
<212> TYPE: DNA
<213> ORGANISM: Artificial Sequence
<220> FEATURE:
<223> OTHER INFORMATION: Synthetic polypeptide
<220> FEATURE:
<221> NAME/KEY: CDS
<222> LOCATION: (1)..(51)

<400> SEQUENCE: 83 aaa agc agc cag agc gtg ctg tac agc agc aac aac aaa aac tac ctg    48
Lys Ser Ser Gln Ser Val Leu Tyr Ser Ser Asn Asn Lys Asn Tyr Leu
1               5                   10                  15 gcg                                                                51
Ala

<210> SEQ ID NO 84
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 84

Lys Ser Ser Gln Ser Val Leu Tyr Ser Ser Asn Asn Lys Asn Tyr Leu
1               5                   10                  15

Ala

<210> SEQ ID NO 85
<211> LENGTH: 21
<212> TYPE: DNA
<213> ORGANISM: Artificial Sequence
<220> FEATURE:
<223> OTHER INFORMATION: Synthetic polypeptide
<220> FEATURE:
<221> NAME/KEY: CDS
<222> LOCATION: (1)..(21)

<400> SEQUENCE: 85 tgg gcg agc acc cgt gaa agc                                        21
Trp Ala Ser Thr Arg Glu Ser
1               5

<210> SEQ ID NO 86
<211> LENGTH: 7
<212> TYPE: PRT
```

```
<213> ORGANISM: Artificial Sequence
<220> FEATURE:
<223> OTHER INFORMATION: Synthetic polypeptide

<400> SEQUENCE: 86

Trp Ala Ser Thr Arg Glu Ser
1               5

<210> SEQ ID NO 87
<211> LENGTH: 27
<212> TYPE: DNA
<213> ORGANISM: Artificial Sequence
<220> FEATURE:
<223> OTHER INFORMATION: Synthetic polypeptide
<220> FEATURE:
<221> NAME/KEY: CDS
<222> LOCATION: (1)..(27)

<400> SEQUENCE: 87 cag caa tac tac tcc acc cct ttt acg                              27
Gln Gln Tyr Tyr Ser Thr Pro Phe Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 88

Gln Gln Tyr Tyr Ser Thr Pro Phe Thr
1               5

<210> SEQ ID NO 89
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ile His Lys Val Met Arg Leu Gly Gln Val Thr Asp Lys Lys Ile Glu
1               5                   10                  15

Pro Arg Gly Pro Thr Ile Lys Pro Cys Pro Pro Cys Lys Cys
            20                  25                  30

<210> SEQ ID NO 90
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ile Asn Lys Val Met Gln Leu Glu Gln Val Thr Asp Lys Lys Ile Glu
1               5                   10                  15

Pro Arg Gly Pro Thr Ile Lys Pro Cys Pro Pro Cys Lys Cys
            20                  25                  30

<210> SEQ ID NO 91
<211> LENGTH: 26
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 91

Ile Asn Lys Val Met Gln Leu Glu Lys Lys Ile Glu Pro Arg Gly Pro
1               5                   10                  15

Thr Ile Lys Pro Cys Pro Pro Cys Lys Cys
            20                  25

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ile Asn Lys Val Met Gln Leu Glu Pro Arg Gly Pro Thr Ile Lys Pro
1               5                   10                  15

Cys Pro Pro Cys Lys Cys
            20

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Asn Lys Val Met Gln Leu Glu Thr Ile Lys Pro Cys Pro Pro Cys
1               5                   10                  15

Lys Cys
```

METHOD OF REDUCING BLOOD GLUCOSE BY ADMINISTERING RON AGONISTS

CROSS REFERENCE TO RELATED APPLICATIONS

This application is a continuation of International Application No. PCT/US13/72364 having an international filing date of Nov. 27, 2013, the entire contents of which are incorporated herein by reference, and which claims benefit under 35 U.S.C § 119 to U.S. Provisional Application No. 61/732,048, filed on Nov. 30, 2012 and 61/823,744, filed on May 15, 2013, which are incorporated by reference herein in their entireties.

SEQUENCE LISTING

The instant application contains a Sequence Listing submitted via EFS-Web and is hereby incorporated by reference in its entirety. Said ASCII copy, created on Oct. 12, 2015, is named P05505US2_SeqList.txt, and is 391,412 bytes in size.

BACKGROUND OF RELATED ART

Crohn's disease (CD) and ulcerative colitis (UC) are two forms of inflammatory bowel disease (IBD) characterized by chronic inflammatory responses within the intestinal tract. Genome-wide association studies (GWAS) examining the frequencies of single nucleotide polymorphisms (SNPs) in CD and UC patients have identified a large number of shared and unique susceptibility alleles. Using both GWAS and candidate gene approaches, polymorphisms in macrophage stimulating protein (MSP) have been identified that were thought to associate with susceptibility to both CD and UC. See e.g., Barrett et al., 2008, Nat Genet 40:955-62, and Consortium WTCC. 2007, Nature 447:661-78.

The likely causative allele responsible for this increased genetic risk is a non-synonymous coding SNP in MSP (rs3197999) that leads to an arginine to cysteine change at amino acid 689 (689R to 689C). See Goyette et al. 2008, Mucosal Immunol 1:131-8.

MSP is a plasminogen-related soluble growth factor expressed by the liver and secreted into the serum as an inactive single-chain protein (pro-MSP) incapable of binding its receptor, the Met-family receptor tyrosine kinase, Recepteur d'Origine Nantais (RON). Proteolytic cleavage of pro-MSP between R483 and V484 converts it into an active, two-chain disulfide-linked α/β heterodimer able to bind RON with high affinity and induce receptor signaling. See Gaudino et al., 1994, EMBO J 13:3524-32, and Wang et al., 1994, Science 266:117-9. The α-chain comprises an N-terminal PAN domain followed by four Kringle domains and the β-chain contains a C-terminal trypsin-like serine protease domain. pro-MSP can be proteolytically activated by a number of different serine proteases, including those involved in the coagulation cascade and induced during inflammatory responses. See e.g., Wang et al., 1994, J Biol Chem 269:3436-40. Thus, cleavage of MSP at sites of tissue damage leads to local activation of RON.

RON expression has been reported in epithelial cells, subsets of macrophages, neuroendocrine tissues, and developing bone, and has been linked to induction of epithelial cell proliferation, survival, migration and adherence to extracellular matrix. See e.g., Iwama et al., 1995, Blood 86:3394-403, Gaudino et al., 1995, Oncogene 11:2627-37, Danilkovitch et al., 1999, Exp Cell Res 248:575-82, and Danilkovitch et al., 2000, Mol Cell Biol 20:2218-27. More recently, the MSP-RON pathway has been proposed as a key negative regulator of inflammatory responses. Based primarily on studies of murine peritoneal macrophages stimulated with lipopolysaccharide and interferon-γ, RON signaling was found to suppress expression of pro-inflammatory factors and upregulate pathways that may be involved in tissue repair. See e.g., Chen et al., 1998, J Immunol, 161: 4950-9, and Wilson et al., 2008, J Immunol, 181:2303-10. The suppressive role of RON in innate inflammatory responses has been supported by in vivo studies demonstrating that mice with targeted mutations in RON exhibit enhanced sensitivity to endotoxin challenge. See Waltz et al., 2001, J Clin Invest, 108:567-76. These in vitro and in vivo studies have led to the speculation that the increased genetic risk for IBD associated with the MSP 689C polymorphism is a direct consequence of altered binding between MSP and RON, and defects in RON-mediated inhibition of macrophage activation. See Khor et al., 2011, Nature 474:307-17, Gorlatova et al., 2011, PLoS One 6:e27269. Paradoxically, a more recent study found that the 689C polymorphism increases MSP stimulatory activity in a human monocytic cell line, inducing greater in vitro migration and proliferation. Hauser et al., 2012, Genes Immun 13:321-7.

Thus, a better understanding of the role of the MSP polymorphism in RON signaling and RON associated diseases, including IBD, and a better therapeutic for treatment is needed.

SUMMARY OF THE INVENTION

The instant application provides reagents and compositions relating to Receptor d'Origine Nantais (RON), in particular RON agonists, and methods of using and methods of producing thereof. In one aspect, the invention provides a RON agonist comprising an anti-RON agonist antibody, or an antigen-binding fragment thereof, or a Macrophage Stimulating Protein (MSP) fusion protein that binds to RON, or a functional fragment thereof. In certain embodiments, the RON agonist comprises an MSP fusion protein or a functional fragment thereof. In certain embodiments, the MSP fusion protein comprises MSP β and a fusion moiety. In certain preferred embodiments, the fusion moiety comprises a dimerization domain, including without limitation, an immunoglobulin Fc domain. In certain embodiments, the immunoglobulin Fc domain comprises an IgG Fc domain; and in certain further embodiments, the Fc domain is an IgG1, IgG2, IgG3 or IgG4 Fc domain. In certain other embodiments, the Fc domain is an IgG1 Fc domain. In certain embodiments, the Fc domain further comprises the D265A and N297A (DANA) mutations. In certain particular embodiments, the MSP fusion protein is a dimer. In certain other embodiments, the MSP fusion protein is bivalent with respect to RON binding. In certain other embodiments, the MSP fusion protein further comprises a linker, preferably a peptide linker that links MSP β and the fusion moiety. In certain embodiments, the peptide linker is 2 to 20 amino acid residues in length, preferably 4-16 amino acid residues in length, and more preferably 8-16 amino acid residues in length. In certain embodiments, the peptide linker is 16 amino acid residues in length. In certain other embodiments, the peptide linker is 4 amino acid residues in length. In certain particular embodiments, the MSP fusion protein is a human MSP fusion protein. In other embodiments, the MSP fusion protein comprises a human MSP β. In certain other embodiments, the MSP fusion protein comprises a human IgG1 Fc domain. In certain embodiments, the RON agonist comprises an MSP fusion protein having at least 85%, 88%, 90%, 91%, 92%, 93%, 94%, 95%, 96%, 97%, 98% or 99% sequence identity to the amino acid sequence of SEQ ID NO:20, 22 or 24. In certain other embodiments, the RON agonist comprises an MSP fusion protein having at least 85%, 88%, 90%, 91%, 92%, 93%, 94%, 95%, 96%, 97%, 98% or 99% sequence identity to the amino acid sequence of SEQ ID NO:20. In certain particular embodiments, the MSP fusion protein comprises the amino acid sequence of SEQ ID NO:20.

In yet other embodiments, the RON agonist comprises an anti-RON agonist antibody or an antigen binding fragment thereof. In certain embodiments, the anti-RON agonist antibody comprises the one or more hypervariable regions of monoclonal antibody YW651.1 or 2E5.8.1. In certain other embodiments, the antibody is an anti-human RON agonist antibody. In certain other embodiments, the antibody is a monoclonal, a chimeric, a human, a bispecific or a humanized antibody.

In another aspect, the invention provides pharmaceutical compositions comprising one or more RON agonists described herein and a pharmaceutically acceptable carrier, diluent or excipient. In certain embodiments, the pharmaceutical composition comprises a human MSP fusion protein, or a functional fragment thereof. In certain embodiment, the pharmaceutical composition comprises a human MSP fusion protein comprising the amino acid sequence of SEQ ID NO:20. In certain other embodiments, the pharmaceutical composition comprises an anti-human RON agonist antibody, or an antigen-binding fragment thereof.

In yet another aspect, the invention provides methods of treating MSP-associated or RON-associated diseases or disorders in a subject in need thereof comprising the step of administering to the subject an RON agonist, or a pharmaceutical composition comprising the RON agonist, as described herein. In certain embodiments, the RON-associated disease or disorder is associated with reduced RON activity. In certain particular embodiments, the reduced RON activity is associated with epithelial cell proliferation, survival or migration. In certain embodiments, the reduced RON activity is associated with a defect, condition or impairment in wound healing. In certain further embodiments, the reduced RON activity is associated with a defect, condition or impairment in epithelial wound healing in the gut or skin. In certain other embodiments, the RON-associated diseases or disorders include without limitation inflammatory bowel disease (IBD) (including ulcerative colitis and Crohn's disease), primary sclerosing cholangitis, or a defect, condition or impairment in wound healing. In certain other embodiments, the IBD is ulcerative colitis. In yet other embodiments, the IBD is Crohn's disease.

In certain embodiments, the defect, condition or impairment in wound healing is a fibrotic disease. In certain other embodiments, the defect, condition or impairment in wound healing is associated with chronic epithelial damage, including without limitation, idiopathic pulmonary fibrosis, scleroderma, and primary biliary cirrhosis. In certain other embodiments, the wound healing is epithelial wound healing. In certain particular embodiments, the defect in epithelial wound healing occurs in the epithelial lining of a lumen, a tract or duct. In certain embodiments, the defect in epithelial wound healing occurs in the epithelial lining of the intestine. In certain embodiments, the defect in epithelial wound healing occurs in the epithelial lining of the colon. Without being limited to particular mechanism(s), in certain embodiments, the enhanced epithelial wound healing is reflected or achieved by the increased epithelial proliferation, survival and/or migration. In certain other embodiments, the wound healing is measured by the degree of wound closure. In certain other embodiments, the defect in epithelial wound healing occurs in the skin. In certain embodiments, the wound is chronic wound, pressure wound or pressure ulcer. In certain other embodiments, the defect in epithelial wound healing is associated with diabetes mellitus. In certain embodiments, the wound is diabetic wound or diabetic ulcer including diabetic foot ulcer. In certain particular embodiments, the subject is a diabetic subject. In certain further embodiments, the subject is a human diabetic patient. In certain embodiments, the RON agonist comprises a human MSP fusion protein, or a functional fragment thereof, or an anti-human RON antibody, or an antigen-binding fragment thereof. In certain other embodiments, the RON agonist comprises the amino acid sequence of SEQ ID NO:20.

In certain embodiments, the method further comprises the steps of detecting the serum MSP level in the subject, optionally detecting the serum MSP level in a normal control, and administering the RON agonist, or a pharmaceutical composition comprising the RON agonist, to the subject when the serum MSP level is lower in the subject as compared to the serum MSP level in a normal control. In certain other embodiments, the method further comprises the steps of detecting the serum MSP level in the subject, and administering the RON agonist, or a pharmaceutical composition comprising the RON agonist, to the subject when the serum MSP level is lower in the subject as compared to a predetermined serum MSP level in a normal control. In certain embodiments, the method further comprises the step of detecting the serum MSP level in a normal control. In certain other embodiments, the method further comprises the steps of detecting the presence of the rs3197999 polymorphism in the subject, and administering the RON agonist to the subject when the rs3197999 polymorphism is detected in the subject and/or when the serum MSP level is lower in the subject than in a normal control. In certain other embodiments, the method further comprises the step of administering the RON agonist to the subject when both the rs3197999 polymorphism is detected in the subject and the serum MSP level is lower in the subject than in a normal control. In certain embodiments, the RON agonist comprises a human MSP fusion protein, or a functional fragment thereof, or an anti-human RON antibody, or an antigen-binding fragment thereof. In certain other embodiments, the RON agonist comprises the amino acid sequence of SEQ ID NO:20. The serum MSP levels can be measured by any methods known in the art, including without limitation, an ELISA assay. The rs3197999 polymorphism can be detected by any method known in the art; exemplary methods include detecting using a sequencing based or PCR based assay such as the TaqMan platform provided by Applied Biosystem (TaqMan SNP Genotyping Assay, Catalog #4351379, Carlsbad, Calif.).

In another aspect, the invention provides method of enhancing epithelial wound healing in a subject in need thereof, comprising the step of administering to the subject a RON agonist or a pharmaceutical composition comprising the RON agonist. In a further aspect, the invention provides a method of increasing epithelial cell proliferation, survival and/or migration comprising contacting the cell with a RON agonist. In a further aspect, the invention provides a method of increasing epithelial cell proliferation, survival and/or migration in a subject in need thereof comprising administering to the subject a RON agonist, or a pharmaceutical composition comprising the RON agonist. In certain embodiments, the subject has IBD. In certain other embodiments, the IBD is ulcerative colitis. In certain further embodiments, the IBD is Crohn's disease. In certain embodiments, the RON agonist or a pharmaceutical composition comprising the agonist of the invention is advantageously applied to a subject that has undergone a surgical operation to enhance wound healing after an internal or external surgical incision. In certain other embodiments, the subject is a diabetic subject. In yet other embodiments, the subject is a human diabetic patient. Accordingly, in a further aspect, the invention provides a method of enhancing epithelial wound healing in a diabetic subject. In certain embodiments, the epithelial wound healing occurs in the skin of the diabetic subject. In certain embodiments, the RON agonist comprises a human MSP fusion protein, or a functional fragment thereof, or an anti-human RON antibody, or an antigen-binding fragment thereof. In certain other embodiments, the RON agonist comprises the amino acid sequence of SEQ ID NO:20.

In certain embodiments of these aspects, the method further comprises detecting (1) the presence of the rs3197999 polymorphism and/or (2) the serum MSP level of the subject, and administering the RON agonist to the subject when the rs3197999 polymorphism is detected in the subject or when the serum MSP level is lower in the subject than in a normal control. In certain embodiments, the method further comprises the step of detecting the serum MSP level in a normal control. In certain embodiments, the method further comprises the steps of (a) detecting the presence of the rs3197999 polymorphism in the subject and administering the RON agonist to the subject when the rs3197999 polymorphism is detected in the subject, or (b) detecting the serum MSP level in the subject, and administering the RON agonist to the subject when the serum MSP level is lower in the subject as compared to the serum MSP level in a normal control. In certain other embodiments, the method further comprises the step of administering the RON agonist to the subject when both the rs3197999 polymorphism is detected in the subject and the serum MSP level is lower in the subject than in the normal control.

In yet a further aspect, the invention provides methods of treating diabetes mellitus in a subject in need thereof comprising the step of administering to the subject a RON agonist or the pharmaceutical composition comprising the RON agonist. In another aspect, the invention provides methods of reducing blood glucose in a subject in need thereof comprising the step of administering to the subject the RON agonist, or the pharmaceutical composition comprising the RON agonist. In a further aspect, the invention provides methods of treating a condition associated with diabetes. In certain embodiments, the condition is, without limitation, diabetic ketoacidosis, metabolic acidosis, hyperglycemia, hyperglycemic hyperosmolar syndrome, or metabolic syndrome. In certain embodiments of these aspects, the RON agonist comprises a human MSP fusion protein, or a functional fragment thereof, or an anti-human RON antibody, or an antigen-binding fragment thereof. In certain other embodiments, the RON agonist comprises the amino acid sequence of SEQ ID NO:20.

In certain other embodiments of these aspects, the method of treating diabetes further comprises the steps of (a) detecting the presence of the rs3197999 polymorphism in the subject and administering the RON agonist to the subject when the rs3197999 polymorphism is detected in the subject, and/or (b) detecting the serum MSP level in the subject, and administering the RON agonist to the subject when the serum MSP level is lower in the subject as compared to the serum MSP level in a normal control.

In certain embodiments further comprises the steps of detecting the presence of the rs3197999 polymorphism in the subject, detecting the serum MSP level in the subject, and administering the RON agonist to the subject when the rs3197999 polymorphism is detected in the subject and/or when the serum MSP level is lower in the subject than in a normal control. In yet other embodiments, the method further comprises the steps of detecting the presence of the rs3197999 polymorphism in the subject, detecting the serum MSP level in the subject, and administering the RON agonist to the subject when the rs3197999 polymorphism is detected in the subject and/or when the serum MSP level is lower in the subject than in a normal control.

In a further aspect, the invention provides a method of diagnosing IBD in a test subject suspected of having IBD comprising the steps of (a) detecting or determining the serum MSP level of the subject, (b) optionally detecting or determining the serum MSP level of a normal control, and (c) diagnosing the subject of having IBD if the serum MSP level of the subject is lower than the serum MSP level of the control. In yet another aspect, the invention provides a method of diagnosing IBD in a test subject suspected of at risk of having IBD comprising the steps of (a) detecting or determining the serum MSP level of the subject, (b) optionally detecting or determining the serum MSP level of a normal control, and (c) diagnosing the subject of at risk of having IBD if the serum MSP level of the subject is lower than the serum MSP level of the control. In certain embodiments, the method further comprises the steps of determining the presence of the rs3197999 polymorphism in the test subject, and diagnosing the subject of having IBD or at risk of having IBD when the rs3197999 polymorphism is detected in the subject.

In yet another aspect, the invention provides methods of diagnosing a subject suspected of having or at risk of having a defect, condition or impairment in wound healing comprising the steps of (a) detecting the serum MSP level of the subject or detecting the presence of the rs3197999 polymorphism in the subject; (b) optionally detecting the serum MSP level of a normal control; and (c) diagnosing the subject of having or at risk of having a defect in wound healing if the serum MSP level of the subject is lower than the serum MSP level of the normal control. In certain embodiments, the method further comprises the step of detecting the serum MSP level of a normal control. In certain embodiments, the method further comprises the steps of detecting the serum MSP level of the subject and detecting the presence of the rs3197999 polymorphism in the subject, and diagnosing the subject of having or at risk of having a defect, condition or impairment in wound healing when the rs3197999 polymorphism is detected in the subject or when the serum MSP level of the subject is lower than the serum MSP level of the normal control. In certain other embodiments, the method further comprises the steps of detecting the serum MSP level of the subject and detecting the presence of the rs3197999 polymorphism in the subject, and diagnosing the subject of having or at risk of having a defect, condition or impairment in wound healing when the rs3197999 polymorphism is detected in the subject and when the serum MSP level of the subject is lower than the serum MSP level of the normal control. In certain embodiments, the wound healing is epithelial cell wound healing. In certain embodiments, the subject has or is at risk of having IBD. In certain other embodiments, the subject is a diabetic subject.

In another aspect, the invention provides methods of detecting RON in a sample using the anti-RON antibody or MSP fusion protein of the invention. In a further aspect, the invention provides methods of diagnosis in a subject, or a sample from the subject, of a disease or a condition associated with altered RON expression levels using the anti-RON antibody or MSP fusion protein.

In certain embodiments of all the above aspects, the subject is a mammal. In certain other embodiments of all the above aspects, the subject is a human. In certain further embodiments of all the above aspects, the subject is a human with diabetes.

In a further aspect, the invention provides isolated nucleic acid molecules having the polynucleotide sequences encoding a RON agonist. In certain embodiments, the isolated nucleic acid molecules comprise the polynucleotide sequences encoding an anti-RON antibody. In certain other embodiments, the isolated nucleic acid molecules comprise the polynucleotide sequences encoding the MSP fusion proteins. In certain embodiments, the nucleic acid molecule comprises the polynucleotide sequence that is at least 80%, 85%, 90%, 91%, 92%, 93%, 94%, 95%, 96%, 97%, 98% or 99% identical to the polynucleotide sequence of SEQ ID NO:19, 21 or 23. In certain embodiments, the nucleic acid molecule comprises the polynucleotide sequence of SEQ ID NO:19, 21 or 23. In certain particular embodiments, the nucleic acid molecule comprises the polynucleotide sequence of SEQ ID NO:19.

In another aspect, the invention provides a vector comprising the polynucleotide sequence that encodes a RON agonist. In yet another aspect, the invention provides a host cell comprises the nucleic acid molecule comprising the polynucleotide sequence, or the vector comprising the polynucleotide sequence, wherein the polynucleotide sequence encodes a RON agonist. In certain embodiments, the vector is an expression vector that comprises the polynucleotide sequence that encodes an anti-RON antibody. In certain other embodiments, the vector is an expression vector that comprises the polynucleotide sequence, which encodes the MSP fusion protein. In certain particular embodiments, the fusion protein comprises the amino acid sequence of SEQ ID NO:20. The invention also provides a method of producing an MSP fusion protein, comprising the steps of (a) culturing the host cell under conditions that allow expression the MSP fusion protein; and (b) recovering the MSP fusion protein.

In another aspect, the invention provides an isolated RON agonist antibody. In certain embodiments, the RON agonist antibody comprises the hypervariable domain sequence that is at least 95% identity to the hypervariable domain sequence of monoclonal antibody YW651.1 or 2E5.8.1. In certain embodiments, the antibody is an anti-human RON agonist antibody.

In further aspects, the invention provides an isolated nucleic acid molecule comprising the polynucleotide sequence encoding an RON agonist antibody. In certain embodiments, the antibody is an anti-human RON agonist antibody. In another aspect, the invention provides a vector comprising the polynucleotide sequence encoding the anti-human RON antibody. In a further aspect, the invention provides a host cell comprising the nucleic acid molecule that comprises the polynucleotide encoding the antibody or the vector comprising the polynucleotide sequence encoding the antibody. In certain embodiments, the vector is an expression vector that comprises the polynucleotide sequence, which encodes the isolated antibodies. The invention also provides a method of producing the isolated antibody described herein, comprising the steps of (a) culturing the host cell under conditions that allow expression of the isolated antibody; and (b) recovering the isolated antibody.

In yet another aspect, the invention provides uses of a RON agonist for the preparation of a medicament for treating an MSP-associated or RON-associated disease or disorder. In certain embodiments, the MSP-associated or RON-associated disease or disorder is IBD or a defect in wound healing, particularly epithelial wound healing. In certain other embodiments, the RON agonist is an anti-human RON antibody or a human MSP fusion protein.

Specific embodiments of the present invention will become evident from the following more detailed description of certain preferred embodiments and the claims.

Any and all embodiments described above can be applied to any and all aspects of the invention, unless the context clearly indicates otherwise.

DETAILED DESCRIPTION OF THE INVENTION

Figure 1:
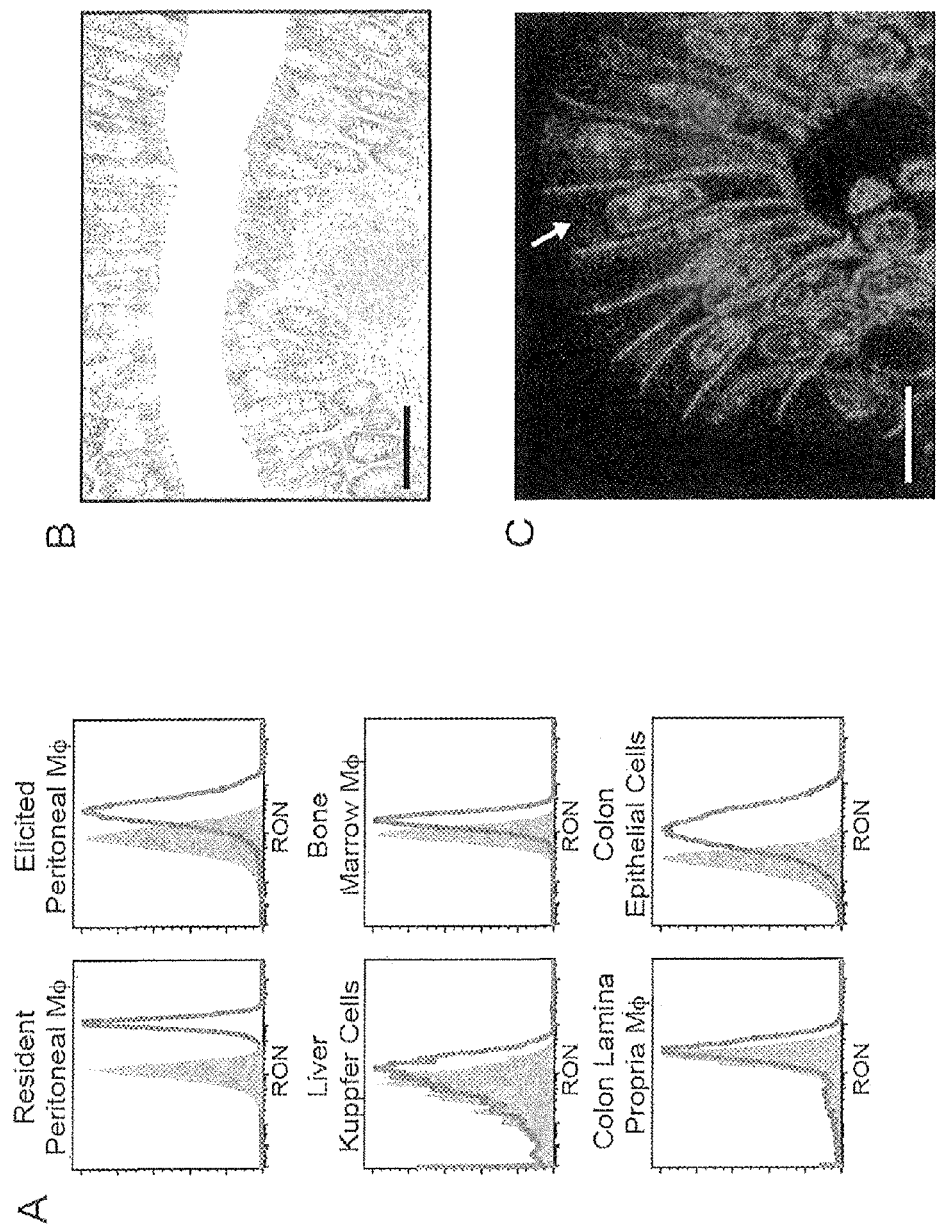
FIG. 1A-E. A-D show results examining the expression of RON in myeloid and epithelial cell populations in mice. A shows histograms of single cell suspension of the indicated cell populations or tissues analyzed by flow cytometry for RON expression using a monoclonal antibody specific for murine RON (Ph4 antibody, Genentech) (Chaudhuri et al., manuscript submitted for publication) or an isotype control antibody (shaded histogram). Macrophage populations were gated as $CD45^+F4/80^+CD11b^+MHC$ class $II^+$ for ex vivo-derived cells and $F4/80^+CD11b^+$ for bone marrow cultured cells. Colonic epithelial cells were gated as $CD45^-$ ECadherin$^+$. B shows a microphotograph of immunohistochemistry staining of a tissue section from normal mouse colon showing RON expression in the basal lateral surface of epithelial cells. C presents a microphotograph of immunofluorescence staining of a tissue section from normal mouse colon stained for RON and counterstained for nuclei. The white arrow indicates the apical surface of a single epithelial cell. D shows microphotographs of immunofluorescence staining of tissue sections from mouse colon taken 6 days post-treatment with dextran sulfate sodium (DSS), stained for RON, MEW class II, F4/80, and counterstained for nuclei (A-D). Individual stains and merged image are shown (A-D). E shows a microphotograph of immunofluorescence staining of RON. Scale bars=100 µm (B), 10 µm (C), 20 µm (D) and 40 µm (E). The figures relate to Example 1.
Figure 1:
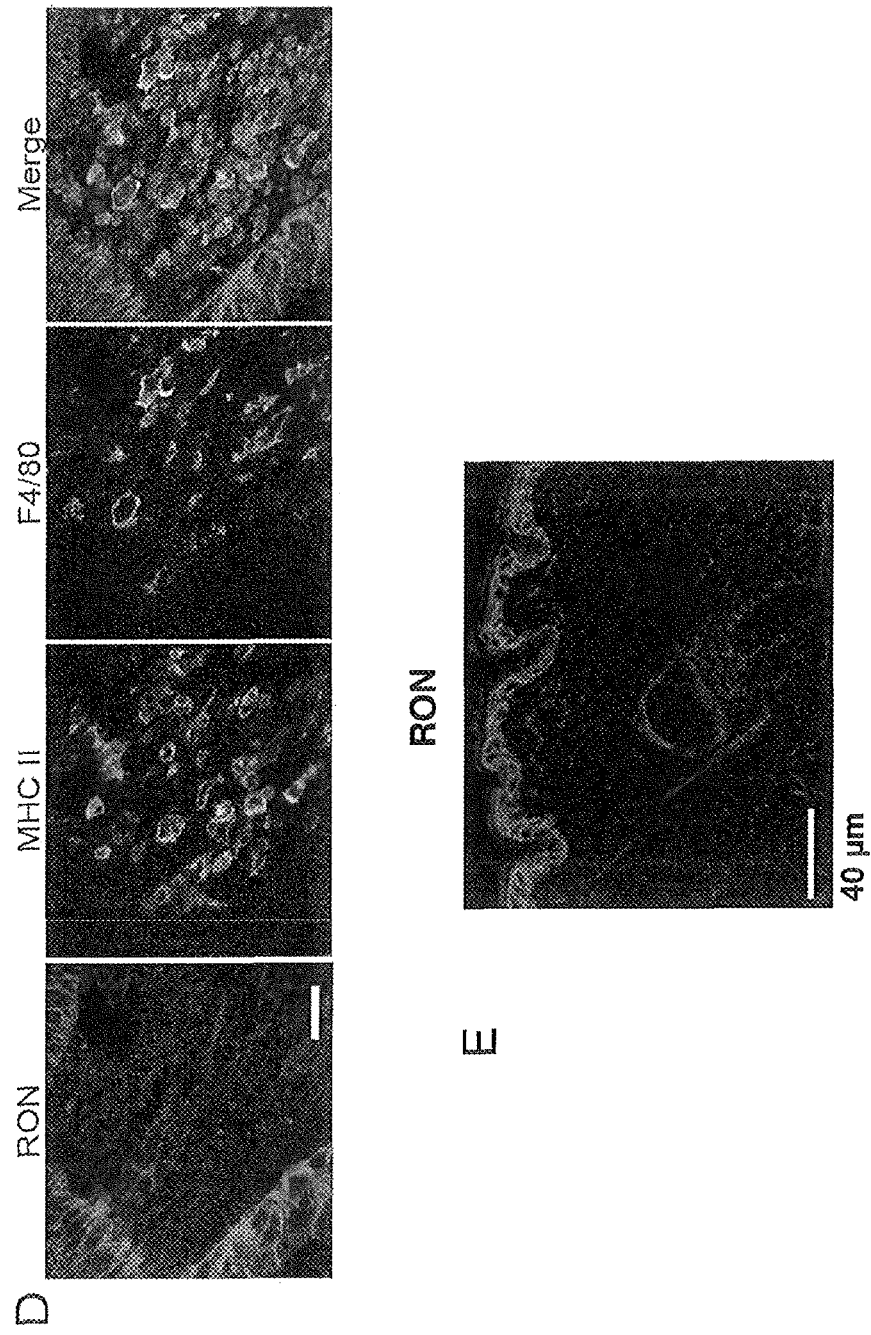

All publications, patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press) and *PCR Protocols: A Guide to Methods and Applications* (Innis, et al. 1990. Academic Press, San Diego, Calif.).

As used herein, the singular forms "a", "an" and "the" include plural referents unless the context clearly dictates otherwise. For example, reference to "an isolated antibody" means one or more isolated antibodies.

Any and every embodiment described below applies to any and every aspect of the invention, unless the context clearly indicates otherwise. All embodiments within and between different aspects can be combined unless the context clearly dictates otherwise.

I. Definition

The term MSP as used herein includes any native MSP from any mammalian source, including mammals such as primates (e.g. humans) and rodents (e.g., mice and rats). The term MSP encompasses "full-length MSP," "pro-MSP," and secreted MSP lacking the leader sequence (e.g., signal peptide or signal sequence). As used herein, full-length MSP and pro-MSP are of the same length, but differ in that pro-MSP represents inactive MSP that has not been proteolytically processed to generate the α chain and β chain. Pro-MSP is proteolytically cleaved by a convertase such as the serine protease hepsin to generate the α and β chains, which form a heterodimer connected by a di-sulfide bond (full length MSP). The leader sequence is cleaved before the mature, active MSP protein is secreted from the cell. In certain embodiments, MSP also encompasses naturally occurring variants of MSP, e.g., splice variants or allelic variants. In certain other embodiments, MSP encompasses one or more of the mutations that facilitate recombinant production of the protein without diminishing the function. Such mutations include, for example, MSP with a histidine tag (His tag), C672A in human MSP and C677A in mouse MSP. In certain particular embodiments, the MSP is human MSP. The amino acid sequence of an exemplary human MSP is shown in SEQ ID NO:2.

MSP β refers to the β chain of MSP, which contains the RON binding site. MSP β alone is sufficient for binding to RON. In certain advantageous embodiments, dimerized MSP β facilitates RON binding and recruitment. In certain embodiments, the MSP β construct contains an exogenous leader sequence (e.g., the HGF leader sequence as shown in SEQ ID NO:55) that is removed before MSP β is secreted from a cell to the extracellular milieu. In certain other embodiments, a mutation is introduced into MSP β to remove the cysteine reside that in the context of full-length MSP forms a di-sulfide bond with the MSP α chain. In certain embodiments, the mutation is a C588S or C588A mutation in human MSP β or a C593S or C593A mutation in mouse MSP β. Through the disclosure, the amino acid residue numbering of MSP or MSP β is based on the amino acid residue numbering of the pro-MSP.

In certain embodiments, the MSP fusion protein comprises MSPβ and a fusion moiety. In certain other embodiments, the MSP fusion protein comprises a functional fragment of MSPβ and a fusion moiety. In certain other embodiments, the MSP fusion protein comprises MSP and a fusion moiety, or a functional fragment thereof.

The term "a functional fragment" of a protein refers to a truncated polypeptide that is short of the full-length protein but nevertheless retains a desired function (such as binding to RON) of the full-length protein. In certain embodiments, the functional fragment of a MSP fusion protein comprises the amino acid sequence from V484-M708, V484-V700 or V484-F694 of human MSP. See Carafoli et al., 2005, *FEBS J* 272(22):5799-807. It is within the ability of an ordinary skill in the art to design and prepare an MSP functional fragment suitable for use in the invention based on the sequence and structure of MSP known in the art and the guidance provided herein.

The term "single chain MSP" of "scMSP" refers to a non-cleavable, inactive pro-MSP that contains a mutation in the P1 position of the pro-MSP cleavage site. For example, the single chain human MSP contains an R483E mutation that blocks hepsin cleavage. The scMSP may contain further mutation (such as R689C) as indicated.

In certain aspects, the invention provides therapeutic or diagnostic methods comprising the step of detecting serum MSP levels in a test subject and administering to the subject a RON agonist or making diagnosis of RON-associated or MSP-associated diseases when the serum MSP levels of the subject is lower than that of a normal control. The level of serum MSP levels MSP level in a normal control can be a known average normal level previously measured or known in a population, or can be measured each time. In certain embodiments, the "normal control" or "control" in this context refers to an individual, preferably a human that has the wild type MSP gene. In certain other embodiments, the control sample is derived from an individual, preferably a human that does not have the rs3197999 polymorphism.

The term "RON agonist" refers to a molecule that stimulates RON activity and/or activates RON downstream signaling event through RON. In certain embodiments, the RON activity is measured by phosphorylation of Akt. It is within the skill in the art to analyze other RON downstream effectors as an indicator of the activity of a RON agonist. In certain embodiments, the RON agonist is an MSP fusion protein. In certain preferred embodiments, the MSP fusion protein comprises a fusion moiety that is capable of forming a dimer. In certain other embodiments, the dimeric MSP fusion protein binds to and recruits RON on the cell surface and stimulates RON signaling. In certain embodiments, the fusion protein is an Fc fusion protein. It is understood that the fusion moiety can be another molecule that is capable of dimerization. Such fusion moiety includes without limitation a leucine zipper motif. In certain other embodiment, the dimeric RON agonist comprises two MSP β domains attached by a linker, preferably a flexible linker, most preferably a flexible peptide linker.

The term "rs3197999 polymorphism" refers to the R689C mutation in human MSP gene locus. The presence of the rs3197999 polymorphism can be detected by any suitable methods known in the art, including without limitation sequencing, restriction fragment length polymorphism analysis, PCR analysis such as the TaqMan-based qPCR assay, or by a microarray approach such as a SNP array. It is within the ability of the skilled in the art to design proper primers and probes for detecting the polymorphism.

A "human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described throughout the application.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-RON antibody" and "an antibody that binds to RON" refer to an antibody that is capable of binding RON with sufficient affinity such that the antibody is useful as a diagnostic and/or therapeutic agent in targeting RON. In one embodiment, the extent of binding of an anti-RON antibody to an unrelated, non-RON protein is less than about 10% of the binding of the antibody to RON as measured, e.g., by a radioimmunoassay (RIA). In certain embodiments, an antibody that binds to RON has a dissociation constant (Kd) of <1 μM, <100 nM, <10 nM, <1 nM, <0.1 nM, <0.01 nM, or <0.001 nM (e.g. $10^{-8}$M or less, e.g. from $10^{-8}$M to $10^{-13}$M, e.g., from $10^{-9}$M to $10^{-13}$M). In certain embodiments, an anti-RON antibody binds to an epitope of RON that is conserved among RON from different species. In certain preferred embodiments, the anti-RON antibody is an agonist anti-RON antibody.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" or "antigen-binding fragment" refers to a molecule other than an intact antibody that comprises a portion of an intact antibody that binds the antigen to which the intact antibody binds. Examples of antibody fragments include but are not limited to Fv; Fab; Fab; Fab'-SH; F(ab')$_2$; diabodies; linear antibodies; single-chain antibody molecules (e.g. scFv); and multispecific (including bispecific) antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "amount effective," "effective amount" or a "therapeutically effective amount" of an agent, e.g., a pharmaceutical formulation, refers to an amount effective, at dosages and for periods of time necessary, to achieve the desired therapeutic or prophylactic result, for example, stimulating RON signaling, promoting epithelial proliferation or enhancing wound healing. The amount of the compound which constitutes an "effective amount" or "therapeutically effective amount" may vary depending on the severity of the disease, the condition or age of the patient to be treated, or the route of administration, but can be determined routinely by one of ordinary skill in the art.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., 2007, *J. Chromatogr. B* 848:79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-RON antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., 1993, *J. Immunol.* 150:880-887; Clarkson et al., 1991, *Nature* 352:624-628.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on RON agonists, and methods of using the agonists for treatment of MSP associated or RON associated-diseases or disorders. In certain embodiments, antibodies that bind to human RON are provided. Antibodies of the invention are useful, e.g., for the diagnosis or treatment of MSP-associated or RON-associated diseases.

A. Exemplary Anti-RON Antibodies

In one aspect, the invention provides isolated antibodies that bind to human RON. In certain embodiments, an anti-RON antibody is an agonist of RON activity. In certain other embodiments, the RON agonist antibody stimulates RON downstream signaling exemplified by Akt phosphorylation. In certain other embodiments, the RON agonist antibody does not trigger down-regulation of surface RON upon binding to RON.

In a further aspect of the invention, an anti-RON antibody according to any of the above embodiments is a monoclonal antibody, including a chimeric, humanized, bispecific or human antibody. In one embodiment, an anti-RON antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-RON antibody according to any of the above embodiments may incorporate any of the features, singly or in combination, as described in Sections 1-7 below:

1. Antibody Affinity

In certain embodiments, an antibody provided herein has a dissociation constant (Kd) of <1 µM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., 1999, *J. Mol. Biol.* 293:865-881). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., 1997, *Cancer Res.* 57:4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CMS chips at ~10 response units (RU). In one embodiment, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., 1999, *J. Mol. Biol.* 293:865-881. If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. 2003, *Nat. Med.* 9:129-134. For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')₂ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage).

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, 2008, *Front. Biosci.* 13:1619-1633, and are further described, e.g., in Riechmann et al., 1998, *Nature* 332:323-329; Queen et al., 1989, *Proc. Nat'l Acad. Sci. USA* 86:10029-10033; U.S. Pat. Nos. 5,821,337, 7,527,791, 6,982,321, and 7,087,409; Kashmiri et al., 2005, *Methods* 36:25-34 (describing specificity determining region (SDR) grafting); Padlan, 1991, *Mol. Immunol.* 28:489-498 (describing "resurfacing"); Dall' Acqua et al., 2005, *Methods* 36:43-60 (describing "FR shuffling"); and Osbourn et al., 2005, *Methods* 36:61-68 and Klimka et al., 2000, *Br. J. Cancer,* 83:252-260 (describing the "guided selection" approach to FR shuffling).

Human framework regions that may be used for humanization include but are not limited to: framework regions selected using the "best-fit" method (see, e.g., Sims et al. 1993, *J. Immunol.* 151:2296); framework regions derived from the consensus sequence of human antibodies of a particular subgroup of light or heavy chain variable regions (see, e.g., Carter et al., 1992, *Proc. Natl. Acad. Sci. USA,* 89:4285; and Presta et al., 1993, *J. Immunol.,* 151:2623); human mature (somatically mutated) framework regions or human germline framework regions (see, e.g., Almagro and Fransson, 2008, *Front. Biosci.* 13:1619-1633); and framework regions derived from screening FR libraries (see, e.g., Baca et al., 1997, *J. Biol. Chem.* 272:10678-10684 and Rosok et al., 1996, *J. Biol. Chem.* 271:22611-22618).

4. Human Antibodies

In certain embodiments, an antibody provided herein is a human antibody. Human antibodies can be produced using various techniques known in the art. Human antibodies are described generally in van Dijk et al., 2001, *Curr. Opin. Pharmacol.* 5: 368-74 and Lonberg, 2008, *Curr. Opin. Immunol.* 20:450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated into the animal's chromosomes. In such transgenic mice, the endogenous immunoglobulin loci have generally been inactivated. For review of methods for obtaining human antibodies from transgenic animals, see Lonberg, 2005, *Nat. Biotech.* 23:1117-1125. See also, e.g., U.S. Pat. Nos. 6,075,181 and 6,150,584 describing XENO-MOUSE' technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, 1984, *J. Immunol.,* 133: 3001; Brodeur et al., *Monoclonal Antibody Production Techniques and Applications,* pp. 51-63 (Marcel Dekker, Inc., New York, 1987); and Boerner et al., 1991, *J. Immunol.,* 147: 86.) Human antibodies generated via human B-cell hybridoma technology are also described in Li et al., 2006, *Proc. Natl. Acad. Sci. USA,* 103:3557-3562. Additional methods include those described, for example, in U.S. Pat. No. 7,189,826 (describing production of monoclonal human IgM antibodies from hybridoma cell lines) and Ni, 2006, *Xiandai Mianyixue,* 26(4):265-268 (describing human-human hybridomas). Human hybridoma technology (Trioma technology) is also described in Vollmers and Brandlein, 2005, *Histology and Histopathology,* 20(3):927-937 and Vollmers and Brandlein, 2005, *Methods and Findings in Experimental and Clinical Pharmacology,* 27(3): 185-91.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., 1991, *Nature* 352: 624-628; Marks et al., 1992, *J. Mol. Biol.* 222: 581-597; Marks and Bradbury, in *Methods in Molecular Biology* 248:161-175 (Lo, ed., Human Press, Totowa, N.J., 2003); Sidhu et al., 2004, *J. Mol. Biol.* 338(2): 299-310; Lee et al., 2004, *J. Mol. Biol.* 340(5): 1073-1093; Fellouse, 2004, *Proc. Natl. Acad. Sci. USA* 101(34): 12467-12472; and Lee et al., 2004, *J. Immunol. Methods* 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al., 1994, *Ann. Rev. Immunol.*, 12: 433-455. Phage typically displays antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., 1993, *EMBO J*, 12: 725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, 1992, *J. Mol. Biol.*, 227: 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for RON, preferably human RON, and the other is for any other antigen. In certain embodiments, bispecific antibodies may bind to two different epitopes of RON, preferably human RON. Bispecific antibodies may also be used to localize cytotoxic agents to cells which express RON. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, 1983, *Nature* 305: 537), WO 93/08829, and Traunecker et al., *EMBO J.* 1991, 10: 3655), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., 1985, *Science*, 229: 81); using leucine zippers to produce bi-specific antibodies (see, e.g., Kostelny et al., 1992, *J. Immunol.*, 148(5):1547-1553); using "diabody" technology for making bispecific antibody fragments (see, e.g., Hollinger et al., 1993, *Proc. Natl. Acad. Sci. USA*, 90:6444-6448); and using single-chain Fv (sFv) dimers (see, e.g. Gruber et al., 1994, *J. Immunol.*, 152:5368); and preparing trispecific antibodies as described, e.g., in Tutt et al. 1991, *J. Immunol.* 147: 60.

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to RON as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;

(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells, 1989, *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. 1997, *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. 1986, *Arch. Biochem. Biophys.*

249:533-545; US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., 2004, *Biotech. Bioeng.* 87: 614; Kanda, Y. et al., 2006, *Biotechnol. Bioeng.*, 94(4):680-688; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.)

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII FcR expression on hematopoietic cells is summarized in Table 3 on page 464 of Ravetch and Kinet, 1991, *Annu. Rev. Immunol.* 9:457-492. Non-limiting examples of in vitro assays to assess ADCC activity of a molecule of interest is described in U.S. Pat. No. 5,500,362 (see, e.g. Hellstrom, I. et al. 1986, *Proc. Nat'l Acad. Sci. USA* 83:7059-7063) and Hellstrom, I et al., 1985, *Proc. Nat'l Acad. Sci. USA* 82:1499-1502; U.S. Pat. No. 5,821,337 (see Bruggemann, M. et al., 1987, *J. Exp. Med.* 166:1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. 1998, *Proc. Nat'l Acad. Sci. USA* 95:652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., 1996, *J. Immunol.* Methods 202:163; Cragg, M. S. et al., 2003, *Blood* 101:1045-1052; and Cragg, M. S. and M. J. Glennie, 2004, *Blood* 103:2738-2743). FcRn binding and in vivo clearance/half-life determinations can also be performed using methods known in the art (see, e.g., Petkova, S. B. et al., 2006, *Int'l. Immunol.* 18(12):1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., 2001, *J. Biol. Chem.* 9(2): 6591-6604.)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. 2000, *J. Immunol.* 164: 4178-4184.

Antibodies with increased half-lives and improved binding to the neonatal Fc receptor (FcRn), which is responsible for the transfer of maternal IgGs to the fetus (Guyer et al., 1976, *I Immunol.* 117:587, and Kim et al., 1994, *J. Immunol.* 24:249), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, 1988, *Nature* 322:738-40; U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., 2005, *Proc. Natl. Acad. Sci. USA* 102: 11600-11605). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-RON agonist antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-RON antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-RON antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, 2004, *Nat. Biotech.* 22:1409-1414, and Li et al., 2006, *Nat. Biotech.* 24:210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., 1977, *J. Gen Virol.* 36:59); baby hamster kidney cells (BHK); mouse sertoli cells (TM4 cells as described, e.g., in Mather, 1980, *Biol. Reprod.* 23:243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., 1982, *Annals N.Y. Acad. Sci.* 383:44-68; MRC 5 cells; and FS4 cells. Other useful mammalian host cell lines include Chinese hamster ovary (CHO) cells, including DHFR⁻ CHO cells (Urlaub et al., 1980, *Proc. Natl. Acad. Sci. USA* 77:4216); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Immunoconjugates

The invention also provides immunoconjugates comprising an anti-RON antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF)

(see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., 1993, *Cancer Res.* 53:3336-3342; and Lode et al., 1998, *Cancer Res.* 58:2925-2928); an anthracycline such as daunomycin or doxorubicin (see Kratz et al., 2006, *Current Med. Chem.* 13:477-523; Jeffrey et al., 2006, *Bioorganic & Med. Chem. Letters* 16:358-362; Torgov et al., 2005, *Bioconj. Chem.* 16:717-721; Nagy et al., 2000, *Proc. Natl. Acad. Sci. USA* 97:829-834; Dubowchik et al., 2002, *Bioorg. & Med. Chem. Letters* 12:1529-1532; King et al., 2002, *J. Med. Chem.* 45:4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene tri aminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

D. Methods and Compositions for Diagnostics and Detection

In certain embodiments, any of the anti-RON antibodies provided herein is useful for detecting the presence of RON in a biological sample. The term "detecting" as used herein encompasses quantitative or qualitative detection. In certain embodiments, a biological sample comprises a cell or tissue, such as intestine, colon, skin, neuroendocrine tissues, developing bone, epithelial cells and resident peritoneal microphage.

In one embodiment, an anti-RON antibody for use in a method of diagnosis or detection is provided. In a further aspect, a method of detecting the presence of RON in a biological sample is provided. In certain embodiments, the method comprises contacting the biological sample with an anti-RON antibody as described herein under conditions permissive for binding of the anti-RON antibody to RON, and detecting whether a complex is formed between the anti-RON antibody and RON. Such method may be an in vitro or in vivo method. In one embodiment, an anti-RON antibody is used to select subjects eligible for therapy with an anti-RON antibody, e.g. where RON is a biomarker for selection of patients.

Exemplary disorders that can be diagnosed using an antibody of the invention include without limitation tumors, tumor progression and tumor metastases. In certain embodiments, labeled anti-RON antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of an anti-RON antibody and/or MSP fusion proteins as described herein are prepared by mixing such antibody or recombinant protein having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an anti-inflammatory therapy or an anti-hyperglycemic therapy, including without limitation, an immunosuppressant such as a TNF inhibitor, mesalazine, steroid, methotrexate, Azathioprine or an anti-hyperglycemia drug such as insulin, an insulin analog, metformin, sulfonylureas, or glitazones. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

F. Therapeutic Methods and Compositions

Any of the RON agonists provided herein may be used in therapeutic methods.

In one aspect, a RON agonist for use as a medicament is provided. In further aspects, a RON agonist for use in treating an MSP-associated or RON associated disease or disorder is provided. In certain embodiments, the disease or disorder is IBD, diabetes or a defect in wound healing. In certain embodiments, an anti-RON agonist antibody for use in a method of treatment is provided. In certain embodiments, the invention provides an anti-RON antibody for use in a method of treating an individual having IBD, diabetes or a defect in wound healing comprising administering to the individual an effective amount of the anti-RON antibody. In one such embodiment, the method further comprises administering to the individual an effective amount of at least one additional therapeutic agent, e.g., as described below. In further embodiments, the invention provides an anti-RON antibody for use in enhancing epithelial wound healing. In certain embodiments, the invention provides an anti-RON antibody for use in a method of enhancing wound healing in an individual comprising administering to the individual an effective of the anti-RON antibody to enhance epithelial wound healing. An "individual" according to any of the above embodiments is preferably a human.

In a further aspect, the invention provides for the use of an anti-RON antibody in the manufacture or preparation of a medicament. In one embodiment, the medicament is for treatment of IBD, a defect in wound healing, or diabetes. In a further embodiment, the medicament is for use in a method of treating IBD, a defect in wound healing or diabetes comprising administering to an individual having IBD, a defect in wound healing or diabetes an effective amount of the medicament. In one such embodiment, the method further comprises administering to the individual an effective amount of at least one additional therapeutic agent. Non-limiting exemplary additional therapeutic agents include an immunosuppressant such as a TNF inhibitor, mesalazine, steroid, methotrexate, Azathioprine or an anti-hyperglycemia therapy such as insulin, insulin analogs, metformin, sulfonylureas, or glitazones. In a further embodiment, the medicament is for enhancing wound healing, epithelial proliferation or migration or reducing blood glucose. In a further embodiment, the medicament is for use in a method of enhancing wound healing, epithelial proliferation or migration or reducing blood glucose in an individual comprising administering to the individual an amount effective of the medicament to enhance wound healing, epithelial proliferation or migration or reducing blood glucose. An "individual" according to any of the above embodiments may be a human.

There are a variety of ways to measure wound healing. Often images are taken to calculate linear dimensions, perimeter and area. The Image J program (NIH) allows measurement of wound areas from an image. The final healing prognosis can be extrapolated from initial healing rates based on the migration of the periphery towards the center. This is done using a number of mathematical equations, the most common of which is a modified Gilman's equation. If healing is slow/inadequate, biopsies of the wound edges may be taken to rule out infection and malignancy.

In a further aspect, the invention provides a method for treating IBD, a defect in wound healing or diabetes. In one embodiment, the method comprises administering to an individual having such diseases an effective amount of an anti-RON antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the RON agonists provided herein, e.g., for use in any of the above therapeutic methods.

In one embodiment, a pharmaceutical formulation comprises any of the RON agonists provided herein and a pharmaceutically acceptable carrier. In another embodiment, a pharmaceutical formulation comprises any of the anti-RON antibodies or MSP fusion proteins provided herein and at least one additional therapeutic agent, e.g., as described below.

RON agonists of the invention can be used either alone or in combination with other agents in a therapy. For instance, an antibody of the invention may be co-administered with at least one additional therapeutic agent. In certain embodiments, an additional therapeutic agent is an immunosuppressant such as a TNF inhibitor, mesalazine, steroid, methotrexate, Azathioprine or an anti-hyperglycemia drug such as insulin, insulin analogs, metformin, sulfonylureas, or glitazones.

Such combination therapies noted above encompass combined administration (where two or more therapeutic agents are included in the same or separate formulations), and separate administration, in which case, administration of the agonist of the invention can occur prior to, simultaneously, and/or following, administration of the additional therapeutic agent or agents. In one embodiment, administration of the anti-RON antibody and administration of an additional therapeutic agent occur within about one month, or within about one, two or three weeks, or within about one, two, three, four, five, or six days, of each other.

A Ron agonist of the invention (and any additional therapeutic agent) can be administered by any suitable means, including parenteral, topical, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein. In certain embodiments, the RON agonist is administered systematically or topically. In certain embodiments, the RON agonist is administered topically.

RON agonists of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

A pharmaceutical composition for topical administration can be formulated, for example, in the form of a topical gel. See e.g., U.S. Pat. No. 5,192,734 (Genentech). In certain embodiments, the composition can be formulated in the presence of cellulose derivatives. In certain other embodiments, the topical formulation can be reconstituted from lyophilized formulation with sufficient buffer or diluent before administration. In certain embodiments, the RON agonist is formulated for topical administration to a subject having a defect in epithelial wound healing. In certain particular embodiments, the epithelial wound healing occurs in the skin. In certain other particular embodiments, the subject is a human having diabetes. In certain other embodiments, the topical formulation comprising a RON agonist of the invention can be used to improve wound healing after internal or external surgical incisions.

For the prevention or treatment of disease, the appropriate dosage of an agonist of the invention (when used alone or in combination with one or more other additional therapeutic agents) will depend on the type of disease to be treated, the type of agonist, the severity and course of the disease, whether the agonist is administered for preventive or therapeutic purposes, previous therapy, the patient's clinical history and response to the agonist, and the discretion of the attending physician. The agonist is suitably administered to the patient at one time or over a series of treatments. Depending on the type and severity of the disease, about 1 µg/kg to 15 mg/kg (e.g. 0.1 mg/kg-10 mg/kg) of agonist can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-RON antibody.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an agonist of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-RON antibody.

The Examples, which follow, are illustrative of specific embodiments of the invention, and various uses thereof. They are set forth for explanatory purposes only, and are not to be taken as limiting the invention.

EXAMPLES

Cloning, Expression and Purification of Recombinant Proteins

Recombinant human pro-MSP 689R or 689C (C672A) (SEQ ID NO:2 or 4, respectively), human MSP β 689R or 689C (HGF leader, V484-G711; C588S, with and without C672A) (SEQ ID NOs:8 and 9) were cloned into pRK expression vectors with C-terminal 6-His tags. The C672A mutation was previously shown to be required in order to obtain properly folded protein (Wahl et al., 1997, *J Biol Chem*, 272:15053-6). An R483E mutation was introduced into the P1 position of the human pro-MSP cleavage site to make scMSP (R483E, C672A) (SEQ ID NO:6) as noncleavable, inactive versions of single-chain pro-MSP (scMSP). All mutations were made with the QuikChange II XL site-directed mutagenesis kit (Agilent Technologies, Santa Clara, Calif.). The natural leader sequence (or signal peptide) of human MSP is M1-G18.

Human full length MSP containing a C672A mutation (SEQ ID NO:2), Human MSP β (HGF leader, V484-G711, C672A, C588S) (SEQ ID NO:9) and murine MSP β (HGF leader, V489-E716, HGF leader C677A, C593A) (SEQ ID NO:16), all with C-terminal His-tags were cloned into a pRK vector. Constructs were expressed transiently in Chinese hamster ovary (CHO) cells for 2 weeks. Secreted proteins were purified by Ni-NTA affinity chromatography followed by size exclusion chromatography on Superdex 200 10/300 GL or Superdex 75 10/300 GL (GE Healthcare, Piscataway, N.J.).

Recombinant human RON comprising the Sema, PSI and IPT1 domains (natural leader sequence+E25-M682) was made as an Fc fusion with human IgG1 (RON-Fc) by expressing in CHO cells (SEQ ID N044). See Ronsin et al., 1993, Oncogene 8(5):1195-202; Gherardi et al., 2003, Proc Natl Acad Sci USA. 100(21):12039-44; and Lu et al., 2007, Cancer Lett. 257(2):157-64. Epub 2007 Sep. 21. Recombinant human MSP β (HGF leader, V484-G711, C672A, C588S) or murine MSP (HGF leader, V489-E716, C677A, C593A) separated by various linker lengths from a C-terminal Fc regions of the heavy chain murine IgG2a or human IgG1 were cloned into a pRK vector containing the human HGF signal sequence (M1-G31) (SEQ ID NO:55)(Ashkenazi et al., 1997, Current Opinion in Immunology 9:195-200). Human MSP can activate both human and mouse RON, while mouse MSP only activates mouse RON.

In order to eliminate the fusion protein binding to Fc receptors, variants were made with two mutations (D265A and N297A in human IgG1, dubbed DANA) in the murine IgG2a and human IgG1 Fc heavy chain (Shields R L et al., 2001, J Biol Chem 276: 6591-6604; and Gong et al., 2005, J Immunol. 174(2):817-26). Constructs were cloned into the pRK vector and expressed in Chinese hamster ovary (CHO) cells as above. MSP β-Fc fusions were purified by affinity chromatography on a Mab Select Sure column (GE Healthcare, Piscataway, N.J.) followed by size exclusion chromatography on Superdex 200 10/300 GL to isolate monomeric proteins based on their elution profile. Protein was purified in Phosphate Buffered Saline (PBS) and stored at 4° C. RON-Fc was purified by affinity chromatography on a MabSelect Sure column (GE Healthcare) followed by size exclusion chromatography (Superdex 200 10/300 GL).

Recombinant human RON Sema/PSI (natural leader sequence+residues E25-P568) containing a C-terminal His-tag was cloned into the Gateway vector pENTR/D-TOPO (Life Technologies), which includes the honeybee melittin secretion signal to generate recombinant baculovirus using the Bac-to-Bac system (Life Technologies). *Trichoplusia ni* insect cells (1×10⁶ cells per ml) were infected with recombinant baculovirus with a multiplicity of infection of three in ESF921 medium (Expression Systems, Woodland, Calif.). After a 72-h incubation, RON Sema/PSI was purified by Ni-NTA affinity chromatography followed by size exclusion chromatography on Superdex 200 10/300 GL (GE Healthcare) and stored in HEPES Buffered Saline (HBS) at −20° C.

Recombinant murine RON Sema/PSI/IPT1 (natural leader sequence+R33-V684) containing the C-terminal Fc region of the heavy chain of human IgG1 (mRON-hFc) (SEQ ID NO:50) or His-tag (mRON-His) (SEQ ID NO:52) was expressed in CHO cells. mRON-His was purified by Ni-NTA affinity chromatography followed by size exclusion chromatography on Superdex 200 10/300 GL (GE Healthcare) and stored in HEPES Buffered Saline (FIBS) at −20° C. The Fc-fusion protein was purified as above.

The extracellular domain of the human recombinant hepsin harboring a C-terminal His-tag (sHepsin) (SEQ ID NO:54) was expressed and purified as described in Moran et al., 2006, J Biol Chem, 281: 30439-46). Antibody25 (Fab25) inhibits hepsin enzymatic activity was generated by using antibody phage display and subsequently expressed in *E. coli* and purified as described previously (Ganesan et al., 2012, Protein Eng Des Sel 25:127-33).

All constructs described herein are summarized in Table 2 below.

TABLE 2

| Sequences | SEQ ID NOs | Comments |
| --- | --- | --- |
| Full length human MSP | SEQ ID NO: 1 (DNA)<br>SEQ ID NO: 2 (protein) | Wild type + C672A + His tag |
| Full length human MSP R689C | SEQ ID NO: 3 (DNA)<br>SEQ ID NO: 4 (protein) | Wild type + C672A + R689C + His tag |
| Human ScMSP | SEQ ID NO: 5 (DNA)<br>SEQ ID NO: 6 (protein) | Wild type + R483E + C672A + His tag |

TABLE 2-continued

| Sequences | SEQ ID NOs | Comments |
|---|---|---|
| Human MSP β | SEQ ID NO: 7 (DNA) | HGF leader + V484-G711 + C588S + |
|  | SEQ ID NO: 8 (protein) | C672C + His tag |
| Human MSP β | SEQ ID NO: 9 (protein) | HGF leader + V484-G711 + C588S + C672A + His tag |
| Human MSP β R689C | SEQ ID NO: 10 (protein) | HGF leader + V484-G711 + C588S + C672C + R689C + His tag |
| Human MSP β R689C | SEQ ID NO: 11 (protein) | HGF leader + V484-G711 + C588S + C672A + R689C + His tag |
| Wild type human MSP | SEQ ID NO: 12 (protein) | Wild type sequence |
| Full length mouse MSP | SEQ ID NO: 13 (DNA) | Wild type sequence |
|  | SEQ ID NO: 14 (protein) |  |
| Mouse MSP β | SEQ ID NO: 15 (DNA) | HGF leader + V489-E716 + C593A + |
|  | SEQ ID NO: 16 (protein) | C677A + His tag |
| Mouse MSP β | SEQ ID NO: 17 (protein) | HGF leader + V489-E716 + C593A + C677C + His tag |
| Wild type mouse MSP | SEQ ID NO: 18 (protein) | Wild type sequence |
| Human MSP β-L4-hIgG1 Fc | SEQ ID NO: 19 (DNA) | h4h |
|  | SEQ ID NO: 20 (protein) |  |
| Human MSP β-L16-mIgG2a Fc | SEQ ID NO: 21 (DNA) | h16m |
|  | SEQ ID NO: 22 (protein) |  |
| Human MSP β-L16-mIgG2a Fc (DANA) | SEQ ID NO: 23 (DNA) | h16m (DANA) |
|  | SEQ ID NO: 24 (protein) |  |
| Mouse MSP β-L4-mIgG2a Fc | SEQ ID NO: 25 (DNA) | m4m |
|  | SEQ ID NO: 26 (protein) |  |
| Mouse MSP β-L8-mIgG2a Fc | SEQ ID NO: 27 (DNA) | m8m |
|  | SEQ ID NO: 28 (protein) |  |
| Mouse MSP β-L12-mIgG2a Fc | SEQ ID NO: 29 (DNA) | m12m |
|  | SEQ ID NO: 30 (protein) |  |
| Mouse MSP β-L16-mIgG2a Fc | SEQ ID NO: 31 (DNA) | m16m |
|  | SEQ ID NO: 32 (protein) |  |
| Mouse MSP β-L4-mIgG2a Fc (DANA) | SEQ ID NO: 33 (DNA) | m4m (DANA) |
|  | SEQ ID NO: 34 (protein) |  |
| Mouse MSP β-L8-mIgG2a Fc (DANA) | SEQ ID NO: 35 (DNA) | m8m (DANA) |
|  | SEQ ID NO: 36 (protein) |  |
| Mouse MSP β-L12-mIgG2a Fc (DANA) | SEQ ID NO: 37 (DNA) | m12m (DANA) |
|  | SEQ ID NO: 38 (protein) |  |
| Mouse MSP β-L16-mIgG2a Fc (DANA) | SEQ ID NO: 39 (DNA) | m16m (DANA) |
|  | SEQ ID NO: 40 (protein) |  |
| Human RON | SEQ ID NO: 41 (DNA) |  |
|  | SEQ ID NO: 42 (protein) |  |
| Human RON-hIgG1 Fc | SEQ ID NO: 43 (DNA) | RON Sema/PSI/IPT1 (leader |
|  | SEQ ID NO: 44 (protein) | sequence + R33-V684) |
| Human RON-His | SEQ ID NO: 45 (DNA) | RON Sema/PSI/IPT1 + His tag |
|  | SEQ ID NO: 46 (protein) |  |
| Mouse RON | SEQ ID NO: 47 (DNA) |  |
|  | SEQ ID NO: 48 (protein) |  |
| Mouse RON-hIgG1 Fc | SEQ ID NO: 49 (DNA) | RON Sema/PSI/IPT1 |
|  | SEQ ID NO: 50 (protein) |  |
| Mouse RON-His | SEQ ID NO: 51 (DNA) | RON Sema/PSI/IPT1 + His tag |
|  | SEQ ID NO: 52 (protein) |  |
| sHepsin | SEQ ID NO: 53 (DNA) |  |
|  | SEQ ID NO: 54 (protein) |  |
| HGF leader sequence | SEQ ID NO: 55 (protein) |  |
| MSP PCR sense primer | SEQ ID NO: 56 |  |
| MSP PCR anti-sense primer | SEQ ID NO: 57 |  |
| MSP PCR TaqMan probe | SEQ ID NO: 58 |  |
| RON amplification sense primer | SEQ ID NO: 59 |  |
| RON amplification anti-sense primer | SEQ ID NO: 60 |  |
| RON TaqMan probe | SEQ ID NO: 61 |  |
| RPL19 amplification sense primer | SEQ ID NO: 62 |  |
| RPL19 amplification anti-sense primer | SEQ ID NO: 63 |  |
| RPL19 TaqMan probe | SEQ ID NO: 64 |  |
| Anti-mRON mAb 2E5.8.1 CDRH1 | SEQ ID NO: 65 (DNA) |  |
|  | SEQ ID NO: 66 (protein) |  |
| Anti-mRON mAb 2E5.8.1 CDRH2 | SEQ ID NO: 67 (DNA) |  |
|  | SEQ ID NO: 68 (protein) |  |
| Anti-mRON mAb 2E5.8.1 CHRH3 | SEQ ID NO: 69 (DNA) |  |
|  | SEQ ID NO: 70 (protein) |  |
| Anti-mRON mAb 2E5.8.1 CDRL1 | SEQ ID NO: 71 (DNA) |  |
|  | SEQ ID NO: 72 (protein) |  |
| Anti-mRON mAb 2E5.8.1 CDRL2 | SEQ ID NO: 73 (DNA) |  |
|  | SEQ ID NO: 74 (protein) |  |
| Anti-mRON mAb 2E5.8.1 CDRL3 | SEQ ID NO: 75 (DNA) |  |
|  | SEQ ID NO: 76 (protein) |  |

TABLE 2-continued

| Sequences | SEQ ID NOs | Comments |
|---|---|---|
| Anti-mRON mAb YW651.1CDRH1 | SEQ ID NO: 77 (DNA) | |
| Anti-mRON mAb YW651.1CDRH1 | SEQ ID NO: 78 (protein) | |
| Anti-mRON mAb YW651.1CDRH2 | SEQ ID NO: 79 (DNA) | |
| Anti-mRON mAb YW651.1CDRH2 | SEQ ID NO: 80 (protein) | |
| Anti-mRON mAb YW651.1CDRH3 | SEQ ID NO: 81 (DNA) | |
| Anti-mRON mAb YW651.1CDRH3 | SEQ ID NO: 82 (protein) | |
| Anti-mRON mAb YW651.1CDRL1 | SEQ ID NO: 83 (DNA) | |
| Anti-mRON mAb YW651.1CDRL1 | SEQ ID NO: 84 (protein) | |
| Anti-mRON mAb YW651.1CDRL2 | SEQ ID NO: 85 (DNA) | |
| Anti-mRON mAb YW651.1CDRL2 | SEQ ID NO: 86 (protein) | |
| Anti-mRON mAb YW651.1CDRL3 | SEQ ID NO: 87 (DNA) | |
| Anti-mRON mAb YW651.1CDRL3 | SEQ ID NO: 88 (protein) | |

Cell Isolation, Differentiation and Culture

Cell lines were cultured according to standard protocols. 3T3 cells were cultured in high glucose DMEM (Cellgro) with 10% bovine calf serum (Sigma). Human primary colon cells (Celprogen) were maintained in colon cell culture medium (Celprogen). Parental 3T3 and A2780 cells were stably transfected with murine RON to generate 3T3-mRON and A2780-mRON cells respectively (Chaudhuri et al., 2011, J Biol Chem 286:32762-74), for which medium was supplemented with 400 µg/ml G418. Cell lines stably transfected with MSP were generated using the Flp-In system (Life Technologies) according to the manufacturer's instructions. Recombinant human pro-MSP 689R or 689C (Q19-G711) with the wild-type residue at position 672 was cloned into pcDNA5/FRT (Life Technologies) and used to transfect 293 Flp-In cells (Life Technologies). Transfected cells were plated in medium supplemented with 100 µg/ml Zeocin (Life Technologies) and Zeocin-resistant colonies were picked with cloning discs (Sigma-Aldrich) after three weeks. Clones were re-plated to confirm hygromycin sensitivity and Zeocin resistance.

Human peripheral blood mononuclear cells (PBMCs) were isolated from blood by density gradient centrifugation with Ficoll-Paque PLUS (GE Healthcare). Monocytes were purified from PBMCs with the Monocyte Isolation Kit II (Miltenyi Biotec). Human monocyte-derived macrophages were obtained by incubation of CD14+ monocytes for one week in RPMI supplemented with 20% fetal bovine serum (FBS), 100 U/ml penicillin, 100 µg/ml streptomycin, 2 mM L-glutamine, and 100 ng/ml M-CSF (R&D Systems). Macrophages were treated with 100 ng/ml LPS and 20 ng/ml IFN-γ, or 20 ng/ml IL-4 for 18 h in RPMI plus 5% FBS, or with 100 ng/ml LPS on IgG-coated plates for 24 h in RPMI plus 20% FBS.

Murine bone marrow derived macrophages were obtained by incubating unfractionated bone marrow cells in DMEM plus 10% FBS, 100 U/ml penicillin, 100 µg/ml streptomycin, 2 mM L-glutamine, and 30% conditioned media from L929 cells. Fresh growth media was added on day 3 of the culture and adherent macrophages were harvested on day 7. Cells were uniformly F4/80 and CD11b positive at this time point.

Peritoneal exudate cells were harvested from mice under steady-state conditions or 4 days after intraperitoneal injection with 1 ml of 3% thioglycollate by peritoneal lavage with 9 ml of RPMI. Cells were washed once with RPMI and resuspended in FACS buffer. Liver mononuclear cells were obtained as described (Egen et al., 2008, Immunity 28:271-84), with some modification. Briefly, livers were perfused through the portal vein with 3 ml of digest buffer consisting of RPMI plus 0.2 mg/ml of Liberase TL and 0.1 mg/ml DNase I (Roche Applied Science). Livers were excised and further incubated in digest buffer for 40 min at 37° C. After manual disruption by repeated pipetting, liver cell suspensions were washed in Hanks' balanced salt solution (HBSS) (Life Technologies), resuspended in 35% Percoll, and centrifuged at 800×g for 20 min, collecting the cell pellet. Red blood cells were lysed with Ack lysis buffer (Lonza) and cells were resuspended in FACS buffer. For single cell suspensions of murine colon, colons were removed from the animals, flushed with HBSS, cut into 2 cm pieces, and incubated in HBSS containing EDTA and DTT for 15 min at 37° C. with constant shaking. This incubation period was kept short to avoid loss of epithelial cells. The tissue was washed 2 times in RPMI, minced, and incubated in RPMI plus 0.2 mg/ml of Liberase TL and 0.1 mg/ml DNase I for 20 min at 37° C. with constant shaking. The suspension, containing both mononuclear cells and epithelial cells, was filtered through 100 µm and 70 µm filters, washed, and resuspended in FACS buffer.

Human intestinal resection samples were obtained from 1 colon carcinoma patient, 2 UC, and 3 CD patients through collaboration with the Mayo Clinic (Rochester, Minn.). Matched serum, DNA, and intestinal biopsy RNA samples were collected as part of the multi-center EMBARK observational clinical trial in IBD sponsored by Genentech. Informed consent was obtained from all human subjects.

Single cell suspensions of resected intestinal tissues were prepared by dissecting out serosa, lamina muscularis, and submucosa, leaving approximately three grams of tissue including lamina propria and epithelium. This was incubated for 15 min at 30° C. on an orbital shaker in 50 ml HBSS with 5 mM DTT, then in 50 ml HBSS with 1 mM EDTA. Tissue was washed twice in 50 ml RPMI plus 10% FBS, minced into 0.5 cm pieces, and digested 20 min in 50 ml RPMI, 10% FBS, 1.5 mg/ml collagenase VIII (Sigma-Aldrich), 0.1 mg/ml DNase I at 37° C. on an orbital shaker. Digested tissue was filtered through a 70 µm pore filter, washed, and resuspended in FACS buffer (PBS plus 2% FBS). For leukocyte purification, cells were pelleted, resuspended in 7 ml isotonic 35% Percoll (GE Healthcare), underlayed with 6 ml isotonic 60% Percoll, and centrifuged 20 min at 2000 RPM at 4° C. Cells at the Percoll interface were collected, washed, and resuspended in FACS buffer.

Mice

C57Bl/6, C57Bl/6 Recombinase Activating Gene (RAG)-2 deficient, and db/db mice were obtained from the Jackson Laboratory. RON.ko mice (described in Waltz et al, 2001, J Clin Invest. 108(4):567-76) lack the tyrosine kinase domain of RON, which has been removed through gene targeting. All animal experiments were approved by the Genentech Institutional Animal Care and Use Committee Flow Cytometry Murine cells were stained with fluorochrome-labeled antibodies against F4/80 (clone BM8), CD11b (clone M1/70), MHC class II (clone M5/114.15.2), and either mouse RON (clone PH4, Genentech, Inc., South San Francisco, Calif.) or a murine IgG2a isotype control antibody (Genentech, Inc). Human cells were stained with fluorochrome-labeled antibodies against CD14 (clone 61D3), CD16 (clone 3G8), CD45 (clone HI30) EpCAM (clone VU1D9), MHC class II (LN3), and either human RON (Clone 1A2.2, Genentech, Inc.) or a murine IgG2a isotype control antibody (Genentech, Inc). Unless specified, all other antibodies were purchased from Abcam, BD Biosciences, Biolegend, or eBioscience. Ex vivo analyzed murine and human cells were stained with a LIVE/DEAD Aqua or Violet viability stain (Life Technologies). Cells were analyzed on a LSRII flow cytometer (BD Biosciences). Live cells were identified based on size and the viability stain and RON expression was determined by gating on the indicated population of cells using Flowjo software (Treestar, Ashland, Oreg.).

MSP Binding Assays a. MSP Binding to Plate Immobilized RON

MaxiSorp plates (Nalge Nunc International) were coated overnight at 4° C. with 2 µg/ml of rabbit anti-human IgG Fc specific antibody (Jackson ImmunoResearch Laboratories) in 50 mM sodium carbonate buffer, pH 9.6. After blocking with assay buffer (50 mM HEPES pH 7.2, 150 mM NaCl, 5 mM $CaCl_2$, 1% BSA and 0.1% Tween-20), 1 µg/ml RON-Fc fusion protein in assay buffer was added and plates were incubated for 1 h with gentle shaking at room temperature. After washing with PBS+0.05% Tween-20, MSP (1000 nM-0.2 pM, 2-fold dilution series) was added for 1 h. Bound MSP was detected using anti-His-HRP (Qiagen Inc.) followed by addition of $TMB/H_2O_2$ substrate (Thermo Scientific). The reaction was stopped with 1M $H_3PO_4$ and the absorbance at 450 nm ($A_{450}$) was measured on a SpectraMax Plus[384] plate reader (Molecular Devices, LLC). The half maximal effective concentration of MSP ($EC_{50}$) was determined by a 4-parameter fit using Kaleidagraph (Synergy Software).

b. Kinetic Measurement of MSP Binding to RON by Surface Plasmon Resonance (SPR)

Binding kinetics of RON to MSP 13-Fc fusion proteins and MSP proteins to RON-Fc fusions were determined using a Biacore 3000 optical biosensor equipped with a research-grade CMS sensor chip (GE Healthcare). Amine coupling reagents, N-ethyl-N'-dimethylamino-propylcarbodiimide (EDC), N-hydroxy-succinimide (NETS) and sodium ethanolamine HCl, pH 8.5, were obtained from GE Healthcare. Standard coupling protocols were used to tether a rabbit anti-human IgG1 or rabbit anti-murine IgG2a (Jackson ImmunoResearch Laboratories) onto the biosensor surface. A biosensor chip that was subjected to the amine coupling procedure with no protein coupled was used to correct for non-specific binding. To determine RON binding affinities to MSP 13-Fc fusions, between 50 and 100 response units (RU) of MSP 13-Fc were captured on each of three immobilized anti-Fc surfaces. Various concentrations (500-3.9 nM, 2-fold dilution series) of RON-His, were injected in HBS-P buffer (10 mM HEPES, pH 7.5, 150 mM NaCl, 0.005% P20) at 25° C. with a flow rate of 30 µL/min and dissociation monitored for 240 sec. Between measurements, the biosensor surfaces were regenerated with a 120 s pulse of 10 mM glycine-HCl pH 1.5 followed by a 120 s wash with running buffer.

To determine MSP protein binding kinetics to hRON-Fc or mRON-Fc fusion proteins, between 50 and 100 response units (RU) were captured on each of three immobilized anti-human Fc surfaces. Various concentrations (50-0.78 nM, 2-fold dilution series) of MSP, MSP β, MSP α or scMSP were injected in HBS-P buffer (10 mM HEPES, pH 7.5, 150 mM NaCl, 0.005% P20) at 25° C. with a flow rate of 30 µL/min and dissociation monitored for 4 min. Between measurements, the biosensor surfaces were regenerated with a 2 min pulse of 10 mM glycine-HCl pH 1.5.

Each data set was fit globally to a simple one-to-one Langmuir binding model (BIA evaluation 4.1, GE Healthcare) to determine the kinetic parameters $k_{on}$ and $k_{off}$. The equilibrium dissociation constants ($K_D$) were then calculated as a ratio ($k_{off}/k_{on}$) of these rate constants.

c. Kinetic Measurement of YW651.1-IgG2a Binding to RON by Surface Plasmon Resonance A BIAcore-3000 instrument was used. Briefly, CMS biosensor chip was activated with N-ethyl-N'-(3-dimethylaminopropyl)-carbodiimide hydrochloride (EDC) and N-hydroxysuccinimide (NHS) reagents according to the supplier's (GE Healthcare Biosciences) instructions, and human antibody capture kit was applied to couple goat anti-human Fc IgGs to achieve approximately 10000 response units (RU) on each flow cell, then following by blocking unreacted groups with 1M ethanolamine.

For kinetics measurements, mRON-Fc (catalog #431-MS, mRON extracellular domain fused to human IgG1, R&D System) antigens were captured to achieve approximately 250 RU, and then two-fold serial dilutions of anti-mRON Fab (0.49 nM to 250 nM) were injected in HBS-P buffer (0.01M HEPES pH 7.4, 0.15M NaCl, 0.005% surfactant P20) at 25° C. with a flow rate of 30 µl/min. Association rates ($k_{on}$) and dissociation rates ($k_{off}$) were calculated using a simple one-to-one Langmuir binding model (BIAcore Evaluation Software version 3.2). The equilibrium dissociation constant (KD) was calculated as the ratio $k_{off}/k_{on}$.

d. Kinetic Measurement of MSP Binding to RON by Biolayer Interferometry (BLI)

Real-time kinetic measurements of MSP binding to RON were conducted using an Octet RED384 (ForteBio, Inc). Samples or buffer were dispensed into 96-well microtiter plates (Greiner Bio-One North America, Inc.) at a volume of 200 µl per well. Anti-human IgG Fc Biosensors were used for the experiments. Each experiment consisted of three steps: incubation with ForteBio Kinetic buffer diluted 1:10 in PBS assay buffer to establish an equilibrium for 120 s (baseline), incubation with 10 µg/ml RON-Fc in assay buffer to coat the biosensor with binding target for 900 s (load), incubation with MSP, MSP β or scMSP in assay buffer containing various concentrations (75-4.7 nM, 2-fold dilution series) for 400 s (association), and incubation with assay buffer to measure the off-rate of MSP for 400 s (dissociation). Operating temperature was maintained at 30° C. Data were generated automatically by the Octet Data Acquisition 7.0 software. Each data set was fitted globally to a simple one-to-one binding model using ForteBio Analysis Software 7.0 to determine the kinetic parameters $k_a$ and $k_d$. The equilibrium dissociation constants ($K_D$) were then calculated as a ratio ($k_{off}/k_{on}$) of these rate constants.

e. Equilibrium Measurement of MSP Binding to RON by Radioligand Binding Assay

MSP proteins were iodinated using the Iodogen method (Thermo Scientific) and purified from free $Na^{125}I$ by gel filtration using a NAP-5 column. Specific activities ranged from 12.26 to 18.65 µCi/µg. Competition reaction mixtures were made of a fixed concentration of iodinated MSP and unlabeled MSP serially diluted 1- to 2-fold ten times starting at 5 µM in a volume of 3T3-hRon cells were washed with binding buffer, consisting of DMEM with 1% bovine serum albumin, 325 nM human IgG, 50 mM HEPES (pH 7.2) and 0.1% sodium azide. 150,000 cells in 0.2 ml binding buffer were added to competition reaction mixtures. Competition reactions with cells were incubated for 2 h at room temperature and transferred to a Multiscreen filter plate (Millipore) and washed 4 times with binding buffer. Filters were counted on a Wallac Wizard 1470 gamma counter (PerkinElmer Life and Analytical Sciences). Binding affinities were determined using NewLigand software (Genentech, Inc) (Munson et al., 1980, Anal Biochem 107:220-39).

Western Blotting for Akt Phosphorylation

A2780-hRON and BxPC3 cells were grown overnight in media containing 0.5% BSA.

Cells were treated with 100 ng/ml MSP 689R, MSP 689C or nothing for 20 min at 37° C. Samples were prepared by washing the cell monolayer twice with ice cold PBS followed by the addition of SDS-PAGE sample buffer and quantified by BCA Protein Assay (Thermo Scientific, Rockford, Ill.). Proteins (20 µg) were electrophoresed on 4%-20% Tris-glycine gels (Life Technologies), transferred to nitrocellulose membranes and blocked with Odyssey blocking buffer (Li-Cor Biosciences) for 1 h at room temperature. Membrane was probed with Akt Polyclonal Antibody (Cell Signaling Technology), and Phospho-Akt Monoclonal Antibody, Ser473 (Cell Signaling Technology) overnight at 4° C. After washing, the membrane was incubated with IRDye™ 800 conjugated goat anti-mouse IgG (Rockland Immunochemicals) and AlexaFluor 680 goat anti-rabbit IgG (Life Technologies) for 1 h. The amount of phosphorylated and total kinase expression was detected using the Odyssey Infrared Imaging System (Li-Cor Biosciences).

For MSPβ-Fc activation of mRON in mRON-expressing 3T3 cells, 10-50 ug of protein lysate supernatant was separated by SDS-PAGE using the Mini-Protein Tetra Cell (Biorad) and transferred to PVDF membrane (Millipore) in the Tetra Cell according to the manufacturer's instructions. Blots were probed with anti-phospho Akt antibody (clone D9E, Cell Signaling Technology) or polyclonal anti-Akt antibody (Cell Signaling Technology) followed by HRP-conjugated goat anti-rabbit antibody according to the manufacturer's instructions. Protein bands were visualized by incubation of membrane with SuperSignal West Pico solution (Thermo Fisher) and exposure to film.

Immunofluorescence and Immunohistochemistry on Fixed Tissue Sections

For immunofluorescence staining, mouse colons were excised, thoroughly flushed with PBS, and fixed overnight in PLP buffer (0.05 M phosphate buffer containing 0.1 M L-lysine [pH 7.4], 2 mg/ml NaIO$_4$, and 10 mg/ml paraformaldehyde), followed by dehydration in 30% sucrose, and embedding in OCT freezing media (Sakura Finetek). Sections in 12 µm thickness were cut on a CM3050S cryostat (Leica Microsystems) and adhered to Superfrost Plus slides (VWR). Sections were blocked in 10% donkey serum (Jackson ImmunoResearch Laboratories) and stained using the following primary antibodies: F4/80-AlexaFluor 647 (clone BM8, eBiosciences), MHC class II-FITC (clone M5/114.15.2, BD Biosciences), and goat anti-mouse RON (R&D Systems). Goat antibodies were visualized with Donkey anti-Goat AlexaFluor 568 (Life Technologies). Nuclei were counterstained with Hoechst 33342 (Life Technologies) and slides were mounted with Prolong Gold (Life Technologies). Images were acquired using a Leica SPE confocal microscope (Leica Microsystems).

Mouse skin was excised and fixed overnight in PLP buffer (0.05 M phosphate buffer containing 0.1 M L-lysine [pH 7.4], 2 mg/ml NaIO$_4$, and 10 mg/ml paraformaldehyde), followed by dehydration in 30% sucrose, and embedding in OCT freezing media (Sakura Finetek). Sections of 12 µm thickness were cut on a CM3050S cryostat (Leica Microsystems) and adhered to Superfrost Plus slides (VWR). Sections were blocked in 10% donkey serum (Jackson ImmunoResearch Laboratories) containing 0.2% TritonX-100 (Sigma) and stained using the following primary antibodies: F4/80-FITC (clone BM8, eBiosciences), E-cadherin-Alexa Fluor 647 (clone DECMA-1, e Biosciences), and goat anti-mouse RON (R&D Systems). Goat antibodies were visualized with Donkey anti-Goat AlexaFluor 568 (Life Technologies). Nuclei were counterstained with Hoechst 33342 (Life Technologies) and slides were mounted with Prolong Gold (Life Technologies). Images were acquired using an LSM 510 confocal microscope (Carl Zeiss Microimaging).

For immunohistochemistry on human tissues, 4 µm sections were cut from formalin fixed, paraffin-embedded intestinal tissue. Staining was performed on the Ventana Discovery XT Autostainer platform (Ventana Medical Systems). Deparaffinization, endogenous peroxidase blocking as well as pretreatment using CC1 standard antigen retrieval was performed using Ventana ready to use reagents. Goat polyclonal anti-human RON antibody (R&D Systems) was then diluted to 0.5 µg/ml in 3% BSA/PBS and sections were incubated for 32 min at 37° C. Sections were subsequently incubated with an unconjugated rabbit-anti-goat secondary linker antibody (Vector Labs) followed by an anti-rabbit-OMNIMAP-HRP kit (Ventana Medical Systems) and ChromoMap DAB colorimetric reagents (Ventana Medical Systems). Slides were counterstained with hematoxylin (Ventana Medical Systems) and dehydrated, cleared and mounted for viewing.

For immunohistochemistry on murine tissues, 4 µm sections were cut from formalin fixed, paraffin-embedded intestinal tissues. Sections were deparaffinized in xylenes and rehydrated through a graded series of alcohols. Sections were then pre-treated for antigen retrieval using Target Retrieval Solution (DAKO). Sections were blocked for endogenous peroxidase activity using KPL blocking solution (KPL, Inc.), for avidin/biotin using an avidin/biotin blocking kit (Vector Labs), and for IgG binding with TNB Blocking buffer (Perkin Elmer). Sections were incubated overnight at 4° C. with anti-murine RON goat polyclonal antibody (R&D Systems) at 2.5 µg/ml. Sections were then incubated with a biotinylated donkey-anti-goat secondary antibody (Jackson ImmunoResearch Laboratories) followed by ABC-HRP Elite reagents (Vector Labs). Chromogenic development was accomplished using a metal enhanced DAB colorimetric peroxidase substrate (Thermo Scientific). Sections were then counterstained with Myer's Hematoxylin (Rowley Biochemical Institute), dehydrated, cleared with xylenes and mounted for viewing.

Quantitative PCR or RT-PCR

To determine the rs3197999 genotype of EMBARK cohort members, 10 ng of genomic DNA was used in the Taqman SNP Genotyping Assay (Applied Biosystems). To compare quantities of the MSP expression cassette in stably transfected 293 Flp-In cells, genomic DNA was isolated with the DNeasy kit (Qiagen) and 50 ng was assayed with the Taqman Universal PCR Master Mix (Applied Biosystems). Primers specific for MSP expression cassette DNA, 5'-CCACTGCTTACTGGCTTATCG-3' (SEQ ID NO:56), 5'-TCTTCAGCATCTGCCACATC-3' (SEQ ID NO:57), and taqman probe 5'-TAGCGCTACCGGACTCAGAT-3' (SEQ ID NO:58), were used. MSP DNA quantity was normalized to GAPDH DNA quantified with the Taqman Gene Expression Assay (Applied Biosystems) using the $\Delta C_T$ method. For analysis of RON mRNA expression in epithelial cell lines and myeloid cells, total RNA was isolated with the RNeasy kit with on-column DNase digestion (Qiagen). 80 ng RNA was assayed with the Quantitect Probe RT-PCR kit (Qiagen), and RON expression was normalized to RPL19 expression using the $\Delta C_T$ method. For RON amplification, primers 5'-AGGGCAGTCCTGCAACAT-3' (SEQ ID NO:59), 5'-GAGTCCACTGTGCCCAGAA-3' (SEQ ID NO:60), and taqman probe 5'-ACAGGGTCCACAGCAGGCACTC-3' (SEQ ID NO:61) were used. For RPL19 amplification, primers 5'-CAATGCCAACTCCCGTCAG-3' (SEQ ID NO:62), 5'-GTCACAGGCTTGCGGATGA-3' (SEQ ID NO:63), and taqman probe 5'-AGATCCGGAAGCTCAT-CAAAGATGGGCT-3' (SEQ ID NO:64) were used. Reactions were run on the ABI 7500 Real Time PCR system and analyzed with the 7500 Software (Applied Biosystems).

For analysis of mRNA expression in intestinal biopsies, tissue samples were homogenized with 3 mm using a TissueLyzer (Qiagen) and RNA isolated using the RNeasy kit (Qiagen). RNA integrity was assessed with the Agilent 2100 Bioanalyzer using the Agilent RNA 6000 Pico Kit (Agilent Technologies). Reactions were run on the BioMark HD System (Fluidigm) using human RON primer set Hs00899925_m1 (Applied Biosystems) and GAPDH primer set Hs99999905_m1 (Applied Biosystems). RON expression was normalized to GAPDH and a reference human RNA sample using the $A\Delta C_T$ method.

ELISA Assay for MSP

For assays of human serum, MaxiSorp plates were coated overnight at 4° C. with 1 µg/ml of anti-hMSP α antibody (R&D Systems) in 0.05 M carbonate/bicarbonate buffer, pH 9.6, then incubated 1 h at room temperature in blocking buffer (PBS, 0.5% BSA, 15 ppm Proclin pH 7.4). Samples were diluted in Assay Diluent (PBS, 0.5% BSA, 0.05% Tween 20, 15 ppm Proclin), added to plate, and incubated 2 h at room temperature. Biotinylated polyclonal goat anti-human MSP (R&D Systems) was diluted in Assay Diluent to 100 ng/ml, added to plate, and incubated 1 h at room temperature. Amdex streptavidin-HRP (GE Healthcare) was diluted in Assay Diluent to 50 ng/ml, added to the plate, and incubated 30 min at room temperature. Binding was read by incubation with TMB/$H_2O_2$ substrate (KPL, Inc) for 15 min, addition of 1 M $H_3PO_4$, and measurement of the absorbance at 450 nm ($A_{450}$). The MSP concentration was calculated by comparison to standard curves of MSP 689R, MSP 689C, scMSP 689R, and scMSP 689C that were titrated from 2 to 0.0082 ng/ml in 2.5-fold increments.

To assay supernatants from cells stably transfected with pro-MSP, Microtest ELISA plates (BD Falcon) were coated overnight at 4° C. with 1 µg/ml of anti-hMSP α antibody (R&D Systems) in PBS, then incubated 1 h at room temperature in Starting Block buffer (Thermo Scientific). Samples were diluted in Starting Block buffer, added to plate, and incubated 2 h at room temperature. Biotinylated polyclonal goat anti-human MSP (R&D Systems) was diluted in Starting Block buffer to 1 µg/ml, added to plate, and incubated for 1 h at room temperature. Streptavidin-HRP (EMD Millipore) was diluted 1:10,000 in Starting Block buffer, added to the plate, and incubated 20 min at room temperature. Binding was read by incubation with TMB/$H_2O_2$ substrate (R&D Systems) for 15 min, addition of 1M $H_3PO_4$, and measurement of $A_{450}$. To control for differences in cell quantity, relative cell densities were quantified by addition of CellTiter-Glo and measurement of luminescence with the Glomax luminometer (Promega). ELISA results were divided by luminescence to control for cell density.

RON Agonism by MSPβ-IgG2a Agonists and Anti-RON Agonist Antibodies in 3T3 and 3T3-mRON Cells 3T3 or 3T3-mRON cells were seeded in DMEM with 0.5% bovine calf serum and allowed to adhere overnight. The next day, medium was removed and cells were treated for 30 minutes at 37° C. with medium alone, anti-ragweed IgG2a isotype control, MSP, h16m, m16m, m4m, m8m, m12m, or m16m MSPβ-IgG2a agonists (15 nM to 1 pM, 5-fold dilution series in medium), RON agonist antibody 2E5.8.1 or YW651.1 (15 nM to 1 pM, 5-fold dilution series in medium). Cells were lysed on ice for 15 minutes in MSD lysis buffer. For detection of Akt phosphorylation, lysates were added to MULTI-SPOT 96-Well 4-Spot Phospho (Ser473)/Total Akt plates (Meso Scale Discovery) which were incubated according to manufacturer's instructions and read in a SECTOR Imager 6000 (Meso Scale Discovery). $EC_{50}$ values were calculated using the Prism software package (GraphPad).

In Vivo Analysis of MSPβ-IgG2a and RON Antibody Agonist Activity in Murine Colon and Skin To measure Akt phosphorylation in colon lysates, five female C57Bl/6 mice per group were inoculated intravenously with 5 mg/kg m12m MSPβ-IgG2a agonist, RON agonist antibody 2E5.8.1-IgG2a, RON agonist antibody YW651.1-IgG2a, or anti-ragweed control antibody of the same isotype diluted in PBS to a volume of 100 ul. After one hour, colons were harvested from mice, flushed with cold PBS, and homogenized in 500 ul MSD lysis buffer using GentleMACS M tubes (Miltenyi Biotec). For detection of Akt phosphorylation, supernatants were assayed by western blot analysis or added to MULTI-SPOT 96-Well 4-Spot Phospho(Ser473)/Total Akt plates (Meso Scale Discovery) which were incubated according to manufacturer's instructions and read in a SECTOR Imager 6000 (Meso Scale Discovery). To measure Akt phosphorylation in skin lysates, at day 0 female db/db mice were anaesthetized with isofluorane and the dorsal portion of the back (from the scapular to lumbar area) was shaved, stubble removed with Nair, and rinsed with sterile water, alcohol, betadine, and repeat alcohol. Animals were placed in ventral recumbency and a 6 mm punch device was used to make two 6 mm diameter full thickness skin wounds, 1 cm left and 1 cm right of midline. A 0.5 mm thick silicone frame, 10-12 mm inside diameter, was placed around each wound with frame held in place by superglue. A 2 cm square of Tegaderm or Op-site was placed over the wound and frame. At day four, mice were inoculated intraperitoneally with 5 mg/kg RON agonist antibody YW651.1-IgG2a, or anti-ragweed control antibody of the same isotype diluted in PBS to a volume of 100 ul. After one hour, a 2 mm ring of skin around the wound and a 6 mm piece of skin from a non-wounded area were harvested and homogenized in 300 ul MSD lysis buffer using GentleMACS M tubes.

To measure Akt phosphorylation in sectioned colon tissue, four female C57Bl/6 mice per group were inoculated intravenously with 5 mg/kg m12m MSPβ-IgG2a agonist or anti-ragweed control antibody of the same isotype diluted in PBS to a volume of 100 ul. Immunohistochemistry was performed on freshly cut 4 um thick formalin-fixed paraffin embedded (FFPE) tissue sections mounted on glass slides. Slides were de-paraffinized in xylenes and rehydrated through graded alcohols to distilled water. Slides were pretreated with Target Retrieval solution (Dako) for 20 minutes at 99° C. and cooled down for 20 minutes. Slides were then treated with KPL blocking solution (Kierkegaard and Perry Laboratories, MD, USA) and avidin/biotin block (Vector Laboratories) respectively. Non-specific IgG binding was blocked for 30 minutes at room temperature with blocking serum made of 10% normal goat serum in 3% BSA. Primary antibody, anti-pAKT clone D9E (Rabbit monoclonal, #4060L, Cell Signaling Technologies) was incubated on slides at 0.375 ug/ml in blocking serum for 60 minutes at room temperature. Slides were rinsed, incubated with goat anti-rabbit biotinylated secondary antibody (Vector Laboratories, CA, USA) at 7.5 µg/ml for 30 minutes at room temperature, followed by incubation in Vectastain ABC Elite reagent (Vector Laboratories). Slides were then incubated in Pierce metal enhanced DAB (Thermo Scientific). Subsequently, the slides were counterstained, dehydrated and covered with coverslips.

In Vitro Wound Healing Assay

Parental 3T3 or 3T3-mRON cells were suspended in DMEM with 0.5% BCS and seeded in collagen-coated 96 well plates. The next day, scratch wounds were made in each well using the WoundMaker 96 (Essen Bioscience). After two washes in PBS, medium alone or medium containing 15 nM MSP 689R, MSP 689C, scMSP, anti-ragweed IgG2a (0.6 nM, 0.12 nM, or 3 nM), MSP (3 nM), RON agonist antibody 2E5.8.1-IgG2a (0.6 nM or 0.12 nM), RON agonist antibody YW651.1-IgG2a (0.6 nM or 0.12 nM), or nothing as control was added to the wells. Cells were incubated 32 h in the IncuCyte Imaging System (Essen Bioscience) with imaging every few hours. Using the IncuCyte software package (Essen Bioscience), cell density within the wound was calculated relative to density outside the wound. Images were uniformly processed post-analysis with a Gaussian filter, contrast enhancement, and shadowing using ImageJ (National Institute of Health) See also Abramoff et al., 2004, Biophotonics International 11:36-42.

In Vivo Wound Healing Assay and Glucose Measurement in Diabetic Mice

At day 0, female db/db mice were anaesthetized with isofluorane and the dorsal portion of the back (from the scapular to lumbar area) was shaved, stubble removed with Nair, and rinsed with sterile water, alcohol, betadine, and repeat alcohol. Animals were placed in ventral recumbency and a 6 mm punch device was used to make two 6 mm diameter full thickness skin wounds, 1 cm left and 1 cm right of midline. A 0.5 mm thick silicone frame, 10-12 mm inside diameter, was placed around each wound with frame held in place by superglue. A 2 cm square of Tegaderm or Op-site was placed over the wound and frame. Six animals per group were inoculated intraperitoneally with 100 ug of anti-ragweed IgG2a or RON agonist antibody YW651.1 every four days starting at day −4. Every four days, the horizontal and vertical size of each wound was measured using digital calipers and the mean was determined. Wounds were photographed with a Nikon D200 digital camera. Every four days, 2 ul of blood was drawn via a tail nick and blood glucose was measured with the One Touch Glucometer.

Example 1 RON is Primarily Expressed by Epithelial Cells in Intestine and Skin

The MSP 689C polymorphism has been hypothesized to increase IBD risk by interfering with RON-mediated inhibition of macrophage activity (see e.g., Goyette et al., 2008, Mucosal Immunol 1:131-8, Gorlatova et al., 2011, PLoS One 6:e27269). However, while RON expression and inhibitory activity on macrophages has been demonstrated (see e.g., Chen et al., 1998, J Immunol 161:4950-9), these reports have primarily relied on studies using murine peritoneal macrophage populations that may have limited relevance to IBD. Thus, in order to identify cell types likely to be affected by alterations in MSP activity stemming from the 689C polymorphism, RON expression in a variety of murine and human cell types under both steady-state and inflammatory conditions were characterized.

RON expression patterns in mice were first examined using flow cytometry. Consistent with prior reports (e.g., Iwama et al., Blood 1995, 86:3394-403), resident and thioglycollate-elicited peritoneal macrophages expressed high levels of the RON receptor. Lower levels of RON were also found on other murine macrophage populations, including liver Kupffer cells and in vitro cultured bone marrow-derived macrophages (BMMs) (FIG. 1 panel A). RON expression on cells isolated from disassociated colon tissue was also examined. Only weak staining for RON on the lamina propria macrophage population was observed, but relatively high staining was observed on colon epithelial cells (FIG. 1 panel A). To further define RON expression patterns in intestinal and skin tissue, immunohistochemistry (IHC) staining on tissue sections from murine colon and immunofluorescence (IF) staining on tissue sections from murine colon and skin were performed. Robust RON staining on the intestinal epithelium was detected to localize to the basolateral surface of individual epithelial cells (FIG. 1 panels B and C). Robust RON staining on the skin also localized to epithelial cells (FIG. 1 panel E). Consistent with flow cytometry analysis, RON staining in the lamina propria was weak and could not be distinguished over background. Notably, the relative expression of RON on colon epithelium and lamina propria cells did not change under conditions of inflammation. Colons harvested from mice provided 3% dextran sulfate sodium (DSS) in their drinking water for 6 days to induce colitis showed predominate epithelial RON expression and co-staining with macrophage markers failed to reveal detectable expression by this cell type (FIG. 1 panel D).

Figure 2:
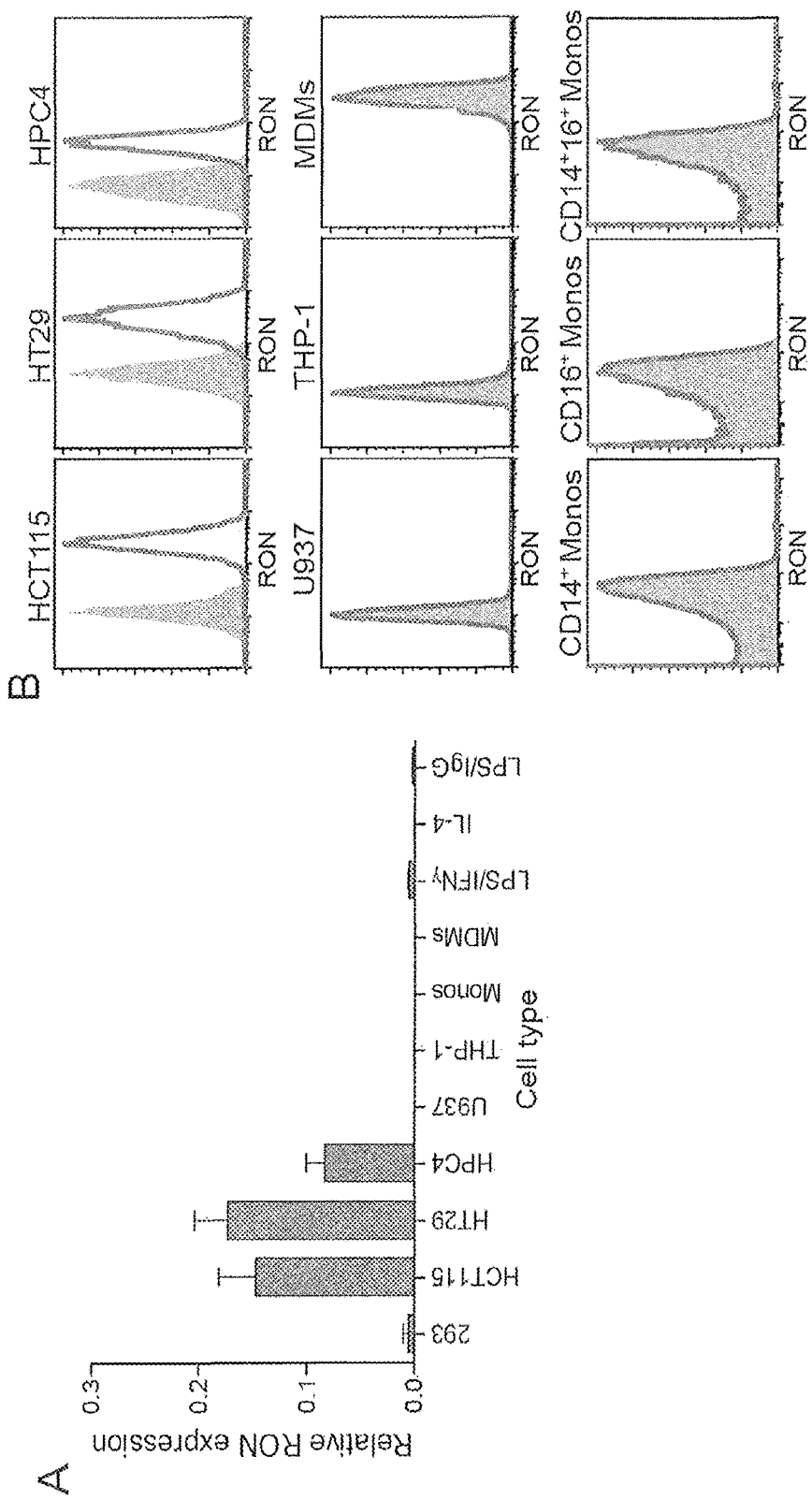
FIG. 2A-G. A-D present results described in Example 1 showing that RON is preferentially expressed by epithelial cells in humans. A shows results of quantitative RT-PCR survey of RON expression in human cell lines and primary cells. Columns 1: HEK293 control, columns 2-4: epithelial cell lines (HCT115, HT29, HPC4), columns 5-6: monocytic cell lines (U937, THP-1), column 7: human $CD14^+$monocytes (monos), and columns 8-11: monocyte-derived macrophages (MDMs) left untreated or treated with the indicated stimuli. Data in columns 1-7 are the mean+/−SD of three independent samples and data in columns 8-11 are the mean of two donors. B shows histograms of flow cytometry analysis of single-cell suspensions for RON expression. Cells were stained with a monoclonal antibody specific for human RON (clone 1A2.2, Chaudhuri et al., 2011, J Biol Chem. 286(37):32762-74) or an isotype control antibody (shaded histogram). MDMs were gated as $CD14^+CD33^+$. C shows microphotographs of tissue sections from normal, UC, and CD colon immunohistochemically stained for RON expression. Scale bars=100 µm. D summarizes the data of quantitative RT-PCR analysis of RON expression in human intestinal biopsy samples taken from normal individuals as well as un-inflamed and inflamed regions of UC and CD patients. E shows histograms of flow cytometry analysis of RON expression in single cell suspensions of resected intestinal tissues from an ulcerative colitis patient using a monoclonal antibody specific for human RON (clone 1A2.2) or an isotype control antibody (shaded histogram). Macrophages were gated as $CD45^+CD14^+HLADR^+$ and epithelial cells were gated as $CD45^-EpCAM^+$ cells. Macrophage data are representative of six donors and epithelial cell data are representative of three donors. F shows quantitative results of RON expression in macrophages and epithelial cells from resected intestinal tissue of multiple donors. Patient numbers are indicated. Data represents the mean fluorescence intensity ratio of RON staining to isotype control staining. Dashed line indicates a ratio of 1:1, i.e. lack of RON expression. N, non-IBD. G depicts histograms showing RON expression levels in untreated cells or cells treated with the digestion conditions identical to E.
Figure 2:
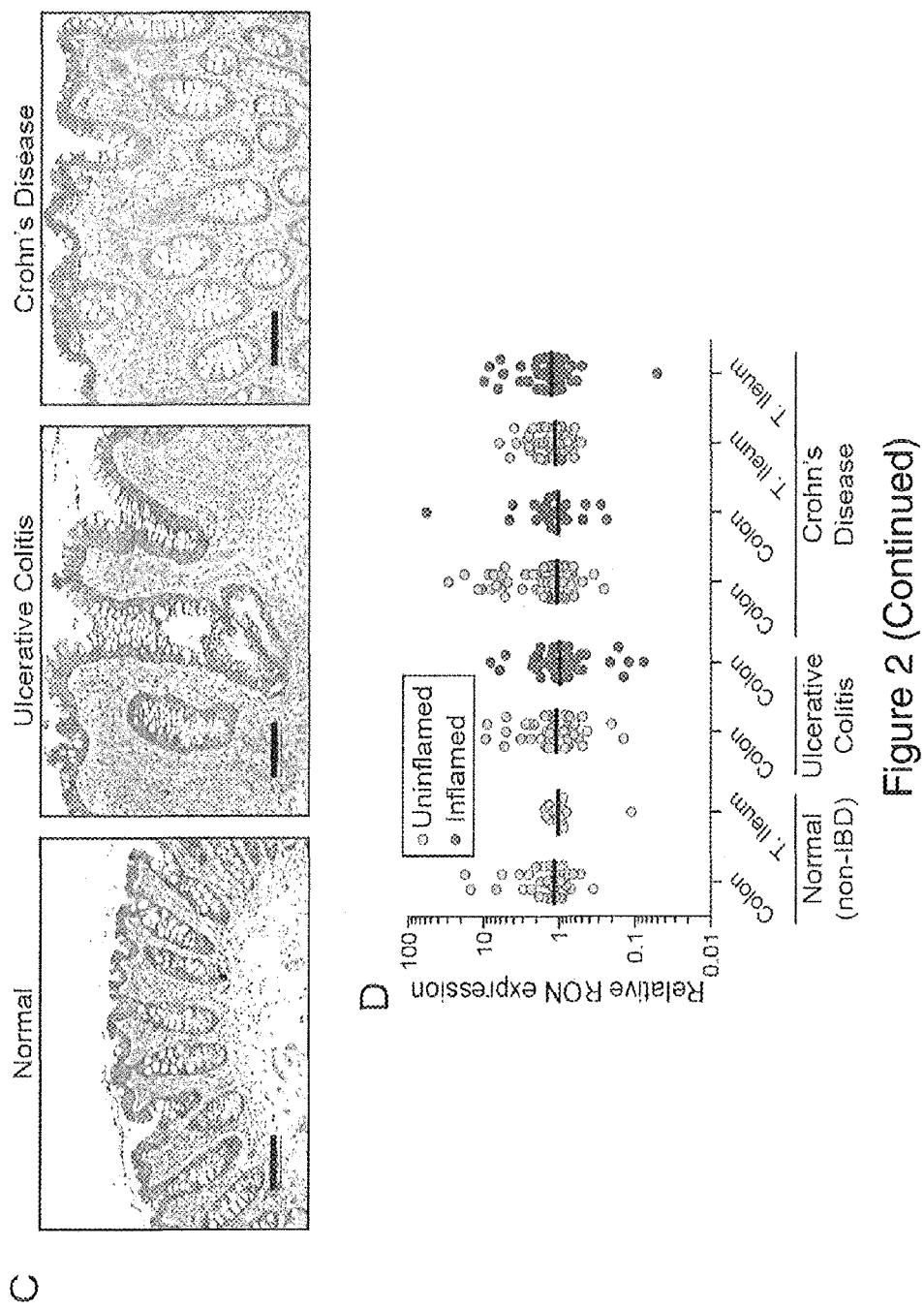
Figure 2:
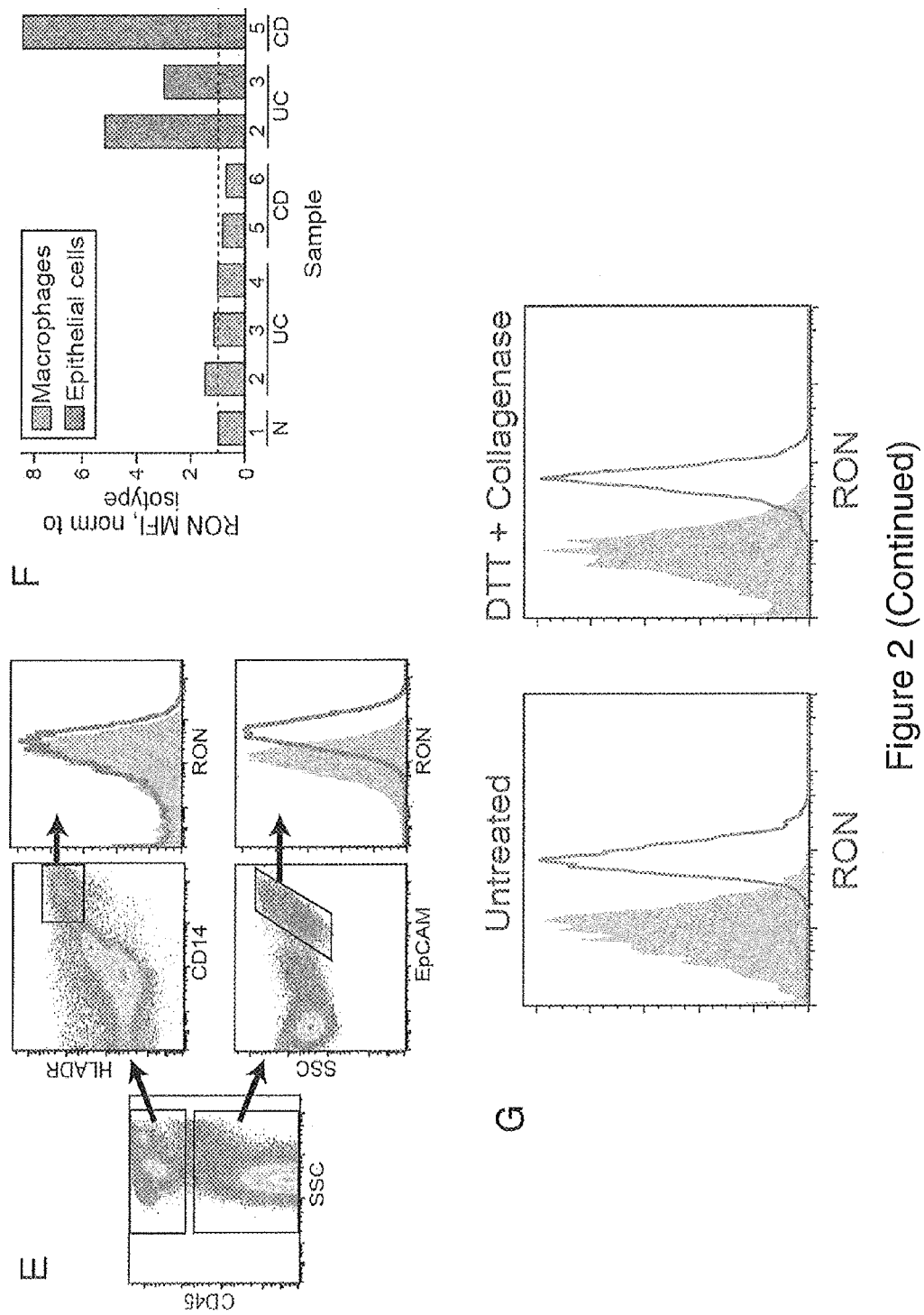

Given the robust expression of murine RON by intestinal epithelial cells, but not intestinal macrophages, the role of RON in regulating macrophage activity within the context of intestinal inflammation was revisited. To extend these findings to humans and IBD, RON expression across different human cell types and tissues were characterized. Substantially higher levels of RON transcript were detected in multiple human epithelial cell lines, compared to human myeloid cell populations that included primary CD14+ monocytes, monocyte-derived macrophages (MDMs), and monocytic cell lines (FIG. 2 panel A). Treatment of MDM cultures with various stimuli, such as interferon-γ, LPS, or IL4 failed to induce substantial upregulation of RON (FIG. 2 panel A). These data are consistent with flow cytometric analysis demonstrating RON protein expression on the surface of epithelial cells but not monocyte/macrophage populations (FIG. 2 panel B).

While the above data suggest that RON is not expressed under steady-state conditions in human monocyte/macrophage populations, these expression patterns could change in the setting of IBD. IHC analysis of RON expression in normal, UC, and CD tissues demonstrated predominant localization to epithelial cells, similar to what was observed in mice (FIG. 2 panel C, representative images from tissue sections from 11 UC patients, 9 CD patients and 8 normal individuals). However, some lamina propria staining was also observed on these sections, which could represent background staining or RON expression on additional cell types. Notably, RON expression did not substantially vary between normal and disease tissue, either by IHC or by quantitative analysis of RON transcripts in intestinal biopsies obtained from normal, UC, and CD patients (FIG. 2 panels C and D). These later data are consistent with RON being expressed by epithelial cells but not a recruited population of inflammatory cells associated with inflamed biopsy samples.

To further define RON expression patterns in IBD tissue, single cell suspensions of human resected intestinal samples from IBD patients (FIG. 2 panel E) and control were examined by flow cytometry. RON expression on macrophages and epithelial cells from resected intestinal tissue of multiple donors was quantified and the results are shown FIG. 2 panel F.

In accord with earlier observations, RON was robustly expressed on epithelial cells but expressed poorly if at all on macrophage populations (FIG. 2 panels E and F). The possibility that the tissue processing and enzymatic digestion procedures would have affected RON staining was ruled out by flow cytometry analysis as shown in FIG. 2 panel G, which shows that the enzymatic digestion protocols used to generate single cell suspensions from intestinal resections did not affect the levels of RON expression. These data indicate that in humans, RON is highly expressed by epithelial, but not myeloid, cell populations. In contrast to the murine immune system, high level of RON receptor expression was not detected in human macrophage populations, either under steady-state or disease conditions. In both mouse and human, RON is constitutively and highly expressed by the intestinal epithelium, localized to the basolateral surface of the cell. The results suggest that the 689C MSP polymorphism likely confers increased risk for developing IBD through epithelial-intrinsic effects.

Example 2 MSP 689R and 689C Variants Bind RON with Similar Affinities

Having determined that epithelial cells are the likely target of MSP activity in human intestine, the consequences of the 689C polymorphism for RON activation were examined. Several forms of recombinant MSP were expressed and purified from mammalian cells (FIG. 3 panels A-B), including full-length versions of the 689R and 689C MSP variants that, consistent with previously published studies, required a cysteine to alanine substitution at amino acid 672 (C672A) in order to obtain properly folded protein. See Gorlatova et al. 2011, PLoS One, 6:e27269 and Wahl et al. 1997, J Biol Chem 272:15053-6. Constitutively inactive, single-chain MSP (scMSP) proteins bearing an arginine to glutamic acid mutation at amino acid 483 (R483E) that prevents proteolytic cleavage to the active two-chain form, were also expressed and purified as controls. Finally, recombinant 689R and 689C versions of the MSP β-chain (MSP (3), the domain responsible for high affinity interactions with RON were generated. See Danilkovitch et al., 1999, J Biol Chem 274:29937-43 and Wang et al., 1997, J Biol Chem 272:16999-7004. Importantly, MSP β proteins were successfully expressed and purified without the mutation at position 672 and thus represent the wild-type sequence of this domain.

Figure 3:
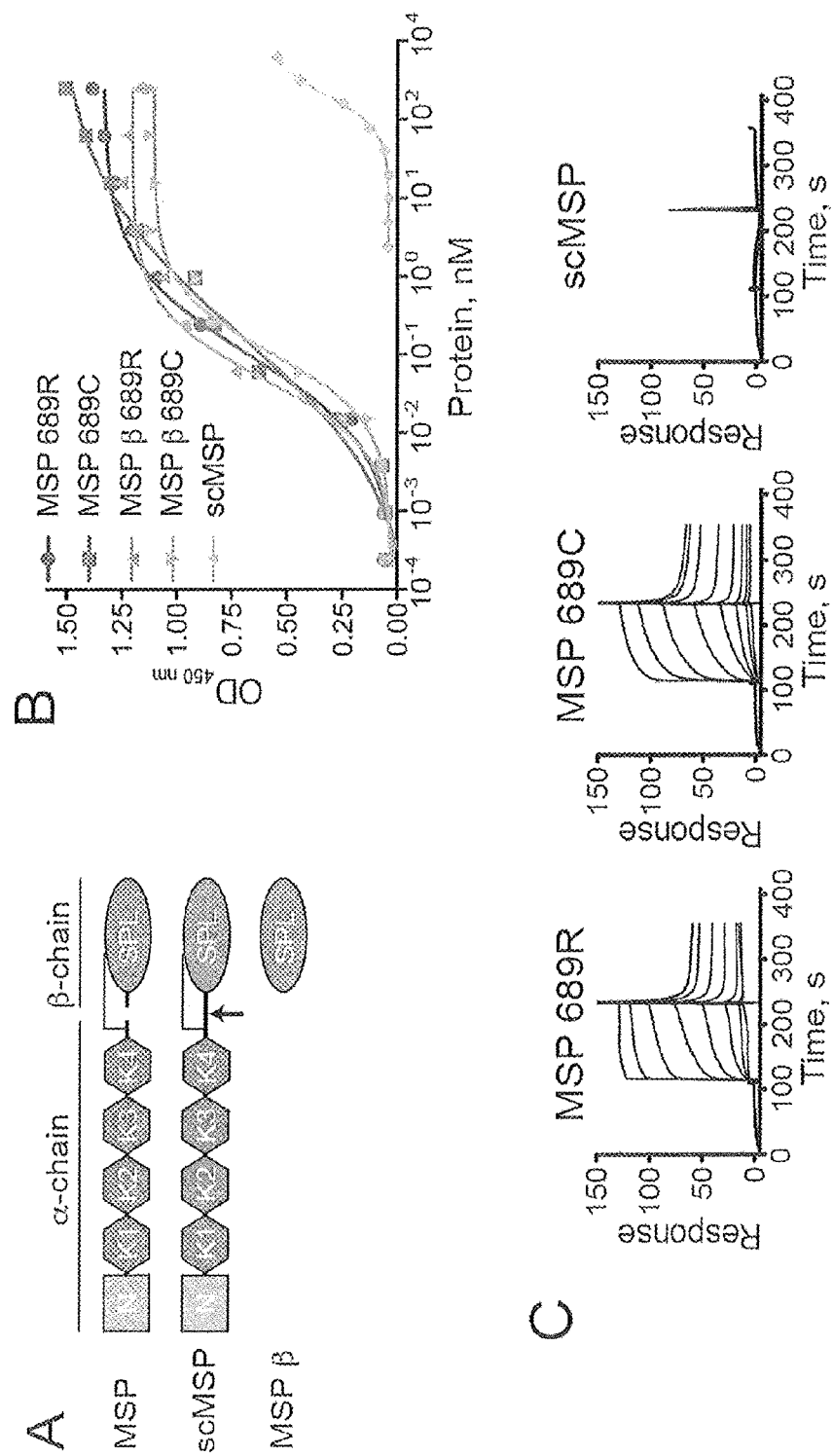
FIG. 3A-E. A-E show results of Example 2 binding studies of recombinant human MSP proteins. A is diagram of recombinant human MSP proteins used in this study. Wild type MSP protein containing the α and β chains connected by a disulfide bond and the PAN domain (N), kringle domains (K), serine protease-like domain (SPL) are indicated (SEQ ID NO:12). Single chain MSP (scMSP) (SEQ ID NO:6) is constitutively inactive due to the R483E mutation at the proteolytic cleavage site (arrow). 689R and 689C versions of the full length MSP protein and MSP β protein were generated (SEQ ID NO:4 and SEQ ID NO:10, respectively). B shows the results of cell-free binding assays using plate bound RON-Fc (SEQ ID NO:44) and soluble MSP. Means of three replicates per group are shown. Lines represent dose-response curves fit to a 4 parameter equation, which yielded $EC_{50}$ values of 0.1, 0.2, 0.05 and 0.1 nM for MSP 689R, 689C, MSP β 689R (SEQ ID NOs:2, 4 and 8) and MSP β 689C (SEQ ID NO:10), respectively. C presents results of SPR analysis of MSP proteins binding to immobilized RON Sema/PSI, showing relative response in response units. Data are representative of three independent experiments. D shows results of radioligand binding assay of MSP binding to RON. Competition binding to 3T3-hRON cells (large graphs) used to generate affinities and Scatchard plots (inset graphs) are shown. Mean+/−standard deviation (SD) of three independent experiments is shown. E is a homology model of the structure of RON Sema/PSI (PDB code 4FWW) shown at the bottom, which binds to MSP β (PDB code 2ASU) shown on top. RON and MSP β were globally aligned to the Met/HGF β complex (PDB code 1SHY). Predicted locations of the MSP β contact residues within 4 Å of RON are marked by asterisks. MSP residue 689 was mutated to a cysteine and is marked by an arrow. Residue A223 of RON sits on top of the pseudo S1 pocket of MSP β.
Figure 3:
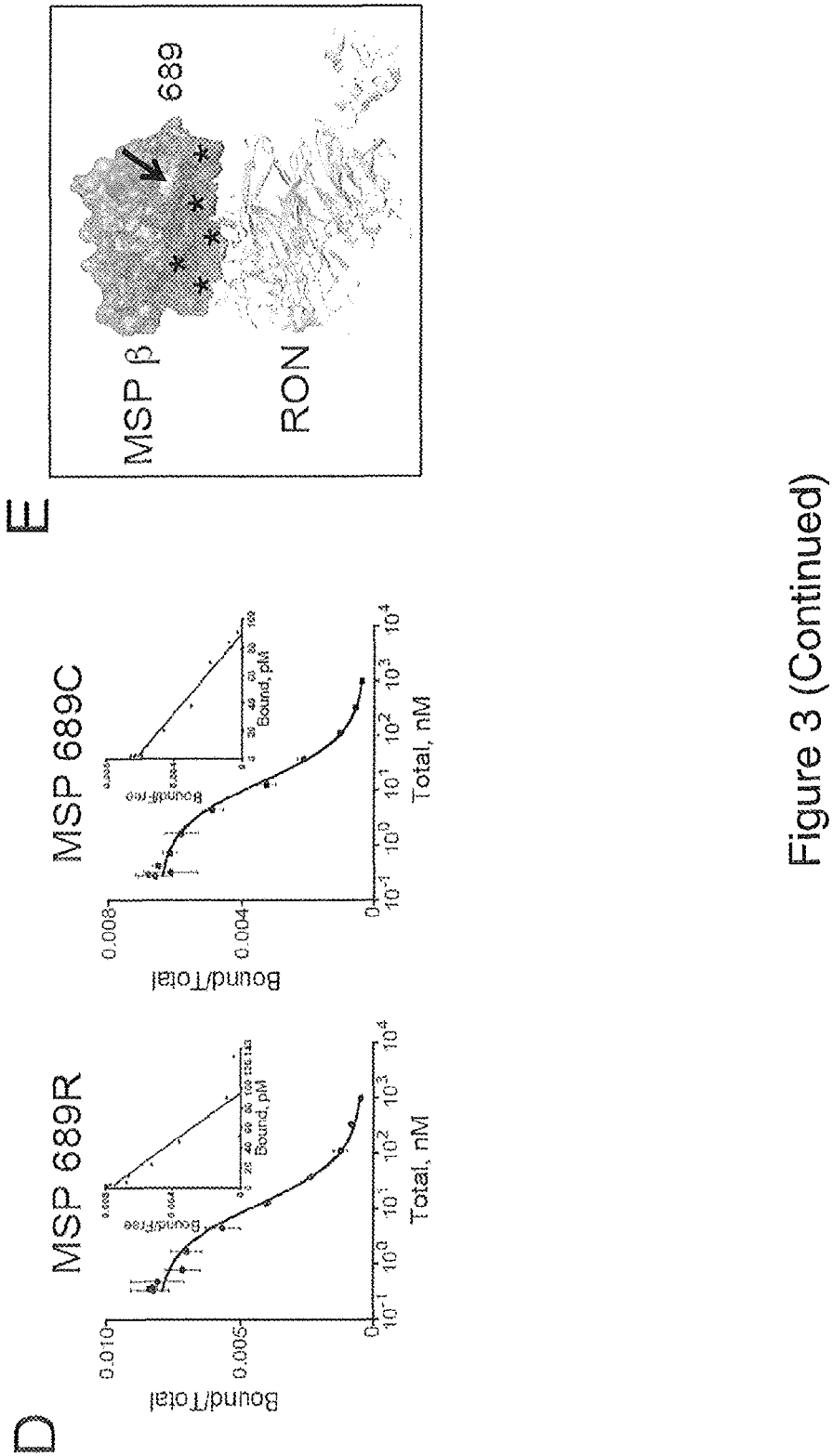

In cell-free assays of MSP binding to immobilized RON, 689R and 689C protein variants showed overlapping dose-response curves. As expected, the scMSP mutant showed minimal binding to RON-coated plates (FIG. 3 panel B). To more precisely quantify MSP interactions with RON, surface plasmon resonance (SPR) was used to determine the affinity of soluble MSP 689R and 689C to immobilized RON. No significant differences in RON binding kinetics were observed between the 689R and 689C versions of either full-length MSP or MSP 13 and no binding was observed for scMSP, using either direct or indirect RON immobilization (FIG. 3 panel C and Table 3). Similar results were obtained using biolayer interferometry (BLI), a related technique used for real-time quantification of molecular interactions (Table 3). No effect of mutating position 672 in MSP β on the ability of either the 689R or 689C variants to bind to RON (Table 3) was observed, suggesting that full-length MSP is not influenced by the C672A mutation necessary for its expression.

TABLE 3

Binding kinetics and affinities of MSP 689R and 689C proteins to RON

| Protein | $k_{on}$ $(M^{-1}s^{-1}) \times 10^{-5}$ | $k_{off}$ $(s^{-1}) \times 10^{2}$ | $K_D$ (nM) | $K_D$ (nM)$^{d,e}$ |
|---|---|---|---|---|
| MSP 689R | $^a$5.11 | $^a$0.33 | $^a$6.4 ± 0.1 | $^d$12.6 ± 1.7 |
|  | $^b$2.03 | $^b$0.13 | $^b$7.1 ± 1.1 | $^e$23.0 ± 2.0 |
|  | $^c$3.46 | $^c$0.07 | $^c$9.9 ± 0.2 |  |
| MSP 689C | $^a$0.17 | $^a$0.002 | $^a$9.6 ± 0.6 | $^d$13.0 ± 2.8 |
|  | $^b$1.16 | $^b$0.12 | $^b$9.6 ± 0.5 | $^e$25.7 ± 6.0 |
|  | $^c$4.28 | $^c$0.07 | $^c$9.4 ± 0.7 |  |
| MSP β 689R | $^a$35.3 | $^a$2.75 | $^a$9.6 ± 0.8 |  |
|  | $^b$24.5 | $^b$1.59 | $^b$6.6 ± 0.1 |  |
|  | $^c$3.88 | $^c$0.25 | $^c$7.5 ± 0.2 |  |
| MSP β 689C | $^a$57.5 | $^a$4.79 | $^a$9.0 ± 1.1 |  |
|  | $^b$13.0 | $^b$1.42 | $^b$9.1 ± 0.2 |  |
|  | $^c$17.5 | $^c$0.93 | $^c$9.1 ± 1.7 |  |
| MSP β 672C 689R | $^a$9.56 | $^a$0.66 | $^a$6.3 ± 0.8 |  |
| MSP β 672C 689C | $^a$8.70 | $^a$0.79 | $^a$9.7 ± 0.7 |  |

$^a$SPR capturing RON-Fc at 25° C.,
$^b$SPR using immobilized RON Sema/PSI at 25° C.,
$^c$BLI using RON-Fc at 30° C.,
$^d$Radioligand binding to 3T3-hRON cells for 2 h at room temperature,
$^e$Radioligand binding to 3T3-hRON cells for 4 h on ice.

To confirm the above results, a radioligand binding assay using labeled MSP 689R and 689C proteins and a cell line expressing human RON was performed. In agreement with the cell-free assays, competition binding and Scatchard analysis revealed no significant difference in the RON binding affinities between the MSP variants (FIG. 3 panel D and Table 3). Taken together, these data indicate that the 689C polymorphism does not affect the binding between MSP and RON. This conclusion is in accord with a homology model of RON bound to MSP β. Briefly, a homology model of MSP β bound to human RON Sema/PSI was made using the coordinates from the protein data bank for MSP β (2ASU), for RON Sema/PSI (4FWW), and the Met Sema/PSI in complex with HGF β (1SHY). See Carafoli et al., 2005, FEBS J 272:5799-807; Chao et al., 2012, PLoS One 7:e41912; and Stamos et al., 2004, EMBO J 23:2325-35. RON and MSP β were globally aligned to the Met/hepatocyte growth factor (HGF β) complex using Pymol (the PyMOL Molecular Graphics System, Version 1.4.1 Schrödinger, LLC), which was used to show all structures. MSP 13 residue 689 was mutated to a cysteine using Pymol. The homology model shows that residue 689 is distal from the putative MSP-RON interface (FIG. 3 panel E).

Example 3 Pro-MSP 689R and 689C Variants Undergo Similar Proteolytic Activation

As proteolytic activation of MSP represents a critical regulatory point controlling in vivo RON activity, whether this process differs between MSP 689R and 689C was next examined. Recombinant MSP exists in both inactive pro-MSP (uncleaved) and active MSP (cleaved) forms following purification from transfected cell supernatants, presumably due to endogenous protease activity present during expression. The ability of hepsin, a protease that cleaves and activates pro-MSP, to cleave the 689R or 689C single-chain proteins to completion was examined. See Ganesan et al., 2011, Mol Cancer Res 9:1175-86.

pro-MSP was incubated overnight with sHepsin at a 1:100 ratio in activation buffer (50 mM Tris-HCl, pH 8.0, 150 mM NaCl, 0.05% Chaps) at room temperature to produce active MSP. sHepsin was removed by adding a 10-fold molar excess of anti-hepsin (Fab25) followed by Protein A-Sepharose Chromatography (GE Healthcare). This resulted in complete conversion of pro-MSP to the active two-chain form. To determine activation kinetics, pro-MSP (100 µg/mL, 1.25 µM) was incubated 1 h at 37° C. with various concentrations (100 nM-97 pM, 2-fold dilution series) of sHepsin or 1.25 µM pro-MSP was incubated with 12.5 nM sHepsin for 0.5, 1, 2, 4, 6, 8, 16 or 24 h at room temperature in activation buffer. The reaction stopped by adding SDS-PAGE sample buffer followed by electrophoretic analysis on 4%-20% Tris-glycine gels (Life Technologies) under reducing conditions.

Figure 4:
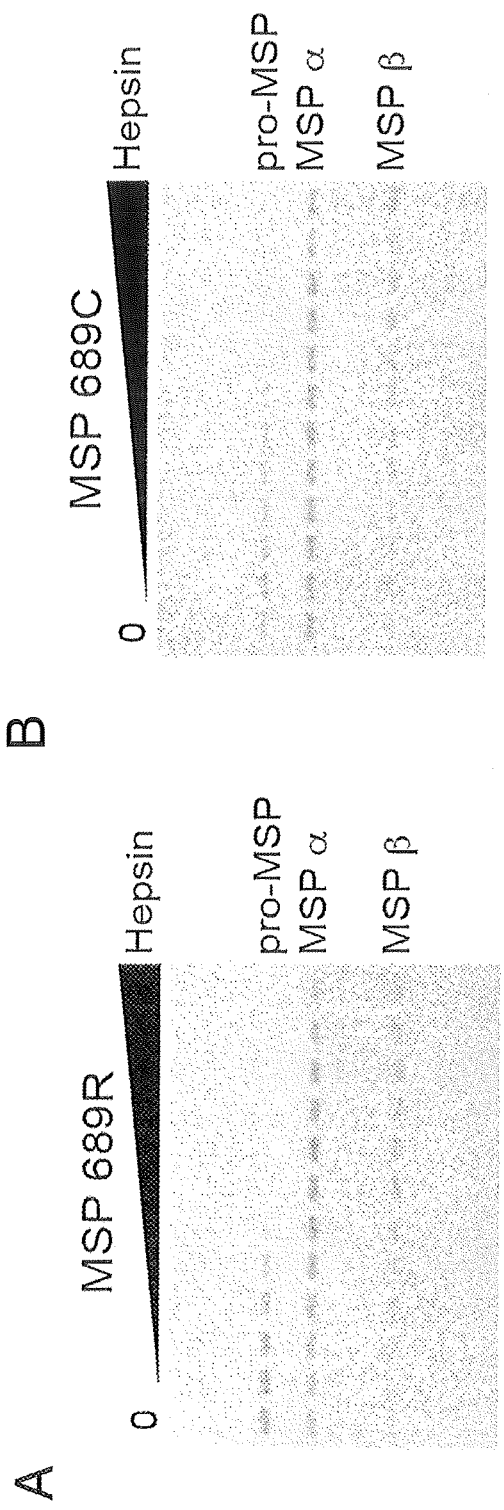
FIG. 4A-B. A-B present images of gel electrophoresis stained by Coomassie Brilliant Blue showing proteolytic processing of pro-MSP. Purified MSP 689R (A) and MSP 689C (B) consisting of both pro-MSP and MSP were mixed with increasing amounts of hepsin and analyzed by gel electrophoresis under reducing conditions. Relative mobilities corresponding to pro-MSP, MSP α, and MSP β are indicated. Data are representative of three independent experiments. The data refer to Example 3.

No obvious difference was observed in the concentration of hepsin required to completely cleave these variants over a 1-hour period (FIG. 4). These data suggest that the 689C polymorphism does not alter RON signaling through differential effects on proteolytic activation of pro-MSP.

Example 4 MSP 689R and 689C Variants Induce Similar Robust RON Signaling

While the studies presented herein revealed no difference in proteolytic activation or RON binding between the MSP variants, the 689C polymorphism could still affect MSP-dependent signal transduction through the RON receptor. To address this point, down-stream biological effects of MSP variants on several RON-expressing cell lines were determined. In vitro stimulation of A2780-hRON (Chaudhuri et al., 2011, J Biol Chem 286:32762-74) and BxPC3 with either full-length activated MSP 689R or 689C protein induced similar levels of phosphorylated Akt (pAkt) by western blot analysis (FIG. 5 panel A).

Figure 5:
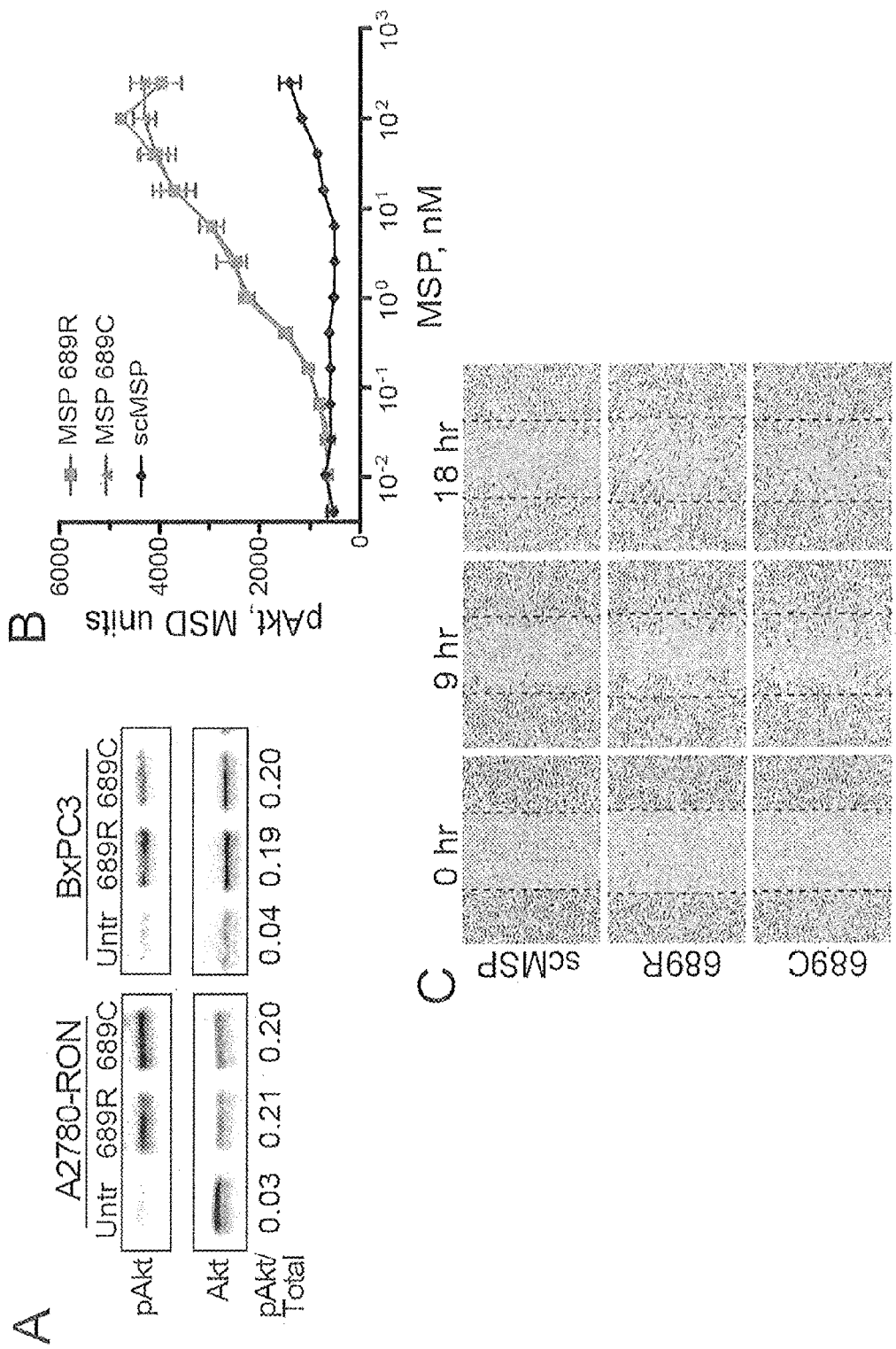
FIG. 5A-E. A presents photographs of western blot analysis of total Akt and pAkt in A2780-hRON and BxPC3 cells treated as indicated. Blot was performed in triplicate and mean of the pAkt/total ratios is shown. B shows results of MSD analysis of 3T3-hRON cells treated with scMSP or MSP variants. Mean+/−SD of three treatments is shown. Data are representative of three independent experiments. C presents images from scratch wound assay of 3T3-hRON cells treated with scMSP or MSP variants. Images are from the same cell culture at the indicated times after scratch wounding. Dashed lines represent position of initial scratch. D shows the quantification of the results of scratch wound assay from 3T3-hRON cells treated with medium-alone, scMSP, or MSP variants. Mean+/−SD of three treatments is shown. Data are representative of three independent experiments. E shows the quantification of the results of scratch wound assay from parental 3T3 cells, which do not express the RON receptor, treated with scMSP or MSP variants. Mean of three treatments is shown and error bars signify standard deviation. Data are representative of three independent experiments. The figures relate to Example 4.
Figure 5:
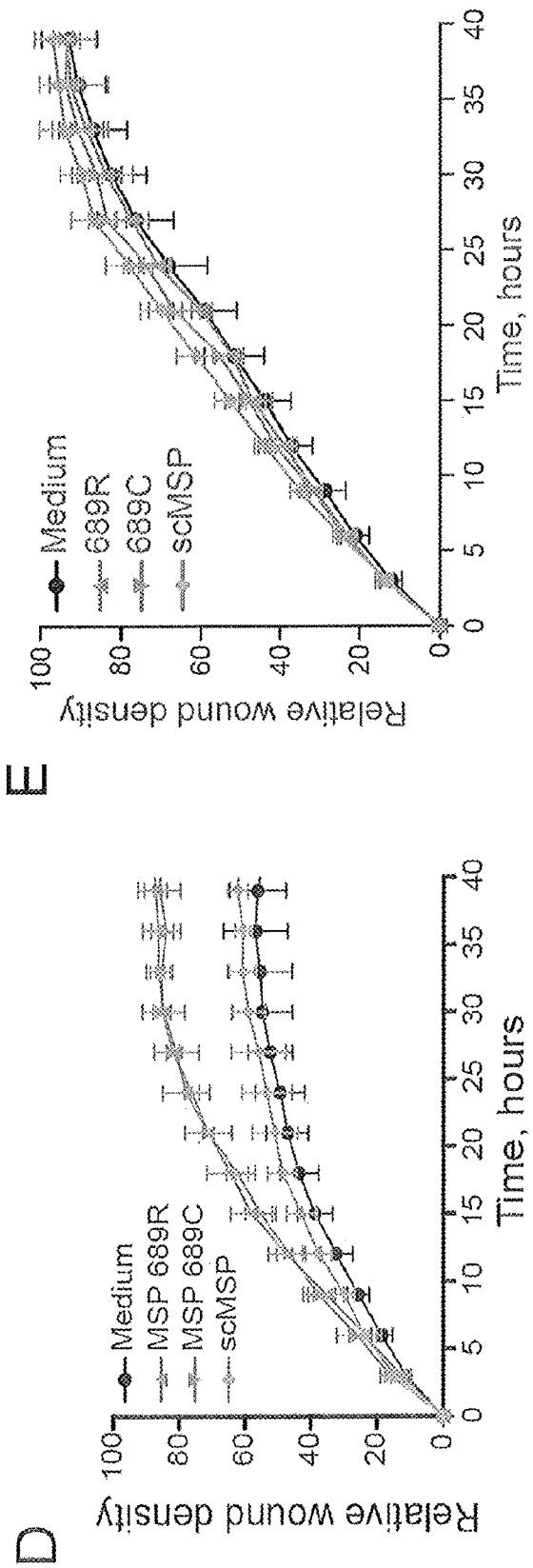

Furthermore, quantitative Meso Scale Discovery (MSD) analysis of pAkt induction in 3T3-hRON cells failed to reveal a difference in the activity of MSP 689R and 689C across a wide range of doses (FIG. 5 panel B). Briefly, 3T3-RON cells were seeded in DMEM with 0.5% bovine calf serum (BCS). The next day, cells were treated with titrations of MSP 689R, MSP 689C, scMSP (250 nM to 4 pM, 1.5-fold dilution series in medium), or medium alone for 30 min and lysed in MSD lysis buffer (Meso Scale Discovery). For detection of Akt phosphorylation, lysates were added to MULTI-SPOT 96-Well 4-Spot Phospho (Ser473)/Total Akt plates (Meso Scale Discovery) which were incubated according to manufacturer's instructions and read in a SECTOR Imager 6000 (Meso Scale Discovery). Consistent with its lack of RON binding, scMSP did not induce a robust pAkt signal as shown by the MSD analysis.

RON signaling has been reported to induce cell proliferation, survival, and migration, which play important roles in wound repair processes. See Nanney et al., 1998, J Invest Dermatol 111:573-81 and Santoro et al., 2003, Dev Cell 2003; 5:257-71. To determine whether the 689C polymorphism affects these down-stream cellular responses to MSP, an in vitro cell monolayer scratch-wounding model was used to evaluate wound closure in the presence or absence of MSP variants. Scratch wounds were made in confluent monolayers of 3T3-mRON cells and cultures were subsequently treated with MSP 689R, MSP 689C, medium alone, or inactive scMSP. Treatment with MSP 689R or 689C resulted in similar wound widths that were smaller than the untreated or scMSP-treated cultures (FIG. 5 panels C and D). These MSP-induced responses were dependent on RON expression, as no effects of treatment were observed in RON-negative 3T3 cells (FIG. 5 panel E). Taken together, these data indicate that the 689C polymorphism does not alter the ability of MSP to bind to, signal through, or elicit functional responses from the RON receptor. In addition, they confirm the ability of MSP-dependent RON signaling to drive cellular responses that are relevant for wound repair.

Figure 6:
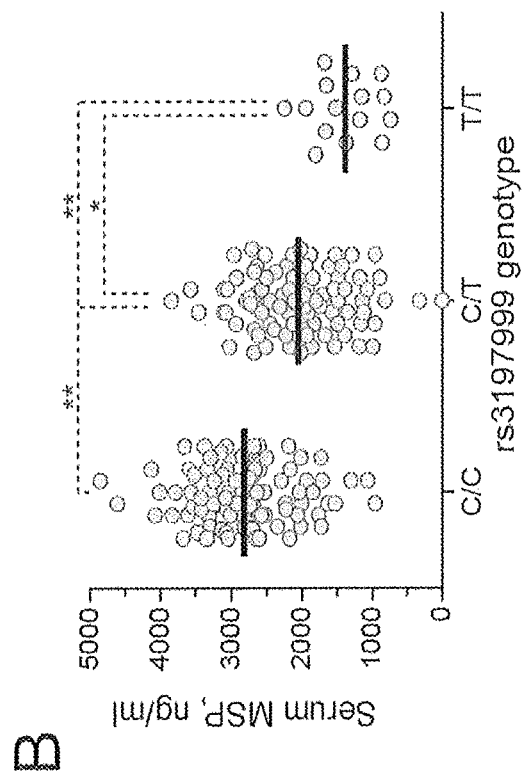
FIG. 6A-D. A summarizes the results of Example 5 analyzing the rs3197999 alleles in DNA samples from normal, UC, and CD patients from the EMBARK cohort. The C allele encodes MSP 689R and T allele encodes MSP 689C. Allele frequency and number are indicated for each group. B shows serum MSP concentrations in matched serum samples of EMBARK subjects determined by ELISA, with results grouped by rs3197999 genotype. *, p=0.0009; **, p<0.001. C shows serum MSP concentrations grouped by genotype and disease status. D shows the sensitivity of the MSP ELISA assay on recombinant human MSP variants and scMSP. Error bars represent standard deviation.
Figure 6:
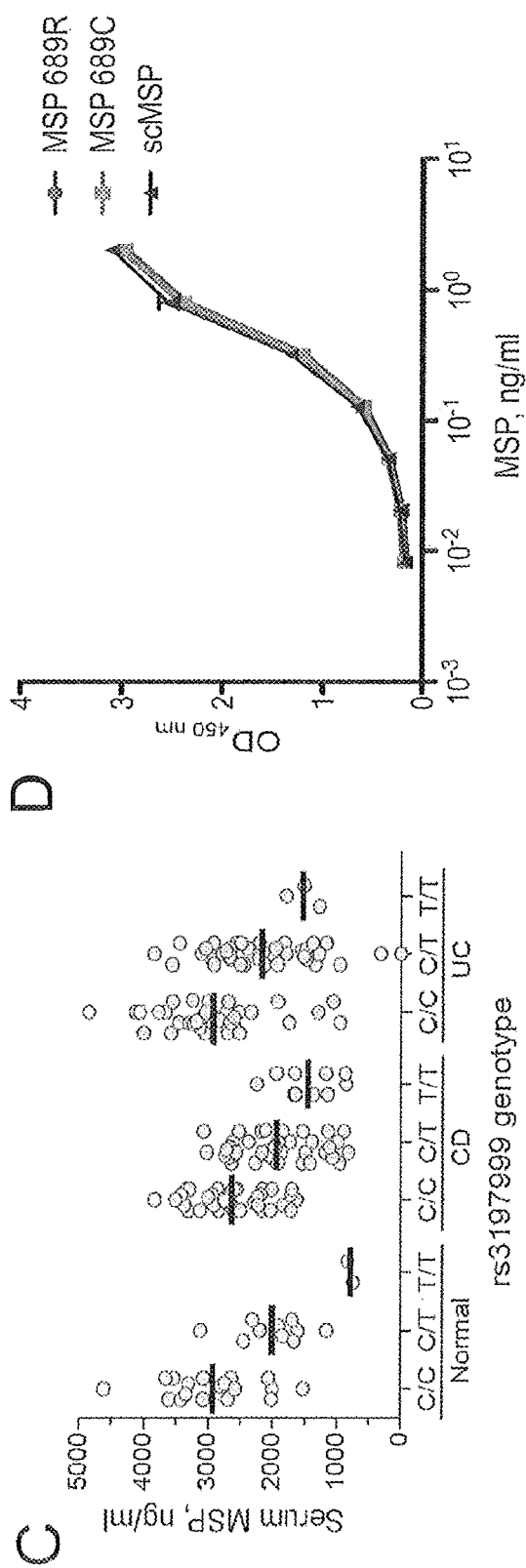
Figure 7:
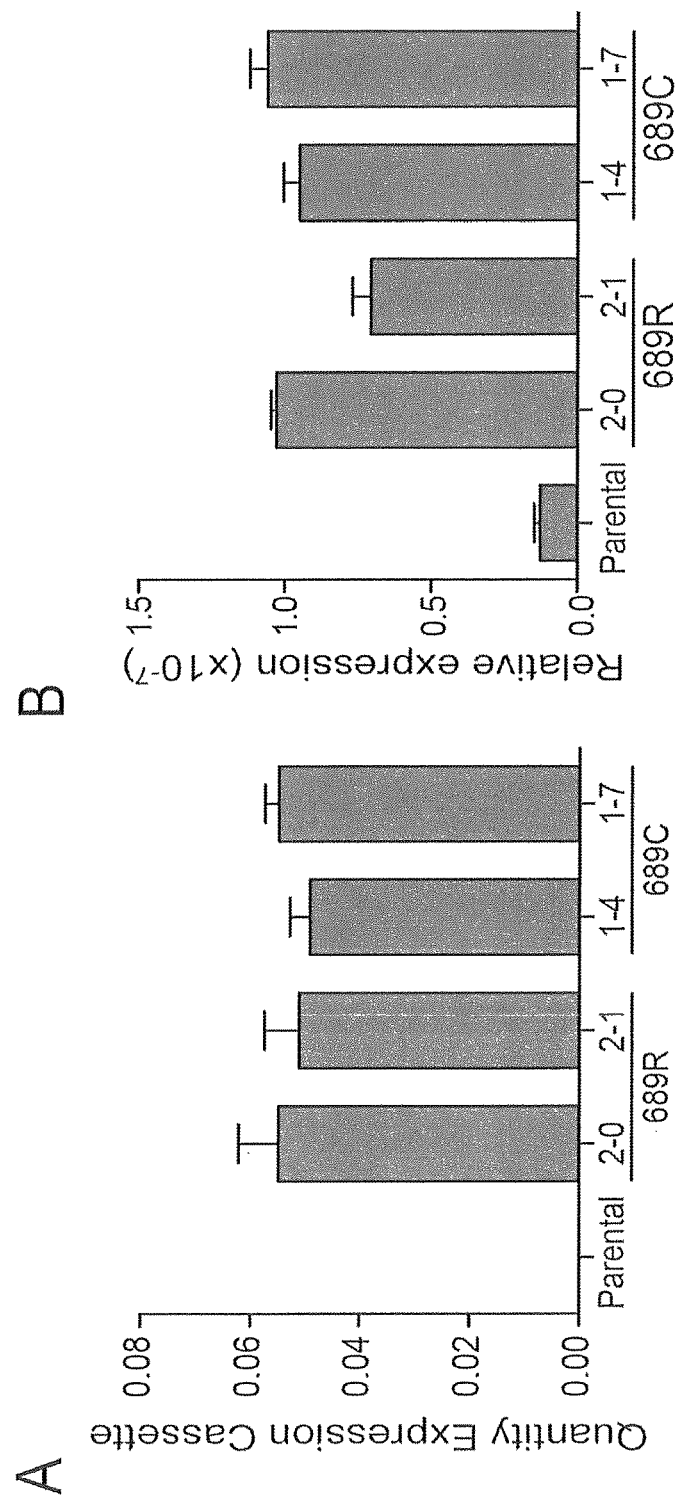
FIG. 7A-B. A relates to Example 5 showing a bar graph of quantitative PCR data on stably transfected cells using primers specific for the MSP expression cassette in pcDNA5/FRT. Values for the MSP cassette were normalized to total DNA using the $\Delta C_T$ method. Values for two 689R- and two 689C-expressing clones are shown. Data are the mean of three independent samples and error bars represent standard deviation. Parental, 293 FlpIn cells. B presents a bar graph showing the results of ELISA assay measuring MSP secretion into cell supernatant by stably transfected cell clones. ELISA values are controlled for differences in cell quantity, as measured by the CellTiter-Glo assay (Promega). Values for two 689R- and two 689C-expressing clones are shown. Data are the mean of three independent samples and error bars represent standard deviation. Parental, 293 FlpIn cells.
Figure 8:
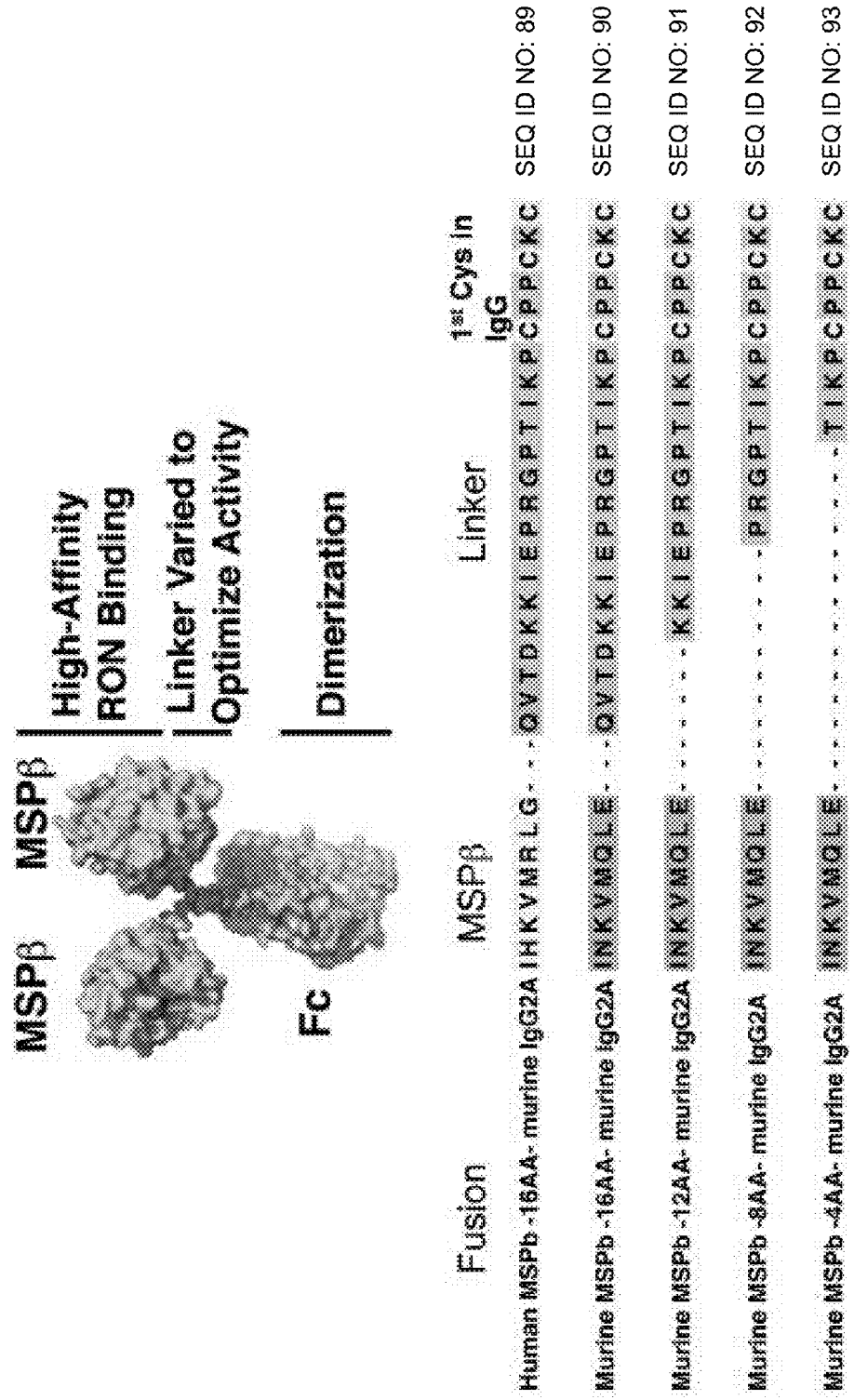
FIG. 8 describes the design of MSP β-IgG Fc fusion proteins. Either human or mouse MSP β was fused to the Fc domain of mouse IgG2a with or without a peptide linker 4, 8, 12 or 16 amino acid residues in length. The cloning of the fusion proteins is described in the Example section.

Example 5 Carriers of the MSP 689C Polymorphism have Reduced Quantities of Serum MSP MSP is predominately expressed by the liver, where it is secreted into the serum and circulates at relatively high concentrations. See Yoshimura et al., 1993, J Biol Chem 268:15461-8. The quantities of circulating MSP were next examined for MSP 689R and MSP 689C. Matched human serum and DNA samples from 204 donors were analyzed for both the rs3197999 genotype and MSP serum concentrations. Consistent with previous genetic studies, the minor allele of MSP was enriched in UC and CD patients compared to individuals without disease (FIG. 6 panel A). See e.g. Anderson et al., 2011, Nat Genet 43:246-52; Anderson et al., 2009, Gastroenterology 136:523-9 e3; Barrett et al., 2008, Nat Genet 40:955-62. However, given the modest contribution of this allele to overall IBD risk and the relatively small size of our study group compared to GWAS cohorts, these results failed to meet statistical significance.

To establish the relationship between rs3197999 genotype and serum MSP concentrations, an ELISA assay to measure MSP in human serum was developed. This assay had equal sensitivity for detecting MSP 689R and MSP 689C proteins and was unaffected by the activation state of the protein (FIG. 6 panel D). Analysis of the serum MSP concentrations in the rs3197999 genotyped cohort revealed that heterozygous carriers of the MSP 689C polymorphism had 27 percent ($p<0.0001$) and homozygous carriers had 50 percent ($p<0.0001$) lower quantities of MSP compared to individuals carrying two copies of MSP 689R variant (FIG. 6 panel B). These decreased concentrations of serum MSP were not a secondary effect of IBD, as normal individuals and patients diagnosed with CD or UC showed similar genotype-dependent reductions in MSP concentrations (FIG. 6 panel C).

To investigate the mechanism by which the 689C polymorphism leads to decreased levels of serum MSP, stably transfected cell lines that bearing a single copy of MSP 689R or 689C cDNA downstream of a constitutive promoter located at the same genomic locus were generated. Quantitative PCR analysis was used to confirm that individual clones harbored the same amount of integrated MSP DNA and MSP protein quantities were measured in cell culture supernatants by ELISA (FIG. 6 panel D). These studies revealed that the 689C polymorphism does not impact the quantity of MSP produced by cells, arguing against an effect of the polymorphism on protein synthesis or secretion.

Taken together, these data indicate that the 689C polymorphism is associated with decreased levels of circulating MSP and suggest that the resulting reduction in RON pathway activity impacts the efficiency of wound repair in intestinal epithelial cells, leading to increased susceptibility to IBD.

Example 6 MSPβ-IgG2a Proteins Bind RON with High Affinity

Figure 9:
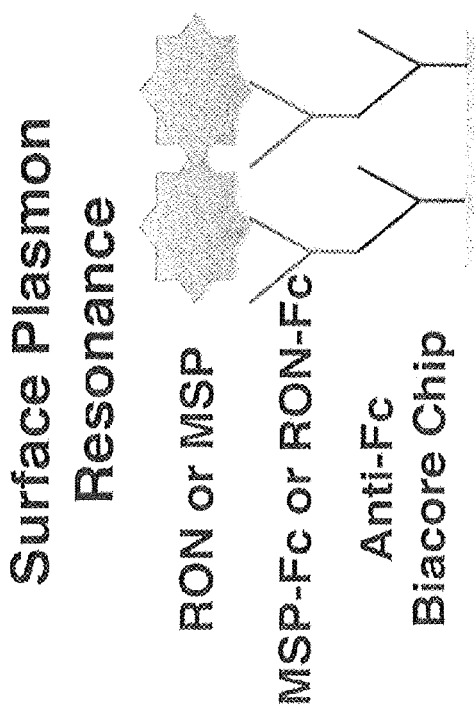
FIG. 9 shows the experimental design and results of the binding assay examining the binding activity of human full-length MSP, human and murine MSPβ, and different MSPβ-Fc fusion proteins for murine RON-Fc. This figure relates to Example 6.

To function as a RON agonist, MSPβ-IgG2a fusion proteins must bind the RON receptor. To assay binding, surface plasmon resonance was used to measure the affinity of full-length human MSP, human and mouse MSP β, and a number of human and mouse MSPβ-IgG2a fusions for immobilized RON receptor. The results showed that most MSPβ-IgG2a fusion proteins bound RON with high affinities in the single-digit nanomolar range, similar to that of MSP, the native RON ligand (FIG. 9). Fusion proteins with mutant IgG2a domains (D265A and N297A) that lack effector function had similar affinity for RON as those with wild type IgG2a (FIG. 9).

Example 7 MSPβ-IgG2a Proteins Function as RON Agonists In Vitro

To induce RON signaling in cells, MSPβ-IgG2a fusion proteins must bind full-length RON expressed on the cell surface. To determine if this occurs, 3T3 cells stably transfected with murine RON (3T3-mRON cells) were incubated with titrations of the fusion proteins or of an anti-ragweed IgG2a antibody as an isotype control. Flow cytometry analysis of 3T3-mRON cells after incubation showed that the MSPβ-IgG2a proteins bind RON on the cell surface at a wide range of concentrations, from 2 ng/ml to 5 ug/ml. Binding of an anti-ragweed control antibody of the same isotype was minimal and observed only at high concentration (FIG. 10. A). Binding is RON-dependent because binding did not occur with RON-negative parental 3T3 cells (FIG. 10. B).

The binding of MSP to RON induces RON signaling, and if MSPβ-IgG2a proteins are to function as RON agonists, their binding to RON should induce signaling as well. To ensure that an MSPβ-IgG2a protein induces signaling in a biologically relevant cell type, human primary colon cells that endogenously expresses RON were stimulated with the m12m agonist.

Human primary colon cell line HPC1 (Celprogen) was seeded in plates in RPMI medium with 0.5% fetal bovine serum and adhered overnight. The next day, medium was removed and cells were treated for 30 minutes at 37° C. with 0.5 ml medium or the m12m MSPβ-IgG2a agonist diluted to a concentration of 0.4 or 0.75 nM in medium. Cells were lysed on ice for 15 minutes in MSD lysis buffer (Meso Scale Discovery). For detection of Akt phosphorylation, supernatants were assayed by western blot analysis. Western blot analysis of cell lysates showed an induction of Akt phosphorylation at serine 473 (FIG. 10 panel C), a modification that is downstream of RON signaling.

Figure 10:
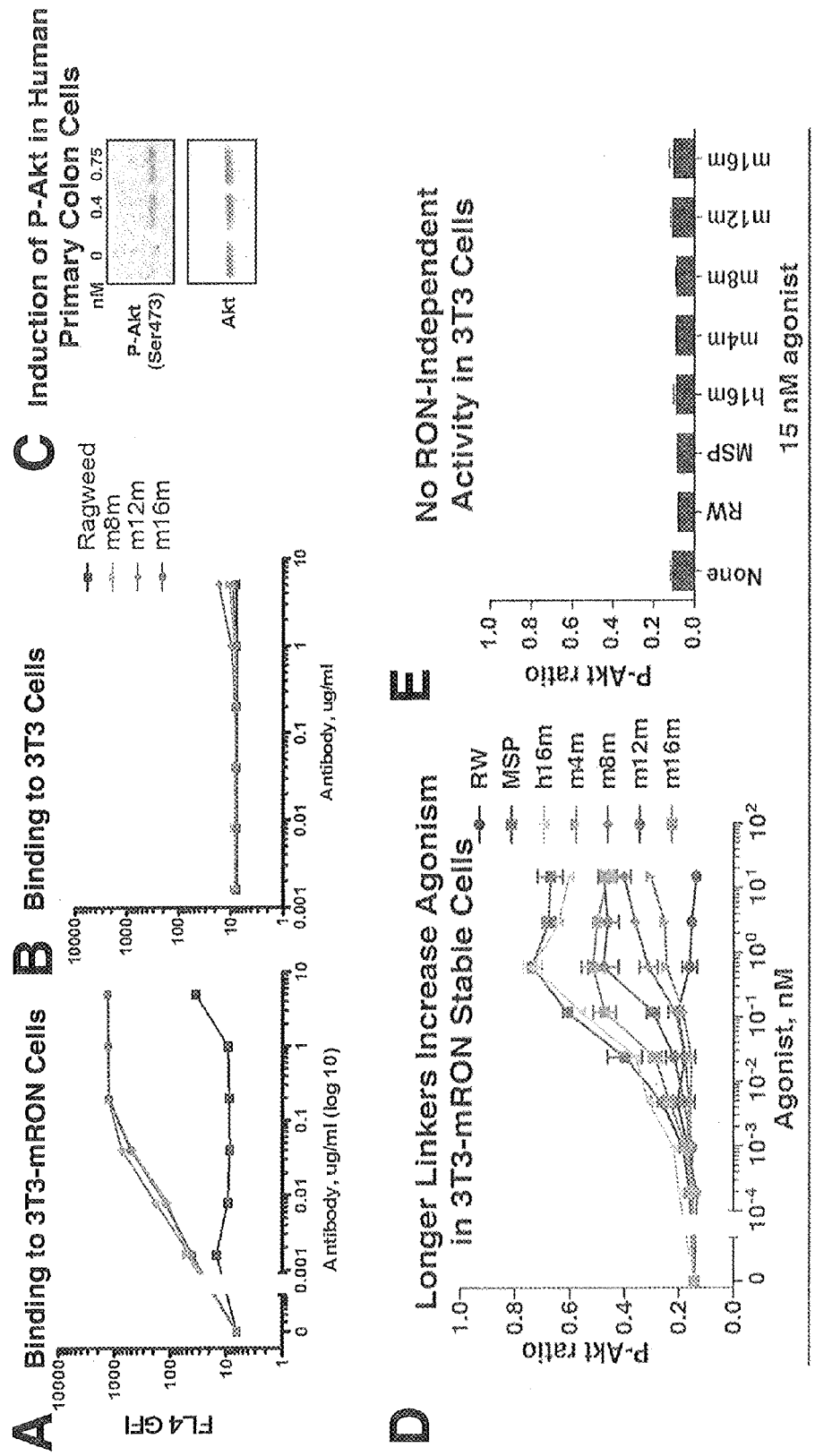
FIG. 10A-E shows results of Example 7 demonstrating MSPβ-Fc fusion proteins binding to mouse RON (mRON) and activation of mRON signaling in vitro. A-B show the binding data of various mMSPβ-IgG2a proteins binding to 3T3 cell expressing mRON on the cell surface (A) or parental 3T3 cells (B). C shows images of western blot analysis detecting phosphorylated-Akt (top panel) or total Akt (bottom panel) in human primary colon cells induced by the m12m (mMSPβ-L12-mIgG2a, SEQ ID NO:30) fusion protein. D shows a graph summarizing the effect of linker length on the activation of mRON in 3T3-mRON stable cells. E shows a bar graph demonstrating that the activation is dependent on mRON expression in the 3T3 cells.

To evaluate the RON agonist activity of MSPβ-IgG2a fusion proteins in more detail, 3T3-mRON cells were stimulated over a range of concentrations with fusion proteins, MSP, or an anti-ragweed control antibody of the same isotype. Quantitative Meso Scale Discovery (MSD) analysis of Akt phosphorylation at serine 473 in these cells showed that, like MSP, fusion proteins induce Akt phosphorylation in a dose-dependent manner. Furthermore, a longer spacer between MSP β and IgG2a is associated with greater potency as a RON agonist (FIG. 10 panel D). The anti-ragweed control antibody had no activity in this assay (FIG. 10 panel D). The observed signaling is RON-dependent, as Akt phosphorylation was not induced in RON-negative parental 3T3 cells (FIG. 10 panel E).

Example 8 MSPβ-IgG2a Proteins Bind the Intestinal Epithelium In Vivo

Figure 11:
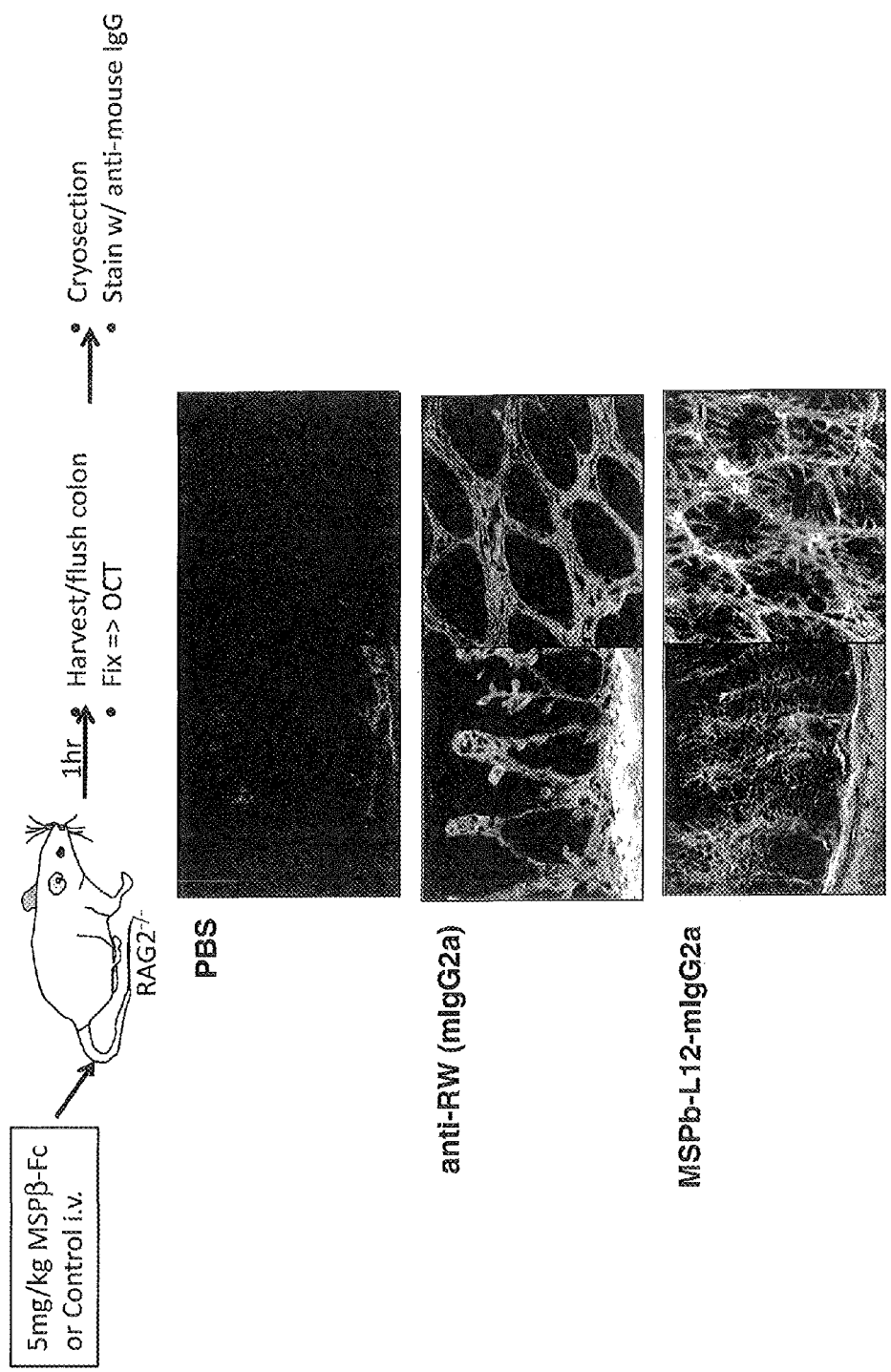
FIG. 11 shows the experimental design and results of Example 8 examining the binding of MSP fusion protein in vivo on mouse colon epithelial cells. Colon epithelial sections of PBS-injected, anti-ragweed isotype control-injected, and MSPβ-L12-mIgG2a-injected mice were stained with goat anti-mouse conjugated to Alexa Fluor 647 (Invitrogen) and the signals were detected using a Leica SPE confocal microscope (Leica Microsystems).

To induce repair pathways in the intestinal epithelium, MSPβ-IgG2a fusion proteins should reach this tissue and bind cells within this tissue. In order to identify cells bound by systemically dosed MSPβ-IgG2a fusion protein, RAG2$^{-/-}$ mice were injected intravenously with PBS, MSPβ-IgG2a fusion, or an anti-ragweed control antibody of the same isotype. Specifically, RAG-2 deficient mice were administered PBS or 5 mg/kg of the m12m MSPβ-IgG2a agonist or anti-ragweed IgG2a as a control. One hour later, animals were sacrificed (FIG. 11). Colons were harvested from all mice, flushed with PBS, and fixed overnight in PLP buffer (0.05 M phosphate buffer containing 0.1 M L-lysine [pH 7.4], 2 mg/ml NaIO$_4$, and 10 mg/ml paraformaldehyde), followed by dehydration in 30% sucrose, and embedding in OCT freezing media (Sakura Finetek). Twelve μm sections were cut on a CM3050S cryostat (Leica Microsystems) and adhered to Superfrost Plus slides (VWR). Sections were blocked in 10% goat serum (Jackson ImmunoResearch Laboratories) and stained with goat anti-mouse conjugated to Alexa Fluor 647 (Invitrogen). Images were acquired using a Leica SPE confocal microscope (Leica Microsystems).

Staining of cryosectioned intestinal tissue with anti-mouse IgG showed specific binding of MSPβ-IgG2a to the colon epithelium (FIG. 11, bottom panel), while the isotype control had a non-specific staining pattern localized to blood vessels and tissue parenchyma (FIG. 11, middle panel). Minimal staining was observed in the colon of mice injected with PBS (FIG. 11, top panel). These data indicate that systemically dosed MSPβ-IgG2a was able to reach the intestinal parenchyma and bound the epithelium. Furthermore, as this is the principal site of RON expression in the intestine, fusion proteins had access to a cell type that should respond to their activity.

Example 9, MSPβ-IgG2a Proteins Function as RON Agonists In Vivo

Figure 12:
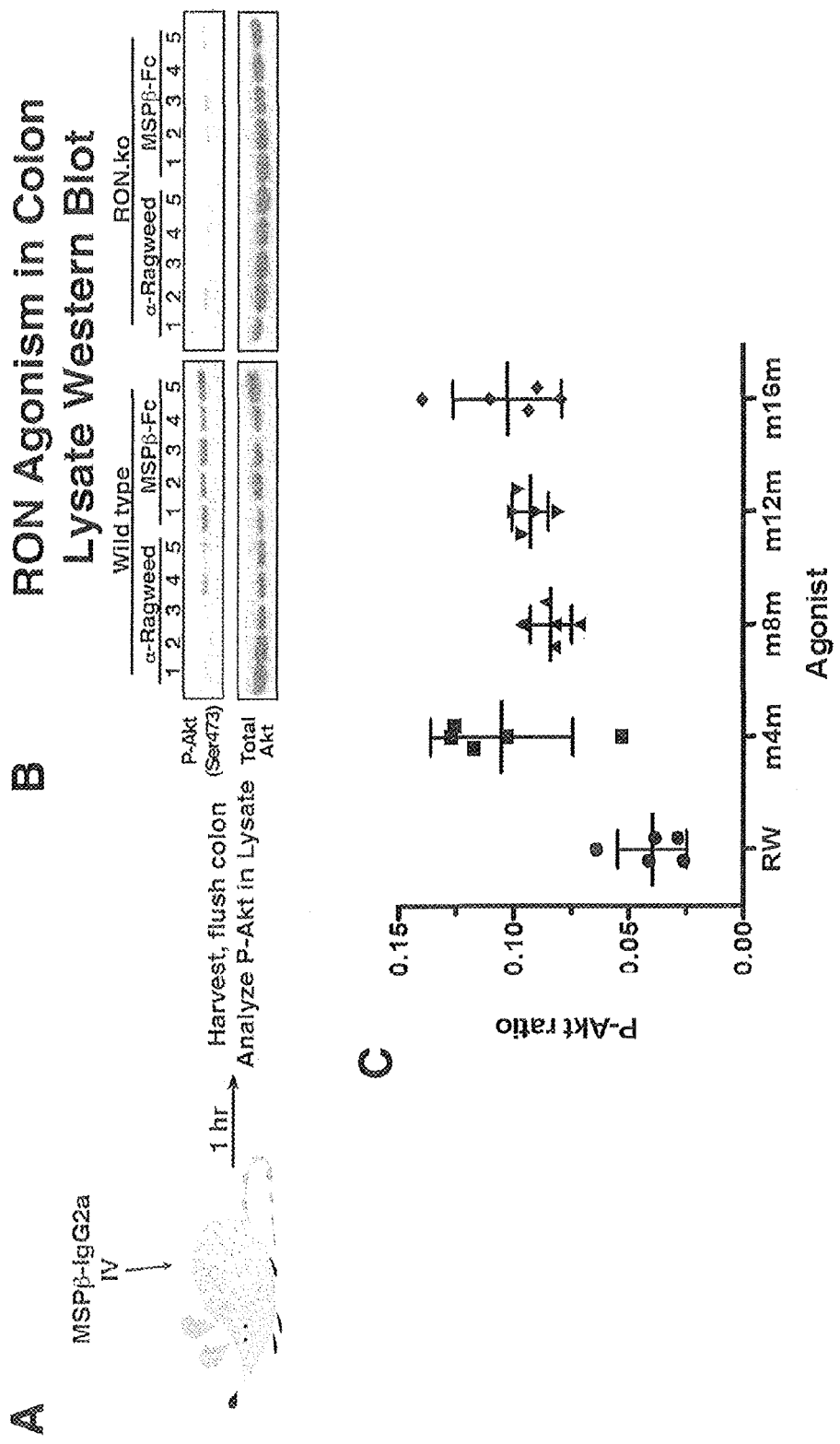
FIG. 12A-C. A shows experimental design of Example 9 examining RON agonism in vivo. B shows images of western blot analysis detecting phosphorylated Akt in mice colon lysate induced by MSPβ-Fc fusion or anti-ragweed isotype control in wild type or RON knockout mice. C summarizes the levels of RON activation by measuring Akt phosphorylation by various mMSPβ-Fc fusion proteins.

Immunohistochemistry data demonstrate that systemically dosed MSPβ-IgG2a proteins have access to the intestinal epithelium and can bind RON-expressing cells. To determine if MSPβ-IgG2a proteins induce RON signaling in vivo, mice were injected intravenously with fusion protein (FIG. 12 panel A). Western blot analysis showed increased Akt phosphorylation in whole tissue lysates of colons from mice that received MSPβ-IgG2a compared to an anti-ragweed control antibody of the same isotype (FIG. 12 panel B). This signaling was RON dependent, for no increase in Akt phosphorylation was observed in the colon of RON.ko mice that lack the RON tyrosine kinase domain (FIG. 12 panel B). RON signaling in the colon was confirmed by quantitative MSD analysis of Akt phosphorylation in the colon of mice injected with fusion proteins having spacers of 4, 8, 12, or 16 amino acids between MSPβ and IgG2a. This analysis detected approximately 2.6-, 2-, 2.3-, and 2.5-fold increases in Akt phosphorylation, respectively (FIG. 12 panel C). Unlike in 3T3-mRON cells, in colon the agonist activity of the MSPβ-IgG2a proteins is not related to the size of the spacer between MSPβ and IgG2a. These data demonstrate that MSPβ-IgG2a proteins reach the colon in a functional state and induce RON-dependent signaling in this tissue.

Figure 13:
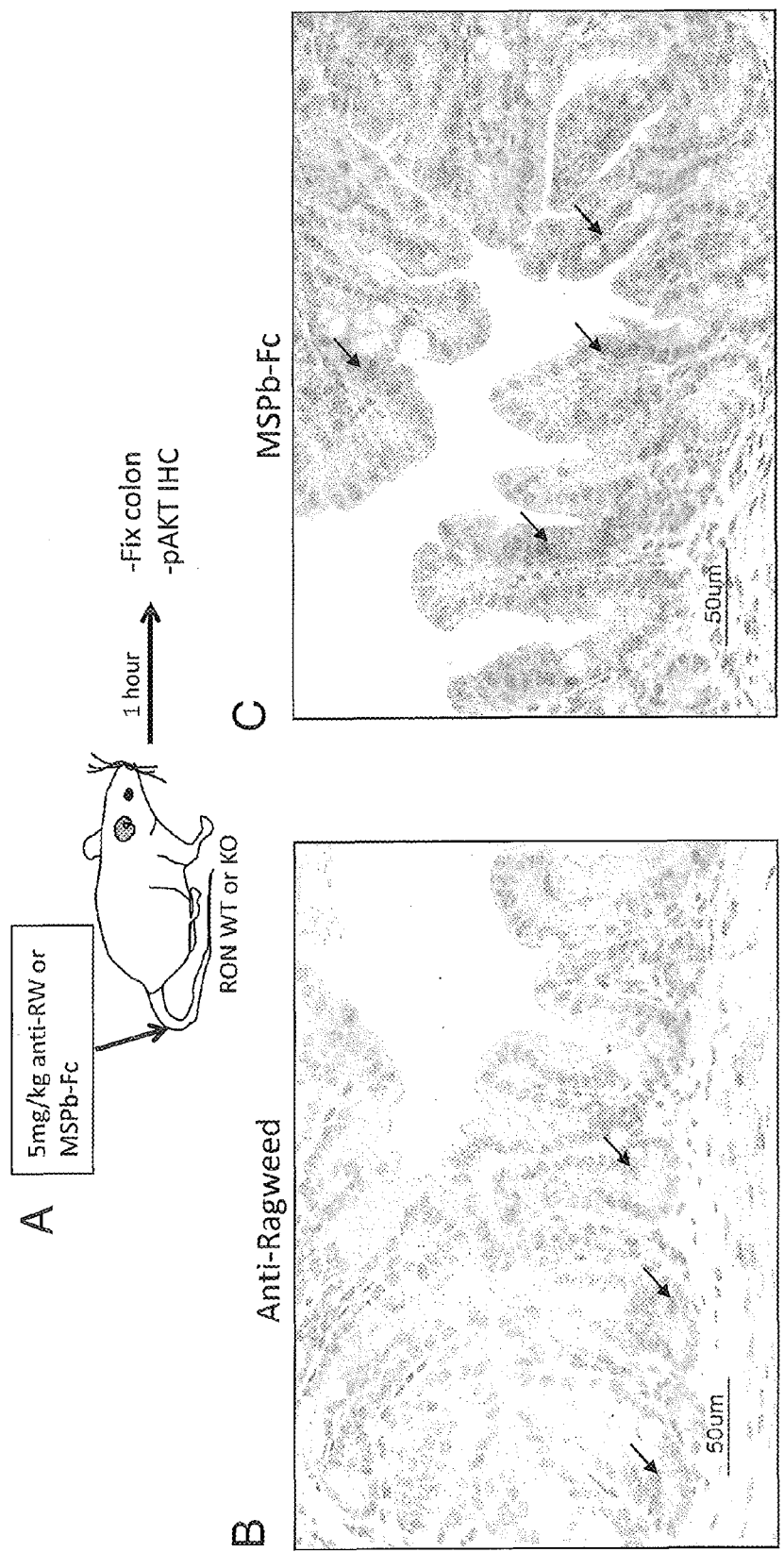
FIG. 13A-B. A shows the experimental design examining RON signaling in colon epithelial tissue. The colon tissue sections from MSPβ-Fc fusion protein-injected mice (C) or anti-ragweed isotype control-injected mice (B) were stained by immunohistochemistry using an anti-phospho-Akt antibody. These figures relate to Example 9.

Western and MSD analysis of mouse colon demonstrated that RON agonists induce RON signaling in this tissue. The colon epithelium would be a relevant tissue in which to induce RON signaling and stimulate repair pathways. To identify if signaling is induced in these cells, mice were injected intravenously with either RON agonist protein or an anti-ragweed control antibody of the same isotype (FIG. 13 panel A). Colon tissue from these mice was then sectioned and stained for phosphorylated Akt. In control antibody treated animals the colon showed weak, scattered nuclear phosphorylated Akt staining in crypt cells (FIG. 13 panel B). In contrast, the colons of mice receiving RON agonists showed stronger nuclear and cytoplasmic staining that was more predominately localized to the surface and upper crypt epithelial cells (FIG. 13 panel C). These results indicate that RON agonists induce signaling in a relevant cell type for the induction of repair pathways.

Example 10 RON Agonist Antibodies Bind RON Expressed on Cell Surface

Figure 14:
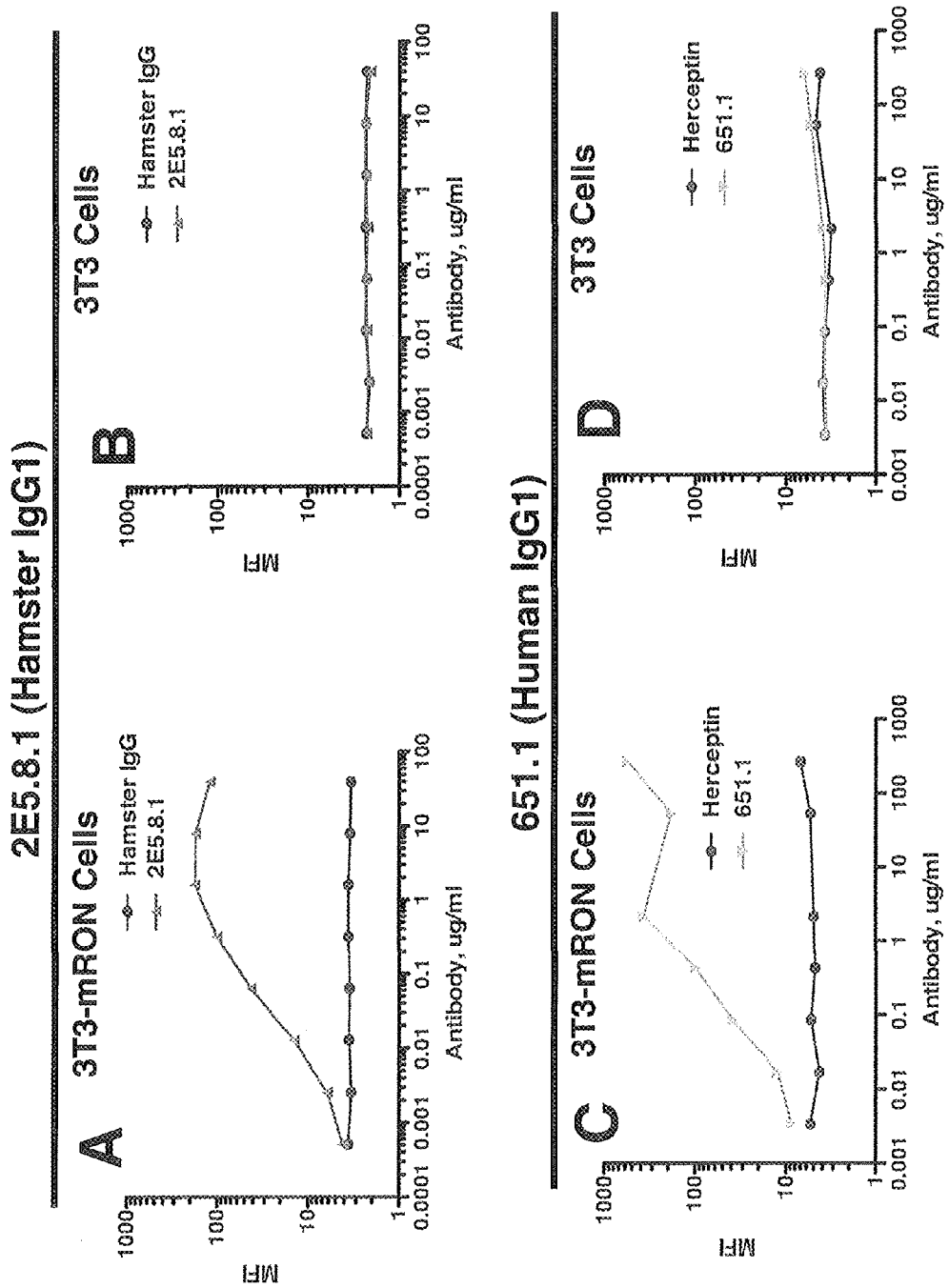
FIG. 14A-D. A and C present graphs showing that anti-RON monoclonal antibodies 2E5.8.1 and YW651.1 bound to mRON expressed on the surface of 3T3-mRON cells. B and D show results demonstrating that the binding is RON specific because no binding was detected in parent 3T3 cells that did not express mRON. These figures relate to Example 10.

Anti-mRON agonist antibodies were generated using mRON as antigen. After screening, two clones were identified and further analyzed. To function as RON agonists in vivo, RON agonist antibodies must bind full-length RON expressed on the cell surface. To determine if this occurs, 3T3-mRON cells were incubated with titrations of the hamster anti-RON antibody 2E5.8.1-hamster IgG1 or human anti-RON antibody YW651.1-IgG1. Flow cytometric analysis of 3T3-mRON cells after this incubation showed that both agonist antibodies bind RON on the cell surface at a wide range of concentrations, from about 2 ng/ml to 40 ug/ml (FIG. 14 panels A and C). Control hamster and human antibodies of the same isotype as the agonists did not bind 3T3-mRON cells (data not shown). Agonist antibody binding is specific for RON, because they did not bind RON-negative parental 3T3 cells (FIG. 14 panels B and D).

Example 11 RON Agonist Antibodies Function as RON Agonists In Vitro

Figure 15:
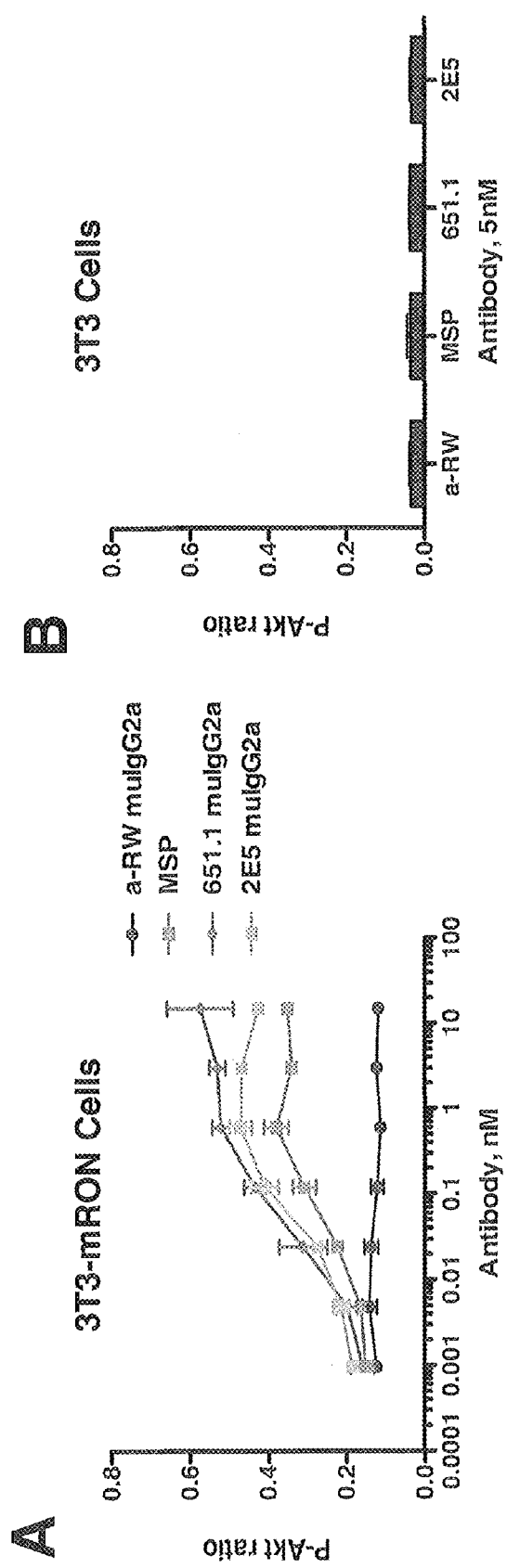
FIG. 15. A-B present results of Example 11 showing Akt phosphorylation in 3T3-mRON cells or control cells induced by MSP fusion proteins and anti-mRON agonist antibodies.

To evaluate the agonist activity of anti-RON antibodies, 2E5.8.1 and YW651.1 antibody clones were reformatted to contain the mouse IgG2a Fc region. 3T3-mRON cells were stimulated with a range of concentrations of 2E5.8.1-IgG2a, YW651.1-IgG2a, MSP, or an anti-ragweed control antibody of the same isotype. Quantitative Meso Scale Discovery (MSD) analysis of Akt phosphorylation at serine 473 in these cells showed that, like MSP, agonist antibodies induce Akt phosphorylation in a dose-dependent manner (FIG. 15 panel A). The anti-ragweed control antibody had no activity in this assay (FIG. 15 panel A). Akt phosphorylation was not induced in RON-negative parental 3T3 cells (FIG. 15 panel B), indicating that observed signaling is RON-dependent.

Example 12 Certain RON Agonist Antibodies do not Block MSP Binding to RON

Figure 16:
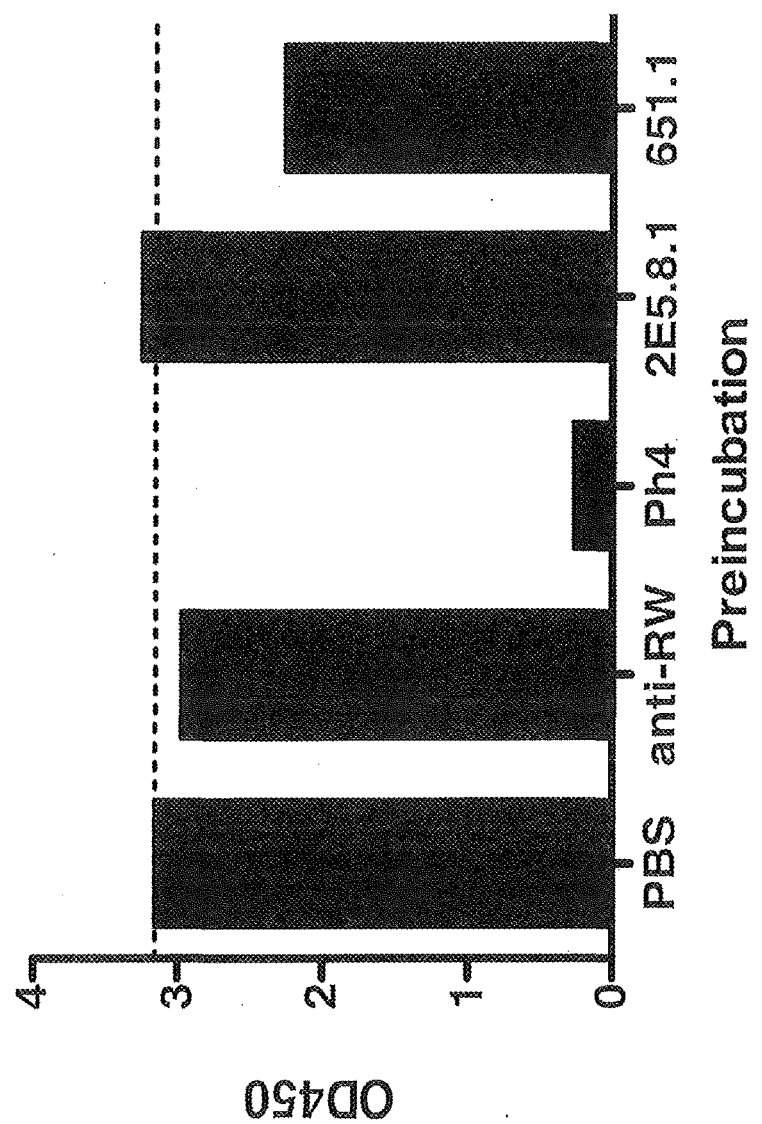
FIG. 16 shows a bar graph summarizing the results of RON blocking assay by anti-RON antibodies as described in Example 12.

RON agonist antibodies, like MSP, bind RON. Therefore they could interfere with MSP binding to RON and lead to decreased RON signaling by MSP in some situations. To determine if such interference occurs, a plate-based binding assay was used to measure MSP binding to RON (FIG. 16). In this assay, Microtest ELISA plates (BD Falcon) were coated overnight at 4° C. with 2 ug/ml mRON-hFc fusion (SEQ ID NO:50) in PBS, and MSP binding to wells pre-incubated with PBS was considered to be the maximum. Plates were washed (PBS with 0.05% Tween 20) and blocked for one hour with 1X Reagent Diluent (R&D Systems). Plates were washed and incubated 30 minutes with 30 ug/ml PBS, anti-ragweed IgG2a, Ph4 anti-RON IgG2a antibody, or agonist antibodies 2E5.8.1 or YW651.1 diluted in 1X Reagent Diluent. Hexahistidine-tagged murine MSP β was added to a final concentration of 0.1 ug/ml and plates were incubated for 1 hour. Plates were washed and incubated with HRP conjugated anti-His antibody (Miltenyi Biotec) diluted 1:2000 dilution in 1X Reagent Diluent. Plates were washed and binding was read by incubation with TMB/$H_2O_2$ substrate (R&D Systems) for 15 min, 1M $H_3PO_4$ was added, and $A_{450}$ was measured.

As expected, preincubation with anti-ragweed antibody, which does not bind RON, failed to reduce MSP binding. Also as expected, preincubation with Ph4 anti-RON antibody, which competes with MSP for RON binding, reduced MSP binding (FIG. 16). RON agonist antibody 2E5.8.1 did not reduce MSP binding, and agonist antibody YW651.1 modestly reduced MSP binding. These results indicate that the binding of these two agonist antibodies to RON likely differs, with one in competition with MSP and the other not.

The characteristics of the reformatted monoclonal antibodies 2E5.8.1 and YW651.1 are summarized below in Table 4.

TABLE 4

| Antibody | Source | Isotype | RON Affinity, nM | EC50 in vitro (MSD pAKT), nM | Agonist Activity in vivo | MSP Ligand Blocking |
|---|---|---|---|---|---|---|
| YW651.1 | Phage | muIgG2a | 0.9 | 0.04 | ++++ | +/− |
| 2E5.8.1 | Hamster | muIgG2a | nt | 0.04 | ++++ | − | nt—not tested

Figure 17:
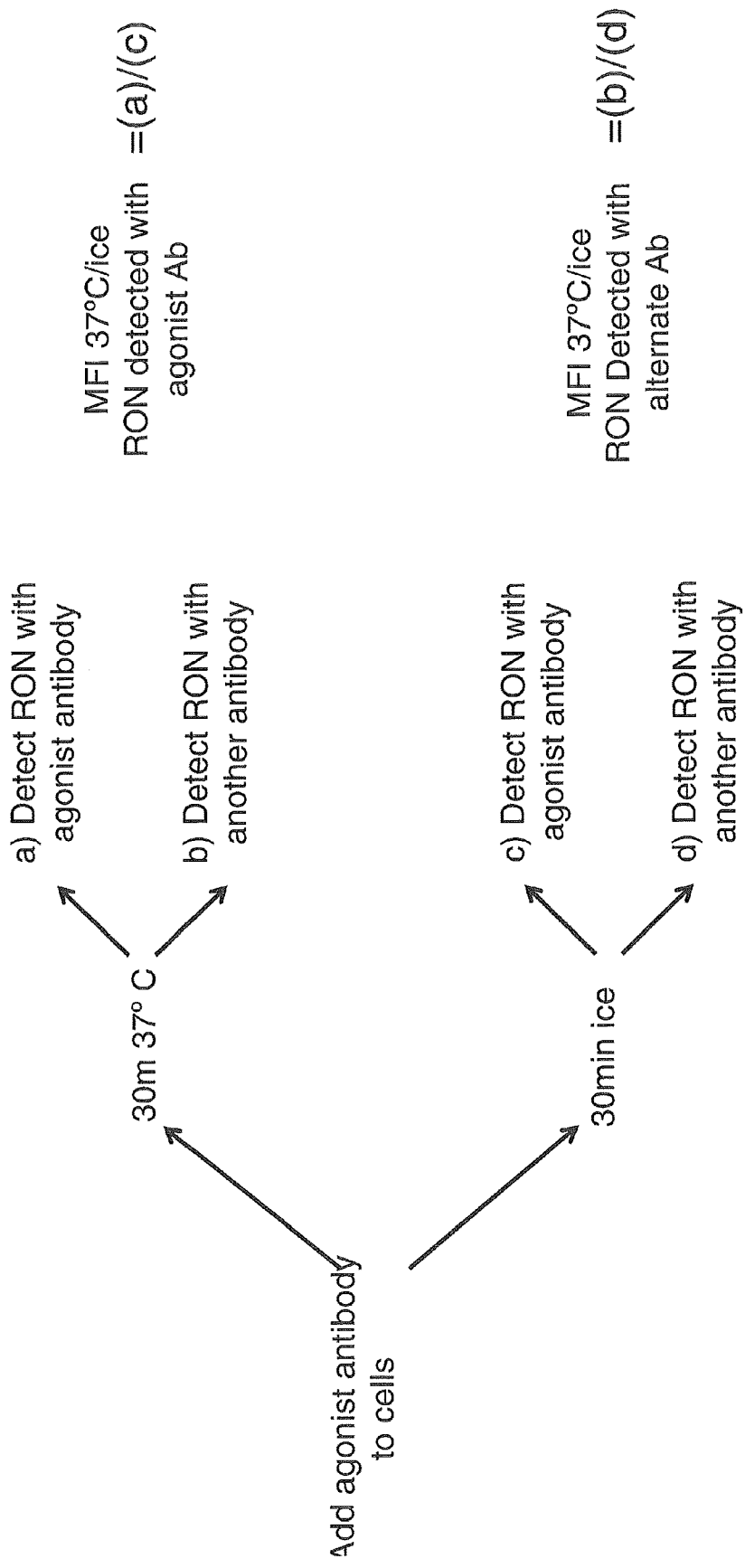
FIG. 17 presents the experimental design of Example 13 examining RON downregulation by RON agonist antibodies.
Figure 18:
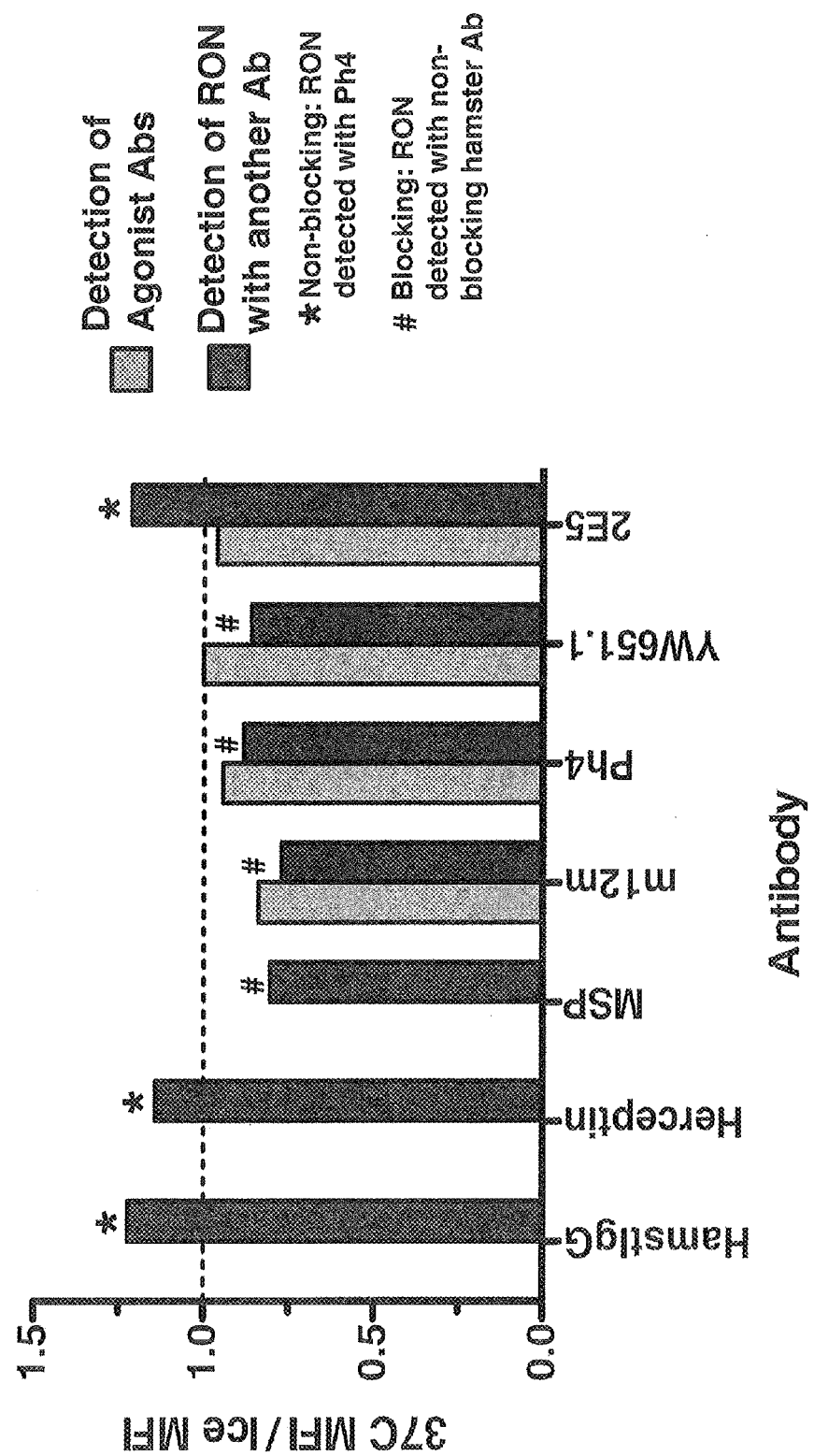
FIG. 18 presents a bar graph summarizing the results of Example 13 showing that the agonist antibodies did not downregulate RON.

Example 13 RON Agonist Antibodies do not Induce Down-Regulation of RON from Cell Surface Next, whether RON activation would induce removal of the receptor from the cell surface, leading to decreased responsiveness to MSP or agonist antibody was examined. A cell-based assay was used to address whether agonist antibodies induce down-regulation of RON (FIGS. 17 and 18). Flow cytometry was used to determine if incubation with the agonist antibody at 37° C. would decrease the amount of RON on the cell surface compared to control in which incubation was conducted on ice (FIG. 17).

200,000 3T3-mRON cells were pelleted and incubated 30 minutes either at 37° C. or on ice with hamster IgG, Herceptin®, MSP, m12m MSPβ-IgG2a, Ph4-IgG2a, YW651.1-human IgG1, or 2E5.8.1-hamster IgG1 diluted to 20 ug/ml in FACS buffer. Cells were washed twice in FACS buffer (PBS plus 2% FBS).

For RON detection via agonist reagent, cells were incubated 30 minutes either at 37° C. or on ice with the following—for hamster IgG and 2E5.8.1: R-phycoerythrin-conjugated goat anti-hamster IgG (Jackson Immunoresearch) diluted 1:500 in FACS buffer; for Herceptin® and YW651.1: phycoerythrin-conjugated goat anti-human IgG (BD Pharmingen) diluted 1:250 in FACS buffer; for Ph4 and MSPβ-IgG2a: Alexa Fluor 647-conjugated goat anti-mouse IgG diluted 1:500 in FACS buffer. RON down-regulation was determined by calculating the ratio of RON signal after incubation at 37° C. to the signal after incubation on ice, with a ratio of less than one indicating down-regulation.

To detect RON with an alternate antibody, cells were incubated 30 minutes either at 37° C. or on ice with the following: for cells treated with hamster IgG, Herceptin®, and 2E5.8.1, RON was detected with Alexa Fluor 647-conjugated Ph4 antibody diluted 1:1000 in FACS buffer; for cells treated with MSP, MSPβ-IgG2a, Ph4, and YW651.1, the 2E5.8.1 antibody was used at a concentration of 1 ug/ml in FACS buffer. 2E5.8.1 was then detected with R-phycoerythrin-conjugated goat anti-hamster IgG diluted 1:500 in FACS buffer. RON down-regulation was determined by calculating the ratio of RON signal after incubation at 37° C. to the signal after incubation on ice, with a ratio of less than one indicating down-regulation.

Two experiments were performed in parallel using different methods to measure cell surface RON. In one, RON was detected using a secondary antibody specific for the agonist. In the other, RON was detected using a different antibody. Importantly, blocking data were used to select a detection antibody that does not compete with the agonist for RON binding. As expected, hamster IgG and Herceptin®, which do not bind RON, did not induce RON down-regulation. Assays using both RON detection methods showed the level of cell surface RON was relatively unchanged after incubation at 37° C. with the m12m MSPβ-IgG2a fusion, anti-RON antibody Ph4, or the RON agonist antibodies YW651.1, and 2E5.8.1. Reagents were not available to detect MSP binding to the cell surface, but RON levels were unchanged when the 2E5.8.1 antibody was used to detect RON after incubation with MSP. These data suggest that RON antibodies behave similarly to MSP in terms of modulation of RON surface receptor expression and did not induce down-regulation of RON from cell surface.

Figure 19:
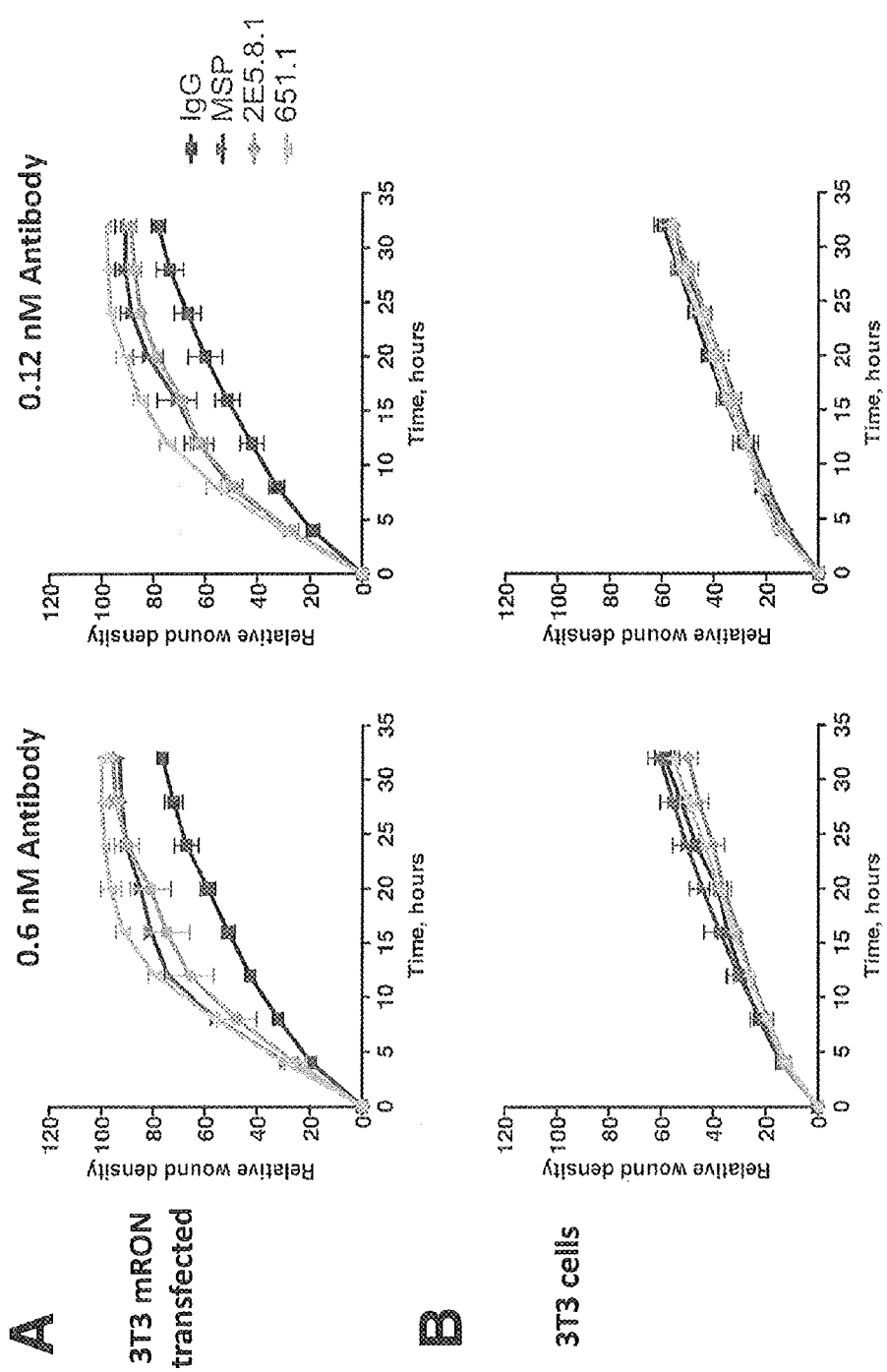
FIG. 19A-B. A presents the results of Example 14 showing the effect of MSP fusion proteins and Ron agonist antibodies on wound healing in 3T3-mRON cells. No effect is shown in RON negative parental 3T3 cells (B).

Example 14 RON Agonist Antibodies Induce Repair in an In Vitro Scratch Wound Assay As shown above, in scratch wound experiments utilizing cell monolayers, MSP can induce a repair response that models wound healing. To determine if RON agonist antibodies induce downstream effects in cells that are similar to those induced by MSP, antibodies were evaluated for their ability to induce repair in the scratch wound assay. As shown above, 12 hours of human MSP treatment (either MSP 689R or MSP 689C) induced wound healing in 3T3 cells expressing hRON, visualized as a greater cell density within the wound area compared to the anti-ragweed antibody control (FIG. 5 panel C). Similarly, mMSP-Fc fusion protein and RON agonist antibodies induced a similar repair response in the in vitro system using 3T3 cells expressing mRON (FIG. 19 panel A). Quantitative analysis of cell density in scratch-wounded 3T3-mRON cells over a 32 hour time course shows that RON agonist antibodies YW651.1 and 2E5.8.1 induced scratch wound repair similar to that induced by MSP and greater than that observed in cells treated with control IgG antibody. This stimulation of wound repair is RON-dependent, because neither MSP nor agonist antibodies induce repair in RON-negative parental 3T3 cells (FIG. 19 panel B).

Example 15 RON Agonist Antibodies Induce RON Signaling in Mouse Colon and Skin

Figure 20:
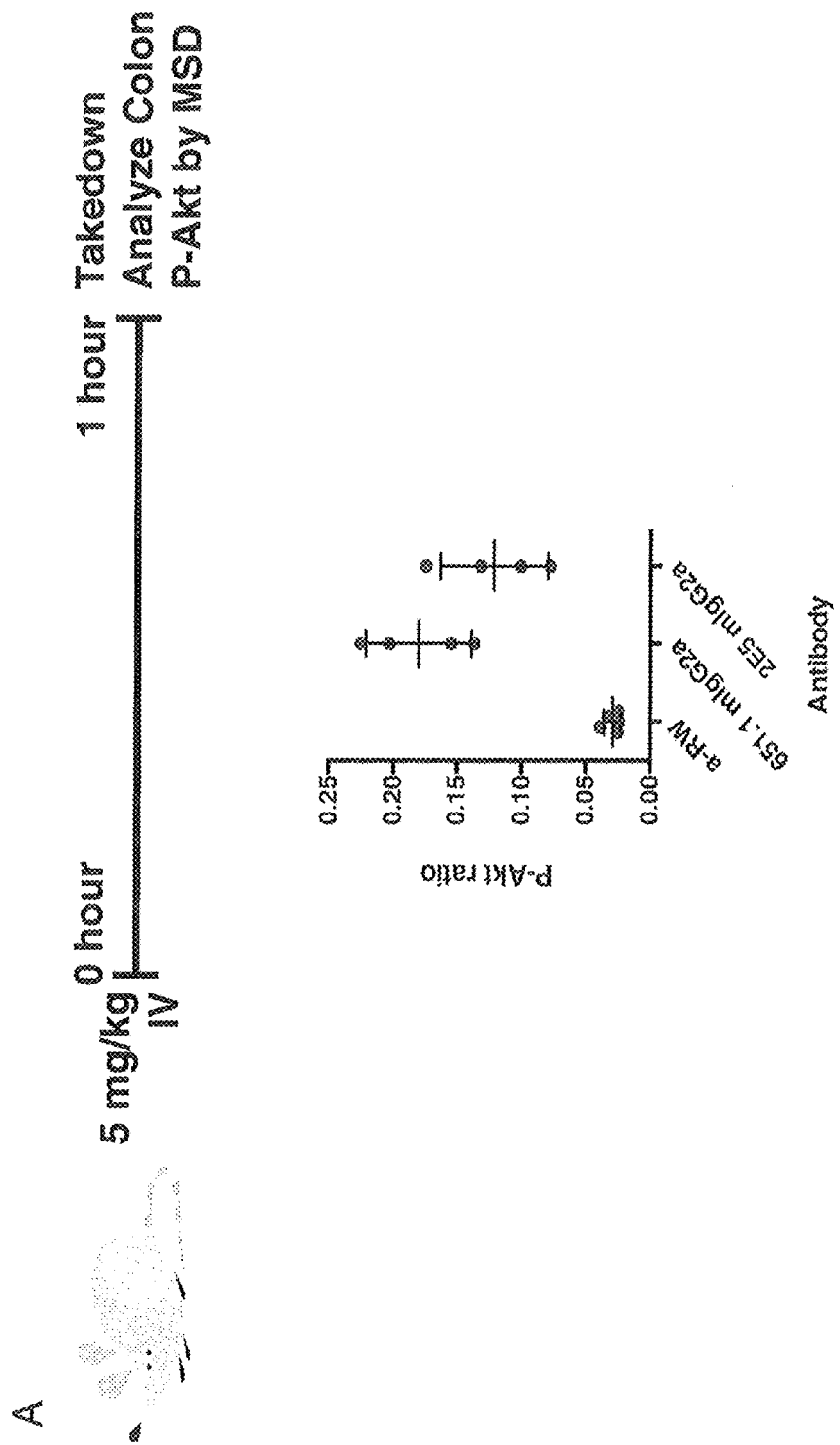
FIG. 20A-C. A shows the experimental design of Example 15 and results of in vivo RON activity assay in colon cells isolated from mice injected with RON agonist antibodies. B-C show results of pAKT induction in non-wounded skin with or without the treatment of agonist antibody YW651.1 in db/db mice (B) or WT and RON TK$^{-/-}$ mice (C). *, p<0.003; **, p<0.0001.
Figure 20:
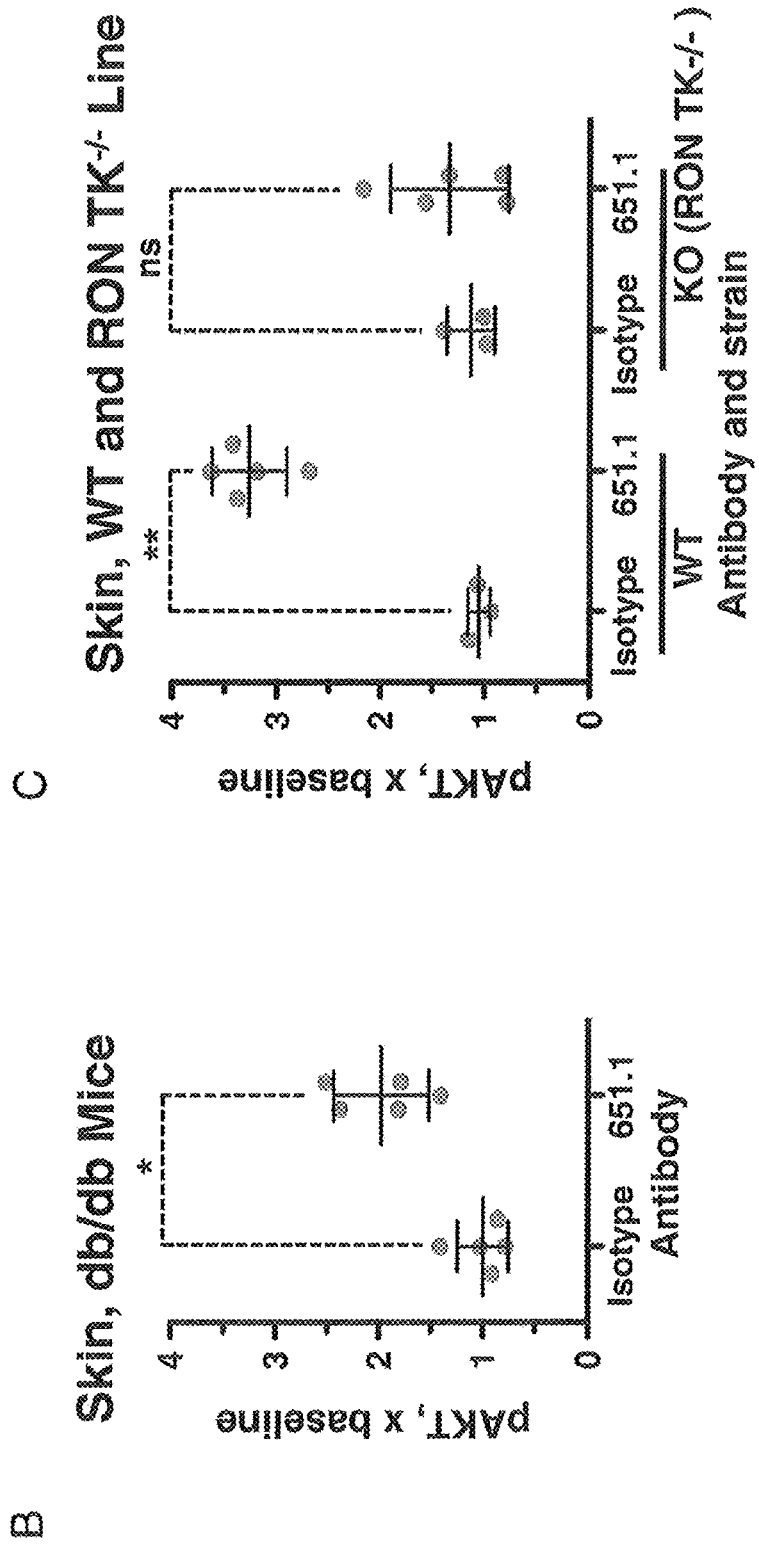

To determine if RON agonist antibodies induce RON signaling in vivo, mice were injected intravenously or intraperitoneally with YW651.1-IgG2a, 2E5.8.1-IgG2a, or an anti-ragweed control antibody of the same isotype. Quantitative MSD (Mesoscale Discovery) analysis of Akt phosphorylation in the colon showed that YW651.1-IgG2a and 2E5.8.1-IgG2a acted as RON agonists in the colon, inducing approximately 7- and 5-fold increases in Akt phosphorylation over control antibody, respectively (FIG. 20 panel A). These data also demonstrate that RON agonist antibodies reached the colon in a functional state and induced RON signaling in the tissues.

Quantitative MSD analysis of Akt phosphorylation in the skin show that YW651.1-IgG2a acted as a RON agonist in non-wounded skin from diabetic mice (db/db) (FIG. 20 panel B) and wild type controls ("WT", i.e., RON TK$^{-/-}$ line littermate, RON TK$^{+/+}$or RON positive mice) (FIG. 20 panel C), inducing over control antibody an approximately 2- and 3-fold increases in Akt phosphorylation, respectively. YW651.1-IgG2a did not induce RON signaling in RON TK$^{-/-}$ mice (RON deficient mice with deletion in the tyrosine kinase domain of RON), indicating that the signaling was RON-dependent (FIG. 20 panel C).

Example 16 RON Agonist Antibody Induces Wound Healing and Reduces Blood Glucose in Diabetic db/db Mice Having shown that RON agonist antibodies bound RON in vitro and induced signaling in the murine colon, it was then determined whether this signaling could induce repair of damaged epithelial tissue in vivo. MSP has been shown to induce healing in a skin-wounding model of epithelial damage (Santoro et al, 2003, Dev Cell. 5(2):257-71), and a similar model was used in this experiment in diabetic mice (db/db mice) to assay RON agonist antibody YW651.1-IgG2a for the induction of repair (FIG. 21 panels A-B).

Figure 21:
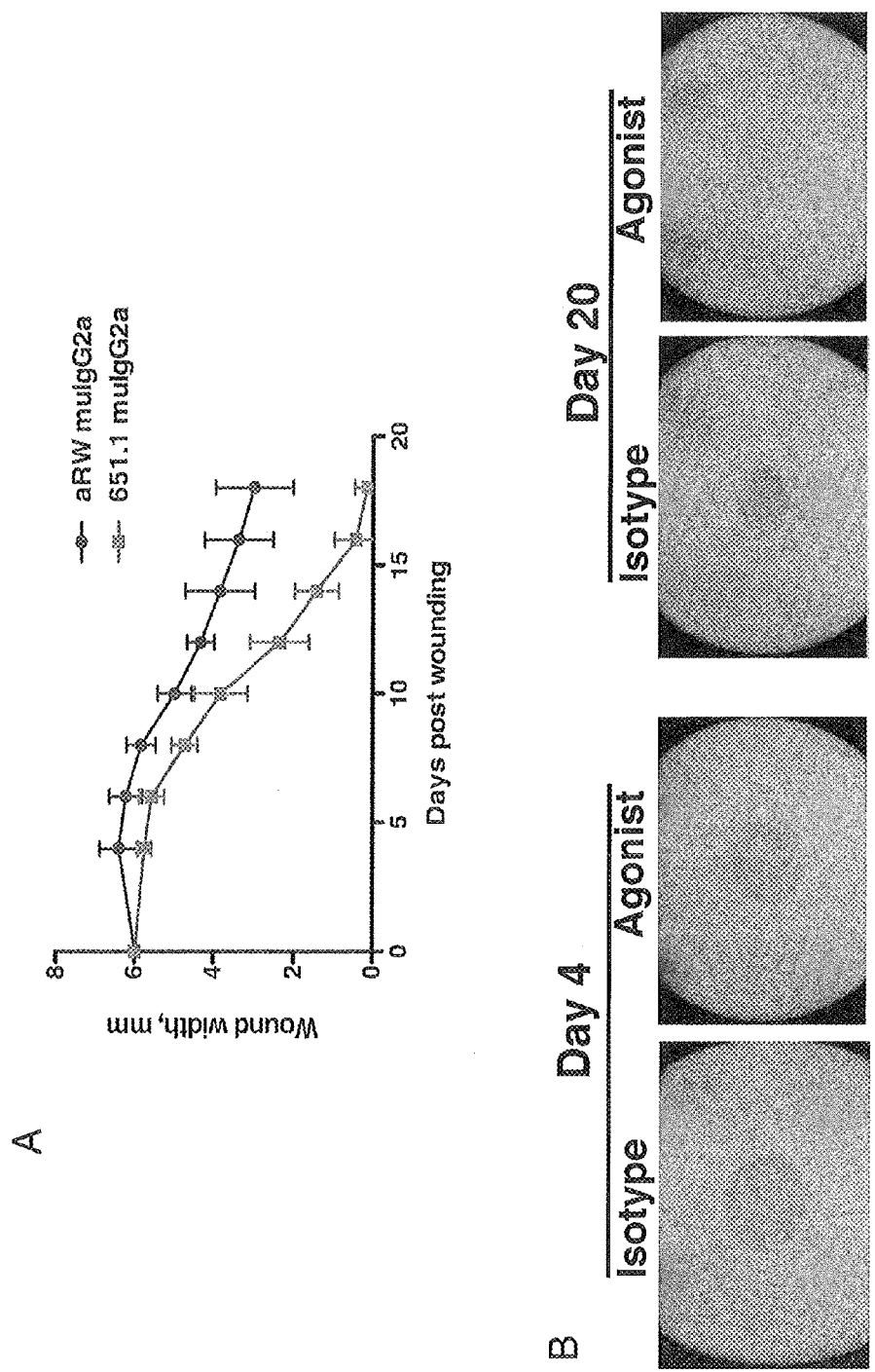
FIG. 21A-C. A shows a graph summarizing the data of in vivo wound healing assay of Example 16 in db/db diabetic mice using the RON agonist antibody YW651.1. B shows photographic images of skin wound closure on Day 4 or Day 20 in db/db mice treated with control antibody or the agonist antibody YW651.1-IgG2a. Quantitative data of pAKT induction by the agonist antibody in the wounded tissue are presented in C.
Figure 21:
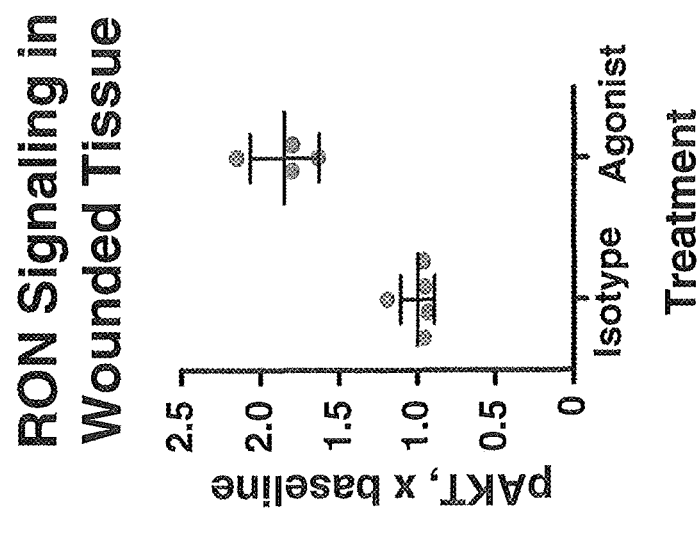

During the course of the study, wound size decreased to near zero for mice that received RON agonist antibody, meaning that the wounds had healed to the point of closure (FIG. 21 panel A). In sharp contrast, wounds did not close for mice that received control antibody of the same isotype. In fact, wound size decreased by only 50 percent. This result demonstrates that systemically dosed RON agonist antibody induced repair of a damaged epithelium. In addition, YW651.1-IgG2a induced Akt phosphorylation over control antibody in wounded skin from db/db mice (FIG. 21 panel C). Thus, consistent with the results of the scratch assay described above, quantitative MSD analysis of Akt phosphorylation in the skin show that YW651.1-IgG2a acted as a RON agonist in non-wounded skin from diabetic mice (db/db) (FIG. 20 panel B), wild type RON-positive mice (FIG. 20 panel C), as well as wounded skin from db/db mice (FIG. 21 panel C).

Figure 22:
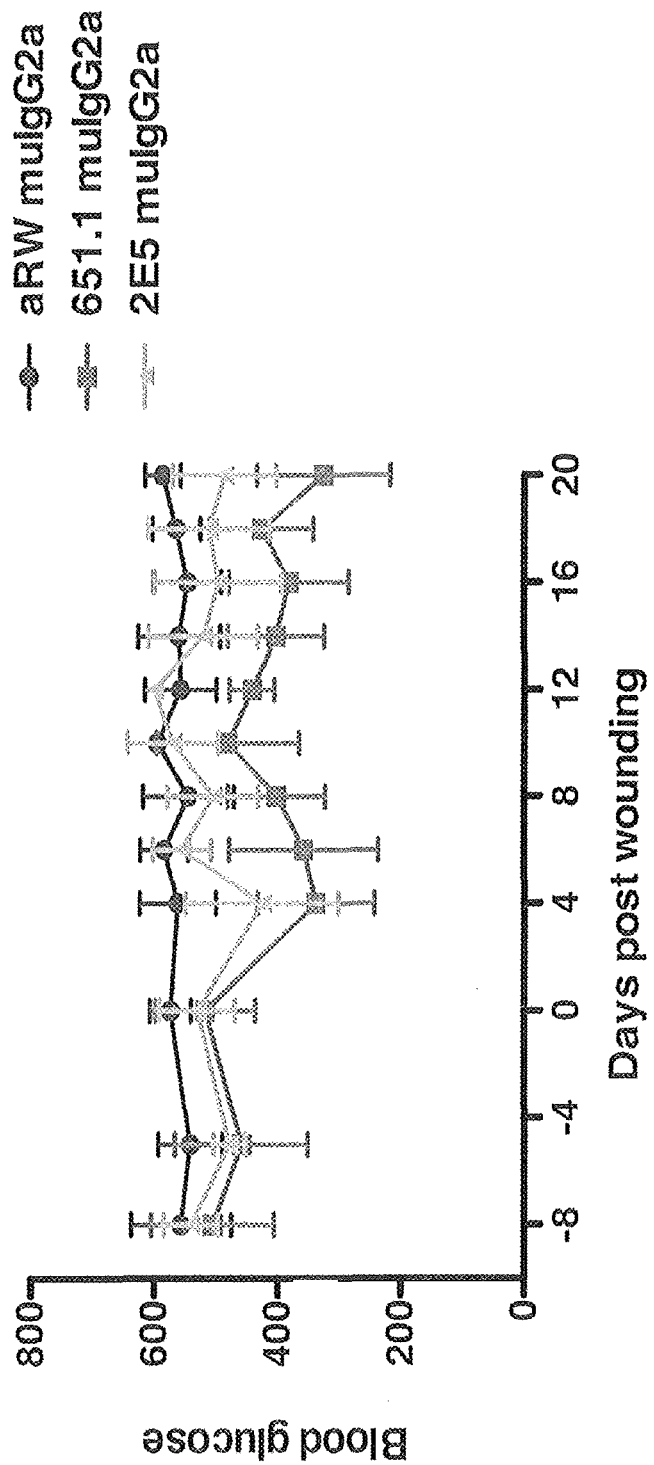
FIG. 22 summarizes the results of Example 16 showing the effect of RON agonist antibodies on reducing blood glucose levels in db/db mice.

In addition to impaired wound healing, db/db mice have other phenotypes resembling diabetes in humans, such as elevated non-fasting blood glucose levels. To establish whether RON agonist antibodies modify other db/db mouse phenotypes, the effect of YW651.1-IgG2a or 2E5.8.1-IgG2a on non-fasting blood glucose level was determined. At multiple time points, mice that received RON agonist antibody YW651.1-IgG2a had significantly lower blood glucose levels compared to mice receiving anti-ragweed control antibody of the same isotype (FIG. 22). These results demonstrate that RON antibodies are efficacious in modifying multiple phenotypes in a model of metabolic syndrome.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method of reducing blood glucose in a subject in need thereof comprising the step of administering to the subject an effective amount of a Receptor d'Origine Nantais (RON) agonist comprising an anti-RON agonist antibody, or an antigen-binding fragment thereof, or a Macrophage Stimulating Protein (MSP) fusion protein, or a functional fragment thereof, wherein the MSP fusion protein comprises an MSP-Fc fusion protein.

2. The method of claim 1 further comprising the steps of detecting the serum MSP level in the subject, detecting the serum MSP level in a normal control, and administering the RON agonist to the subject when the serum MSP level is lower in the subject as compared to the serum MSP level in a normal control.

3. The method of claim 1 further comprising the steps of detecting the presence of the rs3197999 polymorphism in the subject, and administering the RON agonist to the subject when the rs3197999 polymorphism is detected in the subject.

4. The method of claim 2 further comprising the steps of detecting the presence of the rs3197999 polymorphism in the subject, and administering the RON agonist to the subject when the rs3197999 polymorphism is detected in the subject and when the serum MSP level is lower in the subject than in a normal control.

5. The method of claim 1, wherein the subject is a diabetic subject.

* * * * *